United States Patent
Wong et al.

(10) Patent No.: US 10,119,972 B2
(45) Date of Patent: Nov. 6, 2018

(54) REACTIVE LABELLING COMPOUNDS AND USES THEREOF

(71) Applicant: Academia Sinica, Taipei (TW)

(72) Inventors: Chi-Huey Wong, Rancho Sante Fe, CA (US); Jim-Min Fang, Taipei (TW); Jiun-Jie Shie, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 15/666,242

(22) Filed: Aug. 1, 2017

(65) Prior Publication Data

US 2018/0011104 A1    Jan. 11, 2018

Related U.S. Application Data

(60) Division of application No. 14/698,660, filed on Apr. 28, 2015, now Pat. No. 9,759,726, which is a continuation-in-part of application No. PCT/US2015/022977, filed on Mar. 27, 2015.

(60) Provisional application No. 61/971,313, filed on Mar. 27, 2014.

(51) Int. Cl.
| | |
|---|---|
| *C07D 311/02* | (2006.01) |
| *G01N 33/58* | (2006.01) |
| *C07F 5/02* | (2006.01) |
| *C07K 7/08* | (2006.01) |
| *G01N 21/64* | (2006.01) |
| *C07D 309/14* | (2006.01) |

(52) U.S. Cl.
CPC .......... *G01N 33/582* (2013.01); *C07D 309/14* (2013.01); *C07D 311/02* (2013.01); *C07F 5/027* (2013.01); *C07K 7/08* (2013.01); *G01N 21/64* (2013.01); *G01N 2333/924* (2013.01); *G01N 2458/30* (2013.01)

(58) Field of Classification Search
CPC .................................................. G01N 33/582
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |

(Continued)

FOREIGN PATENT DOCUMENTS

| | | |
|---|---|---|
| EP | 0404097 A2 | 12/1990 |
| EP | 0341735 B1 | 9/1992 |

(Continued)

OTHER PUBLICATIONS

Tsai et al., Proceedings of the National Academy of Sciences of the United States of America (2013), 110(7), 2466-2471.*

(Continued)

*Primary Examiner* — Paul V Ward
(74) *Attorney, Agent, or Firm* — Duane Morris LLP

(57) ABSTRACT

Provided are azido-BODIPY compounds of formula (I), cyclooctyne-based fluorogenic probes of formula (IV), and activity-based probes of formula (VI). These compounds undergo azide-alkyne cycloadditions (AAC) with to form triazolyl products. The provided compounds are useful for detection and imaging of alkyne-, or azide-containing molecules. Methods for detection and imaging biomolecules using compounds of the present disclosure are disclosed.

7 Claims, 31 Drawing Sheets

(56) References Cited

U.S. PATENT DOCUMENTS

| | | |
|---|---|---|
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,759,726 B2 | 9/2017 | Wong et al. |
| 9,803,177 B2 | 10/2017 | Rossi et al. |
| 9,914,956 B2 | 3/2018 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |

(56) References Cited

U.S. PATENT DOCUMENTS

| | | |
|---|---|---|
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Deckert et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1 | 3/2015 | Wang |
| 2015/0160217 A1 | 6/2015 | Wong et al. |
| 2015/0225766 A1* | 8/2015 | Wong ............ C07H 13/04 435/5 |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |

(56) References Cited

FOREIGN PATENT DOCUMENTS

| | | |
|---|---|---|
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO-2014031498 * 2/2014 ............... C07H 7/00 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |
| WO | WO 2014/031762 A1 | 2/2017 |

OTHER PUBLICATIONS

Tsai et al., PNAS (Feb. 12, 2013), vol. 110, No. 7, pp. 2466-2471.*
U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," Nature, Oct. 31, 1996, 383(6603):787-793.
Abrahmsén et al, "Analysis of signals for secretion in the staphylococcal protein A gene," EMBO J., Dec. 30, 1985, 4(13B):3901-3906.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 51385144, 1983.
Altschul SF et al., "Basic local alignment search tool", J Mol Biol. Oct. 5, 1990;215(3):403-10.
Altschul SF, et al., "Gapped BLAST and PSI-BLAST: a new generation of protein database search programs", Nucleic Acids Res. Sep. 1, 1997;25(17):3389-402.

Amin, M. N. et al. Synthetic glycopeptides reveal the glycan specificity of HIV-neutralizing antibodies. Nat. Chem. Biol. 9, 521-526, (2013).
Anderson et al., "Stimulation of Natural Killer T Cells by Glycolipids", Molecules, May 2013, 18(12), 15662-15688.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," Chem. Rev., Feb. 2002, 102(2):439-469.
Anthony, Robert et al., Recapitulation of IVIG Anti-Inflammatory Activity with a Recombinant lgG Fc, Science Apr. 18, 2008. 320:373-376.
Arase et al., "NK1.1$^+$CD4$^+$CD8$^-$ thymocytes with specific lymphokine secretion," Eur. J. Immunol., Jan. 1993, 23(1):307-310.
Arié et al., "Chaperone function of FkpA, a heat shock prolyl isomerase, in the periplasm of Escherichia coli," Mol. Microbiol., Jan. 2001, 39(1):199-210.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010).
Bachmann, Cellular and Molecular Biology, vol. 2, Chapter 72: Derivations and Genotypes of Some Mutant Derivatives of Escherichia coli K-12, Neidhardt et al., eds., 1987, pp. 1190-1219, American Society for Microbiology, Washington, D.C.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Baldwin et al., "Monoclonal antibodies in cancer treatment," Lancet, Mar. 15, 1986, 327(8481):603-605.
Banchereau et al., "Dendritic cells and the control of immunity," Nature, Mar. 19, 1998, 392(6673):245-252.
Barbas et al., "Assembly of combinatorial antibody libraries on phage surfaces: the gene III site," Proc. Natl. Acad. Sci. U.S.A., Sep. 15, 1991, 88(18):7978-7982.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barbas et al., "Semisynthetic combinatorial antibody libraries: a chemical solution to the diversity problem," Proc. Natl. Acad. Sci. U.S.A., May 15, 1992, 89(10):4457-4461.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barnes et al., "Methods for growth of cultured cells in serum-free medium," Anal. Biochem., Mar. 1, 1980, 102(2):255-270.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baselga J, et al., "Phase II study of weekly intravenous recombinant humanized anti-p185HER2 monoclonal antibody in patients with HER2/neu-overexpressing metastatic breast cancer", J Clin Oncol. Mar. 1996;14(3):737-44.

(56) References Cited

OTHER PUBLICATIONS

Baskin, J.M.; Amacher, S. L.; Bertozzi, C.R." In vivo imaging of membraneassociated glycans in developing zebrafish." Science 2008, 320, 664-667.
Bass et al., "Hormone phage: an enrichment method for variant proteins with altered binding properties," Proteins, 1990, 8(4):309-314.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beck A., "Biosimilar, biobetter and next generation therapeutic antibodies" MAbs. Mar.-Apr. 2011;3(2):107-10. Epub Mar. 1, 2011.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Berra et al., "Correlation between ganglioside distribution and histological grading of human astrocytomas," Int. J. Cancer, Sep. 15, 1985, 36(3):363-366.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," Glycobiology, Feb. 2010, 20(2):148-157.
Birklé et al., "Role of tumor-associated gangliosides in cancer progression," Biochimie, Mar.-Apr. 2003, 85(3-4):455-463.
Blixt, O. et al. Printed covalent glycan array for ligand profiling of diverse glycan binding proteins. Proc. Natl. Acad. Sci. U.S. A. 101, 17033-17038, (2004.
Bobo et al., "Convection-enhanced delivery of macromolecules in the brain," Proc. Natl. Acad. Sci. U.S.A., Mar. 15, 1994, 91(6) 2076-2080.
Boens, N. et al., "Fluorescent indicators based on BODIPY." Chem. Soc. Rev. 2012, 41, 1130-1172.
Boerner et al., "Production of antigen-specific human monoclonal antibodies from in vitro-primed human splenocytes," J. Immunol., Jul. 1, 1991, 147(1):86-95.
Borg et al., "CD1d-lipid-antigen recognition by the semi-invariant NKT T-cell receptor," Nature, Jul. 5, 2007, 448(7149):44-49.
Bosmann et al., "Enzyme activity in invasive tumors of human breast and colon," Proc. Natl. Acad. Sci. USA, May 1974, 71(5):1833-1837.
Bost, Kenneth et al., Antibodies Against a Peptide Sequence Within the HIV Envelope Protein Crossreacts With Human Interleukin-2, Immunol. Invest., 17: 577-586 (1988).
Bothmann et al., "The periplasmic Escherichia coli peptidylprolyl cis,trans-isomerase FkpA. I. Increased functional expression of antibody fragments with and without cis-prolines," J. Biol. Chem., Jun. 2, 2000, 275(22):17100-17105.
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell in Situ Using 16S rRNA-Targeted Probes, Biotechniques, 13, 928-931 (1992).

Brennan et al., "Preparation of bispecific antibodies by chemical recombination of monoclonal immunoglobulin $G_1$ fragments," Science, Jul. 5, 1985, 229(4708):81-83.
Bricard et al., "Enrichment of human CD4+ Vα24/Vβ11 invariant NKT cells in intrahepatic malignant tumors," J. Immunol., Apr. 15, 2009, 182(2):5140-5151.
Brimble et al., "The cell surface glycosphingolipids SSEA-3 and SSEA-4 are not essential for human ESC pluripotency," Stem Cells, Jan. 2007, 25(1):54-62.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Bruchez, Marcel et al. Semiconductor Nanocrystals as Fluorescent Biological Labels, Science 281:2013-2016, 1998.
Brüggemann et al., "Designer mice: the production of human antibody repertoires in transgenic animals," Year in Immunol., 1993, 7:33-40.
Buchini et al., "Towards a new generation of specific Trypanosoma cruzi trans-sialidase inhibitors," Angew. Chem. Int. Ed. Engl., 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Capel PJ et al., "Heterogeneity of human IgG Fc receptors" Immunomethods. Feb. 1994;4(1):25-34.
Carlsson, Jan et al., Protein Thiolation and Reversible Protein-Protein Conjugation, Biochem J 173: 723-737 (1978).
Carter et al., "High level Escherichia coli expression and production of a bivalent humanized antibody fragment," Nature Biotechnology, Feb. 1992, 10(2):163-167.
Carter et al., "Humanization of an anti-p185$^{HER2}$ antibody for human cancer therapy," Proc. Natl. Acad. Sci. U.S.A., May 15, 1992, 89(10):4285-4289.
Carter PJ "Potent antibody therapeutics by design" Nat Rev Immunol. May 2006;6(5):343-357.
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" MMWR, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," Proc. Natl. Acad. Sci. USA, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjugates Containing Novel Maytansinoids: Promising Anticancer Drugs Cancer Research 52: 127-131 (1992).

(56) References Cited

OTHER PUBLICATIONS

Chauhan, D. P.; Saha, T.; Lahiri, M.; Talukdar, P. "BODIPY based 'click on' fluorogenic dyes: application in live cell imaging." Tetrahedron Lett. 2014, 55, 244-247.

Chen et al., "Chaperone activity of DsbC," J. Bio. Chem., Jul. 9. 1999, 274(28): 19601-19605.

Chen et al., "Selection and analysis of an optimized anti-VEGF antibody: crystal structure of an affinity-matured Fab in complex with antigen," J. Mol. Biol., Nov. 5, 1999, 293(4):865-881.

Chen et al., "Selective killing of transformed cells by cyclin/cyclin-dependent kinase 2 antagonists," Proc. Natl. Acad. Sci. U.S.A., Apr. 13, 1999, 96(8):4325-4329.

Cheng, Peter et al., Oseltamivir-and Amandtadine-resistant Influenza Viruses A (H1N1), Emerg. Infect. Dis., Jun. 2009, 15(6): 966-968.

Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.

Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.

Chiari, M. et al., Advanced Polymers for Molecular Recognition and Sensing at the Interface. J Chromatography B, Apr. 15, 2008, 866(1-2):89-103.

Childs et al., Receptor-Binding Specificity of Pandemic Influenza a (H1N1) 2009 Virus Determined by Carbohydrate Microarray. Nat. Biotechnol. 2009, 27(9): 797-799.

Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.

Chong et al., Influenza Virus Sialidase: Effect of Calcium on Steady-State Kinetic Parameters, Biochim. Biophys. Acta, Mar. 8, 1991, 1077(1): 65-71.

Chothia et al., "Canonical structures for the hypervariable regions of immunoglobulins," J. Mol. Biol., Aug. 20, 1987, 196(4):901-917.

Chothia et al., "Domain association in immunoglobulin molecules. The packing of variable domains," J. Mol. Biol., Dec. 5, 1985, 186(3):651-663.

Chu, Kuo-CHINGet al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.

Clackson et al., "Making antibody fragments using phage display libraries," Nature, Aug. 15, 1991, 352(6336):624-628.

Clark EA et al., "Structure, function, and genetics of human B cell-associated surface molecules" Adv Cancer Res. 1989;52:81-149.

Clynes R, et al., "Fc receptors are required in passive and active immunity to melanoma" Proc Natl Acad Sci USA. Jan. 20, 1998;95(2):652-6.

Codelli, J. A. et al., Second-Generation Difluorinated Cyclooctynes for Copper-Free Click Chemistry, J. Am. Chem. Soc. 2008, 130, 11486-11493.

Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.

Coligan et al., Current Protocols in Immunology, sections 2.5.1-2.6.7, 1991.

Collins et al., Crystal Structures of Oseltamivir-Resistant Influenza Virus Neuraminidase Mutants, Nature, Jun. 26, 2008, 453(7199):1258-1261.

Connor, Robert et al., Receptor Specifcity in Human, Avian, and Equine H2 and H3 Influenza Virus Isolates, Virology, 205: 17, 1994.

Cox et al., New Options for the Prevention of Influenza, N. Engl. J. Med. Oct. 28, 1999, 341(18): 1387-1388.

Cragg, M.S. et al., Complement-Mediated Lysis by Anti-CD20 mAb Correlates with Segregation into Lipid Rafts, Blood 101 (2003) 1045-1052.

Cragg, M.S. et al., Antibody Specificity Controls in Vivo Effector Mechanism of Anti-CD20 Reagents, Blood, 103 (2004) 2738-2743.

Craigo, J. K., Montelaro, R. C. Lessons in AIDS vaccine development learned from studies of equine infectious, anemia virus infection and immunity. Viruses 5, 2963-76, (2013.

Crispin et al., "Carbohydrate and domain architecture of an immature antibody glycoform exhibiting enhanced effector functions," J. Mol. Biol., Apr. 17, 2009, 387(5):1061-1066.

Cunningham et al., "High-resolution epitope mapping of hGH-receptor interactions by alanine-scanning mutagenesis," Science, Jun. 2, 1989, 244(4908):1081-1085.

Cyranoski, Threat of Pandemic Brings Flu Drug Back to Life, Nat. Med. Sep. 2005, 11(9): 909.

Daëron, "Fc receptor biology," Annu. Rev. Immunol., 1997, 15:203-234.

Davies, JW et al., Streamlining Lead Discovery by Aligning in Silico and High-Throughput Screening, Curr Opin Chem Biol. Aug. 2006; 10(4):343-51.

Davodeau et al., "Close phenotypic and functional similarities between human and murine $\alpha\beta$ T cells expressing invariant TCR alpha-chains," J. Immunol., Jun. 15, 1997, 158(12):5603-5611.

De Almeida et al., "Thiacycloalkynes for copper-free click chemistry," Angew. Chem. Int. Ed. Engl., Mar. 5, 2012, 51(10):2443-2447.

Debets, M. F. et al., Bioconjugation with Strained Alkenes and Alkynes, Acc. Chem. Res. 2011, 44, 805-815.

De Haas et al., "Fc$\gamma$ receptors of phagocytes," J. Lab. Clin. Med., Oct. 1995, 126(4):330-341.

Dejong et al., Fatal outcome of human influenza A (H5N1) is associated with high viral load and hypercytokinemia. Nat Med Oct. 2006;12(10):1203-7. Epub Sep. 10, 2006.

Delente, Jacqubs, Glycosylation Revisited, Trends in Biotechnology 3, letters to editor, No. 9 (1985).

Dellabona et al., "An invariant V$\alpha$24-J$\alpha$Q/V$\beta$11 T cell receptor is expressed in all individuals by clonally expanded CD4$^-$8$^{-T\ cells}$," J. Exp. Med., Sep. 1, 1994, 180(3):1171-1176.

Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.

Dennis, Carina, Cancer: Off by a whisker, Nature 442: 739-741 (2006).

De Paz, J. L., Horlacher, T. & Seeberger, P.H. Oligosaccharide microarrays to map interactions of carbohydrates in biological systems. Methods Enzymol. 415, 269-292, (2006).

Dhodapkar et al., "$\alpha$-Galactosyl ceramide-loaded dendritic cells for expansion of natural killer T cells" CAPLUS 145:354715 (2006).

Dhodapkar et al., "A reversible defect in natural killer T cell function characterizes the progression of premalignant to malignant multiple myeloma," J. Exp. Med., Jun. 16, 2003, 197(12):1667-1676.

Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.

Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.

Dommerholt, Jan, Readily Accessible Bicyclononynes for Bioorthogonal Labeling and Three-Dimensional Imaging of Living Cells, Angew. Chem. Int. Ed. 2010, 49, 9422-9425.

Doores KJ, et al. A nonself sugar mimic of the HIV glycan shield shows enhanced antigenicity. Proc. Natl. Acad. Sci. US.A. 107(40), 17107-17112, (2010).

Doores, K. J. & Burton, D.R. Variable Loop Glycan Dependency of the Broad and Potent HIV-I-Neutralizing Antibodies PG9 and PG16. J. Virol. 84, 10510-10521, (2010).

Doores, K. J. et al. Envelope glycans of immunodeficiency virions are almost entirely oligomannose antigens. Proc. Natl. Acad. Sci. U. S. A 107, 13800-13805, (2010).

(56) References Cited

OTHER PUBLICATIONS

Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Durrant et al., "Immunology in the clinic review series; focus on cancer: glycolipids as targets for tumour immunotherapy," *Clin. Exp. Immunol.*, Feb. 2012, 167(2):206-215.
Eberl et al., "Selective bystander proliferation of memory CD4$^{+\ and}$ CD8$^{+}$T cells upon NK T or T cell activation," *J. Immunol.*, Oct. 15, 2000, 165(8):4305-4311.
Eberl et al., "Selective induction of NK cell proliferation and cytotoxicity by activated NKT cells," *Eur. J. Immunol.*, Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)],"*Angew. Chem. Int. Ed. Engl.*, Jun. 1989, 28(6):716-734.
European Search Report issued in connection with corresponding European Patent Application No. 15181446.4, dated Dec. 7, 2015, 10 pages.
Evans, Michael et al., "Mechanism-based profiling of enzyme families," *Chem. Rev.*, Aug. 2006, 106(8):3279-3301.
Evans, "The rise of azide-alkyne 1,3-dipolar 'click' cycloaddition and its application to polymer science and surface modification," *Australian J. Chem.*, Jun. 2007, 60(6):384-395.
Extended European Search Report dated Jan. 5, 2016 in European Patent Application No. 13830785.5, in 10 pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from *Streptococcus pneumoniae*, JBC vol. 287, No. 14, pp. 11272-11281, Mar. 30, 2012.
Fazio, F. et al. Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with antiinflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fernandez-Tejada, Alberto et al., Designing synthetic vaccines for HIV. Expert Rev. Vaccines 14, 815-31, 2015.

Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fishwild et al., "High-avidity human IgGκ monoclonal antibodies from a novel strain of minilocus transgenic mice," *Nature Biotechnol.*, Jul. 1996, 14(7):845-851.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Galfrè et al., "Preparation of monoclonal antibodies: strategies and procedures," *Methods Enzymol.*, 1981, 73(Pt B):3-46.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Gazzano-Santoro et al., "A non-radioactive complement-dependent cytotoxicity assay for anti-CD20 nonclonal antibody," *J. Immunol. Methods*, Mar. 28, 1997, 202(2):163-171.
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.

(56) References Cited

OTHER PUBLICATIONS

GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a,e]cyclooxtene Series," Helvetica Chinica Acta, Jan. 1, 1976, 59(6): 2038-2048.
Giaccone, Giuseppe et al., "A phase I study of the natural killer T-cell ligand α-galactosylceramide (KRN7000) in patients with solid tumors," Clin. Cancer Res., Dec. 2002, 8(12):3702-3709.
Gill et al., "Direct brain infusion of glial cell line-derived neurotrophic factor in Parkinson disease," Nature Med., May 2003, 9(5):589-595 and Addendum from Apr. 2006, 12(4):479.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goding, Monoclonal Antibodies: Principles and Practice $2^{nd}$ ed., Chapter 3: Production of Monoclonal Antibodies, 1986, pp. 59-103, Academic Press, London.
Goldenthal et al., "Safety Evaluation of Vaccine Adjuvants: National Cooperative Vaccine Development Working Group," AIDS Res. Hum. Retroviruses, 1993, 9(Supp.1):S47-S51.
Golkowski et al., "Strategy for catch and release of azide-tagged biomolecules utilizing a photolabile strained alkyne construct," Organic and Biomolecular Chemistry, Jan. 1, 2012, 10(23):4496.
Goochee CF et al., "The oligosaccharides of glycoproteins: bioprocess factors affecting oligosaccharide structure and their effect on glycoprotein properties", Biotechnology (N Y). Dec. 1991;9(12):1347-55.
Gordon et al., "Reactivity of biarylazacyclooctynones in copper-free click chemistry," J. Am. Chem. Soc., Jun. 6, 2012, 134(22): 9199-9208.
Gottschling et al., "Stage-specific embryonic antigen-4 is expressed in basaloid lung cancer and associated with poor prognosis," Eur. Respir. J., Mar. 2013, 41(3):656-663.
Govorkova et al, Combination chemotherapy for influenza. Viruses. Aug. 2010;2(8): 1510-29.
Graham et al., "Characteristics of a human cell line transformed by DNA from human adenovirus type 5," J. Gen. Virol., Jul. 1977, 36(1):59-72.
Graham, Duncan et al., Surface-Enhanced Resonance Raman Scattering as a Novel Method of DNA Discrimination, Angew. Chem., 2000, 112(6), 1103-1105.
Gram et al., "In vitro selection and affinity maturation of antibodies from a naive combinatorial immunoglobulin library," Proc. Natl. Acad. Sci. U.S.A., Apr. 15, 1992, 89(8):3576-3580.
Grandjean, C. et al., On the Preparation of Carbohydrate-Protein Conjugates Using the Traceless Staudinger Ligation, J Org Chem 2005, 70, 7123-7132.
Green, "Targeting targeted therapy," N. Engl. J. Med., May 20, 2004, 350(21):2191-2193.

Greenbaum et al., "Chemical approaches for functionally probing the proteome," Mol. Cell. Proteomics, 2002, 1:60-68.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in Escherichia coli," J. Immunol., Jun. 1, 1994, 152(11):5368-5374.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Guss et al., "Structure of the IgG-binding regions of streptococcal protein G," EMBO J., Jul. 1986, 5(7):1567-1575.
Guyer et al., "Immunoglobulin binding by mouse intestinal epithelial cell receptors," J. Immunol., Aug. 1976, 117(2):587-593.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," J. Immuol., May 1, 1995, 154(9):4322-4332.
Hakomori et al., "Glycosphingolipid antigens and cancer therapy," Chem. Biol., Feb. 1997, 4(2):97-104.
Hakomori, "Glycosylation defining cancer malignancy: new wine in an old bottle," Proc. Natl. Acad. Sci. U.S.A., Aug. 6, 2002, 99(16):10231-10233.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hara et al., "Overproduction of penicillin-binding protein 7 suppresses thermosensitive growth defect at low osmolarity due to an spr mutation of Escherichia coli," Microbial Drug Resistance, Spring 1996, 2(1):63-72.
Harris, "Production of humanized monoclonal antibodies for in vivo imaging and therapy," Biochem. Soc. Transactions, Nov. 1995, 23(4):1035-1038.
Hasegawa, Akira, et al., Synthesis of Sialyl Lewis X Ganglioside Analogues Containing Modified L-Fucose Residues, Carbohydr. Res. 1995, 274, 165-181.
Hsu, Nien-Yeen et al., Desorption Ionization of Biomolecules on Metals, Anal. Chem., 80, 5203-5210, 2008.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Hawkins et al., "Selection of phage antibodies by binding affinity. Mimicking affinity maturation," J. Mol. Biol., 1992, 226(3):889-896.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.

(56) References Cited

OTHER PUBLICATIONS

Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Heyman, "Complement and Fc-receptors in regulation of the antibody response," Immunol. Lett., Dec. 1996, 54(2-3):195-199.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hogrefe et al., "A bacteriophage lambda vector for the cloning and expression of immunoglobulin Fab fragments on the surface of filamentous phage," Gene, Jun. 15, 1993, 128(1):119-126.
Holliger et al., "'Diabodies': small bivalent and bispecific antibody fragments," Proc. Natl. Acad. Sci. U.S.A., Jul. 15, 1993, 90(14):6444-6448.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Honegger et al., "Yet another numbering scheme for immunoglobulin variable domains: an automatic modeling and analysis tool," J. Mol. Biol., Jun. 8, 2001, 309:657-670.
Hoogenboom et al., "By-passing immunisation: Human antibodies from synthetic repertoires of germline $V_H$ gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," Immunol. Today, Jun. 1992, 13(6):198-200.
Hsu et al., "Alkynyl sugar analogs for the labeling and visualization of glycoconjugates in cells," Proc. Natl. Acad. Sci. USA, Feb. 20, 2007, 104(8), 2614-2619.
Huang et al., "Carbohydrate-based vaccines with a glycolipid adjuvant for breast cancer," Proc. Natl. Acad. Sci. U.S.A., Feb. 12, 2013, 110(7):2517-2522.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Hung et al., "Investigation of SSEA-4 binding protein in breast cancer cells," J. Am. Chem. Soc., Apr. 24, 2013, 135(16):5934-5937.
Hurle et al., "Protein engineering techniques for antibody humanization," Curr. Opin. Biotechnol., Aug. 1994, 5(4):428-433.
Immunogenicity, Wikipedia p. 1-3. Downloaded on Aug. 16, 2016 from https://en.wikipedia.org/wiki/Immunogenicity. (2016).
Inouye et al., "Single-step purification of F(ab')$_{2\mu}$ , fragments of mouse monoclonal antibodies (immunoglobulins M) by hydrophobic interaction high-performance liquid chromatography using TSKgel Ether-5PW," J. Biochem. Biophys. Methods, Feb. 1993, 26(1):27-39.

International Search Report and Written Opinion issued for International application No. PCT/US2015/011748, dated Aug. 21, 2015, 17 pages.
International Search Report and Written Opinion issued for International application No. PCT/US2015/032737, dated Oct. 1, 2015, 13 pages.
International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.
International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," J. Immunol., Apr. 1, 1995, 154(7):3310-3319.
Jacobs et al., "Metabolic labeling of glycoproteins with chemical tags through unnatural sialic acid biosynthesis," Methods Enzymol., 2000, 327:260-275.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.
Jakobovits et al., "Germ-line transmission and expression of a human-derived yeast artificial chromosome," Nature, Mar. 18, 1993, 362(6417):255-258.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jenkins N, Curling EM., "Glycosylation of recombinant proteins: problems and prospects", Enzyme Microb Technol. May 1994;16(5):354-64.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," Org. Lett., Nov. 18, 2011, 13(22):5937-5939.

(56) References Cited

OTHER PUBLICATIONS

Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jones et al., "Rapid PCR-cloning of full-length mouse immunoglobulin variable regions," Nature Biotechnol., Jan. 1991, 9(1):88-89.
Jones et al., "Replacing the complementarity-determining regions in a human antibody with those from a mouse," Nature, May 29-Jun. 4, 1986, 321(6069):522-525.
Jones, "Analysis of polypeptides and proteins," Adv. Drug Delivery Rev., Jan.-Apr. 1993, 10(1):29-90.
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewis x: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," Chem. Commun., Jan. 28, 2010, 46(4):589-591.
Kamkaew, A. et al., "BODIPY dyes in photodynamic therapy." Chem. Soc. Rev. 2013, 42, 77-88.
Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.
Kaneko et al., "Anti-inflammatory activity of immunoglobulin G resulting from Fc sialylation," Science, Aug. 4, 2006, 313(5787):670-673.
Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Kawakami et al., "Critical role of V$\alpha$14+ natural killer T cells in the innate phase of host protection against Streptococcus pneumoniae infection," Eur. J. Immunol., Dec. 2003, 33(12):3322-3330.
Kawano et al., "CD1d-restricted and TCR-mediated activation of v$_\alpha$14 NKT cells by glycosylceramides," Science, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannagi et al., "New globoseries glycosphingolipids in human teratocarcinoma reactive with the monoclonal antibody directed to a developmentally regulated antigen, stage-specific embryonic antigen 3," J. Biol. Chem., Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," EMBO J., 1983, 2(12):2355-2361.
Kannappan, Ramaswamy et al., "Photoaffinity labeling of sialidase with a biotin-conjugated phenylaminodizairine derivative of 2,3-didehydro-2-deoxy-N-acetylneuraminic acid," Biol. Pharm. Bull., Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karlin S. et al., "Methods for assessing the statistical significance of molecular sequence features by using general scoring schemes", Proc Natl Acad Sci USA. Mar. 1990;87(6):2264-8.
Karmakar, M. et al., Current Trends in Research and Application of Microbial Cellulases, Research Journal of Microbiology, (2001) 6(1): 41-53.
Kato et al., "GMab-1, a high-affinity anti-3'-isoLM1/3'6'-isoLD1 IgG monoclonal antibody, raised in lacto-series ganglioside-defective knockout mice," Biochem. Biophys. Res. Commun., Jan. 1, 2010, 391(1):750-755.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," Biochemistry, Apr. 3, 2001, 40(13):4005-4015.
Kiick, K.L. et al., Identification of an Expanded Set of Translationally Active Methionine Analogues in Escherichia coli, tetrahedron 56:9487, 2001.
Kim et al., "Localization of the site of the murine IgG1 molecule that is involved in binding to the murine intestinal Fc receptor," Eur. J. Immunol., 1994, 24:2429-2434.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "$\alpha$-galactosylceramide induces early B-cell activation through IL-4 production by NKT cells," Cell. Immunol., Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Köhler et al., "Continuous cultures of fused cells secreting antibody of predefined specificity," Nature, Aug. 7, 1975, 256(5517):495-497.
Kolb et al., "Click chemistry: diverse chemical function from a few good reactions," Angew. Chem. Int. Ed. Engl., Jun. 1, 2001, 40(11):2004-2021.
Kolb et al., "The growing impact of click chemistry on drug discovery," Drug Discov. Today, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GalN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kontermann, "Intrabodies as therapeutic agents," Methods, Oct. 2004, 34(2): 163-170.
Kos, "Regulation of adaptive immunity by natural killer cells," Immunol. Res., 1998, 17(3):303-312.

(56) References Cited

OTHER PUBLICATIONS

Koshihara et al., 1984, Biochmica et biophysica acta, 792(1), pp. 92-97.
Kostelny et al., "Formation of a bispecific antibody by the use of leucine zippers," *J. Immunol.*, Mar. 1, 1992, 148(5):1547-1553.
Kotteas et al., Immunotherapy for pancreatic cancer, J cancer Res Clin Oncol, 142(8): 1795-1805, 2016.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kudo et al., "Up-regulation of a set of glycosyltransferase genes in human colorectal cancer," *Lab. Invest.*, Jul. 1998, 78(7):797-811.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific $CD4^+$ and $CD4^-8^-$ T cells in mice and humans," *J. Exp. Med.*, Sep. 1, 1994, 180(3):1097-1106.
Lau et al., "N-Glycans in cancer progression," *Glycobiology*, Oct. 2008, 18(10):750-760.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004).
Lee et al., Immunogenicity Study of Globo H Analogues with Modification at the Reducing or Nonreducing end of the tumor antigen, J Am Chem Soc, 136: 16844-16853 (2014).
Lefranc et al., "IMGT, the international ImMunoGeneTics database," *Nucleic Acids Res.*, Jan. 1, 1999, 27(1):209-212.

Lehninger, *Biochemistry: The Molecular Basis of Cell Structure and Function*, $2^{nd}$ ed., 1975, pp. 73-75, Worth Publishers, New York.
Lemieux, R. U. et al., Halide ion catalyzed glycosidation reactions. Syntheses of a-linked disaccharides. J Am. Chem. Soc. 97(14), 4056-62, (1975).
Leung et al., "A method for random mutagenesis of a defined DNA segment using a modified polymerase chain reaction," *Technique—A Journal of Methods in Cell and Molecular Biology*, Aug. 1989, 1(1):11-15.
Lew et al., Discovery and Development of GS 4104 (oseltamivir): an Orally Active Influenza Neuraminidase Inhibitor, Curr Med Chem, Jun. 2000, 7(6):663-672.
Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification ofxanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).
Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, P. H., Wang, S. K. & Wong, C.-H. Quantitative analysis of carbohydrate-protein interactions using glycan microarrays: Determination of surface and solution dissociation constants. J. Am. Chem. Soc. 129, 11177-11184, (2007).
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.
Lin et al., A common glycan structure on immunoglobulin G for enhancement of effector functions, PNAS, Aug. 25, 2015, vol. 112, No. 34, p. 10611-10616.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood.* May 15, 2007;109(10):4336-42. Epub Jan. 23, 2007.
Liu et al., "Activity-based protein profiling: the serine hydrolases," *Proc. Natl. Acad. Sci. USA*, Dec. 21, 1999, 96(26):14694-14699.
Liu et al., "Eradication of large colon tumor xenografts by targeted delivery of maytansinoids," *Proc. Natl. Acad. Sci. U.S.A.*, Aug. 6, 1996, 93(16):8618-8623.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyene antibiotic calicheamicin $\Theta^I_1$ effectively suppresses growth and dissemination

(56) References Cited

OTHER PUBLICATIONS of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA Pat. No. 2014, 111(7):2482-7.
Loudet, A.; Burgess, K. "BODIPY dyes and their derivatives: syntheses and spectroscopic properties." Chem. Rev. 2007, 107, 4891-4932.
Louis et al., "The 2007 WHO classification of tumours of the central nervous system," *Acta. Neuropathol.*, Aug. 2007, 114(2):97-109.
Lu et al., "Design of a mechanism-based probe for neuraminidase to capture influenza viruses," *Angew. Chem. Int. Ed. Engl.*, Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
Lu et al., "Single chain anti-c-Met antibody conjugated nanoparticles for in vivo tumor-targeted imaging and drug delivery," *Biomaterials*, Apr. 2011, 32(12):3265-3274.
MacBeath, G. and Schreiber, S. L., Printing Proteins as Microarrays for High-Throughput Function Determination, Science, 289, 1760-1763, 2000.
MacFarlane GT, et al., "Formation of glycoprotein degrading enzymes by Bacteroides fragilis" *FEMS Microbiol Lett.* Jan. 15, 1991;61(2-3):289-93.
Makino et al., Predominant expression of invariant $V_\alpha 14^+$ TCR α chain in $NK1.1^+$ T cell populations, *Int. Immunol.*, Jul. 1995, 7(7):1157-1161.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).
Månsson et al., "Characterization of new gangliosides of the lactotetraose series in murine xenografts of a human glioma cell line," *FEBS Lett.*, May 26, 1986, 201(1):109-113.
Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.
Marcato et al., "Chapter 17: The Rocky Road from Cancer Stem Cell Discovery to Diagnostic Applicability," Cancer Stem Cells Theories and Practice, pp. 335-360, Mar. 22, 2011.
Marks et al., "By-passing immunization. Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 1992, 10(7):779-783.

Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 1980, 23(1):243-252.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matsuda et al., "Structure and physical map of 64 variable segments in the 3' 0.8-megabase region of the human immunoglobulin heavy-chain locus," *Nature Genet.*, Jan. 1993, 3(1):88-94.
Matz et al., "Fluorescent proteins from nonbioluminescent *Anthozoa* species," *Nat. Biotechnol.*, Oct. 1999, 17(10):969-973.
McCafferty et al., "Phage antibodies: Filamentous phage displaying antibody variable domains," *Nature*, Dec. 6, 1990, 348:552-554.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
McLellan, J. S. et al. Structure of HIV-I gp120 V1/V2 domain with broadly neutralizing antibody PG9. Nature 480, 336-343, 2011.
Medelson et al., NKp46 O-glycan Sequences that are involved in the interaction with Hemagglutinin Type 1 of Influenza Virus. J. Virol. Feb. 10, 2010, 84(8):3789-3797.
Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.
Merck, MAB4304, Anti-Stage-Specific Embryonic Antigen-4 Antibody, Clone MC-813-70, 4 Pages, 2017.
Meyer, "Malignant gliomas in adults," *N. Engl. J. Med.*, Oct. 23, 2008, 359(17):1850.
Milstein, C & Cuello, AC, Hybrid Hydridomas and their use in immunohistochemistry, Nature 305, 537-540, Oct. 1993.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant Mycobacterium Bovis BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H 2$ bias of natural killer T cells," *Nature*, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.

(56) References Cited

OTHER PUBLICATIONS

Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morelle, W. et al., "The Mass Spectrometric Analysis of Glycoproteins and their Glycan Structures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing Hiv antibodies. Proc. Natl. Acad. Sci. U. S. A 109, E3268-E3277, (2012).
Munson et al., "Ligand: a versatile computerized approach for characterization of ligand-binding systems," *Anal. Biochem.*, Sep. 1, 1980, 107(1):220-239.
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Ni, Jing et al., Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.

Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Noto et al., "CD44 and SSEA-4 positive cells in an oral cancer cell line HSC-4 possess cancer stem-like cell characteristics," *Oral Oncol.*, Aug. 2013, 49(8):787-795.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ domain dimers," *Proc. Natl. Acad. Sci. USA*, Jul. 1985, 82(14):4592-4596.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," *Immunity*, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," *Adv. Immunol.*, 1998, 70:281-312.
Olden, Kenneth et al., Carbohydrate Moieties of Glycoproteins: A Re-Evaluation of Their Function, Biochem et Biophys Acta 650:209-232 (1982).
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pan, Yanbin et al., Synthesis and Immunological Properties of N-Modified GM3 Antigens as Therapeutic Cancer Vaccines, J. Med. Chem., 48(3), 875-883, 2005.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Papanastassiou et al., "The potential for efficacy of the modified (ICP 34.5) herpes simplex virus HSV1716 following intratumoural injection into human malignant glioma: a proof of principle study," *Gene Therapy*, Mar. 2002, 9(6):398-406.

(56) References Cited

OTHER PUBLICATIONS

Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," *Biochemistry*, Jan. 16, 2007, 46(2):350-358.
Paulson, J. C., Blixt, O. & Collins, B. E. Sweet spots in functional glycomics. Nat. Chem. Biol. 2, 238-248, (2006).
Pearlman et al., *Peptide and Protein Drug Delivery*, Chapter 6: Analysis of Protein Drugs, Lee, ed., 1991, pp. 247-301, Marcel Dekker Publishing, New York.
Peelle et al., "Characterization and use of green fluorescent proteins from *Renilla mulleri* and *Ptilosancus guennyi* for the human cell display of functional peptides," *J. Protein Chem.*, Aug. 2001, 20(6):507-519.
Peipp et al., "Antibody fucosylation differentially impacts cytotoxicity mediated by NK and PMN effector cells," *Blood*, 2008, 112(6):2390-2399.
Peiris et al., Re-emergence of fatal human influenza A subtype H5N1disease. Lancet. Feb. 21, 2004;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Pläckthun, "Mono- and bivalent antibody fragments produced in *Escherichia coli*: Engineering, folding and antigen binding," *Immunol. Rev.*, Dec. 1992, 130:151-188.
Pläckthun, *Handbook of Experimental Pharmacology*, vol. 113: The Pharacology of Monoclonal Antibodies, Chapter 11: Antibodies from *Escherichia coli*, Rosenberg et al., eds., 1994, pp. 269-315, Springer-Verlag, Berlin.
Poloukhtine et al., "Selective labeling of living cells by a photo-triggered click reaction, " *J. Am. Chem. Soc.*, Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene*, Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res*. Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Ramm et al., "The periplasmic *Escherichia coli* peptidylprolyl cis, trans-isomerase FkpA. II. Isomerase-independent chaperone activity in vitro," *J. Biol. Chem.*, Jun. 2, 2000, 275(22):17106-17113.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human IgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Natl. Acad. Sci. U.S.A.*, Feb. 1, 1994, 91(3):969-973.
Romagnani, "Induction of $T_H1$ and $T_H2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N.E. et al, Meningococcal Disease, N Engl J Med 2001, 344, 1378-1388.

(56) References Cited

OTHER PUBLICATIONS

Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials, J. Biol. Chem. 267, 5700-5711, 1992.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4G1cNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.

Schenkel-Brunner, *Human Blood Groups*, Chapter 8: P System, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Schmitz, U. et al., Phage Display: A Molecular Tool for the Generation of Antibodies-A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Sell, "Cancer-associated carbohydrates identified by monoclonal antibodies," *Hum. Pathol.*, Oct. 1990, 21(10):1003-1019.
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., CELL vol. 30, Issue 3, Oct. 1982, pp. 697-705.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.

(56) References Cited

OTHER PUBLICATIONS

Sidhu et al., "Phage-displayed antibody libraries of synthetic heavy chain complementarity determining regions," *J. Mol. Biol.*, Apr. 23, 2004, 338(2):299-310.

Siebenlist et al., "*E. coli* RNA polymerase interacts homologously with two different promoters," *Cell*, Jun. 1980, 20(2):269-281.

Sieber et al., "Proteomic profiling of metalloprotease activities with cocktails of active-site probes," *Nat. Chem. Biol.*, May 2006, 2(5):274-281.

Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.

Sivakumar, Krishnamoorthy et al., "A fluorogenic 1,3-dipolar cycloaddition reaction of 3-azidocoumarins and acetylenes." Org. Lett. 2004,24, 4603-4606.

Skehel, John et al., Receptor Binding and Membrane Fusion in Virus Entry: The Influenza Hemagglutinin, Ann. Rev Biochem, 69:531, 2000.

Skerra, "Bacterial expression of immunoglobulin fragments," *Curr. Opinion in Immunol.*, Apr. 1993, 5(2):256-262.

Slamon DJ, et al., Human breast cancer: correlation of relapse and survival with amplification of the HER-2/neu oncogene, *Science*. Jan. 9, 1987; 235(4785):177-82.

Sletten et al., "Bioorthogonal Chemistry: Fishing for Selectivity in a Sea of Functionality," *Angew. Che. Int. Ed. Engl.*, Aug. 27, 2009, 48(38):6974-6998.

Smith RA et al., "The active form of tumor necrosis factor is a trimer" *J Biol Chem.* May 25, 1987;262(15):6951-4.

Smyth MJ, et al., "CD4+CD25+ T regulatory cells suppress NK cell-mediated immunotherapy of cancer" *J Immunol*. Feb. 1, 2006;176(3):1582-7.

Sok, Devin et al., SnapShot: Broadly Neutralizing Antibodies. Cell 155, 728-728, (2013).

Solomons, G. and Fryhle, C., Chapter 5 Titled, Stereochemistry: Chiral Molecules, p. 184-228, in "Organic Chemistry," 7th Edition, Wiley, Jun. 18, 2001.

Soriano del Amo, David et al. Chemoenzymatic synthesis of the sialyl Lewis X glycan and its derivatives. Carbohydr. Res. 345, 1107-13, (2010).

Spinosa, Maria Rita et al., The Neisseria Meningitidis Capsule is Important for Intracellular Survival in Huamn Cells, Infect Immun 2001, 75, 3594-3603.

Srinivasan, Quantitative et al., Biochemical Rationale for Differences in Transmissibility of 1918 Pandemic Influenza A Viruses, Proc. Natl. Acad. Sci., 105, 2800-2805, 2008.

Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.

Stein, K.E., Thymus-Independent and Thymus-Dependent Responses to Polysaccharide Antigens, J Infect Dis 1992, 165 Suppl 1, S49-52.

Stephens, David, Conquering the Meningococcus, FEALS Microbial Rev 2007, 31, 3-14.

Stephens, D.S. et al., Epidemic Meningitis, Meningococcaemia, and Neisseria Meningitidis, Lancet 2007, 369, 2196-2210.

Stephenson et al., "Neuraminidase inhibitor resistance after oseltamivir treatment of acute influenza A and B in children," Clin. Infect. Dis., Feb. 15, 2009, 48(4):389-396.

Stevanovic, Stefan, Identification of Tumour-Associated T-Cell Epitopes for Vaccine Development, Nat. Rev. Cancer, 2002, 2, 514-520.

Stevens, James et al., Structure of the Uncleaved Human H1 Hemagglutinin From the Extinct 1918 Influenza Virus, Science, 303:1866, 2004.

Stevens, James et al., Structure and Receptor Specificity of the Hemagglutinin From an H5N1 Influenza Virus, Science, 312:404, 2006.

Stevens et al., Glycan Microarry Analysis of the Hemagglutinins From Modern and Pandemic Influenza Viruses Reveals Different Receptor Specificities. Journal of Molecular Biology 355.5 (2006): 1143-1155.

Stickings, Paul et al., Transcutaneous Immunization with Cross-Reacting Material CRM197 of Diphtheria Toxin Boosts Functional Antibody Levels in Mice Primed Parenterally with Adsorbed Diphtheria Toxoid Vaccine, Infection and Immunity, 2008, 76, 1766-1773.

Stockmann, H. et al., Development and Evaluation of New Cyclootynes for Cell Surface Glycan Imaging in Cancer Cells, J. Chem. Sci. 2011, 2, 932-936.

Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.

Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.

Su, G. Hahner, W. Zhou "Investigation of the pore formation in anodic aluminum oxide" J Mater. Chem. 2008, 18 5787-5795.

Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).

Supplementary European Search Report in European Application No. EP 13775664.9, dated Oct. 27, 2015, in 7 pages.

Suresh et al., "Bispecific monoclonal antibodies from hybrid hybridomas," *Methods in Enzymology*, 1986, 121:210-228.

Sutton, VR et al., Bc1-2 Prevents Apoptosis Induced by Perforin and Granzyme B, But Not That Mediated by Whole Cytotoxic Lymphocytes, J of Immunology 1997, 158(12), 5783.

Suzuki E, et al., "A nonfucosylated anti-HER2 antibody augments antibody-dependent cellular cytotoxicity in breast cancer patients" *Clin Cancer Res.* Mar. 15, 2007;13(6):1875-82.

Svennerholm et al., "Human brain gangliosides: Developmental changes from early fetal stage to advanced age," *Biochim. Biophys. Acta*, Sep. 25, 1989, 1005(2):109-117.

Syrigos et al., "Antibody directed enzyme prodrug therapy (ADEPT): a review of the experimental and clinical considerations," *Anticancer Research*, Jan.-Feb. 1999, 19(1A):605-614.

Tahir et al., "Loss of IFN-γ production by invariant NK T cells in advanced cancer," *J. Immunol.*, Oct. 1, 2001, 167(7):4046-4050.

Takakura, Yoshimitsu et al., Molecular cloning, expression and properties of an alpha/beta-Galactoside alpha 2,3-sialyltransferase from *Vibrio* sp. JT- FAJ-16. J. Biochem. 142, 403-412, (2007).

Takano, Ryo et al., Sialylation and Malignant Potential in Tumour Cell Glycosylation Mutants, Glycobiology 4, 665-674 (1994).

Takeda et al., "Construction of chimaeric processed immunoglobulin genes containing mouse variable and human constant region sequences," *Nature*, Apr. 4-10, 1985, 314(6010):452-454.

Taki, Takao et al., Glycolipids of Metastatic Tissue in Liver From Colon Cancer: Appearance of Sialylated Lex and Lex Lipids, J. Biochem. 103, 998-1003, 1998.

Talmadge et al., Murine models to evaluate novel and conventional therapeutic strategies for cancer, Am. J. Pathol, 170(3): 793-804 (2007).

Tanaka, Hiroshi et al., An Efficient Convergent Synthesis of GP1c Ganglioside Epitope, J Am Chem Soc. 2008, 130, 17244.

Tanaka, Katsunori et al., Synthesis of a Sialic Acid Containing Complex-Type N-Glycan on a Solid Support, Chemistry-an Asian Journal, 2009, vol. 4 (4), p. 574-580.

Taton, T. Andrew et al., Scanometric DNA Array Detection with Nanoparticle Probes, Science 289 (2000) 1757-1760.

Taton, T. Andrew et al., Two-Color Labeling of Oligonucleotide Arrays Via Size-Selective Scattering of Nanoparticle Probes, J. Am. Chem. Soc. (2001), 123, 5164-5165.

Taylor-Papadimitriou et al., "Exploiting altered glycosylation patterns in cancer: Progress and challenges in diagnosis and therapy," *Trends Biotechnol.*, Jun. 1994, 12(6):227-233.

(56) References Cited

OTHER PUBLICATIONS

Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Trinchieri, "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai TI, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology.* Jan. 1996;6(1):83-93.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.

Ulrich, G.; Ziessel, R.; Harriman, A. "The chemistry of fluorescent bodipy dyes: Versatility unsurpassed." Angew. Chem. Int. Ed. 2008, 47, 1184-1201.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem.* Jul. 5, 1989;264(19):11282-7.
Van Beek et al., "Increased sialic acid density in surface glycoprotein of transformed and malignant cells—a general phenomenon?" *Cancer Res.*, Nov. 1973, 33(11):2913-2922.
Van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," *Nature*, Apr. 26, 2007, 446(7139):1023-1029.
Vasella et al., "Synthesis of a phosphonic acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vaswani et al., "Humanized antibodies as potential therapeutic drugs," *Ann. Allergy, Asthma Immunol.*, Aug. 1998, 81(2):105-116, 119.
Vavricka, Christopher et al., Influenza Neuraminidase Operates Via a Nucleophilic Mechanism and Can Be Targeted by Covalent Inhibitors, Nature Communcations, 4:1491 (2013).
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.

(56) References Cited

OTHER PUBLICATIONS

Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "Glycan microarray of Globo H and related structures for quantitative analysis of breast cancer," Proc. Natl. Acad. Sci. U.S.A., Aug. 19, 2008, 105(33):11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from Escherichia coli," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "Trypanosoma cruzi trans-sialidase operates through a covalent sialyl-enzyme intermediate: tyrosine is the catalytic nucleophile," J. Am. Chem. Soc., Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," Cancer Metastasis Rev., 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." Eur. J. Immunol., Jul. 1993, 23(7):1456-1461.
Wiltshire, S. et al. Proc. Natl. Acad. Sci. (2000) 97, 10113-10119.
Winter et al., "Making antibodies by phage display technology," Annu. Rev. Immunol., 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," Nat. Chem. Biol., Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woof et al., "Human antibody-Fc receptor interactions illuminated by crystal structures," Nat. Rev. Immunol., Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12):3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," Proc. Natl. Acad. Sci. USA, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," Biochem. J., Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yansura et al., "Nucleotide sequence selection for increased expression of heterologous genes in Escherichia coli," Methods: A Companion to Methods in Enzymol., Aug. 1992, 4(2):151-158.
Yates AJ et al., Brain Tumors in Childhood. Childs Brain 5(1), 31-39 (1979).

(56) References Cited

OTHER PUBLICATIONS

Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "$CD4^{pos}$, $NK1.1^{pos}$ T cells promptly produce interleukin 4 in response to in vivo challenge with anti-CD3," *J. Exp. Med.*, Apr. 1, 1994, 179(4):1285-1295.
Yu et al., "Anti-GD2 antibody with GM-CSF, interleukin-2, and isotretinoin for neuroblastoma," *N. Engl. J. Med.*, Sep. 30, 2010, 363(14):1324-1334.
Yuen et al., Human infection by avian influenza a H5N1. Hong Kong Med J. Jun. 2005;1 1(3):189-99.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "New cerebrosides from Acanthopanax gracilistylus," CAPLUS 156:225776 (2011).
Zhang et al., "Selection of tumor antigens as targets for immune attack using immunohistochemistry: I. Focus on gangliosides," *Int. J. Cancer*, Sep. 26, 1997, 73(1):42-49.
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.

Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., CHemoenzymatic Glycoengineering of Intact 1gG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, Aug. 7, 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
Greene, Theodora et al., Protective Groups in Organic Synthesis, pp. 42-51 and 96-100, 1991.
Schelhaas, Michael et al., Protecting Group Strategies in Organic Synthesis, Angew. Chem. Int. Ed. Engl. 1996, 35, 2056-2083.
Unverzagt, Carlo et al., A Double Regio- and Stereoselective Glycosylation Strategy for the Synthesis of N-Glycans, Chem. Eur. J., 2008, 14, 1304-1311.
European Application 14817316.4, Communication pursuant to Article 94(3), dated Apr. 16, 2018, 5 pages.
Cheung et al., Meeting Info: 23rd International Symposium on Glycoconjugates, Glyco 23. Split, Croatia. Sep. 15, 2015-Sep. 20, 2015, vol. 32, No. 5, pp. 323.
International Search Report and Written Opinion in International Application No. PCT/US2017/048074, dated Dec. 26, 2017, 17 pages.
Lei, Jianqing et al., Potential antitumor applications of a monoclonal antibody specifically targeting human papilloma virus 16 E749-57 peptide, Microbiology and Immunology, 2012, vol. 56, pp. 456-462.

\* cited by examiner

T2 X = Et
T9 X = H
T10 X = CO₂Et
T11 X = CN

Az2 X = Et
Az9 X = H
Az10 X = CO₂Et
Az11 X = CN

REACTIVE LABELLING COMPOUNDS AND USES THEREOF

RELATED APPLICATION

This application is a divisional of U.S. patent application Ser. No. 14/698,660, which was filed of Apr. 28, 2015, which is a continuation-in-part of International Application Serial No. PCT/US2015/022977, filed Mar. 27, 2015, which claims the benefit of priority to U.S. provisional application Ser. No. 61/971,313, filed on Mar. 27, 2014. The contents of which is incorporated herein by reference.

FIELD

The present disclosure relates to the field of triazole formation of cyclooctyne-fused fluorogenic probes, azido-BODIPY compounds, and fluorescently-cleaved probes for the diagnosis and imaging of alkyne- or azide-containing biomolecules. The present disclosure relates to a fluorescence enhancement strategy upon azide-alkyne cycloadditions (AAC).

BACKGROUND

Copper-catalyzed azide-alkyne 1,3-dipolar cycloaddition (CuAAC) has gained widespread use in chemical biology for applications such as labeling of biomolecules in complex mixtures and imaging of fixed cells and tissues. (Kolb, et al., *Angew. Chem. Int. Ed.* 2001, 40, 2004; Rostovtsev, et al., *Angew. Chem. Int. Ed.* 2002, 41, 2596; Wu and Fokin, *Aldrichimica Acta* 2007, 40, 7.) Incorporation of fluorescent probes into proteins, DNA, RNA, lipids and glycans within their native cellular environments provides opportunities for imaging and understanding their roles in vivo. (Best, *Biochemistry* 2009, 48, 6571.)

For example, glycans in protein are displayed on the cell surface with implications in numerous physiological and pathological processes. Aberrant glycosylation on the surface of diseased cells is often observed in pathological conditions, such as inflammation and cancer metastasis. In particular, altered terminal sialylation and fucosylation, which are believed to result from changes in expression locations and levels of sialyltransferases and fucosyltransferases, are associated with tumor malignancy. The ability to explore the biological information content of glycans as biomarkers of cancer, attached to either proteins or lipids, has become a major course of glycomics research. (Hsu, et al., *Proc. Nat. Acad. Sci. U.S.A.,* 2007, 104, 2614; Sawa, et al., *Proc. Nat. Acad. Sci. U.S.A.,* 2006, 103, 12371.)

Analysis of changes in glycosylation patterns in living systems is now possible. (Prescher and Bertozzi, *Nat. Chem. Bio.* 2005, 1, 13.) Metabolic incorporation of an unnatural carbohydrate containing unique functional group that acts as a bioorthogonal chemical reporter into the cell biosynthetic machinery initiates the process. The modified glycan is then processed and constructed on the cell surface. Subsequent reaction with a detectable fluorescent probe equipped with a complementary bioorthogonal functional group enables detection of the incorporated unnatural glycan. (Sletten and Bertozzi, *Angew. Chem. Int. Ed.* 2009, 48, 2.)

The concept of bioorthogonal chemical reporter has been applied to proteomic analysis of glycosylation in proteins and chemical remodeling of cell surfaces in living systems. Bioorthogonal chemical reactions have also been used for other applications, such as protein labeling, activity-based protein folding, protein targets identification, posttranslational modifications, and cell proliferation monitoring. Labeling of specific functional groups on living cell via bioorthogonal chemical reporter strategies have become increasingly powerful in cell biology. In the past few years, a tremendous progress has been made in bioorthogonal chemistry, especially that shows biocompatibility and selectivity in living systems. These approaches are often based on cycloadditions as ideal bioorthogonal reactions because of their intrinsic selectivity and tunable electronics. However, there are still many challenges facing the field, particularly from the perspective of cellular and organismal applications. For example, most bioorthogonal reporter strategies entail multistep procedures that use fluorophroe-labeled reactant partners, which often cause high background fluorescent noise that is difficult to remove from intracellular environments or tissues. In addition, these methods require high concentrations of reagents and catalysts in order to achieve detectable signals.

Some recent efforts have been focused on the design of non- or weak fluorescent probe upon CuAAC reactions with non-fluorescent alkynes or azides, which can ligate to afford a highly fluorescent triazole complex (FIG. 2). (Zhou and Fahrni, *J. Am. Chem. Soc.* 2004, 126, 8862; Sivakumar, et al., *Org. Lett.* 2004, 24, 4603; Sawa, et al., *Proc. Nat. Acad. Sci. U.S.A.,* 2006, 103, 12371; Xie, et al., *Tetrahedron* 2008, 64, 2906; Li, et al., *Org. Lett.* 2009, 11, 3008; Le Droumaguet, et al., *Chem. Soc. Rev.* 2010, 39, 1223; Qi, et al, *Bioconjugate Chem.* 2011, 22, 1758; Chao, et al., *Sci. China Chemistry* 2012, 55, 125. Herner, et al., *Org. Biomol. Chem.* 2013, 11, 3297.) This type of CuAAC reaction occurring in high efficiency would have broad applications in the emerging field of cell biology and functional proteomics due to the distinct fluorescence properties in formation of the triazole without background fluorescent noise of the starting materials. However, these azido- and alkynyl-functionalized probes usually require excitation in the UV region and emit blue light with poor quantum yield in aqueous solution; such optical properties are not ideal for biological applications.

The distinct fluorescence enhancement induced by highly efficient CuAAC reactions would have broad applications in the emerging field of cell biology and functional proteomics (Le Droumaguet, C.; Wang, C.; Wang, Q. *Chem. Soc. Rev.* 2010, 39, 1233-1239; Sawa, M.; Hsu, T.-L.; Itoh, T.; Sugiyama, M.; Hanson, S. R.; Vogt, P. K.; Wong, C.-H. *Proc. Natl. Acad. Sci. U.S.A* 2006, 103, 12371-12376, Shie, J.-J.; Liu, Y.-C.; Lee, Y.-M.; Lim, C.; Fang, J.-M.; Wong, C.-H. *J. Am. Chem. Soc.* 2014, 136, 9953-9961, Hsu, T.-L.; Hanson, S. R.; Kishikawa, K.; Wang, S.-K.; Sawa, M.; Wong, C.-H. *Proc. Natl. Acad. Sci. U.S.A* 2007, 104, 2614-2619, Tsai, C.-S.; Liu, P.-Y.; Yen, H.-Y.; Hsu, T.-L.; Wong C.-H. *Chem. Commun.* 2010, 46, 5575-5577). However, the toxicity of Cu(I) has hindered the use of CuAAC in living systems.

To circumvent the cytotoxicity problem associated with the metal catalyst, the ring strain-promoted azide-alkyne cycloadditions (SPAAC) have been developed as an alternative strategy (Jewett, J. C.; Bertozzi, C. R. *Chem. Soc. Rev.* 2010, 39, 1272-1279, Debets, M. F.; van Berkel, S. S.; Dommerholt, J.; Dirks, A. T. J.; Rutjes, F. P. J. T.; van Delft, F. L. *Acc. Chem. Res.* 2011, 44, 805-815). A cyclooctyne moiety is often incorporated as a stem structure into the SPAAC reagents, such as difluorinated cyclooctynes (DIFO) and the derivatives (Agard, N. J.; Prescher, J. A.; Bertozzi, C. R. *J. Am. Chem. Soc.* 2004, 126, 15046-15047, Codelli, J. A.; Baskin, J. M.; Agard, N. J.; Bertozzi, C. R. *J. Am. Chem. Soc.* 2008, 130, 11486-11493). To increase the ring strain, the cyclooctyne moiety can be fused with other rings to give SPAAC reagents with higher reactivity, such as dibenzylcyclooctyne (DIBO) (Ning, X.; Guo, J.; Wolfert, M. A.; Boons, G.-J. *Angew. Chem. Int. Ed.* 2008, 47, 2253-2255, Poloukhtine, A. A.; Mbua, N. E.; Wolfert, M. A.; Boons, G.-J.; Popik, V. V. *J. Am. Chem. Soc.* 2009, 131, 15769-15777, Stöckmann, H.; Neves, A. A.; Stairs, S.; Ireland-Zecchini, H.; Brindle, K. M.; Leeper, F. J. *Chem. Sci.* 2011, 2, 932-936, Friscourt, F.; Ledin, P. A.; Mbua, N. E.; Flanagan-Steet, H. R.; Wolfert, M. A.; Steet, R.; Boons, G.-J. *J. Am. Chem. Soc.* 2012, 134, 5381-5389) diarylazacyclooctynone (BARAC) (Jewett, J. C.; Sletten, E. M.; Bertozzi, C. R. *J. Am. Chem. Soc.* 2010, 132, 3688-3690) and bicyclononynes (BCN) (Dommerholt, J.; Schmidt, S.; Temming, R.; Hendriks, L. J. A.; Rutjes, F. P. J. T.; van Hest, J. C. M.; Lefeber, D. J.; Friedl, P.; van Delft, F. L. *Angew. Chem. Int. Ed.* 2010, 49, 9422-9425). Tetramethylthiacycloheptyne (TMTH) bearing a contracted seven-membered ring also exhibits reactivity in cycloaddition reactions with azides (de Almeida, G.; Sletten, E. M.; Nakamura, H.; Palaniappan, K. K.; Bertozzi, C. R. *Angew. Chem. Int. Ed.* 2012, 51, 2443-2447, King, M., Baati, R.; Wagner, A. *Chem. Commun.* 2012, 48, 9308-9309). Two cyclooctyne-based fluorogenic probes, CoumBARAC (Jewett, J. C.; Bertozzi, C. R. *Org. Lett.* 2011, 13, 5937-5939) and Fl-DIBO (Friscourt, F.; Fahrni, C. J.; Boons, G.-J. *J. Am. Chem. Soc.* 2012, 134, 18809-18815) have been described by the Bertozzi and Boons groups, respectively.

4,4-Difluoro-4-bora-3a,4a-diaza-s-indacene (also known as BODIPY) dyes are a type of popular fluorophores for many biological applications. BODIPY dyes have numerous advantages including great chemical and photophysical stability, relatively high molar absorption coefficients and fluorescence quantum yields ($\Phi_{fl}$), excitation/emission wavelengths in the visible spectral region (longer than 500 nm), and narrow emission bandwidths with high peak intensities. (Loudet and Burgess, *Chem. Rev.* 2007, 107, 4891; Ulrich et al., *Angew. Chem. Int. Ed.* 2008, 47, 1184; Boens, et al., *Chem. Soc. Rev.* 2012, 41, 1130; Kamkaew, et al, *Chem. Soc. Rev.* 2013, 42, 77.)

Some azido-BODIPY derivatives have been developed for fluorescent labeling upon CuAAC reactions. (Li, et al., *J. Org. Chem.* 2008, 73, 1963.) Specifically, the low fluorescence 3-azido-BODIPY derivatives have been shown to undergo a CuAAC reaction to give the corresponding triazole with enhanced fluorescence. Although the triazole product provided a 300-fold increased emission compared to azido-BODIPY, it exhibited a low fluorescence quantum yield ($\Phi_{fl}$<0.03) and the unreacted azido-BODIPY compound is unstable and fails to react with alkynyl biomolecules under physiological conditions, making it is incompatible with many biological applications. (Wang, et al., *Sci. China Chemistry* 2012, 55, 125; Chauhan, et al. *Tetrahedron Lett.* 2014, 55, 244.)

SUMMARY OF THE INVENTION

Accordingly, there is a need for new design of molecular probes pertinent to cell environments for cell labeling, detecting and/or visualizing the localization of biomolecules in cells.

Accordingly, the present disclosure relates to a new series of azido-BODIPY compounds containing a green-emitting BODIPY scaffold pertinent to cell environments. The BODIPY scaffold is used as a starting module for its appealing synthetic and fluorescent features. Exemplary BODIPYs are easily modified at the 8-position. Arylation at this position has no substantial influence on absorption and emission wavelengths because the aryl moiety and BODIPY core are twisted and conjugation uncoupled.

These exemplary compounds are useful for labeling with alkyne -functionalized proteins without washing processes, and are suitable for visualizing the localization of alkyne-tagged glycosyl conjugates in cells by confocal microscopy. Furthermore, the alkynyl -saccharide modified cells can be lysed and analyzed on SDS-PAGE by using AzBOCEt labeling for direct detection of the probe-labeled glycoproteins without enrichment.

The present disclosure also relates to cyclooctyne-based fluorogenic probes which are capable of reacting to alkyne-functionalized moieties. In some aspects, the cyclooctyne-based fluorogenic probes can be present in a cell. In some aspects, the cyclooctyne-based fluorogenic probes can be used to detect azide-glycoconjugates in a cell.

The present disclosure also relates to the dual-imaging of both azido-functionalized glycoconjugates and alkynyl-functinonalized glyconjugates by contacting a sample with azido-BODIPY compounds of formula (I) and/or cyclooctyne-based fluorogenic probes of formula (IV) in a dual imaging mode.

The present disclosure also relates to measuring the activity of enzymes using probes designed to form a covalent bond with the active site of an enzyme wherein said probes comprise an alkyne moiety for further detection by an azide-containing fluorogenic probe. The enzyme can be a sialidase. The fluorogenic sialidase probe can be based on 3-fluorosialyl fluoride as a mechanism-based inhibitor.

Accordingly, the present disclosure relates to exemplary novel azido-BODIPY compounds of formula (I) that undergo azide-alkyne cycloadditions (AAC). The azide-alkyne cycloadditions (AAC) can be strain or catalyst (metal or organic) promoted. In some embodiments, the catalyst is a metal catalyst. In certain embodiments, the metal catalyst is copper(I).

Exemplary azido-BODIPY compounds described herein can react with alkyne compounds to give stable triazole products with enhanced fluorescence to facilitate the detection. The provided exemplary compounds represent a significant advance in cell-imaging without washing processes and are applicable to direct in-gel detection of the alkyne-tagged glycoproteins from cell lysates after SDS-PAGE.

One aspect of the present disclosure relates to an azido-BODIPY compound of Formula (I):

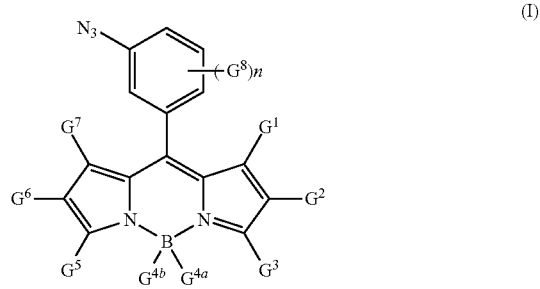

or a pharmaceutically acceptable salt, solvate, or hydrate thereof, and in which $G^1$, $G^2$, $G^3$, $G^{4a}$, $G^{4b}$, $G^5$, $G^6$, $G^7$ and $G^8$ and n are as described herein.

In another aspect, the present disclosure provides synthetic methods for preparation of azido-BODIPY compounds. The present disclosure also demonstrates that the azido-BODIPY compounds described herein can react with organic alkynes to form triazole products with enhanced fluorescence.

In another aspect, the present disclosure provides a triazolyl-BODIPY compound of Formula (III):

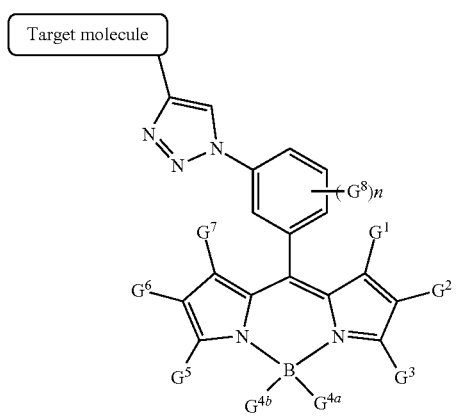

or a pharmaceutically acceptable salt, solvate, or hydrate thereof, and in which $G^1$, $G^2$, $G^3$, $G^{4a}$, $G^{4b}$, $G^5$, $G^6$, $G^7$, $G^8$ and n are as described herein. Target molecule includes, but not limited to, a biomolecule such as a DNA, RNA, protein and glycan.

The azide-alkyne cycloadditions (AAC) can be strain or catalyst (metal or organic) promoted. In some embodiments, the catalyst is a metal catalyst. In certain embodiments, the metal catalyst is copper(I).

In yet another aspect, present disclosure relates to methods for detecting and/or imaging biomolecules.

In certain embodiments, the present disclosure provides a method for imaging an alkyne-containing molecule, the method comprising
  (a) incubating a compound as described herein with a sample containing the alkyne-containing molecule under conditions allowing for ligation of the compound to an alkyne group of the molecule to form a triazole product; and
  (b) detecting a fluorescent signal released from the triazole product.

In certain embodiments, the present disclosure provides a method for detecting an alkyne-containing molecule in a sample, the method comprising:
  (a) contacting a compound as described herein to a sample suspected of having an alkyne-containing molecule;
  (b) detecting a level of a fluorescent signal released from the sample, and
  (c) determining presence of the alkyne-containing molecule in the sample,
wherein an enhanced fluorescent signal as compared to a level of the fluorescent signal in the absence of the molecule indicates presence of the alkyne-containing molecule.

In another aspect, the present disclosure provides a cyclooctyne-based fluorogenic probe of Formula (IV):

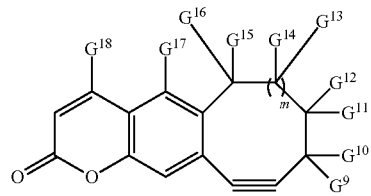

or a pharmaceutically acceptable salt, solvate, or hydrate thereof, and wherein:
  each instance of $G^9$, $G^{10}$, $G^{11}$, $G^{12}$, $G^{13}$, $G^{14}$, $G^{15}$, $G^{16}$, $G^{17}$ and $G^{18}$ is independently hydrogen, optionally substituted $C_{1-6}$ alkyl, optionally substituted $C_{1-6}$ alkenyl, optionally halogen, optionally nitroso, optionally substituted $C_{1-6}$ alkynyl, optionally substituted aryl, optionally substituted acyl, —$OR^A$, —$CH_2OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_3R^A$, —$SO_2N(R^B)_2$, and —$NHSO_2R^B$;
  each instance of R is independently selected from hydrogen, halogen, optionally substituted alkyl, optionally substituted alkenyl, optionally substituted alkynyl, optionally substituted heterocyclyl, optionally substituted aryl, optionally substituted acyl, —$OR^A$, —$CH_2OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_3R^A$, —$SO_2N(R^B)_2$, and —$NHSO_2R^B$;
  each $R^A$ is independently selected from hydrogen, optionally substituted $C_1$-$C_6$ alkyl, optionally substituted alkenyl, optionally substituted alkynyl, optionally substituted heterocyclyl, and optionally substituted aryl; and
  each $R^B$ is independently selected from hydrogen, optionally substituted $C_1$-$C_6$ alkyl, optionally substituted alkenyl, optionally substituted alkynyl, optionally substituted heterocyclyl, and optionally substituted aryl, or two $R^B$ taken together with the intervening nitrogen form a heterocycle;
  each instance of $G^9$ and $G^{10}$ is hydrogen, fluoro, chloro, bromo, iodo, nitroso, alkyl, alkoxy, aryloxy, or alkynyl, and wherein alkyl and alkoxy groups are unbranched, saturated, and have 1-4 carbon atoms; aryl groups and aryl groups of aryloxy can be either carbocyclic aryl or heterocyclic aryl; carbocyclic aryl groups have a total of 6-20 carbon atoms, including carbon atoms of substituents; heterocyclic aryl groups have a total of 5-20 carbon atoms, including carbon atoms of substituents; carboalkoxy groups are alkyl esters of a carboxylic acid wherein alkyl groups are as defined above; each alkyl, aryl, alkoxy, aryloxy, benzo, and carboalkoxy, independently, may be unsubstituted or substituted with one or more substituent; alkyl substituents are halo, hydroxyl, amino, or aryl; aryl substituents are halo, hydroxyl, amino, alkyl, aryl, nitro, or carboxyl; and halo substituents are fluoro or chloro;
  m is 0 or 1;
  n is 0, 1, 2, 3, or 4.

In certain embodiments, cell permeable fluorogenic probes with improved reactivity can be prepared by implementation of additional ring strain or electron-withdrawing substituents to the cyclooctyne moiety. Additional ring strain could be achieved by, for example, altering the given formula from a cyclooctyne ring to a cycloheptyne ring.

In certain embodiments, the present disclosure provides a method for imaging an azide-containing molecule, the method comprising:

(a) incubating a compound of formula (IV) with a sample containing the azide-containing molecule under conditions allowing for ligation of the compound to an azide group of the molecule to form a triazole product; and
(b) detecting a fluorescent signal released from the triazole product.

In certain embodiments, the present disclosure provides a method for detecting an azide-containing molecule in a sample, the method comprising:
(a) contacting a compound of formula (IV) to a sample suspected of having an azide-containing molecule;
(b) detecting a level of a fluorescent signal released from the sample, and
(c) determining presence of the azide-containing molecule in the sample, wherein an enhanced fluorescent signal as compared to a level of the fluorescent signal in the absence of the molecule indicates presence of the azide-containing molecule.

In another aspect, this disclosure relates to compounds of formula (V):

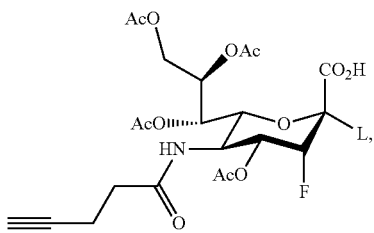

(V)

wherein L is selected from the group consisting of halogen, alkoxy, phenoxy, pentafluorophenoxy, 4-nitrophenoxy, umbelliferyl, alkanoate, benzoate, triflate, mesylate, or tosylate.

In certain embodiments of formula V or IV, L can be a halogen independently including or excluding F, Cl, Br, or I. In certain other embodiments, L is Cl, Br, or I. In certain embodiments, L is halogen but not F.

In certain embodiments, the present disclosure provides a method for imaging the active site of a sialidase enzyme, the method comprising:
(a) contacting a compound of formula (VI):

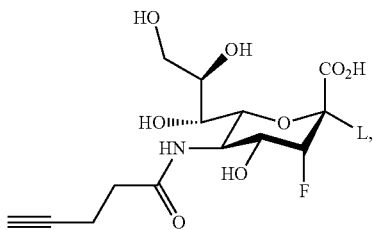

(VI)

wherein L is selected from the group consisting of
halogen, F, Cl, Br, I, alkoxy, phenoxy, pentafluorophenoxy, 4-nitrophenoxy, umbelliferyl, coumarin oxide, alkanoate, benzoate, triflate, mesylate, or tosylate;
with a sample suspected of comprising the sialidase enzyme under conditions for ligation of the compound to the active site of the sialidase enzyme to form a covalent bond product, (b) contacting the covalent bond product with an azide-containing fluorogenic probe as described herein to form a fluorogenic triazole product,
(c) measuring a fluorescent signal released from the triazole product.

In certain embodiments, the present disclosure provides a method for detecting the active site of a sialidase enzyme in a sample, comprising:
(a) contacting the compound 601:

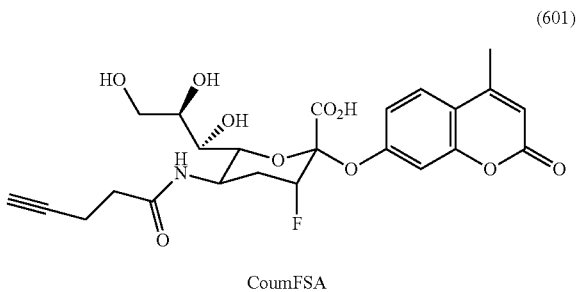 [SMILES: C#CCCC(=O)NC1CC(F)C(Oc2ccc3c(C)cc(=O)oc3c2)(C(=O)O)OC1[C@H](O)[C@H](O)CO]

(601)

CoumFSA with a sample suspected of having an sialidase enzyme molecule;
(b) measuring the level of a fluorescent signal released from the coumadin in the sample mixture, and
(c) determining the presence of the sialidase enzyme molecule in the sample, wherein an enhanced fluorescent signal as compared to a level of the fluorescent signal in the absence of the molecule indicates presence of the azide-containing molecule.

BRIEF DESCRIPTION OF THE DRAWINGS

FIG. 3A shows azido-BODIPYs Az2, Az9-Az11 and FIG. 3B shows the corresponding triazolyl-BODIPYs T2, T9-T11 obtained by CuAAC reactions with 4-pentyn-1-ol.

(FIG. 6A) Illustration of the cell labeling experiments using Ac$_4$ManNAl, Ac$_4$GalNAl and Az10. CL1-5 cells were incubated with 100 μM Ac$_4$ManNAl, Ac$_4$GalNAl or control sugars (Ac$_4$ManNAc and Ac$_4$GalNAc) for 3 days, and then treated with 0.1 μM Az10 for 1 h under CuAAC conditions.

(FIG. 6B) Fluorescence, bright field and overlaid images. Scale bar: 75 µm. (FIG. 6C) Localization of the expressed glycosyl conjugates in CL1-5 cells. These glycosyl conjugates were labeled with fluorogenic probe Az10 (green), anti-GRASP65 (a Golgi marker) followed by Cy3 conjugated anti-rabbit (red), and Hoechst (blue, a nucleus marker). Scale bar: 10 µm.

(FIG. 8A) Fluorescence, bright field and overlaid images. Scale bar: 75 µm. (FIG. 8B) Localization of the expressed glucosyl conjugates in CL1-5 lung cells. These glucosyl conjugates were labeled with fluorogenic probe Az10 (green), anti-GRASP65 (a Golgi marker) followed by Cy3 conjugated anti-rabbit (red), and Hoechst (blue, a nucleus marker). Scale bar: 10 µm.

FIG. 10A shows the chemical structure of the SPAAC-based fluorescence-forming probe coumOCT (101). FIG. 10B shows the chemical structure of compound 102. FIG. 10C shows the chemical structure of the compound 103, a model triazole compound formed from the reaction of compound 102 and an azide-containing compound.

FIG. 11A shows the chemical structure of the compound DFSA (501). FIG. 11B shows the chemical structure of the compound CoumFSA (601).

FIG. 14A shows the interaction of the sialidase active site key amino acids Glu277 and Tyr406 with a difluoro-neuraminic acid compound. FIG. 14B shows the x-ray crystal structure of the sialidase active site interacting with a difluoro-neuraminic acid compound.

FIG. 16A shows the absorbance and emission spectra of fluorogenic probes. FIG. 16B shows the time-course emission spectra of fluorogenic probes.

(FIG. 24A) Illustration of the cell labeling experiments using $Ac_4$ManNAl, $Ac_4$GlcNAz, 101 and AzBOCEt. CL1-5 cells were incubated with 100 µM of $Ac_4$ManNAl and $Ac_4$GlcNAz or control sugars ($Ac_4$ManNAc and $Ac_4$GlcNAc) for 3 days, which were treated with 100 µM of probe 101 for 0.5 h under SPAAC conditions, and then incubated with 0.1 µM of AzBOCEt for 1 h under CuAAC conditions. (B) Dual fluorescence imaging in CL1-5 cells. These glycoconjugates were labeled with probe 101 (cyan) for azido-containing glycoconjugates and AzBOCEt (green) for alkyne-containing glycoconjugates. (Scale bar: 10 µm)

DETAILED DESCRIPTION OF THE INVENTION

Figure 1:
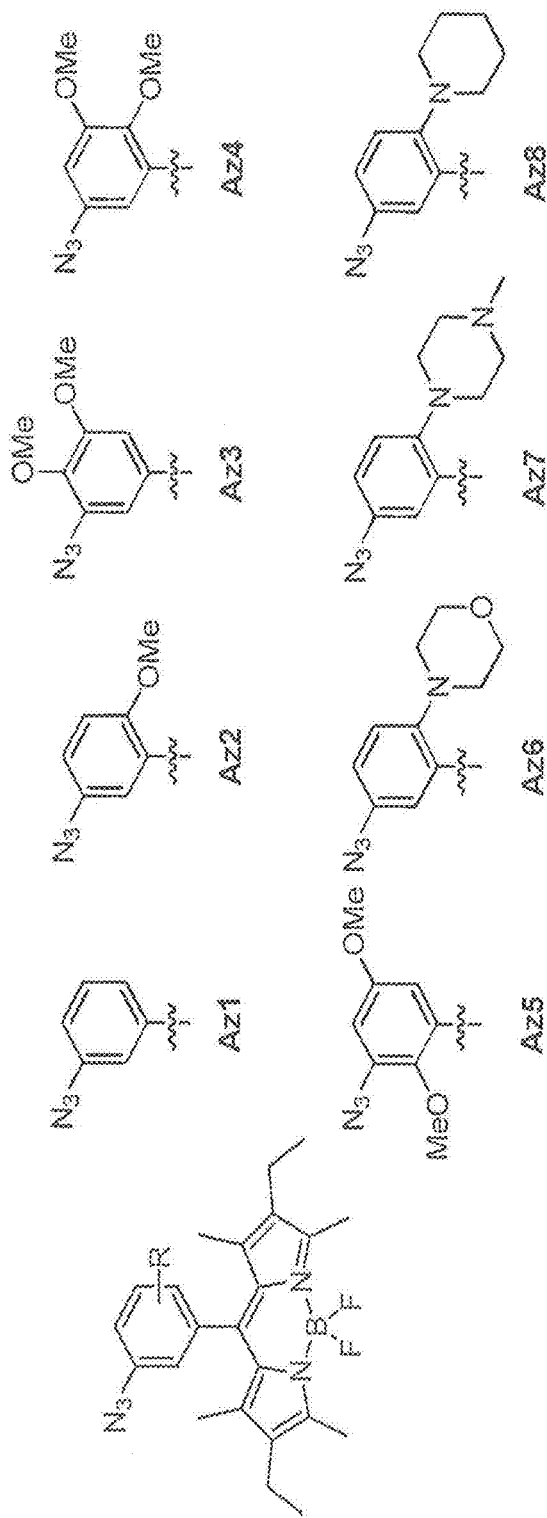
FIG. 1 shows the structures of azido-substituted BODIPY derivatives Az1-Az8 used in the fluorescence screening through the CuAAC reactions.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures using methods including chiral high pressure liquid chromatography (HPLC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The present disclosure additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_1$-3 alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present present disclosure contemplates any and all such combinations in order to arrive at a stable compound. For purposes of this present disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO₂, —N₃, —SO₂H, —SO₃H, —OH, —OR$^{aa}$, —ON(R$^{bb}$)₂, —N(R$^{bb}$)₂, —N(R$^{bb}$)₃⁺X⁻, —N(OR$^{cc}$)R$^{bb}$, —SH, —SR$^{aa}$, —SSR$^{cc}$, —C(=O)R$^{aa}$, —CO₂H, —CHO, —C(OR$^{cc}$)₂, —CO₂R$^{aa}$, —OC(=O)R$^{aa}$, —OCO₂R$^{aa}$, —C(=O)N(R$^{bb}$)₂, —OC(=O)N(R$^{bb}$)₂, —NR$^{bb}$C(=O)R$^{aa}$, —NR$^{bb}$CO₂R$^{aa}$, —NR$^{bb}$C(=O)N(R$^{bb}$)₂, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)₂, —OC(=NR$^{bb}$)N(R$^{bb}$)₂, —NR$^{bb}$C(=NR$^{bb}$)N(R$^{bb}$)₂, —C(=O)NR$^{bb}$SO₂R$^{aa}$, —NR$^{bb}$SO₂R$^{aa}$, —SO₂N(R$^{bb}$)₂, —SO₂R$^{aa}$, —SO₂OR$^{aa}$, —OSO₂R$^{aa}$, —S(=O)R$^{aa}$, —OS(=O)R$^{aa}$, —Si(R$^{aa}$)₃, —OSi(R$^{aa}$)₃ —C(=S)N(R$^{bb}$)₂, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)₂R$^{aa}$, —OP(=O)₂R$^{aa}$, —P(=O)(R$^{aa}$)₂, —OP(=O)(R$^{aa}$)₂, —OP(=O)(OR$^{cc}$)₂, —P(=O)₂N(R$^{bb}$)₂, —OP(=O)₂N(R$^{bb}$)₂, —P(=O)(NR$^{bb}$)₂, —OP(=O)(NR$^{bb}$)₂, —NR$^{bb}$P(=O)(OR$^{cc}$)₂, —NR$^{bb}$P(=O)(NR$^{bb}$)₂, —P(R$^{cc}$)₂, —P(R$^{cc}$)₃, —OP(R$^{cc}$)₂, —OP(R$^{cc}$)₃, —B(R$^{aa}$)₂, —B(OR$^{cc}$)₂, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)₂, =NNR$^{bb}$C(=O)R$^{aa}$, =NNR$^{bb}$C(=O)OR$^{aa}$, =NNR$^{bb}$S(=O)₂R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)₂, —CN, —C(=O)R$^{aa}$, —C(=O)N(R$^{cc}$)₂, —CO₂R$^{aa}$, —SO₂R$^{aa}$, —C(=NR$^{cc}$)OR$^{aa}$, —C(=NR$^{cc}$)N(R$^{cc}$)₂, —SO₂N(R$^{cc}$)₂, —SO₂R$^{cc}$, —SO₂OR$^{cc}$, —SOR$^{aa}$, —C(=S)N(R$^{cc}$)₂, —C(=O)SR$^{cc}$, —C(=S)SR$^{cc}$, —P(=O)₂R$^{aa}$, —P(=O)(R$^{aa}$)₂, —P(=O)₂N(R$^{cc}$)₂, —P(=O)(NR$^{cc}$)₂, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, aryl, and heteroaryl is independently substituted with 0, 1, 2, 3, 4, or 5 R$^{dd}$ groups;

each instance of R$^{dd}$ is, independently, selected from halogen, —CN, —NO₂, —N₃, —SO₂H, —SO₃H, —OH, —OR$^{ee}$, —ON(R$^{ff}$)₂, —N(R$^{ff}$)₂, —N(R$^{ff}$)₃⁺X⁻, —N(OR$^{ee}$)R$^{ff}$, —SH, —SR$^{ee}$, —SSR$^{ee}$, —C(=O)R$^{ee}$, —CO₂H, —CO₂R$^{ee}$, —OC(=O)R$^{ee}$, —OCO₂R$^{ee}$, —C(=O)N(R$^{ff}$)₂, —OC(=O)N(R$^{ff}$)₂, —NR$^{ff}$C(=O)R$^{ee}$, —NR$^{ff}$CO₂R$^{ee}$, —NR$^{ff}$C(=O)N(R$^{ff}$)₂, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)₂, —OC(=NR$^{ff}$)N(R$^{ff}$)₂, —NR$^{ff}$C(=NR$^{ff}$)N(R$^{ff}$)₂, —NR$^{ff}$SO₂R$^{ee}$, —SO₂N(R$^{ff}$)₂, —SO₂R$^{ee}$, —SO₂OR$^{ee}$, —OSO₂R$^{ee}$, —S(=O)R$^{ee}$, —Si(R$^{ee}$)₃, —OSi(R$^{ee}$)₃, —C(=S)N(R$^{ff}$)₂, —C(=O)SR$^{ee}$, —C(=S)SR$^{ee}$, —SC(=S)SR$^{ee}$, —P(=O)₂R$^{ee}$, —P(=O)(R$^{ee}$)₂, —OP(=O)(R$^{ee}$)₂, —OP(=O)(OR$^{ee}$)₂, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO₂, —N₃, —SO₂H, —SO₃H, —OH, —OC$_{1-6}$ alkyl, —ON(C$_{1-6}$ alkyl)₂, —N(C$_{1-6}$ alkyl)₂, —N(C$_{1-6}$ alkyl)₃⁺X⁻, —NH(C$_{1-6}$ alkyl)₂⁺X⁻, —NH₂(C$_{1-6}$ alkyl)⁺X⁻, —NH₃⁺X⁻, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO₂H, —CO₂(C$_{1-6}$ alkyl), —OC(=O)(C$_{1-6}$ alkyl), —OCO₂(C$_{1-6}$ alkyl), —C(=O)NH₂, —C(=O)N(C$_{1-6}$ alkyl)₂, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO₂(C$_{1-6}$ alkyl), —NHC(=O)N(C$_{1-6}$ alkyl)₂, —NHC(=O)NH(C$_{1-6}$ alkyl), —NHC(=O)NH₂, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)₂, —C(=NH)NH(C$_{1-6}$ alkyl), —C(=NH)NH₂, —OC(=NH)N(C$_{1-6}$ alkyl)₂, —OC(NH)NH(C$_{1-6}$ alkyl), —OC(NH)NH₂, —NHC(NH)N(C$_{1-6}$ alkyl)₂, —NHC(=NH)NH₂, —NHSO₂(C$_{1-6}$ alkyl), —SO₂N(C$_{1-6}$ alkyl)₂, —SO₂NH(C$_{1-6}$ alkyl), —SO₂NH₂, —SO₂C$_{1-6}$ alkyl, —SO₂OC$_{1-6}$ alkyl, —OSO₂C$_{1-6}$ alkyl, —SOC$_{1-6}$ alkyl, —Si(C$_{1-6}$ alkyl)₃, —OSi(C$_{1-6}$alkyl)₃ —C(=S)N(C$_{1-6}$ alkyl)₂, C(=S)NH(C$_{1-6}$ alkyl), C(=S)NH₂, —C(=O)S(C$_{1-6}$ alkyl), —C(=S)SC$_{1-6}$ alkyl, —SC(=S)SC$_{1-6}$ alkyl, —P(=O)₂(C$_{1-6}$ alkyl), —P(=O)(C$_{1-6}$ alkyl)₂, —OP(=O)(C$_{1-6}$alkyl)₂, —OP(=O)(OC$_{1-6}$ alkyl)₂, C$_{1-6}$ alkyl, C$_{1-6}$ perhaloalkyl, C$_{2-6}$ alkenyl, C$_{2-6}$ alkynyl, C$_{1-6}$heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein $X^-$ is a counterion.

As used herein, the term "halo" or "halogen" refers to fluorine (fluoro, —F), chlorine (chloro, —Cl), bromine (bromo, —Br), or iodine (iodo, —I). In certain embodiments, L can independently include or exclude F, Cl, Br, or I.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups include those described in detail in *Protecting Groups in Organic Synthesis*, T. W. Greene and P. G. M. Wuts, 3$^d$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethyl carboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethyl silyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups include those described in detail in *Protecting Groups in Organic Synthesis*, T. W. Greene and P. G. M. Wuts, 3' edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups include those described in detail in *Protecting Groups in Organic Synthesis*, T. W. Greene and P. G. M. Wuts, $3^{rd}$ edition, John Wiley & Sons, 1999, incorporated herein by reference.

As used herein, when two entities are "conjugated" or "ligated" to one another, they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. In certain embodiments, two entities are covalently connected, optionally through a linker group.

As used herein, the term "salt" refers to any and all salts, including pharmaceutically acceptable salt which refers to those salts within the scope of sound medical judgment, suitable for use in contact with the tissues of humans and lower animals without undue toxicity, irritation, allergic response and the like, and are commensurate with a reasonable benefit/risk ratio (see Berge et al. describes pharmaceutically acceptable salts in detail in *J. Pharmaceutical Sciences* (1977) 66:1-19). Examples of pharmaceutically acceptable, nontoxic acid salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

As used herein, the terms "condition," "disease," and "disorder" are used interchangeably.

As used herein "inhibition", "inhibiting", "inhibit" and "inhibitor", and the like, refer to the ability of a compound to reduce, slow, halt, or prevent the activity of a particular biological process.

As used herein, the term "cell" present disclosure is meant to encompass eukaryotic and prokaryotic cells of any genus or species, with mammalian cells being of particular interest. "Cell" is also meant to encompass both normal cells and diseased cells, e.g., cancerous cells. In certain embodiments, the cells described herein are living cells.

As used herein the term "sample" includes any chemical sample or biological sample. Chemical sample refers to any chemical mixtures or chemical compounds. Biological sample includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

The term "physiological conditions" is meant to encompass those conditions compatible with living cells, e.g., predominantly aqueous conditions of a temperature, pH, salinity, etc. that are compatible with living cells.

The present disclosure is based on the design and chemical synthesis of a new series of reactive labelling compounds. The compounds can be azido-BODIPY compounds containing a green-emitting BODIPY scaffold pertinent to cell environments. The BODIPY scaffold is used as a starting module for its appealing synthetic and fluorescent features. BODIPYs are easily modified at the 8-position. Arylation at this position has no substantial influence on absorption and emission wavelengths because the aryl moiety and BODIPY core are twisted and conjugation uncoupled.

Described herein are azido-BODIPY compounds that undergo azide-alkyne cycloadditions (AAC) in the presence of catalysts with alkyne-containing molecules to form triazolyl products that exhibit enhanced fluorescence to facilitate the detection of the molecules. The azido-BODIPY compounds represent an advance in cell-imaging without washing processes and are applicable to direct in-gel detection of the alkyne-tagged glycoproteins from cell lysates after SDS-PAGE.

The reactive labelling compounds can also be cyclooctyne-based fluorogenic probes. The cyclooctyne-based fluorogenic probes can further comprise cyclooctynes linked to a coumarin moiety. Also, described herein are cyclooctyne-based fluorogenic probes compounds that undergo azide-alkyne cycloadditions (AAC) in the presence of catalysts with azide-containing molecules to form triazolyl products that exhibit enhanced fluorescence to facilitate the detection of the molecules.

Described herein are methods of using both azido-BODIPY and cyclooctyne-based fluorogenic probes for imaging azido-containing glycoconjugates and alkynyl-containing glycoconjugates in living cells.

Described herein are compounds and methods of using said compounds for conjugation to the active site of enzymes. In some embodiments, the enzyme is a sialidase enzyme. In some embodiments, the compounds are alkynyl-containing compounds. In some embodiments, the compounds form a covalent bond with the active site of the sialidase enzyme.

Azido-BODIPY Compounds

An azido-BOBIPY compound is the Formula (I):

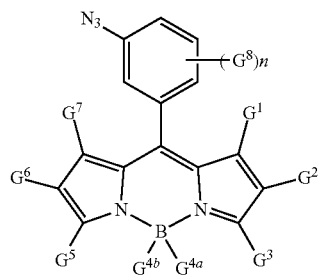

(I)

or a pharmaceutically acceptable salt, solvate, or hydrate thereof, and wherein:

each instance of $G^1$, $G^2$, $G^3$, $G^5$, $G^6$, $G^7$ and $G^8$ is independently hydrogen, optionally substituted $C_{1-6}$ alkyl, optionally substituted $C_{1-6}$ alkenyl, optionally substituted $C_{1-6}$ alkynyl, optionally substituted aryl, optionally substituted acyl, —$OR^A$, —$CH_2OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_3R^A$, —$SO_2N(R^B)_2$, and —$NHSO_2R^B$;

each instance of R is independently selected from hydrogen, halogen, optionally substituted alkyl, optionally substituted alkenyl, optionally substituted alkynyl, optionally substituted heterocyclyl, optionally substituted aryl, optionally substituted acyl, —$OR^A$, —$CH_2OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_3R^A$, —$SO_2N(R^B)_2$, and —$NHSO_2R^B$;

each $R^A$ is independently selected from hydrogen, optionally substituted $C_1$-$C_6$ alkyl, optionally substituted alkenyl, optionally substituted alkynyl, optionally substituted heterocyclyl, and optionally substituted aryl; and each $R^B$ is independently selected from hydrogen, optionally substituted $C_1$-$C_6$ alkyl, optionally substituted alkenyl, optionally substituted alkynyl, optionally substituted heterocyclyl, and optionally substituted aryl, or two $R^B$ taken together with the intervening nitrogen form a heterocycle.

each instance of $G^{4a}$ and $G^{4b}$ is fluoro, alkyl, alkoxy, aryloxy, or alkynyl, and wherein alkyl and alkoxy groups are unbranched, saturated, and have 1-4 carbon atoms; aryl groups and aryl groups of aryloxy can be either carbocyclic aryl or heterocyclic aryl; carbocyclic aryl groups have a total of 6-20 carbon atoms, including carbon atoms of substituents; heterocyclic aryl groups have a total of 5-20 carbon atoms, including carbon atoms of substituents; carboalkoxy groups are alkyl esters of a carboxylic acid wherein alkyl groups are as defined above; each alkyl, aryl, alkoxy, aryloxy, benzo, and carboalkoxy, independently, may be unsubstituted or substituted with one or more substituent; alkyl substituents are halo, hydroxyl, amino, or aryl; aryl substituents are halo, hydroxyl, amino, alkyl, aryl, nitro, or carboxyl; and halo substituents are fluoro or chloro;

n is 0, 1, 2, 3, or 4.

As generally defined herein, $G^1$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, =O, =NOH, =N—$OR^A$, =N—$NH_2$, =N—$NHR^A$, =N—$N(R^B)_2$, and —$NHSO_2R^A$. In certain embodiments, $G^1$ is H. In certain embodiments, $G^1$ is halogen. In certain embodiments, $G^1$ is optionally substituted $C_1$-$C_6$ alkyl. In certain embodiments, $G^1$ is methyl, ethyl, or n-propyl. In certain embodiments, $G^1$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or an oxygen protecting group when attached to an oxygen, or a sulfur protecting group when attaching to sulfur. In certain embodiments, $G^1$ is —OH. In certain embodiments, $G^1$ is —$OR^A$, wherein $R^A$ is optionally substituted $C_1$-$C_6$ alkyl. In certain embodiments, $G^1$ is —$OCH_3$ or —$OC_2H_5$. In certain embodiments, $G^1$ is —$OR^A$, wherein $R^A$ is an oxygen protecting group. In certain embodiments, $G^1$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^1$ is $NH_2$. In certain embodiments, $G^1$ is $NHR^B$, wherein $R^B$ is optionally substituted $C_1$-$C_6$ alkyl. In certain embodiments, $G^1$ is $NHCH_3$ or $NHC_2H_5$. In certain embodiments, $G^1$ is $NHR^B$, wherein $R^B$ is a nitrogen protecting group.

As generally defined herein, $G^2$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, =O, =NOH, =N—$OR^A$, =N—$NH_2$, =N—$NHR^A$, =N—$N(R^B)_2$, and —$NHSO_2R^A$. In certain embodiments, $G^2$ is H. In certain embodiments, $G^2$ is halogen. In certain embodiments, $G^2$ is optionally substituted $C_1$-$C_6$ alkyl. In certain embodiments, $G^2$ is methyl, ethyl, or n-propyl. In certain embodiments, $G^7$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^2$ is —OH. In certain embodiments, $G^2$ is —$OR^A$, wherein $R^A$ is optionally substituted $C_1$-$C_6$ alkyl. In certain embodiments, $G^2$ is —$OCH_3$ or —$OC_2H_5$. In certain embodiments, $G^2$ is —$OR^A$, wherein $R^A$ is an oxygen protecting group. In certain embodiments, $G^2$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^2$ is $NH_2$. In certain embodiments, $G^2$ is $NHR^B$, wherein $R^B$ is optionally substituted $C_1$-$C_6$ alkyl. In certain embodiments, $G^2$ is $NHCH_3$ or $NHC_2H_5$. In certain embodiments, $G^2$ is $NHR^B$, wherein $R^B$ is a nitrogen protecting group.

As generally defined herein, $G^3$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —$CN$, —$NO_2$, —$C(O)R^C$, —$C(O)OR^A$, —$S(O)R^C$, —$SO_2R^A$, —$SO_2N(R^B)_2$, =$O$, =$NOH$, =$N$—$OR^A$, =$N$—$NH_2$, =$N$—$NHR^A$, =$N$—$N(R^B)_2$, and —$NHSO_2R^A$. In certain embodiments, $G^3$ is H. In certain embodiments, $G^3$ is halogen. In certain embodiments, $G^3$ is optionally substituted $C_1$-$C_6$ alkyl. In certain embodiments, $G^3$ is methyl, ethyl, or n-propyl. In certain embodiments, $G^3$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^3$ is —OH. In certain embodiments, $G^3$ is —$OR^A$, wherein $R^A$ is optionally substituted $C_1$-$C_6$ alkyl. In certain embodiments, $G^3$ is —$OCH_3$ or —$OC_2H_5$. In certain embodiments, $G^3$ is —$OR^A$, wherein $R^A$ is an oxygen protecting group. In certain embodiments, $G^3$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^3$ is $NH_2$. In certain embodiments, $G^3$ is $NHR^B$, wherein $R^B$ is optionally substituted $C_1$-$C_6$ alkyl. In certain embodiments, $G^3$ is $NHCH_3$ or $NHC_2H_5$. In certain embodiments, $G^3$ is $NHR^B$, wherein $R^B$ is a nitrogen protecting group.

As generally defined herein, $G^5$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —$CN$, —$NO_2$, —$C(O)R^C$, —$C(O)OR^A$, —$S(O)R^C$, —$SO_2R^A$, —$SO_2N(R^B)_2$, =$O$, =$NOH$, =$N$—$OR^A$, =$N$—$NH_2$, =$N$—$NHR^A$, =$N$—$N(R^B)_2$, and —$NHSO_2R^A$. In certain embodiments, $G^5$ is H. In certain embodiments, $G^5$ is halogen. In certain embodiments, $G^5$ is optionally substituted $C_1$-$C_6$ alkyl. In certain embodiments, $G^5$ is methyl, ethyl, or n-propyl. In certain embodiments, $G^5$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^5$ is —OH. In certain embodiments, $G^5$ is —$OR^A$, wherein $R^A$ is optionally substituted $C_1$-$C_6$ alkyl. In certain embodiments, $G^5$ is —$OCH_3$ or —$OC_2H_5$. In certain embodiments, $G^5$ is —$OR^A$, wherein $R^A$ is an oxygen protecting group. In certain embodiments, $G^5$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^5$ is $NH_2$. In certain embodiments, $G^5$ is $NHR^B$, wherein $R^B$ is optionally substituted $C_1$-$C_6$ alkyl. In certain embodiments, $G^5$ is $NHCH_3$ or $NHC_2H_5$. In certain embodiments, $G^5$ is $NHR^B$, wherein $R^B$ is a nitrogen protecting group.

As generally defined herein, $G^6$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —$CN$, —$NO_2$, —$C(O)R^C$, —$C(O)OR^A$, —$S(O)R^C$, —$SO_2R^A$, —$SO_2N(R^B)_2$, =$O$, =$NOH$, =$N$—$OR^A$, =$N$—$NH_2$, =$N$—$NHR^A$, =$N$—$N(R^B)_2$, and —$NHSO_2R^A$. In certain embodiments, $G^6$ is H. In certain embodiments, $G^6$ is halogen. In certain embodiments, $G^6$ is optionally substituted $C_1$-$C_6$ alkyl. In certain embodiments, $G^6$ is methyl, ethyl, or n-propyl. In certain embodiments, $G^6$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^6$ is —OH. In certain embodiments, $G^6$ is —$OR^A$, wherein $R^A$ is optionally substituted $C_1$-$C_6$ alkyl. In certain embodiments, $G^6$ is —$OCH_3$ or —$OC_2H_5$. In certain embodiments, $G^6$ is —$OR^A$, wherein $R^A$ is an oxygen protecting group. In certain embodiments, $G^6$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^6$ is $NH_2$. In certain embodiments, $G^6$ is $NHR^B$, wherein $R^B$ is optionally substituted $C_1$-$C_6$ alkyl. In certain embodiments, $G^6$ is $NHCH_3$ or $NHC_2H_5$. In certain embodiments, $G^6$ is $NHR^B$, wherein $R^B$ is a nitrogen protecting group.

As generally defined herein, $G^7$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —$CN$, —$NO_2$, —$C(O)R^C$, —$C(O)OR^A$, —$S(O)R^C$, —$SO_2R^A$, —$SO_2N(R^B)_2$, =$O$, =$NOH$, =$N$—$OR^A$, =$N$—$NH_2$, =$N$—$NHR^A$, =$N$—$N(R^B)_2$, and —$NHSO_2R^A$. In certain embodiments, $G^7$ is H. In certain embodiments, $G^7$ is halogen. In certain embodiments, $G^7$ is optionally substituted $C_1$-$C_6$ alkyl. In certain embodiments, $G^7$ is methyl, ethyl, or n-propyl. In certain embodiments, $G^7$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^7$ is —OH. In certain embodiments, $G^7$ is —OR$^A$, wherein R$^A$ is optionally substituted $C_1$-$C_6$ alkyl. In certain embodiments, $G^7$ is —OCH$_3$ or —OC$_2$H$_5$. In certain embodiments, $G^7$ is —OR$^A$, wherein R$^A$ is an oxygen protecting group. In certain embodiments, $G^7$ is —N(R$^B$)$_2$, wherein each instance of R$^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two R$^B$ taken together with the intervening nitrogen form a heterocycle. In certain embodiments, $G^7$ is NH$_2$. In certain embodiments, $G^7$ is NHR$^B$, wherein R$^B$ is optionally substituted $C_1$-$C_6$ alkyl. In certain embodiments, $G^7$ is NHCH$_3$ or NHC$_2$H$_5$. In certain embodiments, $G^7$ is NHR$^B$, wherein R$^B$ is a nitrogen protecting group.

As generally defined herein, $G^8$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —OR$^A$, —CH$_2$OR$^A$, —OC(O)R$^C$, —SR$^A$, —N(R$^B$)$_2$, —N(R$^A$)C(O)R$^C$, —C(O)N(R$^B$)$_2$, —CN, —NO$_2$, —C(O)R$^C$, —C(O)OR$^A$, —S(O)R$^C$, —SO$_2$R$^A$, —SO$_2$N(R$^B$)$_2$, =O, =NOH, =N—OR$^A$, =N—NH$_2$, =N—NHR$^A$, =N—N(R$^B$)$_2$, and —NHSO$_2$R$^A$. In certain embodiments, $G^8$ is H. In certain embodiments, $G^8$ is halogen. In certain embodiments, $G^8$ is optionally substituted $C_1$-$C_6$ alkyl. In certain embodiments, $G^8$ is methyl, ethyl, or n-propyl. In certain embodiments, $G^8$ is —OR$^A$, wherein R$^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^8$ is —OH. In certain embodiments, $G^8$ is —OR$^A$, wherein R$^A$ is optionally substituted $C_1$-$C_6$ alkyl. In certain embodiments, $G^8$ is —OCH$_3$ or —OC$_2$H$_5$. In certain embodiments, $G^8$ is —OR$^A$, wherein R$^A$ is an oxygen protecting group. In certain embodiments, $G^8$ is —N(R$^B$)$_2$, wherein each instance of R$^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two R$^B$ taken together with the intervening nitrogen form a heterocycle. In certain embodiments, $G^8$ is NH$_2$. In certain embodiments, $G^8$ is NHR$^B$, wherein R$^B$ is optionally substituted $C_1$-$C_6$ alkyl. In certain embodiments, $G^8$ is NHCH$_3$ or NHC$_2$H$_5$. In certain embodiments, $G^8$ is NHR$^B$, wherein R$^B$ is a nitrogen protecting group.

In certain embodiments, two of $G^8$ groups adjacent to each other are taken together with their intervening atoms to form an optionally substituted carbocycle or heterocycle. In certain embodiments, two of $G^8$ groups adjacent to each other are taken together with their intervening atoms to form an optionally substituted carbocycle. In certain embodiments, two of $G^8$ groups adjacent to each other are taken together with their intervening atoms to form an optionally substituted 5-membered carbocycle. In certain embodiments, two of $G^8$ groups adjacent to each other are taken together with their intervening atoms to form an optionally substituted 6-membered carbocycle. In certain embodiments, two of $G^8$ groups adjacent to each other are taken together with their intervening atoms to form an optionally substituted phenyl. In certain embodiments, two of $G^8$ groups adjacent to each other are taken together with their intervening atoms to form an unsubstituted phenyl. In certain embodiments, two of $G^8$ groups adjacent to each other are taken together with their intervening atoms to form an optionally substituted heterocycle. In certain embodiments, two of $G^8$ groups adjacent to each other are taken together with their intervening atoms to form an optionally substituted 5-membered heterocycle with one heteroatom of S, N, or O. In certain embodiments, two of $G^8$ groups adjacent to each other are taken together with their intervening atoms to form an optionally substituted 5-membered heterocycle with two heteroatom each independently selected from the group of S, N, and O. In certain embodiments, two of $G^8$ groups adjacent to each other are taken together with their intervening atoms to form an optionally substituted 6-membered carbocycle with one heteroatom of S, N, or O. In certain embodiments, two of $G^8$ groups adjacent to each other are taken together with their intervening atoms to form an optionally substituted 6-membered carbocycle with two heteroatoms each independently selected from the group consisting of S, N, and O.

In some embodiments, at least two of $G^1$, $G^3$, $G^5$ and $G^7$ are $C_1$-$C_6$ alkyl. In certain embodiments, at least two of $G^1$, $G^3$, $G^5$ and $G^7$ is methyl, ethyl, or n-propyl. In some embodiments, each of $G^1$, $G^3$, $G^5$ and $G^7$ is $C_1$-$C_6$ alkyl. In certain embodiments, each of $G^1$, $G^3$, $G^5$ and $G^7$ is methyl, ethyl, or n-propyl. In certain embodiments, each of $G^1$, $G^3$, $G^5$ and $G^7$ is methyl. In certain embodiments, the present disclosure is directed to a compound of Formula (II):

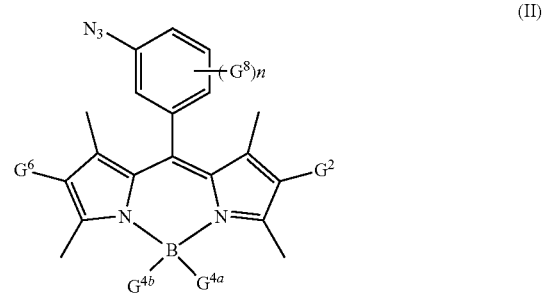

(II)

or a pharmaceutically acceptable salt, solvate, or hydrate thereof, wherein $G^2$, $G^{4a}$, $G^{4b}$, $G^6$, $G^8$ and n are as described herein.

In certain embodiments,

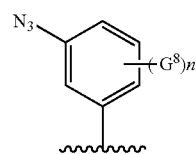

is of the formula:

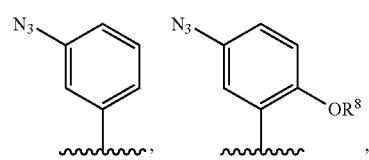

-continued

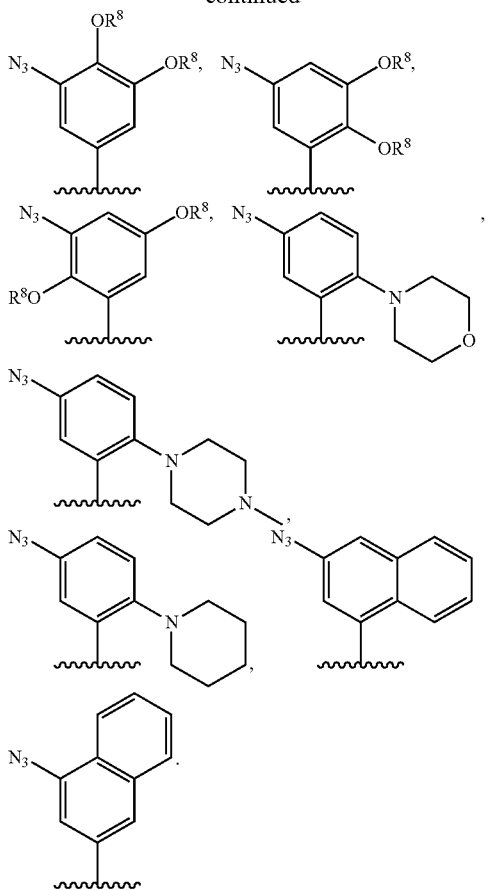

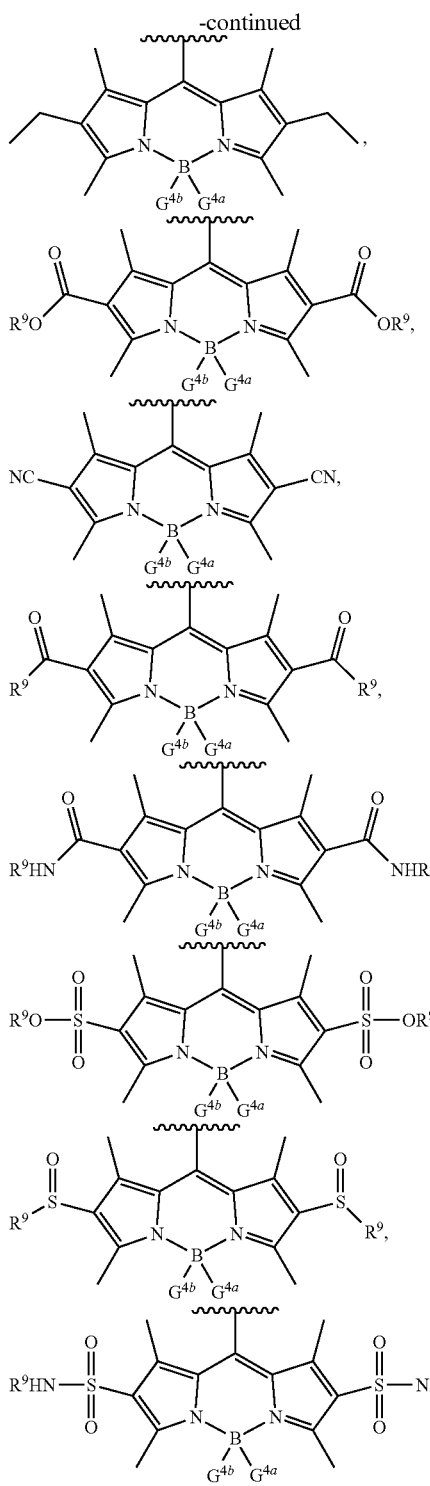

As used herein, each instance of $R^8$ is independently hydrogen, optionally substituted $C_1$-$C_6$ alkyl, optionally substituted alkenyl, optionally substituted heterocyclyl, optionally substituted aryl, optionally substituted heteroaryl, or an oxygen protecting group. In certain embodiments, $R^8$ is hydrogen. In certain embodiments, $R^8$ is optionally substituted $C_1$-$C_6$ alkyl. In certain embodiments, $R^8$ is methyl or ethyl. In certain embodiments, $R^8$ is an oxygen protecting group.

In certain embodiments,

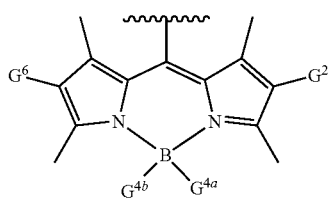

is of the formula:

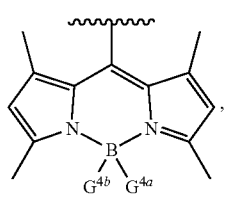

As used herein, each instance of $R^9$ is independently hydrogen, optionally substituted $C_1$-$C_6$ alkyl, optionally substituted alkenyl, optionally substituted heterocyclyl, optionally substituted aryl, optionally substituted heteroaryl, or an oxygen protecting group when attached to an oxygen. In certain embodiments, $R^9$ is hydrogen. In certain embodiments, $R^9$ is optionally substituted $C_1$-$C_6$ alkyl. In certain embodiments, $R^9$ is methyl or ethyl. In certain embodiments, $R^9$ is an oxygen protecting group.

each instance of $G^{4a}$ and $G^{4b}$ is fluoro, alkyl, alkoxy, aryloxy, or alkynyl, In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug, and isomer forms thereof, including the pharmaceutically acceptable salts, solvates, hydrates, prodrugs, and isomers thereof. In certain embodiments, a compound may be a metabolized into a pharmaceutically active derivative.

Exemplary compounds of formulae (I) and (II) are shown in Table 1:

TABLE 1

Exemplary compounds of formulae (I) and (II).

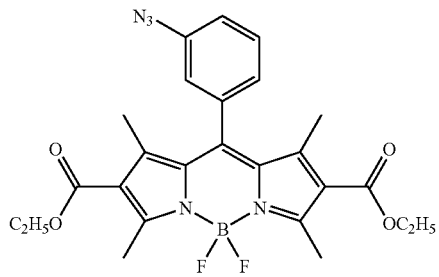

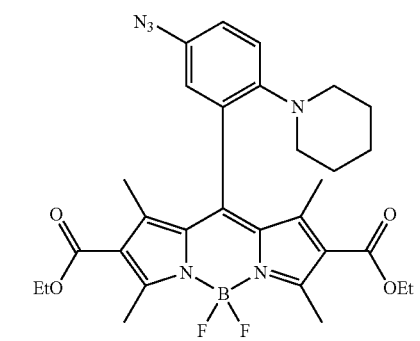

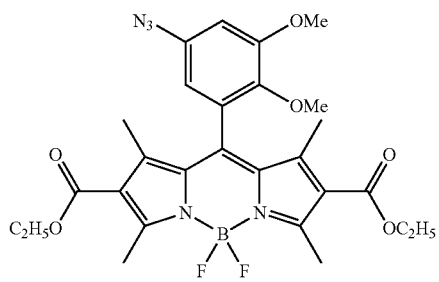

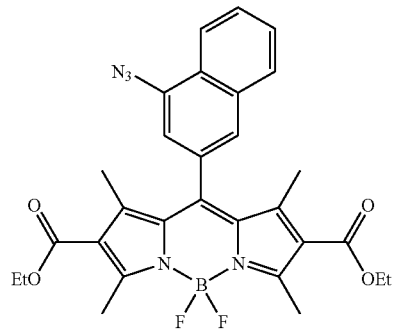

TABLE 1-continued

Exemplary compounds of formulae (I) and (II).

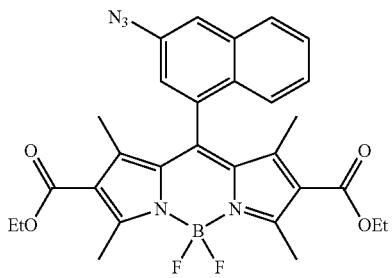

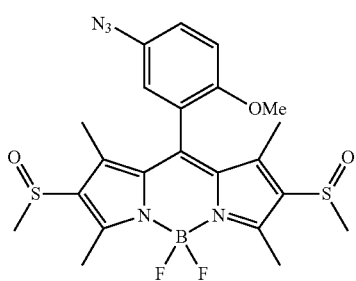

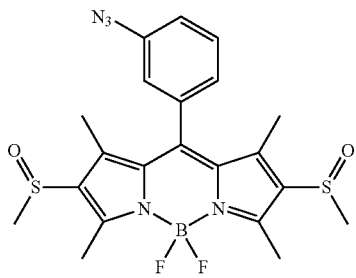

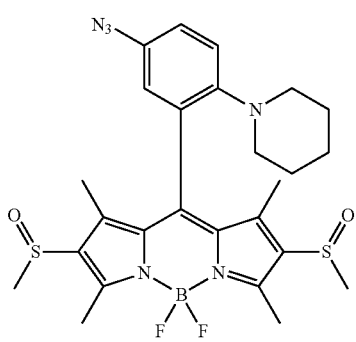

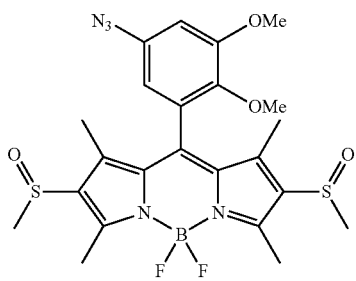

TABLE 1-continued
Exemplary compounds of formulae (I) and (II).
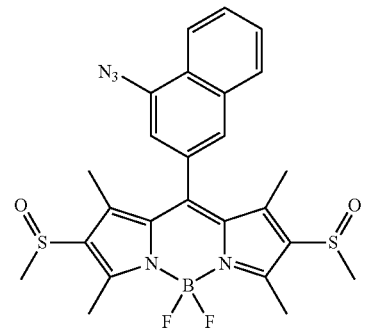
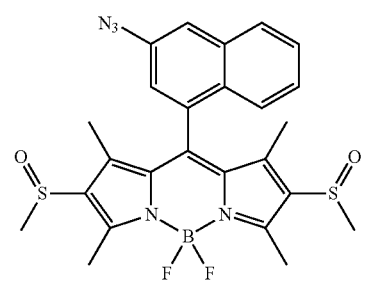
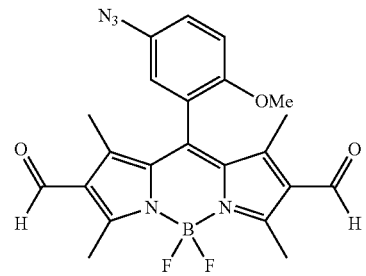
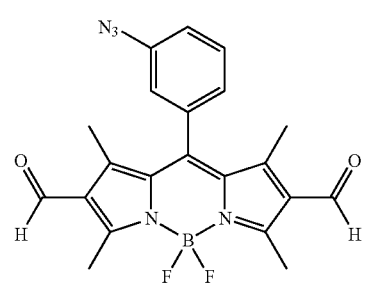
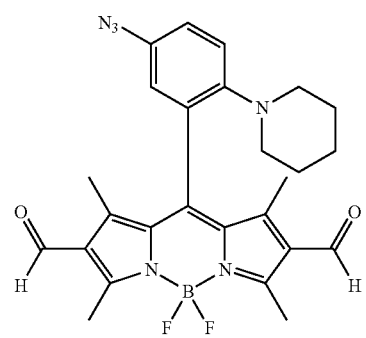
TABLE 1-continued
Exemplary compounds of formulae (I) and (II).
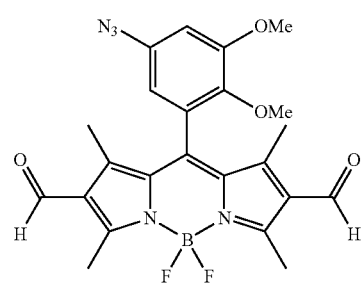
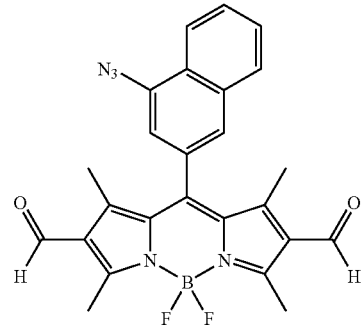
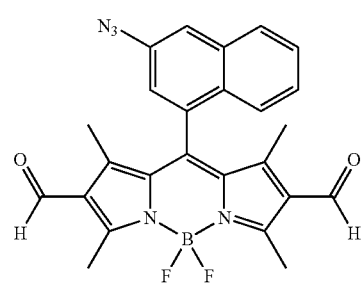
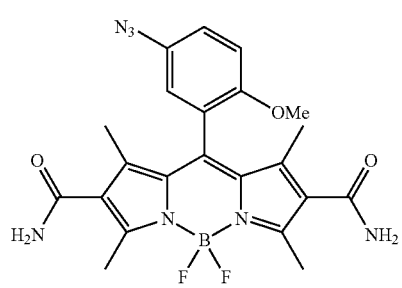
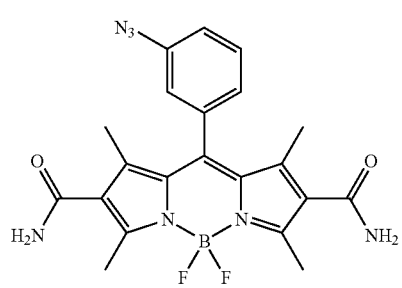

TABLE 1-continued
Exemplary compounds of formulae (I) and (II).
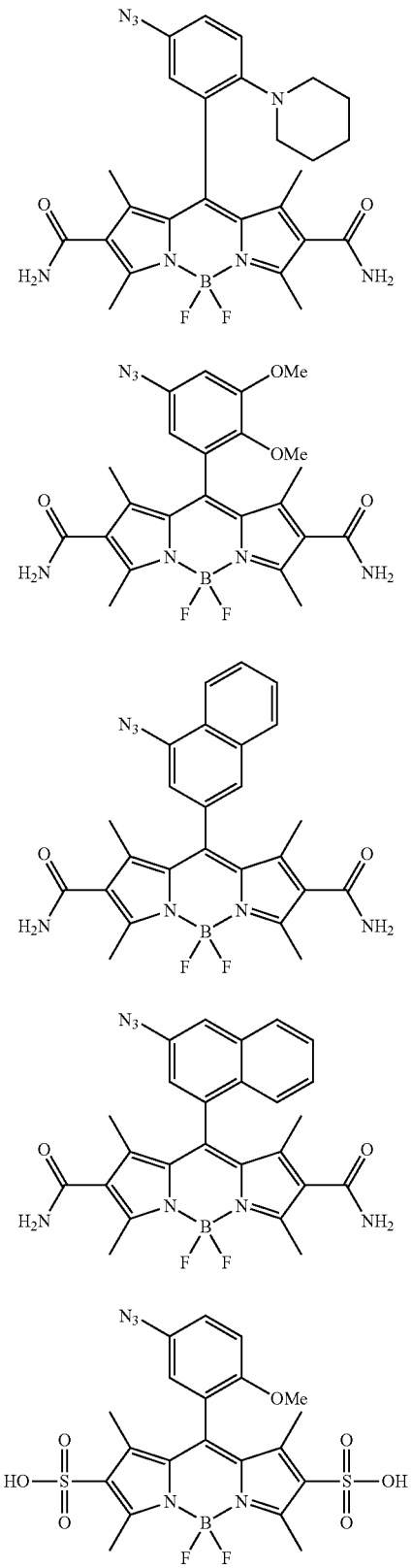
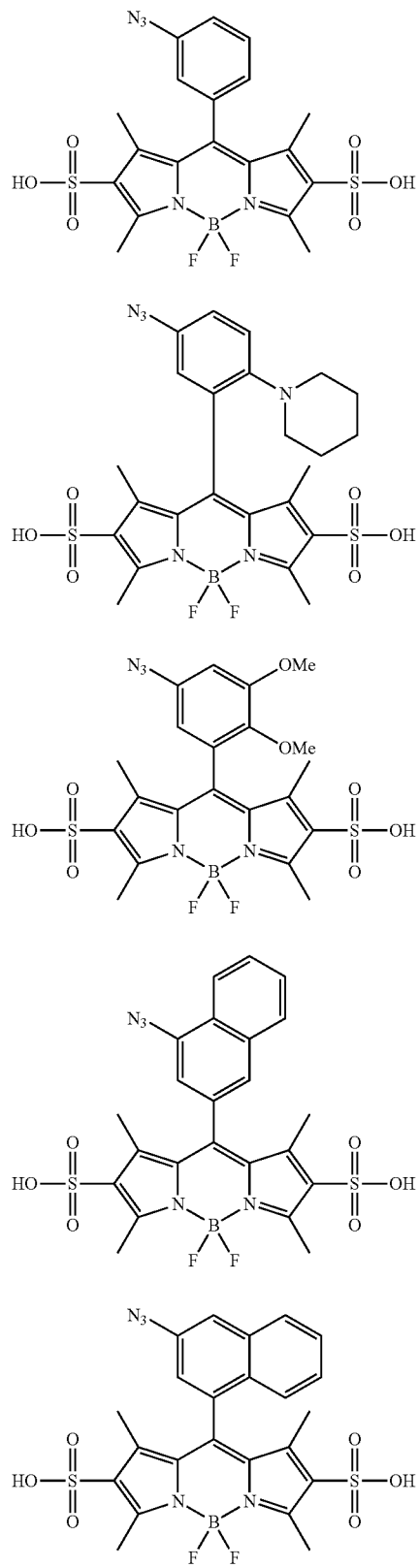

TABLE 1-continued
Exemplary compounds of formulae (I) and (II).
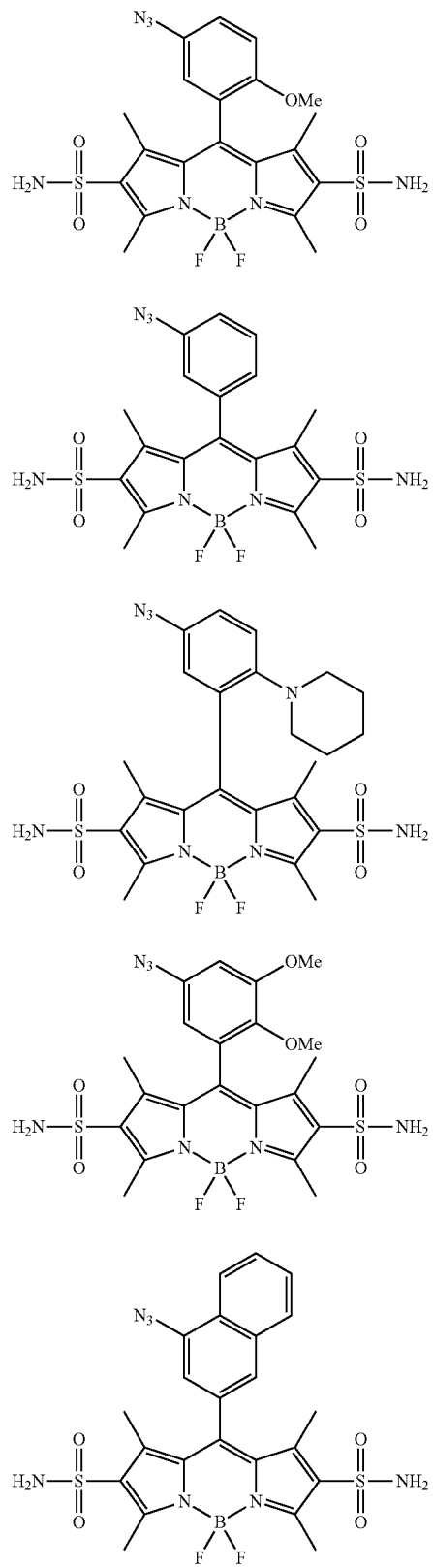
TABLE 1-continued
Exemplary compounds of formulae (I) and (II).
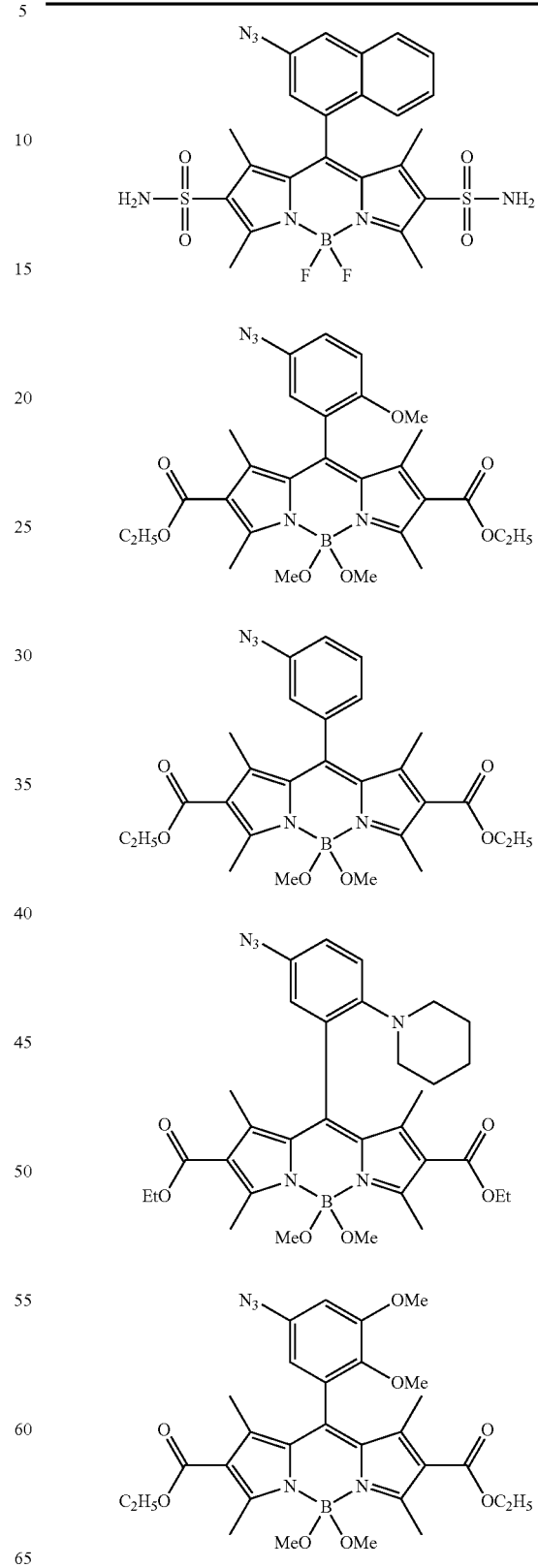

TABLE 1-continued
Exemplary compounds of formulae (I) and (II).
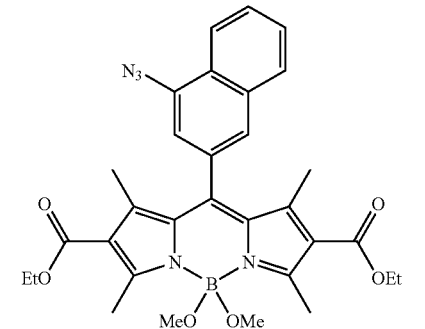
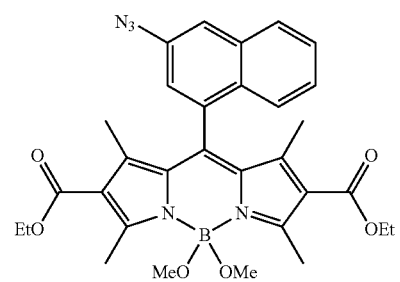
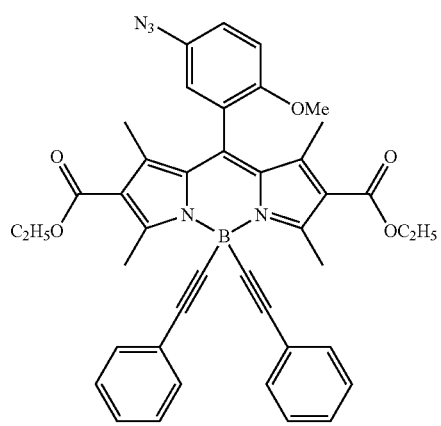
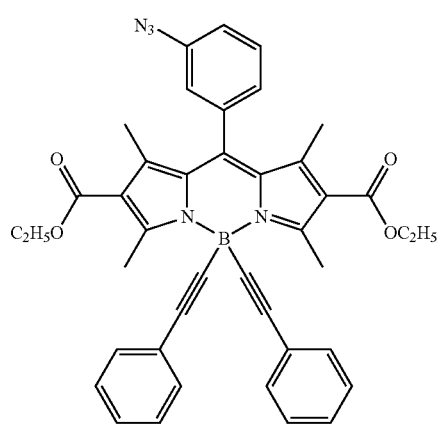
TABLE 1-continued
Exemplary compounds of formulae (I) and (II).
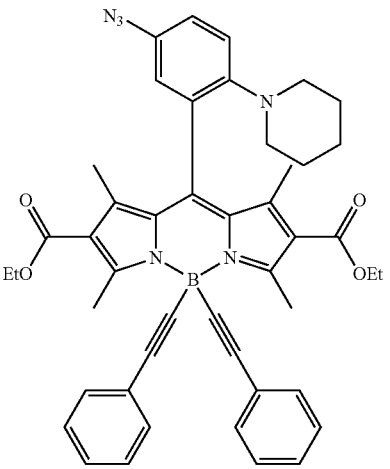
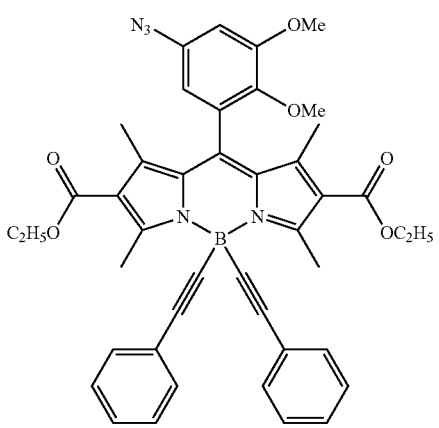
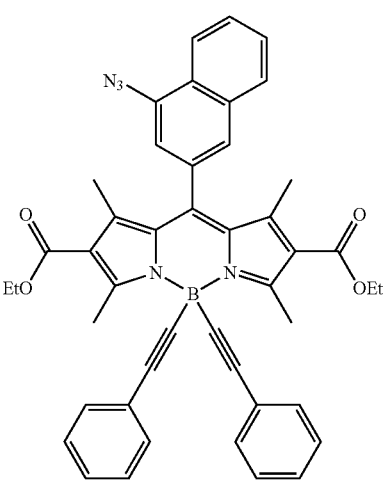

TABLE 1-continued
Exemplary compounds of formulae (I) and (II).
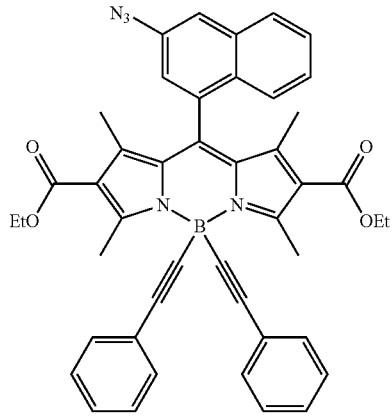
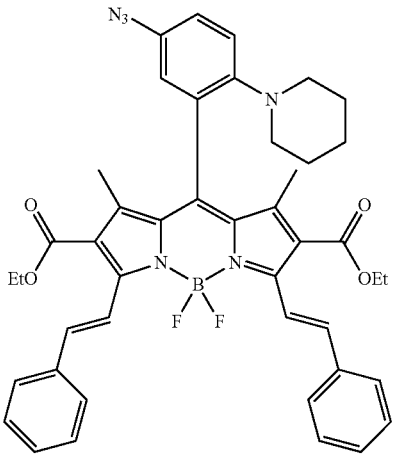
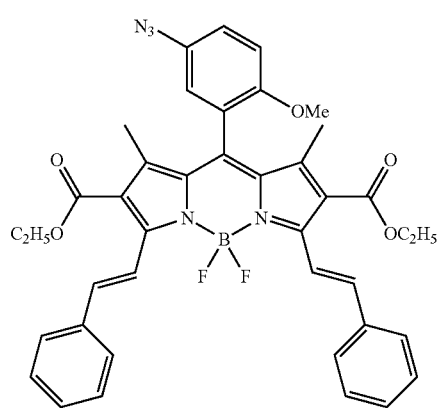
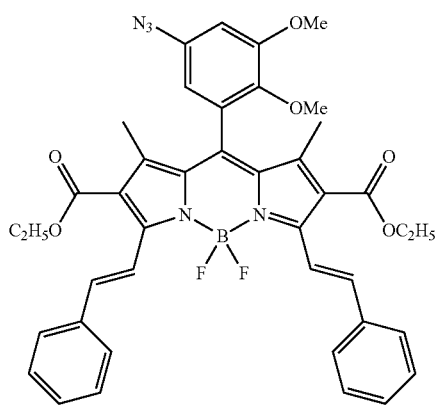
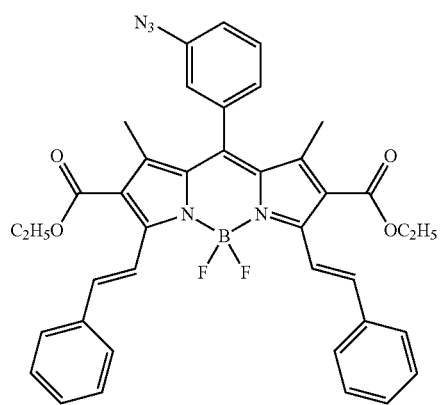
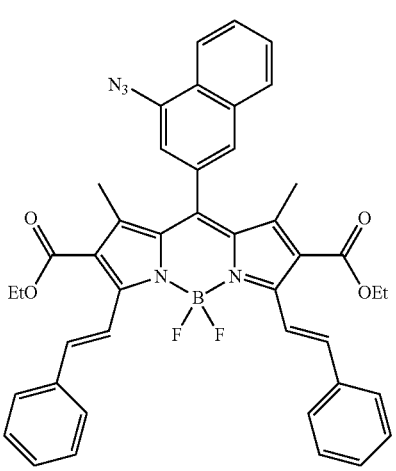

TABLE 1-continued
Exemplary compounds of formulae (I) and (II).
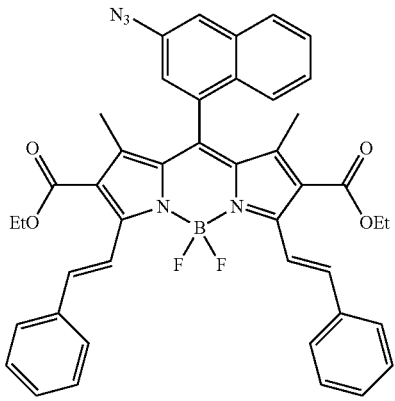
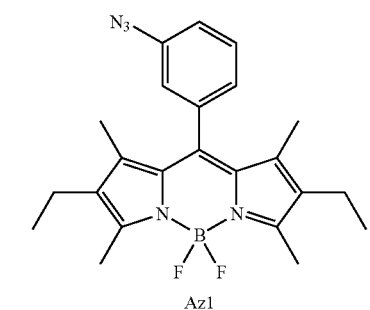
Az1
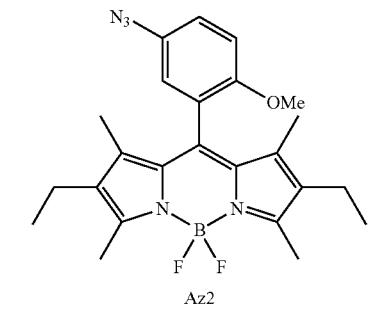
Az2
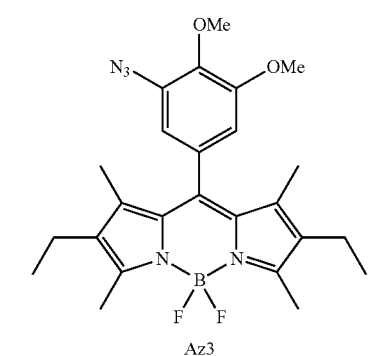
Az3
TABLE 1-continued
Exemplary compounds of formulae (I) and (II).
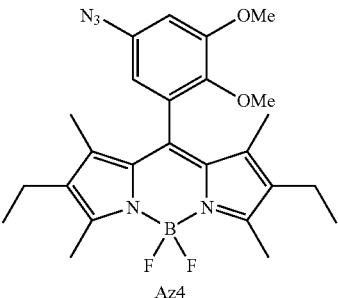
Az4
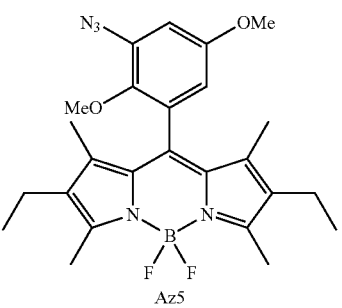
Az5
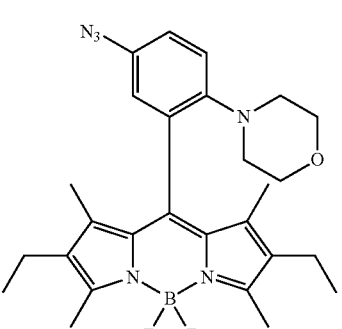
Az6
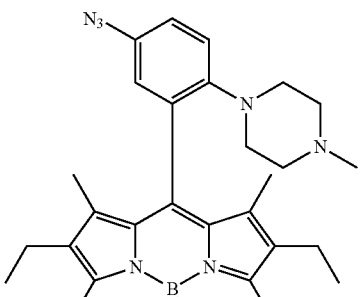
Az7

TABLE 1-continued

Exemplary compounds of formulae (I) and (II).

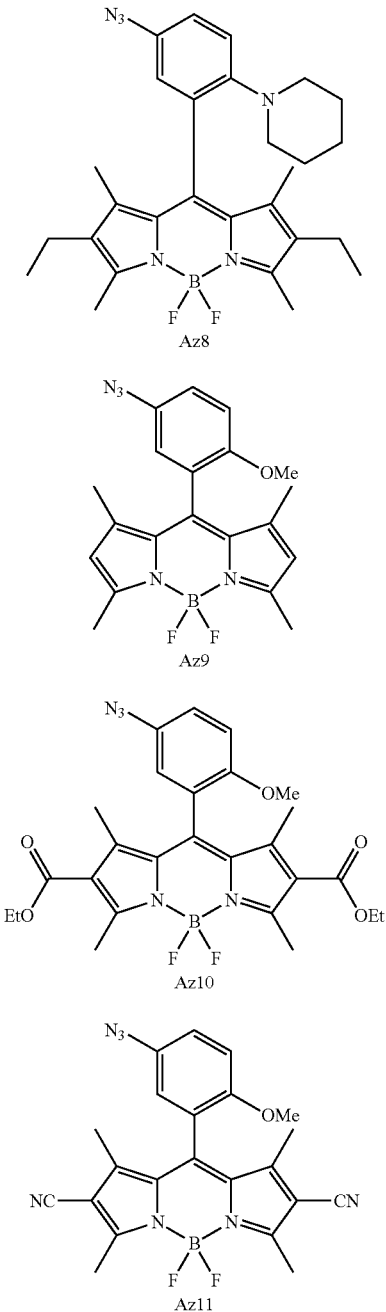

Az8

Az9

Az10

Az11

Exemplary Azido-BODIPY compounds were used to detect alkyne compounds, including the alkynyl-annexed biomolecules. After AAC reaction with an alkyne compound, the formation of triazole ring releases the fluorescence quenching, and results in a fluorescence-enhancing phenomenon. Compounds T2 and T9-T11 are examples of such type of probes that undergo AAC with azides to give fluorescent triazole products.

Alkyne-Containing Molecules

Alkyne-containing molecule described in the disclosure is of the formula:

Exemplary alkyne-containing target molecules include, but are not limited to, amino acids and amino acid residues, polypeptides (including peptides and proteins), sugars or sugar residues, and the like, which contain or are modified to contain at least one alkyne.

Exemplary target molecule includes, but not limited to, a biomolecule such as DNA, RNA, protein or glycan, and it can be naturally occurring, or may be synthetically or recombinantly produced, and may be isolated, substantially purified, or present within the native milieu of the unmodified molecule upon which the alkyne-containing target molecule is based (e.g., on a cell surface or within a cell, including within a host animal, e.g., a mammalian animal, such as a murine host (e.g., rat, mouse), hamster, canine, feline, bovine, swine, and the like). In some embodiments, the target molecule is present in vitro in a cell-free reaction. In other embodiments, the target molecule is present in a cell and/or displayed on the surface of a cell. In many embodiments of interest, the target molecule is in a living cell; on the surface of a living cell; in a living organism, e.g., in a living multicellular organism. Suitable living cells include cells that are part of a living multicellular organism; cells isolated from a multicellular organism; immortalized cell lines; and the like.

Where the target molecule is a polypeptide, the polypeptide may be composed of D-amino acids, L-amino acids, or both, and may be further modified, either naturally, synthetically, or recombinantly, to include other moieties. For example, the target polypeptide may be a lipoprotein, a glycoprotein, or other such modified protein.

In general, the target molecule useful comprises at least one alkyne for reaction with modified azido-BODIPY according to the disclosure, but may comprise 2 or more, 3 or more, 5 or more, 10 or more alkynes. The number of alkynes that may be present in a suitable target molecule will vary according to the intended application of the final product of the reaction, the nature of the target molecule itself, and other considerations which will be readily apparent to the ordinarily skilled artisan in practicing the disclosure as disclosed herein.

This embodiment of the disclosure is particularly useful in modification of a target molecule in vivo. In this embodiment, the target substrate is modified to comprise an alkynyl group at the point at which linkage to the modified azido-BODIPY is desired. For example, where the target substrate is a polypeptide, the polypeptide is modified to contain an N-terminal alkyne. Where the target substrate is a glycoprotein, a sugar residue of the glycoprotein can be modified to contain an alkyne. A target molecule that is unmodified with an alkyne, but that is to be modified with an alkyne, is referred to herein as a "target substrate." A target molecule that is modified with an alkyne is referred to herein as "an alkyne-modified target molecule" or "an alkyne-containing target molecule."

The target substrate can be generated in vitro and then introduced into the cell (e.g., via microinjection, liposome or lipofectin-mediated delivery, electroporation, etc.), which methods will vary according to the nature of the substrate to be targeted for modification and can be readily and appropriately selected by the ordinarily skilled artisan. The final target substrate can also be generated in vivo by exploiting a host cell's natural biosynthetic machinery. For example, the cell can be provided with a biocompatible alkyne-derivative of a substrate for synthesis of the desired target molecule, which substrate is processed by the cell to provide an alkyne-derivative of the desired final target substrate. For example, where the target substrate is a cell surface glycoprotein, the cell can be provided with an alkyne derivative of a sugar residue found within the glycoprotein, which is subsequently processed by the cell through natural biosynthetic processes to produce a modified glycoprotein having at least one modified sugar moiety comprising an accessible alkyne group.

The target substrate can also be produced in vivo using methods. For example, unnatural amino acids having alkynes can be incorporated into recombinant polypeptides expressed in *E. coli* (see, e.g., Kiick et al. (2000) *Tetrahedron* 56:9487). Such recombinantly produced polypeptides can be selectively reacted with a modified azido-BODIPY according to the disclosure.

In one example, an alkyne group is incorporated into the target molecule by providing a cell (e.g., a eukaryotic cell that glycosylates biopolymers such as proteins) with a synthetic building block for the desired biopolymer target substrate. For example, the cell can be provided with a sugar molecule comprising an alkyne group to provide for incorporation of the alkyne group in a glycoprotein. In some embodiments, the glycoprotein is expressed on the cell surface. Alternatively, the alkyne group can be incorporated into an amino acid, which is subsequently incorporated into a peptide or polypeptide synthesized by the cell. Several methods are available for incorporating unnatural building blocks into biopolymers; one need not be restricted to cell surface oligosaccharides as target molecules. See, e.g., van-Hest et al. (1998) *FEBS Lett.* 428:68; and Nowak et al. (1995) *Science* 268:439.

In one embodiment, the target molecule is a carbohydrate-containing molecule (e.g., a glycoprotein; a polysaccharide; etc.), and an alkyne group is introduced into the target molecule using a synthetic substrate. In some embodiments, the synthetic substrate is an alkyne derivative of a sugar utilized in production of a glycosylated molecule. In some embodiments, the synthetic substrate is an alkyne derivative of a sugar utilized in production of a cell surface molecule, e.g., in the glycoprotein biosynthetic pathway. For example, the host cell can be provided with a synthetic sialic acid alkynyl-derivative, which is incorporated into the pathway for sialic acid biosynthesis, eventually resulting in the incorporation of the synthetic sugar residue in glycoproteins. In some embodiments, the glycoproteins are displayed on the cell surface.

In one example, the synthetic substrate is an alkynyl derivative of mannosamine of the general formula:

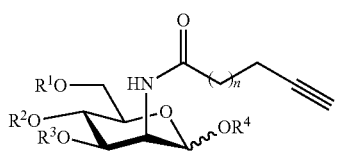

where n is from 0 to 7, generally from 1 to 4, more usually 1 to 2, and $R^1$, $R^2$, $R^3$, and $R^4$ are independently hydrogen or acetyl. In some embodiments, the substrate is N-3-butynoylmannosamine (n=0) or an acetylated derivative thereof, or N-4-pentynoylmannosamine (n=1) or an acetylated form thereof.

In another embodiment, the synthetic substrate is an alkynyl sugar derivative of a general formula of, for example:

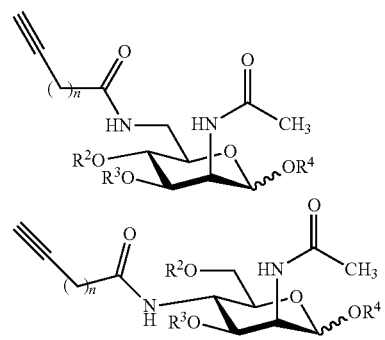

either of which can be incorporated into the sialic acid biosynthesis pathway, and where n is from 1 to 6, generally from 1 to 4, more usually 1 to 2, and $R^2$, $R^3$, and $R^4$ are independently hydrogen or acetyl.

In another embodiment, the synthetic substrate is an alkynyl sugar derivative of a general formula of, for example:

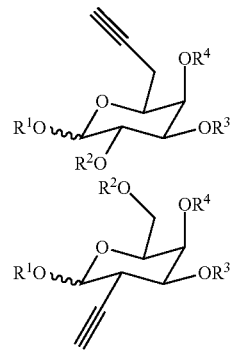

where $R^1$, $R^2$, $R^3$, and $R^4$ are independently hydrogen or acetyl, and where the synthetic substrate is incorporated into biosynthetic pathways involving fucose.

In another embodiment, the synthetic substrate is an alkynyl sugar derivative of a general formula of, for example:

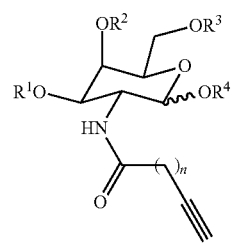

where n is from 1 to 6, generally from 1 to 4, more usually 1 to 2, and $R^1$, $R^2$, $R^3$, and $R^4$ are independently hydrogen or acetyl, and which is incorporated into biosynthetic pathways involving galactose.

In some embodiments, a subject method is used to modify the surface of a cell. Thus, in one aspect, the disclosure features a method of modifying the surface of cell in vitro or in vivo. The method generally involves reacting an alkyne group in a target molecule that comprises an alkynyl group with a modified azido-BODIPY to provide for chemoselective ligation at the cell surface. In many embodiments, the method comprises modifying a target molecule on a cell surface with an alkynyl group; and reacting the alkynyl group in the target molecule with a modified azido-BODIPY. For example, as described above, an alkynyl sugar is provided to a living cell, which alkynyl sugar is incorporated into a glycoprotein that is displayed on the cell surface.

Subject modified azido-BODIPY compounds, and subject modification methods, are useful in a variety of applications, including research applications and diagnostic applications.

In some embodiments, subject modified azido-BODIPY compounds, and subject modification methods, are useful in research applications. Applications of interest include research applications, e.g., exploring functional and physical characteristics of a receptor; proteomics; metabolomics; and the like. Research applications also include drug discovery or other screening applications.

Proteomics aims to detect, identify, and quantify proteins to obtain biologically relevant information. Metabolomics is the detection, identification, and quantification of metabolites and other small molecules such as lipids and carbohydrates. Fiehn (2001) *Comparative and Functional Genomics* 2:155-168; and U.S. Pat. No. 6,873,914.

Drug discovery applications include, but are not limited to, identifying agents that inhibit cancer cell viability and/or growth. Thus, in some embodiments, the instant disclosure provides methods of identifying an agent that inhibits cancer cell viability and/or growth. The methods generally involve modifying a component of the cell to comprise a first reactive partner comprising an alkyne; contacting the cell, in the presence of a test agent, with a second reactive partner comprising a modified azido-BODIPY, the contacting being under physiological conditions; where the contacting results in reaction between the alkynyl group of the first reactive partner and the azido-BODIPY compound of the second reactive partner, thereby synthetically and covalently modifying the cellular component; and determining the effect, if any, of the test agent on the level of modification of the cell with the second reactive partner.

Where the cancer cell is one that produces a higher amount of a carbohydrate than a normal (non-cancerous) cell of the same cell type, the method provides for identifying an agent that reduces growth and/or viability of the cancerous cell.

Applications of interest also include diagnostic applications, e.g., for detection of cancer; and the like, where a subject modified cycloalkyne comprising a detectable label is used to label an alkyne-modified target molecule, e.g., an alkyne-labeled target molecule present on a cancer cell. Applications of interest also include therapeutic applications, where a drug or other therapeutic agent is delivered to an alkyne-modified target molecule, using a subject modified azido-BODIPY compound that comprises a covalently linked drug or other therapeutic agent.

Certain embodiments of the present disclosure are used for in vivo imaging, e.g., to determine the metabolic or other state of a cell in an organism, e.g., an individual. As one non-limiting example, a subject method can be applied to in vivo imaging of cancer cells in an individual (e.g., a mammal, including rodents, lagomorphs, felines, canines, equines, bovines, ovines, caprines, non-human primates, and humans).

One exemplary, non-limiting application of a subject azide-alkyne cycloaddition is in the detection of metabolic change in cells that occur as they alter their phenotype. As one example, altered glycosylation patterns are a hallmark of the tumor phenotype, consisting of both the under- and over-expression of naturally-occurring glycans as well as the presentation of glycans normally restricted to expression during embryonic development. Examples of common antigens associated with transformed cells are sialyl Lewis a, sialyl Lewis x, sialyl T, sialyl Tn, and polysialic acid (PSA). Jørgensen et al. (1995) Cancer Res. 55, 1817-1819; Sell (1990) Hum. Pathology 21, 1003-1019; Taki et al. (1988) J. Biochem. 103, 998-1003; Gabius (1988) Angew. Chem. Int. Ed. Engl. 27, 1267-1276; Feizi (1991) Trends Biochem. Sci. 16, 84-86; Taylor-Papadimitriou and Epenetos (1994) Trends Biotech. 12, 227-233; Hakomori and Zhang (1997) Chem. Biol. 4, 97-104; Dohi et al. (1994) Cancer 73, 1552. These antigens share an important feature—they each contain terminal sialic acid. PSA is a homopolymer of sialic acid residues up to 50 units in length. Elevated levels of sialic acid are highly correlated with the transformed phenotype in many cancers, including gastric (Dohi et al. (1994) Cancer 73, 1552; and Yamashita et al. (1995) J. Natl. Cancer Inst. 87, 441-446), colon (Yamashita et al. (1995) J. Natl. Cancer Inst. 87, 441-446; Hanski et al. (1995) Cancer Res. 55, 928-933; Hanski et al. (1993) Cancer Res. 53, 4082-4088; Yang et al. (1994) Glycobiology 4, 873-884; Saitoh et al. (1992) J. Biol. Chem. 267, 5700-5711), pancreatic (Sawada et al. (1994) Int. J. Cancer 57, 901-907), liver (Sawada et al.(1994) J. Biol. Chem. 269, 1425-1431), lung (Weibel et al. (1988) Cancer Res. 48, 4318-4323), prostate (Jorgensen et al. (1995) Cancer Res. 55, 1817-1819), kidney (Roth et al. (1988) Proc. Natl. Acad. Sci. USA 85, 2999-3000), and breast cancers (Cho et al. (1994) Cancer Res. 54, 6302-6305), as well as several types of leukemia (Joshi et al. (1987) Cancer Res. 47, 3551-3557; Altevogt et al. (1983) Cancer Res. 43, 5138-5144; Okada et al. (1994) Cancer 73, 1811-1816). A strong correlation between the level of cell surface sialic acid and metastatic potential has also been observed in several different tumor types (Kakeji et al. (1995) Brit. J. Cancer 71, 191-195; Takano et al. (1994) Glycobiology 4, 665-674). The collective display of multiple sialylated antigens on a single cancer cell can account for the fact that so many different tumor types share the high sialic acid phenotype without necessarily expressing an identical complement of antigens (Roth et al. (1988) supra). Consequently, diagnostic or therapeutic strategies that target cells on the basis of sialic acid levels have broad applicability to many cancers.

Introduction and incorporation of unnatural alkynylsugars (ManNAl, GalNAl) into living animals provides for detection of changes in metabolic state. Via the attachment of the appropriate epitope tag, the modified azido-BODIPY compound labels these cells in a living organism, and consequently detects changes in metabolic state. Early detection of tumorigenic cells and subsequent intervention reduces the severity and increases survival rates for cancer patients.

Triazolyl-BODIPY Compounds

A triazolyl-BODIPY compound is formed by reacting an azido-BODIPY compound with an alkyne-containing molecule via azide-alkyne cycloadditions (AAC). The triazolyl-BODIPY compound exhibits enhanced fluorescence compared to the corresponding azido-BODIPY compound. Triazolyl-BODIPY compound described in the disclosure is of Formula (III):

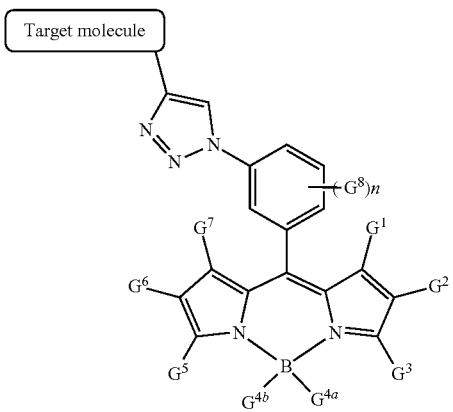

or a pharmaceutically acceptable salt, solvate, or hydrate thereof, wherein:

each instance of $G^1$, $G^2$, $G^3$, $G^5$, $G^6$, $G^7$ and $G^8$ is independently hydrogen, optionally substituted $C_{1-6}$ alkyl, optionally substituted $C_{1-6}$ alkenyl, optionally substituted $C_{1-6}$ alkynyl, optionally substituted aryl, optionally substituted acyl, $-OR^A$, $-CH_2OR^A$, $-OC(O)R^A$, $-SR^A$, $-N(R^B)_2$, $-N(R^A)C(O)R^A$, $-C(O)N(R^B)_2$, $-CN$, $-NO_2$, $-C(O)R^A$, $-C(O)OR^A$, $-S(O)R^A$, $-SO_2R^A$, $-SO_3R^A$, $-SO_2N(R^B)_2$, and $-NHSO_2R^B$;

each instance of R is independently selected from hydrogen, halogen, optionally substituted alkyl, optionally substituted alkenyl, optionally substituted alkynyl, optionally substituted heterocyclyl, optionally substituted aryl, optionally substituted acyl, $-OR^A$, $-CH_2OR^A$, $-OC(O)R^A$, $-SR^A$, $-N(R^B)_2$, $-N(R^A)C(O)R^A$, $-C(O)N(R^B)_2$, $-CN$, $-NO_2$, $-C(O)R^A$, $-C(O)OR^A$, $-S(O)R^A$, $-SO_2R^A$, $-SO_3R^A$, $-SO_2N(R^B)_2$, and $-NHSO_2R^B$;

each $R^A$ is independently selected from hydrogen, optionally substituted $C_1$-$C_6$ alkyl, optionally substituted alkenyl, optionally substituted alkynyl, optionally substituted heterocyclyl, and optionally substituted aryl; and each $R^B$ is independently selected from hydrogen, optionally substituted $C_1$-$C_6$ alkyl, optionally substituted alkenyl, optionally substituted alkynyl, optionally substituted heterocyclyl, and optionally substituted aryl, or two $R^B$ taken together with the intervening nitrogen form a heterocycle.

each instance of $G^{4a}$ and $G^{4b}$ is fluoro, alkyl, alkoxy, aryloxy, or alkynyl, and wherein alkyl and alkoxy groups are unbranched, saturated, and have 1-4 carbon atoms; aryl groups and aryl groups of aryloxy can be either carbocyclic aryl or heterocyclic aryl; carbocyclic aryl groups have a total of 6-20 carbon atoms, including carbon atoms of substituents; heterocyclic aryl groups have a total of 5-20 carbon atoms, including carbon atoms of substituents; carboalkoxy groups are alkyl esters of a carboxylic acid wherein alkyl groups are as defined above; each alkyl, aryl, alkoxy, aryloxy, benzo, and carboalkoxy, independently, may be unsubstituted or substituted with one or more substituent; alkyl substituents are halo, hydroxyl, amino, or aryl; aryl substituents are halo, hydroxyl, amino, alkyl, aryl, nitro, or carboxyl; and halo substituents are fluoro or chloro;

n is 0, 1, 2, 3, or 4.

As generally defined herein, $G^1$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, $-OR^A$, $-CH_2OR^A$, $-OC(O)R^C$, $-SR^A$, $-N(R^B)_2$, $-N(R^A)C(O)R^C$, $-C(O)N(R^B)_2$, $-CN$, $-NO_2$, $-C(O)R^C$, $-C(O)OR^A$, $-S(O)R^C$, $-SO_2R^A$, $-SO_2N(R^B)_2$, $=O$, $=NOH$, $=N-OR^A$, $=N-NH_2$, $=N-NHR^A$, $=N-N(R^B)_2$, and $-NHSO_2R^A$. In certain embodiments, $G^1$ is H. In certain embodiments, $G^1$ is halogen. In certain embodiments, $G^1$ is optionally substituted $C_1$-$C_6$ alkyl. In certain embodiments, $G^1$ is methyl, ethyl, or n-propyl. In certain embodiments, $G^1$ is $-OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or an oxygen protecting group when attached to an oxygen, or a sulfur protecting group when attaching to sulfur. In certain embodiments, $G^1$ is $-OH$. In certain embodiments, $G^1$ is $-OR^A$, wherein $R^A$ is optionally substituted $C_1$-$C_6$ alkyl. In certain embodiments, $G^1$ is $-OCH_3$ or $-OC_2H_5$. In certain embodiments, $G^1$ is $-OR^A$, wherein $R^A$ is an oxygen protecting group. In certain embodiments, $G^1$ is $-N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^1$ is $NH_2$. In certain embodiments, $G^1$ is $NHR^B$, wherein $R^B$ is optionally substituted $C_1$-$C_6$ alkyl. In certain embodiments, $G^1$ is $NHCH_3$ or $NHC_2H_5$. In certain embodiments, $G^1$ is $NHR^B$, wherein $R^B$ is a nitrogen protecting group.

As generally defined herein, $G^2$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, $-OR^A$, $-CH_2OR^A$, $-OC(O)R^C$, $-SR^A$, $-N(R^B)_2$, $-N(R^A)C(O)R^C$, $-C(O)N(R^B)_2$, $-CN$, $-NO_2$, $-C(O)R^C$, $-C(O)OR^A$, $-S(O)R^C$, $-SO_2R^A$, $-SO_2N(R^B)_2$, $=O$, $=NOH$, $=N-OR^A$, $=N-NH_2$, $=N-NHR^A$, $=N-N(R^B)_2$, and $-NHSO_2R^A$. In certain embodiments, $G^2$ is H. In certain embodiments, $G^2$ is halogen. In certain embodiments, $G^2$ is optionally substituted $C_1$-$C_6$ alkyl. In certain embodiments, $G^2$ is methyl, ethyl, or n-propyl. In certain embodiments, $G^7$ is $-OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^2$ is $-OH$. In certain embodiments, $G^2$ is $-OR^A$, wherein $R^A$ is optionally substituted $C_1$-$C_6$ alkyl. In certain embodiments, $G^2$ is $-OCH_3$ or $-OC_2H_5$. In certain embodiments, $G^2$ is $-OR^A$, wherein $R^A$ is an oxygen protecting group. In certain embodiments, $G^2$ is $-N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^2$ is $NH_2$. In certain embodiments, $G^2$ is $NHR^B$, wherein $R^B$ is optionally substituted $C_1$-$C_6$ alkyl. In certain embodiments, $G^2$ is $NHCH_3$ or $NHC_2H_5$. In certain embodiments, $G^2$ is $NHR^B$, wherein $R^B$ is a nitrogen protecting group.

As generally defined herein, $G^3$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, $-OR^A$, $-CH_2OR^A$, $-OC(O)R^C$, $-SR^A$, $-N(R^B)_2$, $-N(R^A)C(O)R^C$, $-C(O)N(R^B)_2$, $-CN$, $-NO_2$, $-C(O)R^C$, $-C(O)OR^A$, $-S(O)R^C$, $-SO_2R^A$, $-SO_2N(R^B)_2$, $=O$, $=NOH$, $=N-OR^A$, $=N-NH_2$, $=N-NHR^A$, $=N-N(R^B)_2$, and $-NHSO_2R^A$. In certain embodiments, $G^3$ is H. In certain embodiments, $G^3$ is halogen. In certain embodiments, $G^3$ is optionally substituted $C_1$-$C_6$ alkyl. In certain embodiments, $G^3$ is methyl, ethyl, or n-propyl. In certain embodiments, $G^7$ is $-OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^3$ is $-OH$. In certain embodiments, $G^3$ is $-OR^A$, wherein $R^A$ is optionally substituted $C_1$-$C_6$ alkyl. In certain embodiments, $G^3$ is $-OCH_3$ or $-OC_2H_5$. In certain embodiments, $G^3$ is $-OR^A$, wherein $R^A$ is an oxygen protecting group. In certain embodiments, $G^3$ is $-N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^3$ is $NH_2$. In certain embodiments, $G^3$ is $NHR^B$, wherein $R^B$ is optionally substituted $C_1$-$C_6$ alkyl. In certain embodiments, $G^3$ is $NHCH_3$ or $NHC_2H_5$. In certain embodiments, $G^3$ is $NHR^B$, wherein $R^B$ is a nitrogen protecting group.

As generally defined herein, $G^5$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, $-OR^A$, $-CH_2OR^A$, $-OC(O)R^C$, $-SR^A$, $-N(R^B)_2$, $-N(R^A)C(O)R^C$, $-C(O)N(R^B)_2$, $-CN$, $-NO_2$, $-C(O)R^C$, $-C(O)OR^A$, $-S(O)R^C$, $-SO_2R^A$, $-SO_2N(R^B)_2$, $=O$, $=NOH$, $=N-OR^A$, $=N-NH_2$, $=N-NHR^A$, $=N-N(R^B)_2$, and $-NHSO_2R^A$. In certain embodiments, $G^5$ is H. In certain embodiments, $G^5$ is halogen. In certain embodiments, $G^5$ is optionally substituted $C_1$-$C_6$ alkyl. In certain embodiments, $G^5$ is methyl, ethyl, or n-propyl. In certain embodiments, $G^5$ is $-OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^5$ is $-OH$. In certain embodiments, $G^5$ is $-OR^A$, wherein $R^A$ is optionally substituted $C_1$-$C_6$ alkyl. In certain embodiments, $G^5$ is $-OCH_3$ or $-OC_2H_5$. In certain embodiments, $G^5$ is $-OR^A$, wherein $R^A$ is an oxygen protecting group. In certain embodiments, $G^5$ is $-N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^5$ is $NH_2$. In certain embodiments, $G^5$ is $NHR^B$, wherein $R^B$ is optionally substituted $C_1$-$C_6$ alkyl. In certain embodiments, $G^5$ is $NHCH_3$ or $NHC_2H_5$. In certain embodiments, $G^5$ is $NHR^B$, wherein $R^B$ is a nitrogen protecting group.

As generally defined herein, $G^6$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, $-OR^A$, $-CH_2OR^A$, $-OC(O)R^C$, $-SR^A$, $-N(R^B)_2$, $-N(R^A)C(O)R^C$, $-C(O)N(R^B)_2$, $-CN$, $-NO_2$, $-C(O)R^C$, $-C(O)OR^A$, $-S(O)R^C$, $-SO_2R^A$, $-SO_2N(R^B)_2$, $=O$, $=NOH$, $=N-OR^A$, $=N-NH_2$, $=N-NHR^A$, $=N-N(R^B)_2$, and $-NHSO_2R^A$. In certain embodiments, $G^6$ is H. In certain embodiments, $G^6$ is halogen. In certain embodiments, $G^6$ is optionally substituted $C_1$-$C_6$ alkyl. In certain embodiments, $G^6$ is methyl, ethyl, or n-propyl. In certain embodiments, $G^6$ is $-OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^6$ is $-OH$. In certain embodiments, $G^6$ is $-OR^A$, wherein $R^A$ is optionally substituted $C_1$-$C_6$ alkyl. In certain embodiments, $G^6$ is $-OCH_3$ or $-OC_2H_5$. In certain embodiments, $G^6$ is $-OR^A$, wherein $R^A$ is an oxygen protecting group. In certain embodiments, $G^6$ is $-N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^6$ is $NH_2$. In certain embodiments, $G^6$ is $NHR^B$, wherein $R^B$ is optionally substituted $C_1$-$C_6$ alkyl. In certain embodiments, $G^6$ is $NHCH_3$ or $NHC_2H_5$. In certain embodiments, $G^6$ is $NHR^B$, wherein $R^B$ is a nitrogen protecting group.

As generally defined herein, $G^7$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, $-OR^A$, $-CH_2OR^A$, $-OC(O)R^C$, $-SR^A$, $-N(R^B)_2$, $-N(R^A)C(O)R^C$, $-C(O)N(R^B)_2$, $-CN$, $-NO_2$, $-C(O)R^C$, $-C(O)OR^A$, $-S(O)R^C$, $-SO_2R^A$, $-SO_2N(R^B)_2$, $=O$, $=NOH$, $=N-OR^A$, $=N-NH_2$, $=N-NHR^A$, $=N-N(R^B)_2$, and $-NHSO_2R^A$. In certain embodiments, $G^7$ is H. In certain embodiments, $G^7$ is halogen. In certain embodiments, $G^7$ is optionally substituted $C_1$-$C_6$ alkyl. In certain embodiments, $G^7$ is methyl, ethyl, or n-propyl. In certain embodiments, $G^7$ is $-OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^7$ is $-OH$. In certain embodiments, $G^7$ is $-OR^A$, wherein $R^A$ is optionally substituted $C_1$-$C_6$ alkyl. In certain embodiments, $G^7$ is $-OCH_3$ or $-OC_2H_5$. In certain embodiments, $G^7$ is $-OR^A$, wherein $R^A$ is an oxygen protecting group. In certain embodiments, $G^7$ is $-N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^7$ is $NH_2$. In certain embodiments, $G^7$ is $NHR^B$, wherein $R^B$ is optionally substituted $C_1$-$C_6$ alkyl. In certain embodiments, $G^7$ is $NHCH_3$ or $NHC_2H_5$. In certain embodiments, $G^7$ is $NHR^B$, wherein $R^B$ is a nitrogen protecting group.

As generally defined herein, $G^8$ is independently selected from hydrogen, halogen, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, =O, =NOH, =N—$OR^A$, =N—$NH_2$, =N—$NHR^A$, =N—$N(R^B)_2$, and —$NHSO_2R^A$. In certain embodiments, $G^8$ is H. In certain embodiments, $G^8$ is halogen. In certain embodiments, $G^8$ is optionally substituted $C_1$-$C_6$ alkyl. In certain embodiments, $G^8$ is methyl, ethyl, or n-propyl. In certain embodiments, $G^8$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur. In certain embodiments, $G^8$ is —OH. In certain embodiments, $G^8$ is —$OR^A$, wherein $R^A$ is optionally substituted $C_1$-$C_6$ alkyl. In certain embodiments, $G^8$ is —$OCH_3$ or —$OC_2H_5$. In certain embodiments, $G^8$ is —$OR^A$, wherein $R^A$ is an oxygen protecting group. In certain embodiments, $G^8$ is —$N(R^B)_2$, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^8$ is $NH_2$. In certain embodiments, $G^8$ is $NHR^B$, wherein $R^B$ is optionally substituted $C_1$-$C_6$ alkyl. In certain embodiments, $G^8$ is $NHCH_3$ or $NHC_2H_5$. In certain embodiments, $G^8$ is $NHR^B$, wherein $R^B$ is a nitrogen protecting group.

In certain embodiments, two of $G^8$ groups adjacent to each other are taken together with their intervening atoms to form an optionally substituted carbocycle or heterocycle. In certain embodiments, two of $G^8$ groups adjacent to each other are taken together with their intervening atoms to form an optionally substituted carbocycle. In certain embodiments, two of $G^8$ groups adjacent to each other are taken together with their intervening atoms to form an optionally substituted 5-membered carbocycle. In certain embodiments, two of $G^8$ groups adjacent to each other are taken together with their intervening atoms to form an optionally substituted 6-membered carbocycle. In certain embodiments, two of $G^8$ groups adjacent to each other are taken together with their intervening atoms to form an optionally substituted phenyl. In certain embodiments, two of $G^8$ groups adjacent to each other are taken together with their intervening atoms to form an unsubstituted phenyl. In certain embodiments, two of $G^8$ groups adjacent to each other are taken together with their intervening atoms to form an optionally substituted heterocycle. In certain embodiments, two of $G^8$ groups adjacent to each other are taken together with their intervening atoms to form an optionally substituted 5-membered heterocycle with one heteroatom of S, N, or O. In certain embodiments, two of $G^8$ groups adjacent to each other are taken together with their intervening atoms to form an optionally substituted 5-membered heterocycle with two heteroatom each independently selected from the group of S, N, and O. In certain embodiments, two of $G^8$ groups adjacent to each other are taken together with their intervening atoms to form an optionally substituted 6-membered carbocycle with one heteroatom of S, N, or O. In certain embodiments, two of $G^8$ groups adjacent to each other are taken together with their intervening atoms to form an optionally substituted 6-membered carbocycle with two heteroatoms each independently selected from the group consisting of S, N, and O.

The efficacy of one or more embodiments of the disclosure are set forth in the description below. Other features or advantages of the present disclosure will be apparent from the following drawings and detailed description of several embodiments, and also from the appending claims.

Cyclooctyne-based Fluorogenic Probes

A cyclooctyne-based fluorogenic probe is the Formula (IV):

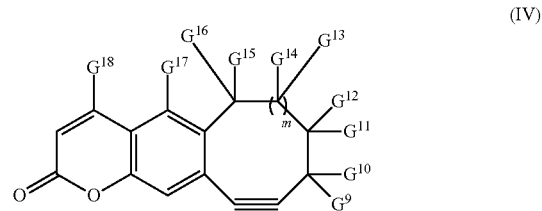

(IV)

or a pharmaceutically acceptable salt, solvate, or hydrate thereof, and wherein:

each instance of $G^9$, $G^{10}$, $G^{11}$, $G^{12}$, $G^{13}$, $G^{14}$, $G^{15}$, $G^{16}$, $G^{17}$ and $G^{18}$ is independently hydrogen, optionally substituted $C_{1-6}$ alkyl, optionally substituted $C_{1-6}$ alkenyl, optionally halogen, optionally nitroso, optionally substituted $C_{1-6}$ alkynyl, optionally substituted aryl, optionally substituted acyl, —$OR^A$, —$CH_2OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_3R^A$, —$SO_2N(R^B)_2$, and —$NHSO_2R^B$;

each instance of R is independently selected from hydrogen, halogen, optionally substituted alkyl, optionally substituted alkenyl, optionally substituted alkynyl, optionally substituted heterocyclyl, optionally substituted aryl, optionally substituted acyl, —$OR^A$, —$CH_2OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_3R^A$, —$SO_2N(R^B)_2$, and —$NHSO_2R^B$;

each $R^A$ is independently selected from hydrogen, optionally substituted $C_1$-$C_6$ alkyl, optionally substituted alkenyl, optionally substituted alkynyl, optionally substituted heterocyclyl, and optionally substituted aryl; and each $R^B$ is independently selected from hydrogen, optionally substituted $C_1$-$C_6$ alkyl, optionally substituted alkenyl, optionally substituted alkynyl, optionally substituted heterocyclyl, and optionally substituted aryl, or two $R^B$ taken together with the intervening nitrogen form a heterocycle;

each instance of $G^9$ and $G^{10}$ is hydrogen, fluoro, chloro, bromo, iodo, nitroso, alkyl, alkoxy, aryloxy, or alkynyl, and wherein alkyl and alkoxy groups are unbranched, saturated, and have 1-4 carbon atoms; aryl groups and aryl groups of aryloxy can be either carbocyclic aryl or heterocyclic aryl; carbocyclic aryl groups have a total of 6-20 carbon atoms, including carbon atoms of substituents; heterocyclic aryl groups have a total of 5-20 carbon atoms, including carbon atoms of substituents; carboalkoxy groups are alkyl esters of a carboxylic acid wherein alkyl groups are as defined above; each alkyl, aryl, alkoxy, aryloxy, benzo, and carboalkoxy, independently, may be unsubstituted or substituted with one or more substituent; alkyl substituents are halo, hydroxyl, amino, or aryl; aryl substituents are halo, hydroxyl, amino, alkyl, aryl, nitro, or carboxyl; and halo substituents are fluoro or chloro;

m is 0 or 1.

As generally defined herein, $G^9$ is independently selected from hydrogen, halogen, nitroso, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^C$, —$SR^A$, —$N(R^B)_2$, —$N(R^A)C(O)R^C$, —$C(O)N(R^B)_2$, —CN, —$NO_2$, —$C(O)R^C$, —$C(O)OR^A$, —$S(O)R^C$, —$SO_2R^A$, —$SO_2N(R^B)_2$, =O, =NOH, =N—$OR^A$, =N—$NH_2$, =N—$NHR^A$, =N—N$(R^B)_2$, and —$NHSO_2R^A$. In certain embodiments, $G^9$ is H. In certain embodiments, $G^9$ is halogen. In certain embodiments, $G^9$ is optionally substituted $C_1$-$C_6$ alkyl. In certain embodiments, $G^1$ is methyl, ethyl, or n-propyl. In certain embodiments, $G^9$ is —$OR^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, optionally substituted heteroaryl, or an oxygen protecting group when attached to an oxygen, or a sulfur protecting group when attaching to sulfur. In certain embodiments, $G^9$ is fluoro.

As generally defined herein, $G^{10}$ is independently selected from hydrogen, halogen, nitroso, optionally substituted $C_1$-$C_6$ alkyl, optionally substituted alkenyl, optionally substituted alkynyl, optionally substituted heterocyclyl, optionally substituted aryl, optionally substituted heteroaryl, —$OR^A$, —$CH_2OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, =O, =NOH, =N—$OR^A$, =N—$NH_2$, =N—$NHR^A$, =N—N$(R^B)_2$, and —$NHSO_2R^A$, wherein $R^A$ is independently hydrogen, optionally substituted $C_1$-$C_6$ alkyl, optionally substituted alkenyl, optionally substituted alkynyl, optionally substituted heterocyclyl, optionally substituted aryl, or an oxygen protecting group when attached to an oxygen, or a sulfur protecting group when attaching to sulfur, wherein each instance of $R^B$ is independently hydrogen, optionally substituted $C_1$-$C_6$ alkyl, optionally substituted alkenyl, optionally substituted alkynyl, optionally substituted heterocyclyl, and optionally substituted aryl, or a nitrogen protecting group, or two $R^B$ taken together with the intervening nitrogen form a heterocycle. In certain embodiments, $G^{10}$ is fluoro.

In certain embodiments, the present disclosure is directed to a compound of 101:

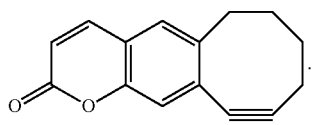

(101)

A new fluorescence-forming probe 101, designed by fusing cyclooctyne with a coumarin fluorophore is described herein for the real-time imaging of azido-containing glycoconjugates in living cells under no-wash and no-fixation as well as catalyst-free conditions. This probe is cell-permeable with low cytotoxicity and generating fluorescence after triazole formation, thus enabling intracellular imaging of glycoprotein localization and trafficking with good fluorescent signal. Moreover, combination of 101 and azido-BODIPY probes described herein allows detection of two different metabolically incorporated azido- and alkyne-containing glycoconjugates, respectively, upon triazole formations in live cells in a dual-labeling experiment.

The low fluorescence 7-alkynylcoumarin 102 has been shown to undergo a CuAAC reaction to give triazole 103 with enhanced fluorescence due to the electron-donating property of the triazole ring.[6c] Thus, incorporation of a cyclooctyne to the coumarin moiety 101 may decrease fluorescence, but the SPAAC reaction of 101 with azides can give highly fluorescent triazole products for sensitive detection. In this disclosure, we report a SPAAC-based fluorescence-forming probe 101, (FIG. 10), namely coumOCT, that can be used for time-course imaging of azido-tagged glycans in living cells under no-wash and no-fixation conditions.

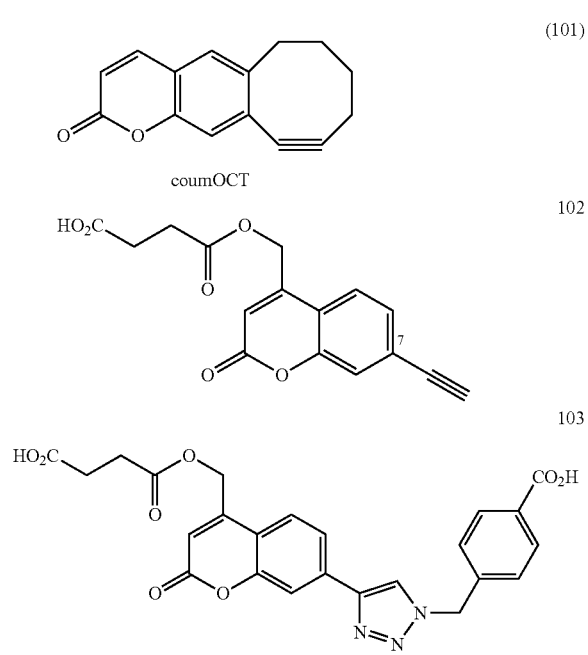

Figures 10A, 10B, 10C:
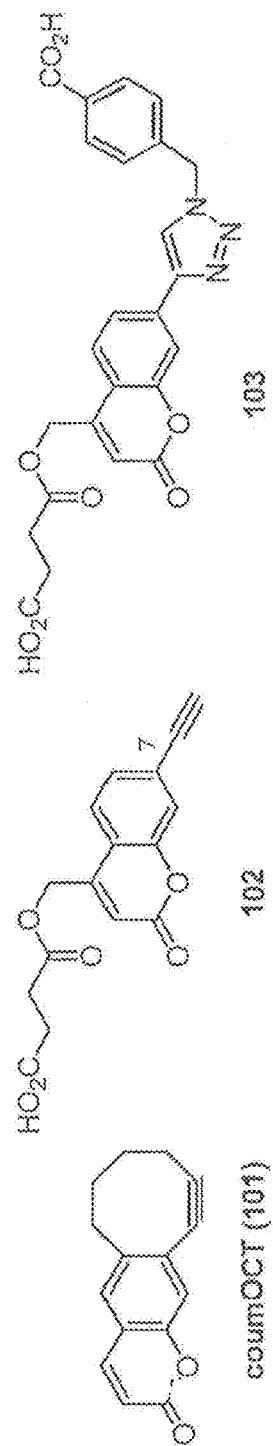
FIG. 10A, 10B, 10C shows a SPAAC-based fluoresence-forming probe, a comparative probe, and the triazole product of the comparative probe.

FIG. 10. Design of the SPAAC-based fluorescence-forming probe 101, showing high fluorescence upon triazole formation for imaging of azido-containing glycoconjugates in living cells. For comparison, 7-alkynylcoumarin 102 is a weakly fluorescent probe that undergoes a CuAAC reaction with azide to form a highly fluorescent triazole 103.

Activity-based Enzyme Probes

This disclosure describes a series of activity-based sialidase probes, DFSA (501), and CoumFSA (601) prepared from 3-fluorosialyl fluoride as the mechanism-based inhibitor and by incorporating an alkyne group for reporter ligation. DFSA (501) is an active-site inactivator of all tested sialidases. In this report, we have described the chemical synthesis of activity-based sialidase probes, CoumFSA (601), and DFSA (501).

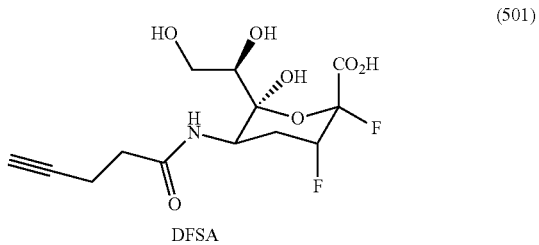

Figure 11B:
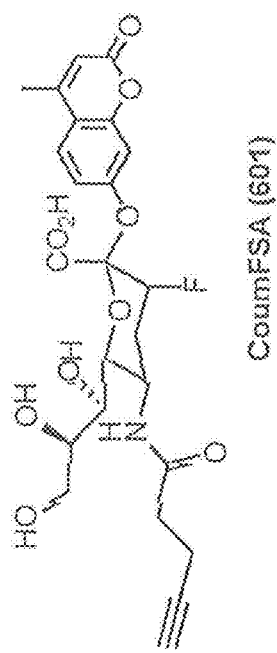
FIG. 11A, 11B shows structures of sialidase probes.
Figure 11A:
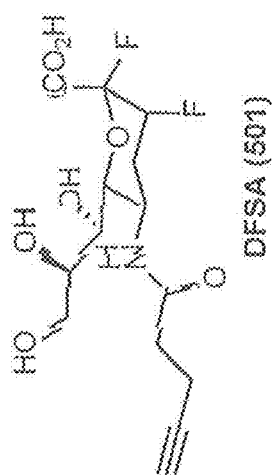

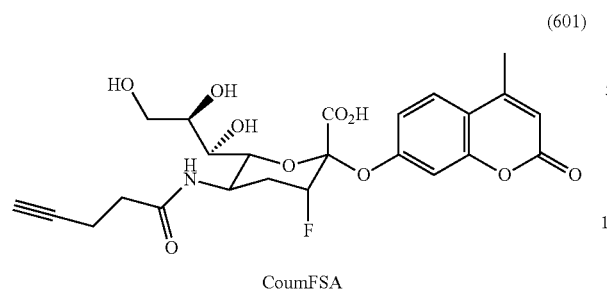
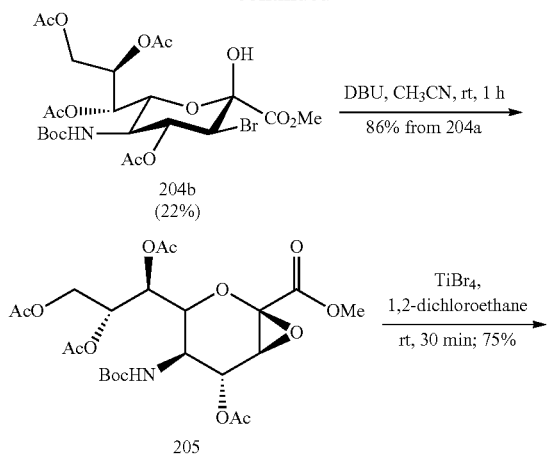
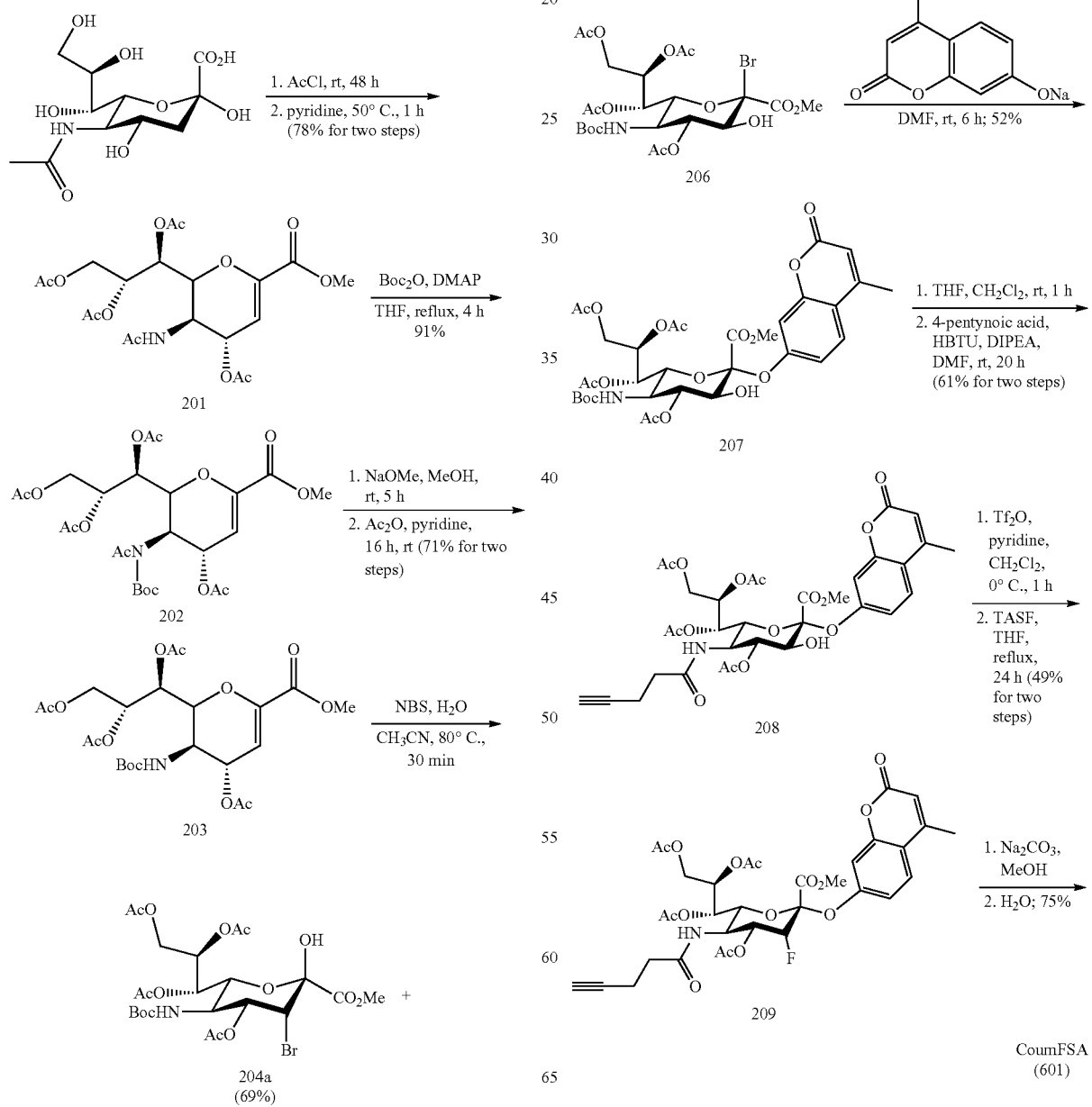
FIG. 11. Structures of sialidase probes DFSA 501 and CoumFSA 601.

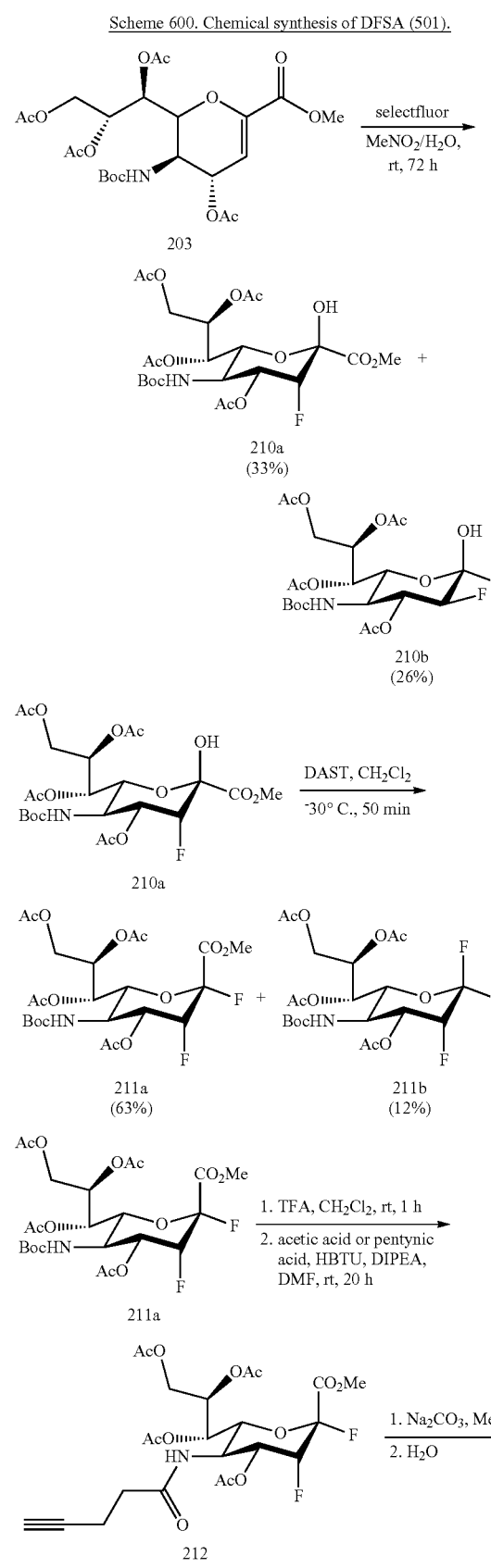

Scheme 600. Chemical synthesis of DFSA (501).

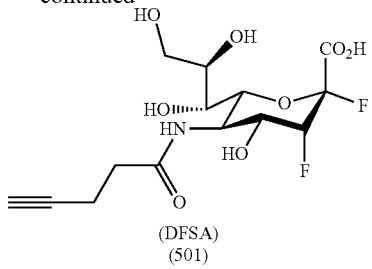

(DFSA)
(501)

In some embodiments, a series of activity-based enzyme probes can be synthesized by varying the leaving group L added to compound 206. As shown in Scheme 700, any selection of a salt (the sodium salt is as shown, but any cation counterion can be used) of a weak acid can be used as an acceptable leaving group. For example, L can be alkoxy, phenoxy, pentafluorophenoxy, 4-nitrophenoxy, coumarin, alkanoate, benzoate, triflate, mesylate, or tosylate.

Scheme 700. Chemical synthesis of variants of the variants of compound 209 by selection of leaving group salt $L^-Na^+$.

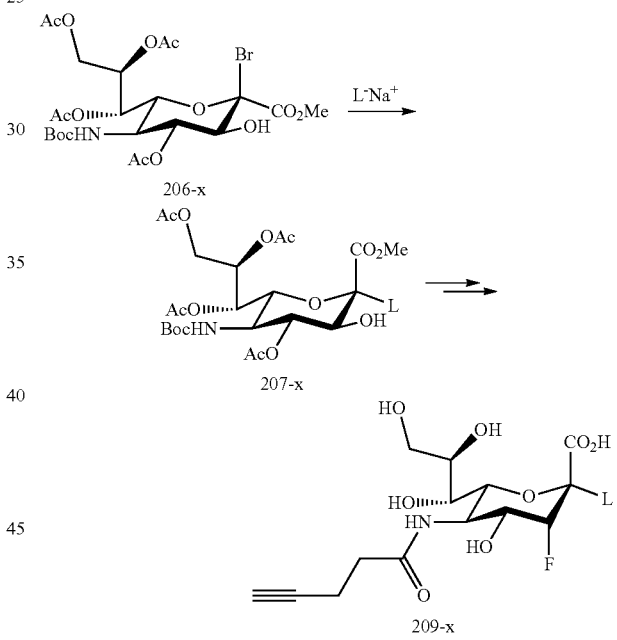

Figure 12:
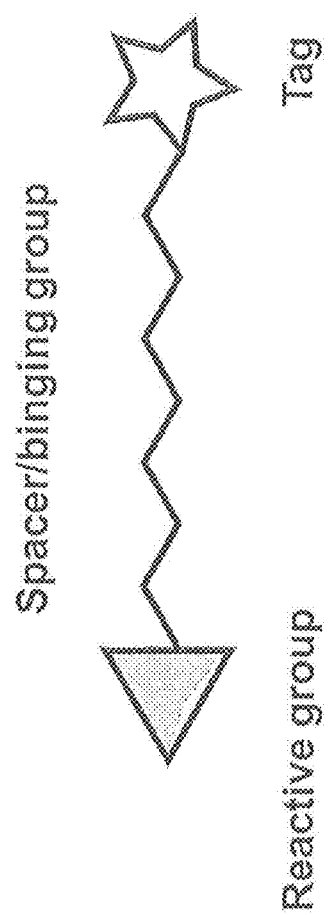
FIG. 12 shows the general structure of an activity-based probe.

FIG. 12 depicts a general structure of an activity-based enzyme probe (ABP). The ABP contains a reactive group, a spacer or binding group, and a reporter tag. The reactive group is designed based on the catalytic mechanism of the enzyme targets, and it can contain an electrophile that can react with a nucleophilic residue in the enzyme active site to form covalent adduct. A variety of reporter tags can be used for enzyme visualization and enrichment, including fluorophores and biotin, as well as "clickable" handles, such as azides and acetylenes.

This disclosure describes the design of an activity-based enzyme probe specifically for sialidases. 3-Fluorosialyl fluoride inactivates wild-type trans-sialidases in a time-dependent manner according to the kinetic model. Because of the strong electron-withdrawing group, the fluorine can destabilize the positively changed oxo-carbenium ion like transition state (FIG. 13), thereby slowing both the formation and hydrolysis of the covalent intermediate.

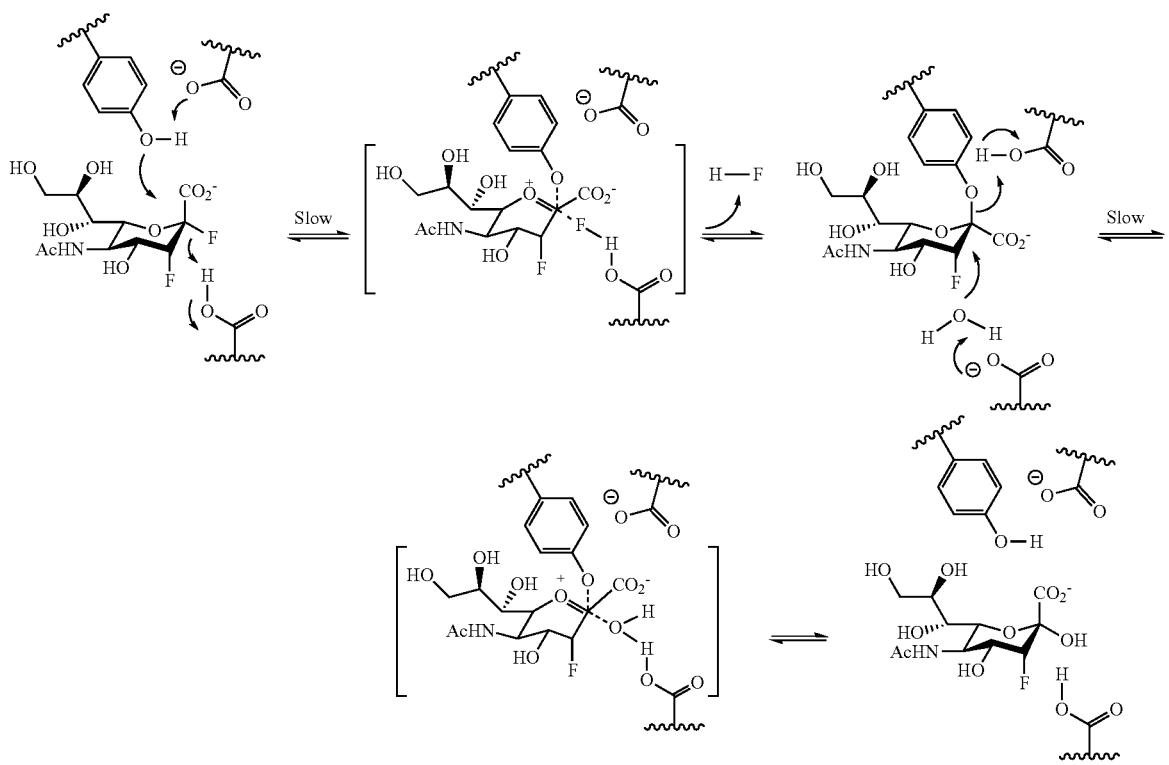

Figure 13:
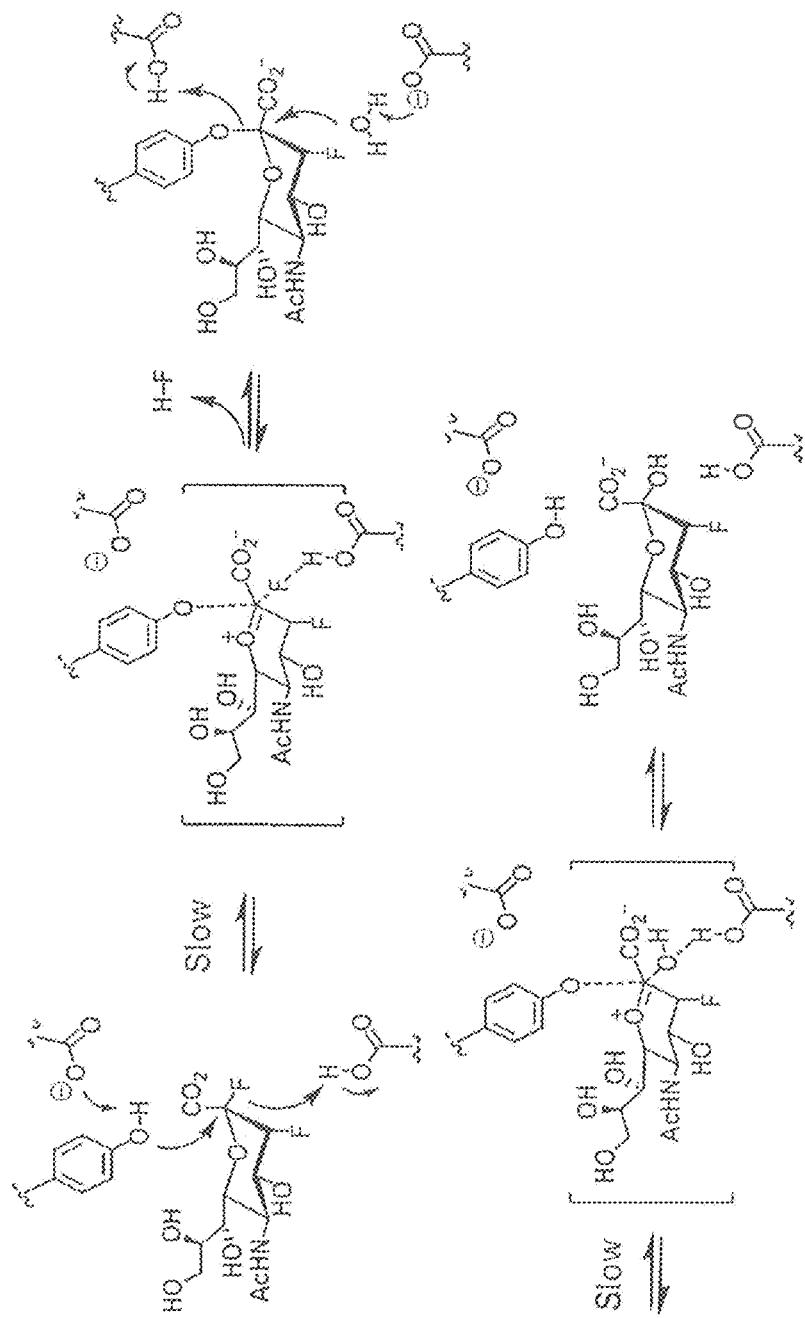
FIG. 13 shows the mechanism and transition state of sialidase enzymes.

FIG. 13. Mechanism and Transition State of Sialidase Enzymes acting on substrates.

Figure 14A:
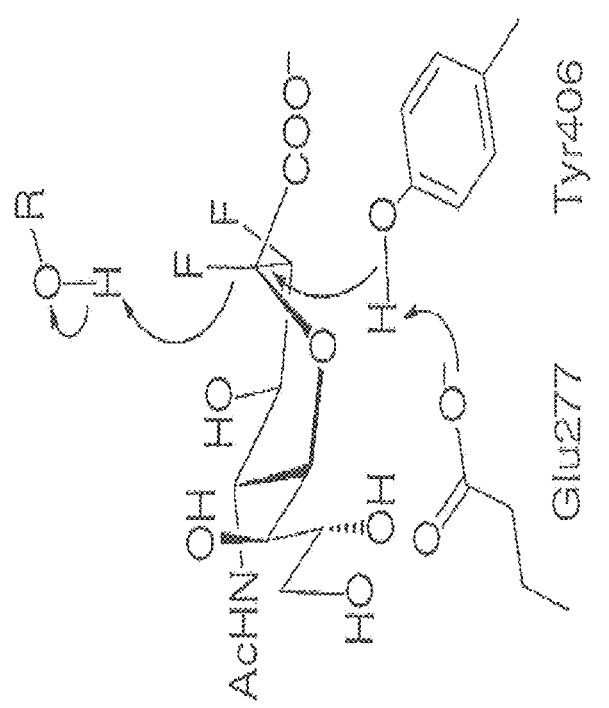
FIG. 14A, 14B shows the x-ray crystal structure of sialidase active site.
Figure 14B:
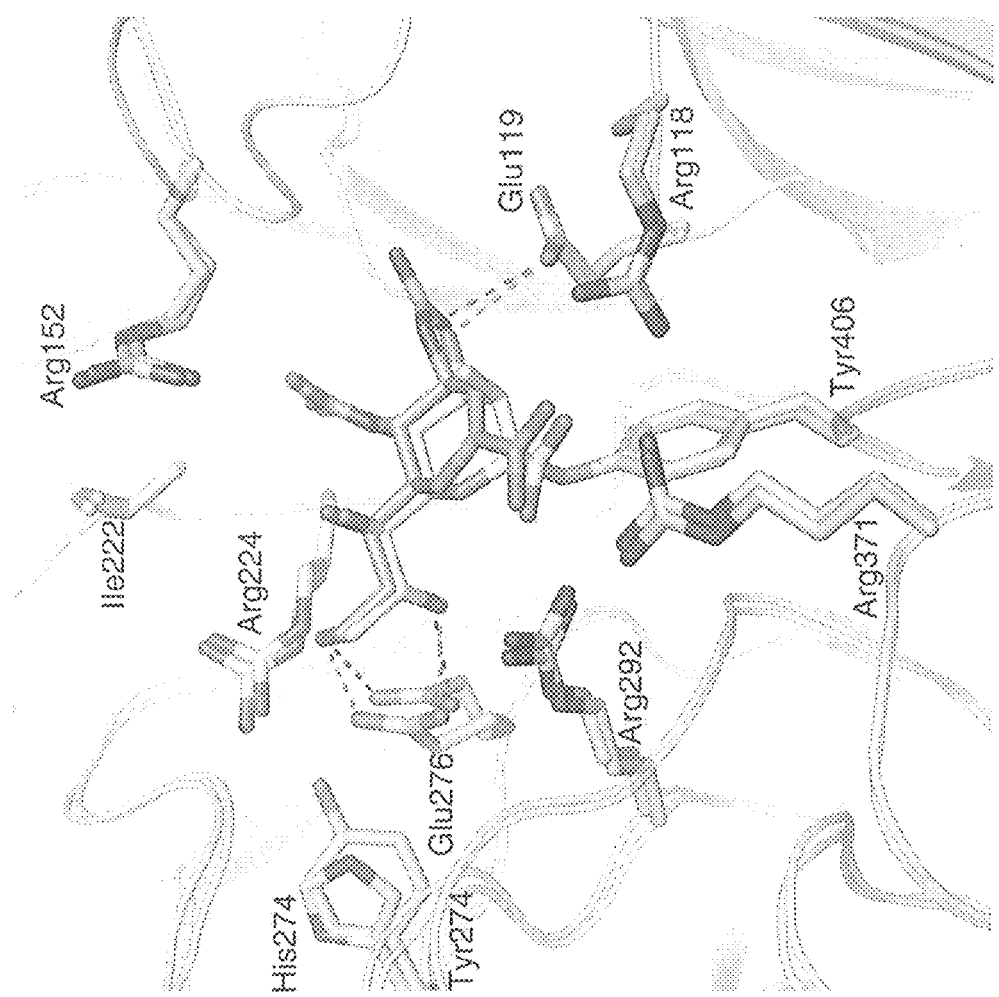

The inventors have recognized that the crystal structure of the sialidase enzyme supports a neuraminidase-covalent complex with 3-fluorosialyl fluoride which can be further modified to incorporate novel chemical functionality into the active site. As shown in FIG. 14, the Tyr406 in the neurminidase (sialidase) active site performs a nucleophilic attack on the C-2 on the 3-fluorosialyl fluoride substrate (*Nat. Commun.* 2013, 4, 1491). Accordingly, modification of the C-2 with leaving groups will yield a covalent bond between the Tyr406 and the 3-fluorosialyl fluoride substrate. Further modification of the 3-fluorosialyl fluoride substrate to include an alkyl functional group enables the covalently-bound substrate to be detected by azide-containing fluorogenic probes, such as those compounds described herein. FIG. 14. The crystal structure of the neurminidase (sialidase) active site with the 3-fluorosialyl fluoride substrate.

Figure 26:
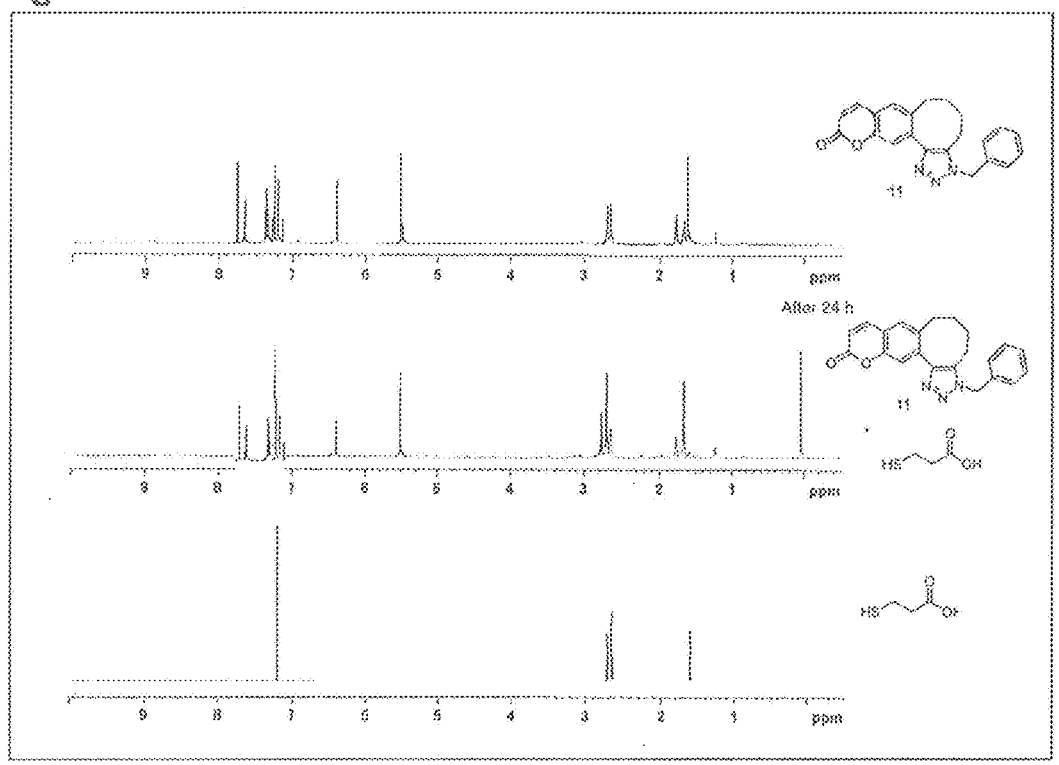
FIG. 26 shows $^1$H-NMR spectrum in $CDCl_3$ of compound 111 and 3-mercaptopropionic acid.

In some embodiments, the activity based probes (ABP) described herein can be used to detect and identify sialidase enzymes. As depicted in FIG. 26, the ABP can react with the active site of the sialidase forming a covalent bond. The cell can optionally be lysed. The ABP can be further reacted with an azide-containing reporter molecule (for example, the azide-containing fluorogenic probes described herein) to form a triazole complex. The triazole complex can then be detected (e.g. by mass-spectroscopy, fluorescence, luminescence, absorption spectroscopy).

Figure 15:
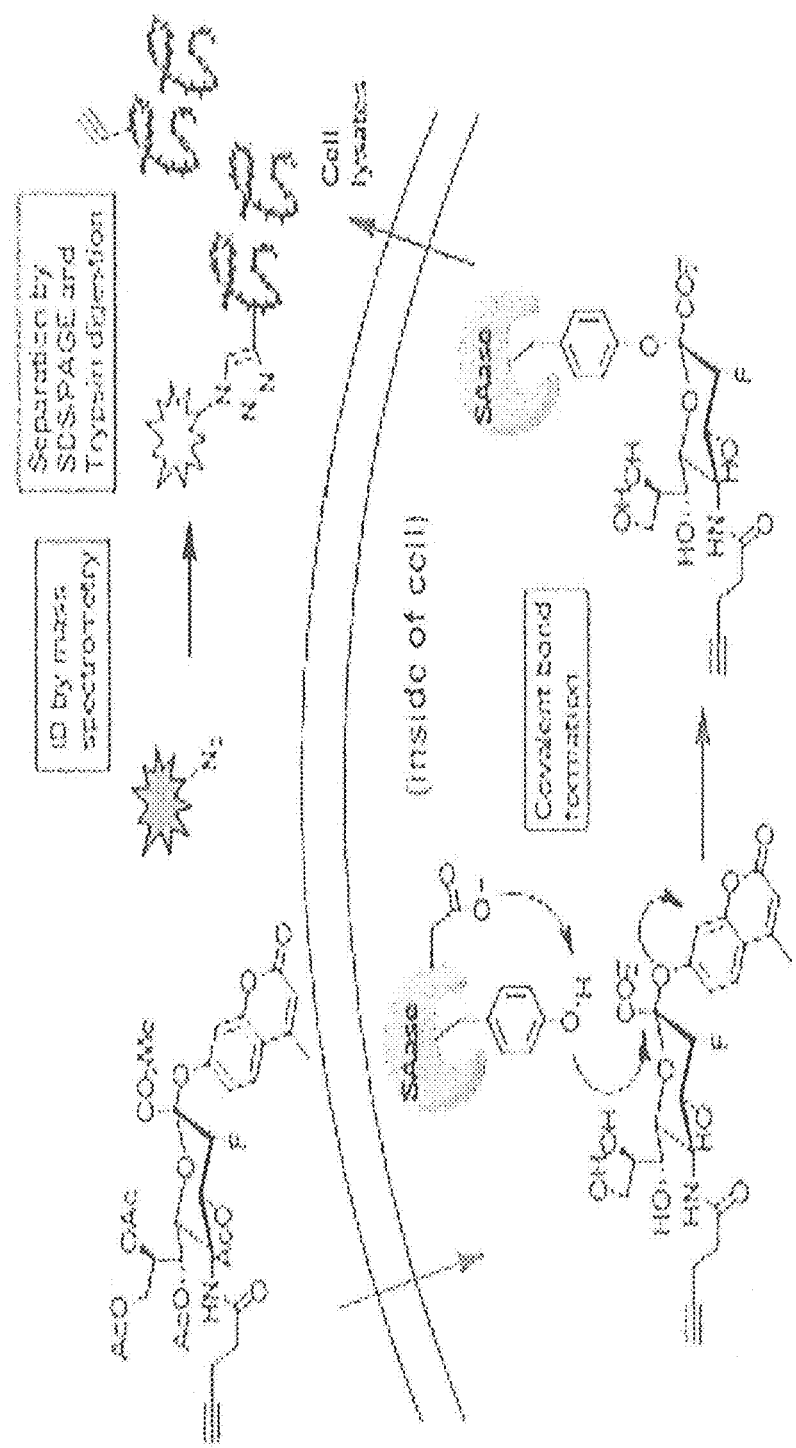
FIG. 15 shows fluorogenic reactions for the identification of sialidases.

FIG. 15. Fluorogenic reactions for identification of sialidases.

EXAMPLES

Example 1

Synthesis of Azido-BODIPY Compounds

Materials

All the reagents were commercially available and used without further purification unless indicated otherwise. All solvents were anhydrous grade unless indicated otherwise. All non-aqueous reactions were carried out in oven-dried glassware under a slightly positive pressure of argon unless otherwise noted. Reactions were magnetically stirred and monitored by thin-layer chromatography on silica gel. Column chromatography was performed on silica gel of 40-63 m particle size. Yields are reported for spectroscopically pure compounds.

Instruments

Melting points were recorded on an Electrothermal MEL-TEMP® 1101D melting point apparatus and were not corrected. NMR spectra were recorded on Bruker AVANCE 600 spectrometer (600 MHz). Chemical shifts are given in δ values relative to tetramethylsilane (TMS); coupling constants J are given in Hz. Internal standards were CDCl$_3$ ($\delta_H$=7.24) for $^1$H-NMR spectra, CDCl$_3$ ($\delta_c$=77.0) for $^{13}$C-NMR spectra. The splitting patterns are reported as s (singlet), d (doublet), t (triplet), q (quartet), m (multiplet), br (broad) and dd (double of doublets). High resolution ESI mass spectra were recorded on a Bruker Daltonics spectrometer. Absorbance spectra were recorded on a Perkin Elmer Lambda 35 UV-Visible spectrophotometer. Fluorescence spectra were recorded on an AMINCO-Bowman Series 2 luminescence spectrometer. All photos were collected on a Leica TCS-SP5 confocal laser-scanning microscope.

A convenient route for the synthesis of azido-BODIPY compounds Az1, Az2, Az3, Az4, Az5, Az6, Az7 and Az8 is disclosed herein. The preparation made use of the key nitro intermediates 1, 2, 3, 4, 5, 6, 7 and 8 which were effectively converted into the corresponding azido-BODIPY compounds. The structure of azido-BODIPY compounds Az1, Az2, Az3, Az4, Az5, Az6, Az7 and Az8 is shown in FIG. 1. Reagents and steps in the synthetic route are as follows.

Step 1. The acid-catalyzed condensation of 2,4-dimethyl-3-ethylpyrrole with substituted nitrobenzaldehydes, followed by oxidation with DDQ in mild conditions, gave dipyrromethene intermediates, which were treated with $BF_3 \cdot OEt_2$ to yield the corresponding nitro-BODIPYs 1-8.

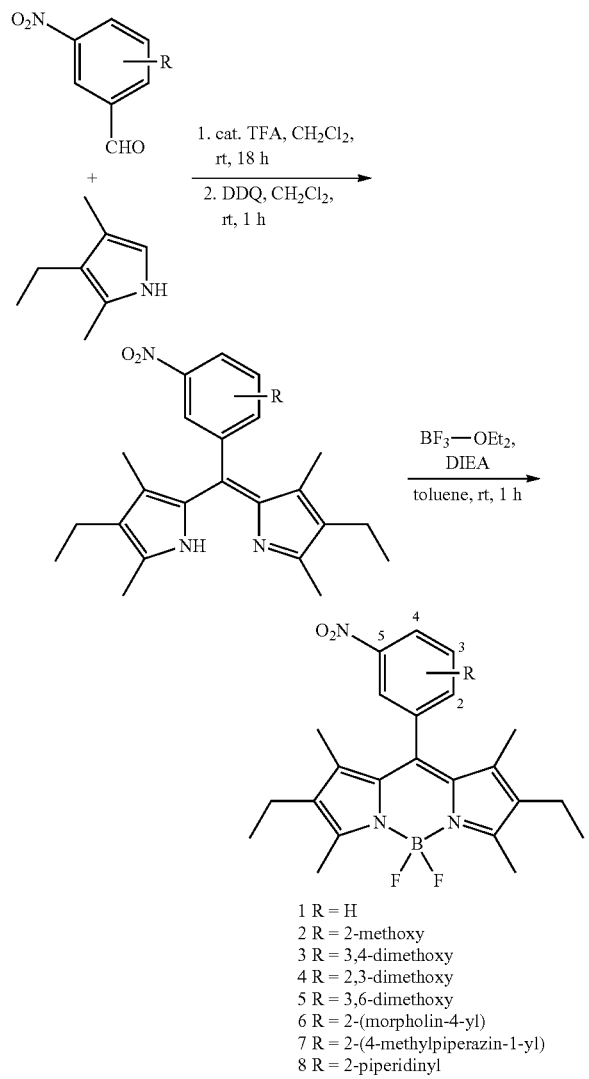

1 R = H
2 R = 2-methoxy
3 R = 3,4-dimethoxy
4 R = 2,3-dimethoxy
5 R = 3,6-dimethoxy
6 R = 2-(morpholin-4-yl)
7 R = 2-(4-methylpiperazin-1-yl)
8 R = 2-piperidinyl Step 2. According to the previously reported method, the amino-BODIPYs Am1-Am8 were obtained in reasonable yields by reduction of the nitro-BODIPYs with hydrazine in the presence of 10% Pd/C. On treatment with triflyl azide ($TfN_3$) in mild conditions, the amino-BODIPYs were converted to the target azido-BODIPYs Az1-Az8. (Li, L.; Han, J.; Nguyen, B.; Burgess, K. *J. Org. Chem.* 2008, 73, 1963-1970.)

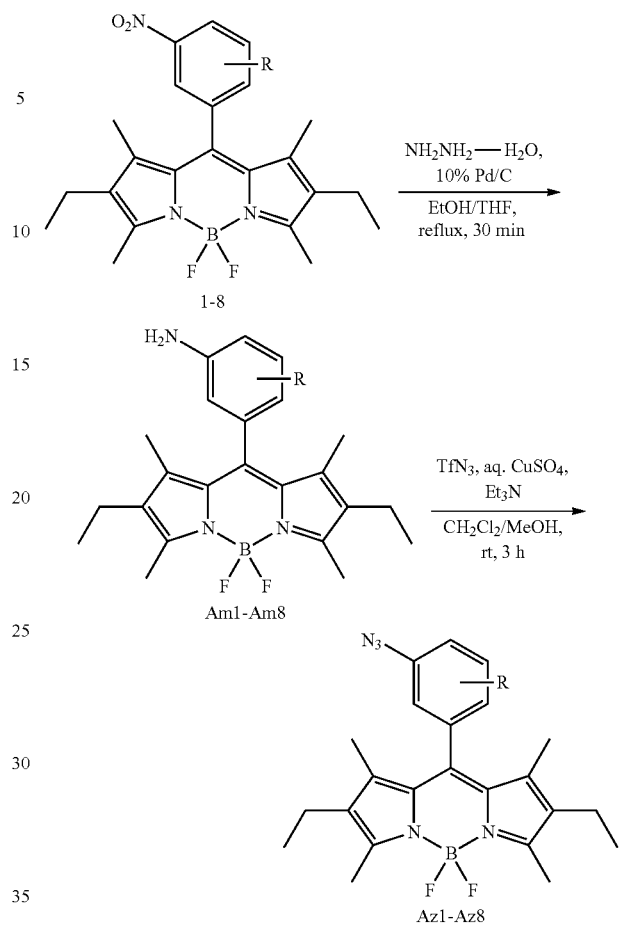

Figure 3C:
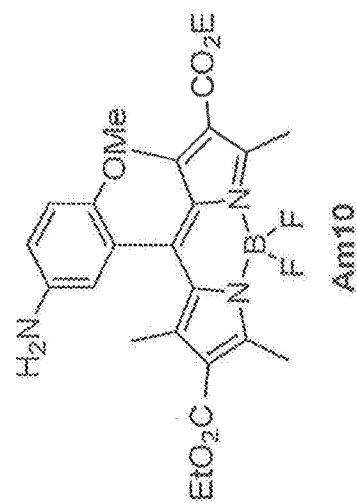
FIG. 3A, 3B, 3C shows the structures of amino-BODIPY Am10 (FIG. 3C)
Figure 3B:
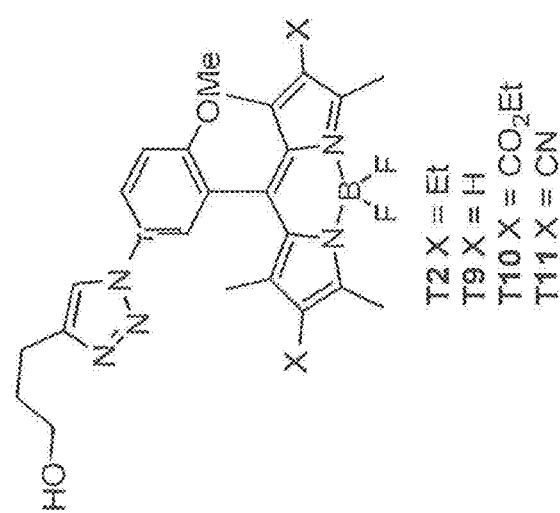
Figure 3A:
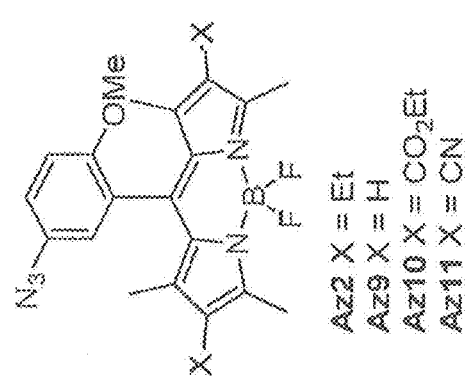
Figure 4:
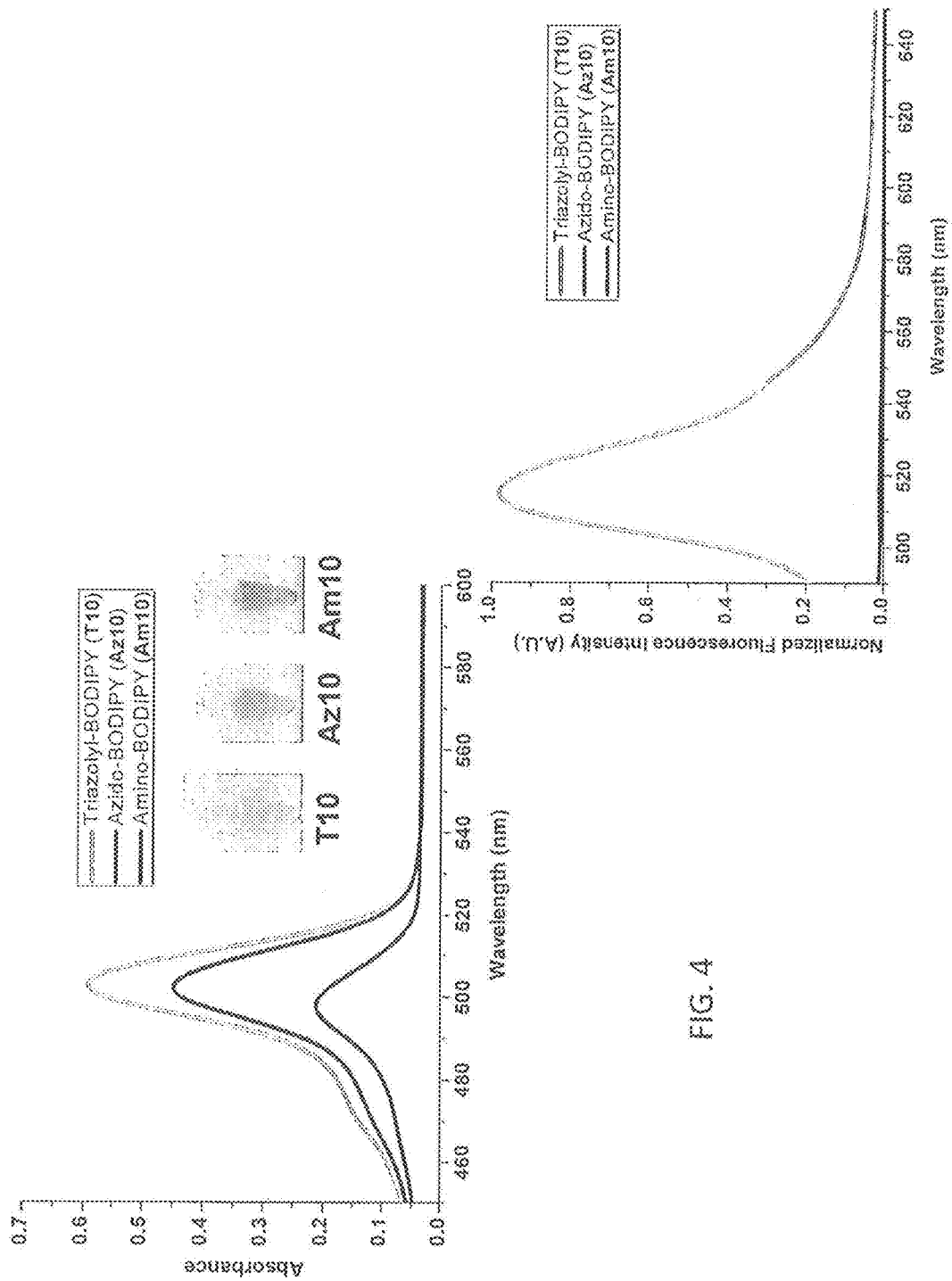
FIG. 4 shows the absorption and normalized emission spectra of triazolyl-BODIPY T10, azido-BODIPY Az10 and amino-BODIPY Am10 in ethanol solution (12 μM) at 25° C. Inset: the images of T10, Az10 and Am10 in ethanol solution (120 μM). The change of yellow Az10 solution to green T10 solution was apparent.

A convenient route for the synthesis of azido-BODIPY compounds Az9, Az10 and Az11 is disclosed herein. The preparation made use of the key nitro intermediates 9, 10 and 11 which were effectively converted into the corresponding azido-BODIPY compounds. The structure of azido-BODIPY compounds Az9, Az10 and Az11 is shown in FIG. 3. Reagents and steps in the synthetic route are as follows.

Step 1. The acid-catalyzed condensation of 2,4-dimethyl-3-substituted pyrroles with 2-methoxy-5-nitrobenzaldehyde, followed by oxidation with DDQ in mild conditions, gave dipyrromethene intermediates, which were treated with $BF_3 \cdot OEt_2$ to yield the corresponding nitro-BODIPYs 9-11.

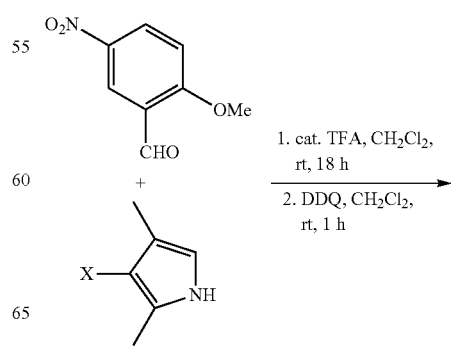

-continued

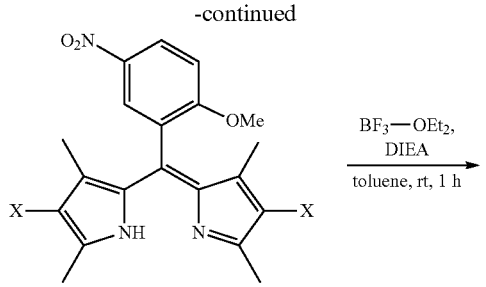

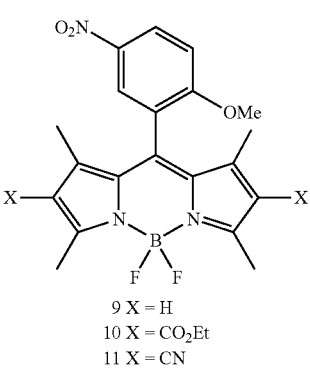

9 X = H
10 X = CO₂Et
11 X = CN

Step 2. According to the previously reported method, the amino-BODIPYs Am9-Am11 were obtained in reasonable yields by reduction of the nitro-BODIPYs with hydrazine in the presence of 10% Pd/C. On treatment with triflyl azide (TfN₃) in mild conditions, the amino-BODIPYs were converted to the target azido-BODIPYs Az9-Az11. (Li, L.; Han, J.; Nguyen, B.; Burgess, K. *J. Org. Chem.* 2008, 73, 1963-1970.)

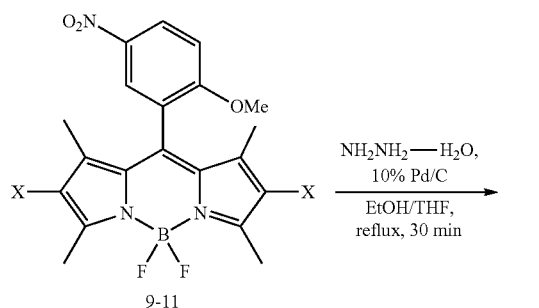

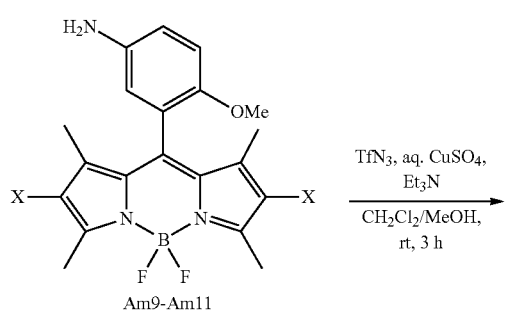

Am9-Am11

-continued

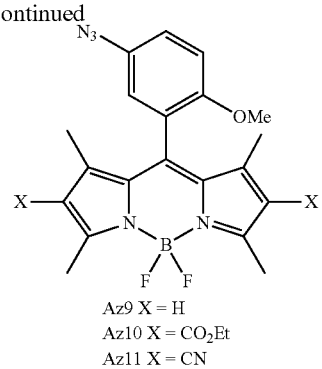

Az9 X = H
Az10 X = CO₂Et
Az11 X = CN

Example 2

Synthesis of Triazolyl-BODIPY Compounds

A convenient route for the synthesis of triazolyl-BODIPY compounds T2, T9, T10 and T11 is disclosed herein. The structure of triazolyl-BODIPY compounds T2, T9, T10 and T11 is shown in FIG. 3. Reagents and step in the synthetic route is as follows.

The triazolyl-BODIPY compounds T2, T9, T10 and T11 were obtained in reasonable yields by 1,3-dipolar cycloaddition of the azido-BODIPY compounds Az2, Az9, Az10 and Az11 with 4-pentyn-1-ol in CuAAC conditions containing CuSO₄, sodium ascorbate and a tris-triazole ligand prepared from tripropargylamine and ethyl azidoacetate. (Zhou, Z.; Fahrni, C. J. *J. Am. Chem. Soc.* 2004, 126, 8862-8863).

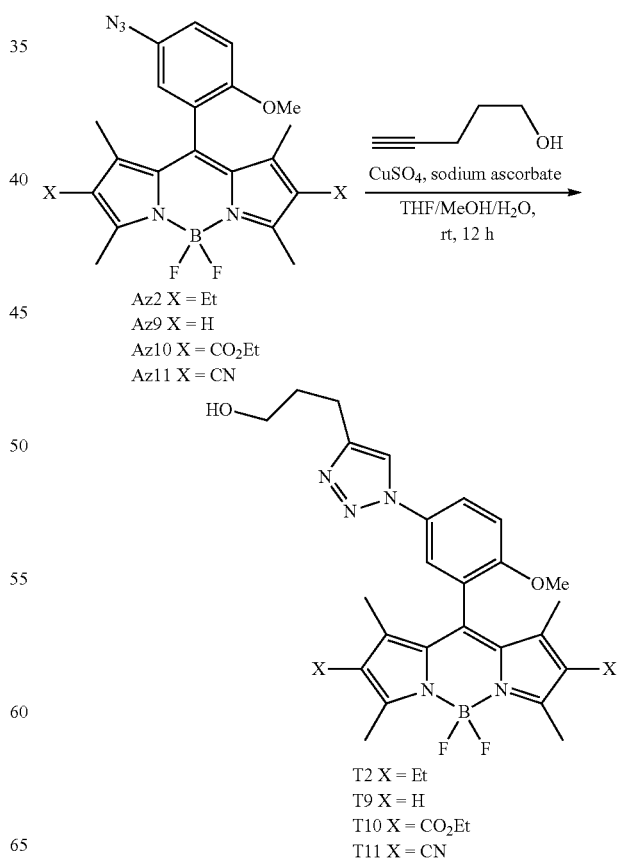

General Synthetic Procedures and Product Characterization of Nitro-BODIPYs.

Substituted nitrobenzaldehyde (3 mmol) and 3-substituted 2,4-dimethylpyrrole (6 mmol) were dissolved in anhydrous $CH_2Cl_2$ (400 mL) under an Ar atmosphere. TFA (1 drop) was added, and the resulting solution was stirred at room temperature overnight. After complete consumption of the reactants in 12-18 h as shown by TLC analysis, 2,3-dichloro-5,6-dicyano-1,4-benzoquinone (DDQ, 3 mmol) was added in one portion. The reaction mixture was stirred at room temperature for 1 h, and then washed with brine (400 mL). The organic fraction was dried over $MgSO_4$, filtered, and concentrated. The crude compound was purified on a short alumina oxide column ($CH_2Cl_2$) to afford brown solids of dipyrromethene. The crude dipyrromethene product and N,N-diisopropylethylamine (DIEA) (40 mmol) were dissolved in anhydrous toluene (150 mL) and stirred at room temperature for 10 min. $BF_3.OEt_2$ (55 mmol) was added slowly, and stirring was continued for 1 h. The reaction mixture was washed with water (3×50 mL) and brine (50 mL), dried over $MgSO_4$, filtered, and concentrated. The crude product was purified by column chromatography on silica gel by elution with $CH_2Cl_2$/hexane or EtOAc/hexane to afford the corresponding nitro-BODIPY product 1-11.

2,6-Diethyl-4,4-difluoro-8-(3-nitrophenyl)-1,3,5,7-tetramethyl-4-bora-3a,4a-diaza-s-indacene (1)

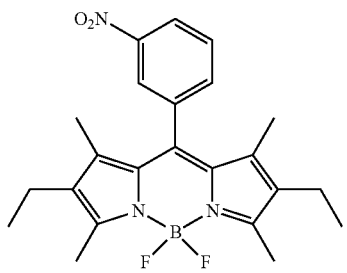

Compound 1 was prepared from 2,4-dimethyl-3-ethylpyrrole and 3-nitrobenzaldehyde in 15% yield for three steps. $C_{23}H_{26}BF_2N_3O_2$, dark red solids, mp 246-248° C.; TLC (EtOAc/hexane, 1:4) $R_f$=0.38; $^1$H NMR (600 MHz, $CDCl_3$) δ 8.36-8.34 (1 H, m), 8.20 (1 H, t, J=1.7 Hz), 7.70-7.64 (2 H, m), 2.52 (6 H, s), 2.28 (4 H, q, J=7.6 Hz), 1.23 (6 H, s), 0.96 (6 H, t, J=7.6 Hz); $^{13}$C NMR (150 MHz, $CDCl_3$) δ 155.0, 148.6, 137.6, 136.3, 134.8, 133.5, 130.4, 130.2, 123.89, 123.85, 17.0, 14.5, 12.6, 12.1; HRMS calcd for $C_{23}H_{27}BF_2N_3O_2$: 426.2164, found: m/z 426.2167 [M+H]$^+$.

2,6-Diethyl-4,4-difluoro-8-(2-methoxy-5-nitrophenyl)-1,3,5,7-tetramethyl-4-bora-3a,4a-diaza-s-indacene (2)

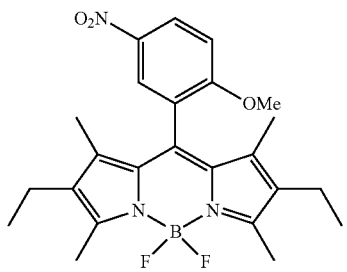

Compound 2 was prepared from 2,4-dimethyl-3-ethylpyrrole and 2-methoxy-5-nitrobenzaldehyde in 51% yield for three steps. $C_{24}H_{28}BF_2N_3O_3$, dark red solids, mp 210-212° C.; TLC (EtOAc/hexane, 1:4) $R_f$=0.33; $^1$H NMR (600 MHz, $CDCl_3$) δ 8.42 (1 H, dd, J=9.1, 2.5 Hz), 8.15 (1 H, d, J=2.5 Hz), 7.11 (1 H, d, J=9.1 Hz), 3.93 (3 H, s), 2.56 (6 H, s), 2.32 (4 H, q, J=7.6 Hz), 1.36 (6 H, s), 1.02 (6 H, t, J=7.6 Hz); $^{13}$C NMR (150 MHz, $CDCl_3$) δ 162.0, 154.4, 141.8, 137.1, 133.5, 133.0, 130.4, 126.8, 126.1, 125.6, 110.9, 56.6, 17.0, 14.6, 12.6, 11.5; HRMS calcd for $C_{24}H_{29}BF_2N_3O_3$: 456.2270, found: m/z 456.2267 [M+H]$^+$.

2,6-Diethyl-4,4-difluoro-8-(3,4-dimethoxy-5-nitrophenyl)-1,3,5,7-tetramethyl-4-bora-3a,4a-diaza-s-indacene (3)

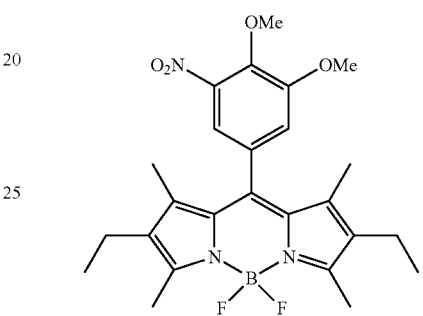

Compound 3 was prepared from 2,4-dimethyl-3-ethylpyrrole and 3,4-dimethoxy-5-nitrobenzaldehyde in 45% yield for three steps. $C_{25}H_{30}BF_2N_3O_4$, dark red solids, mp 190-192° C.; TLC (EtOAc/hexane, 1:3) $R_f$=0.5; $^1$H NMR (600 MHz, $CDCl_3$) δ 7.28 (1 H, s), 7.02 (1 H, s), 4.04 (3 H, s), 3.89 (3 H, s), 2.51 (6 H, s), 2.30 (4 H, q, J=7.5 Hz), 1.38 (6 H, s), 0.98 (6 H, t, J=7.5 Hz); $^{13}$C NMR (150 MHz, $CDCl_3$) δ 154.9, 145.3, 143.2, 137.7, 136.4, 133.4, 131.4, 130.4, 116.16, 116.12, 62.5, 56.8, 17.0, 14.5, 12.6, 12.0; HRMS calcd for $C_{25}H_{31}BF_2N_3O_4$: 486.2376, found: m/z 486.2377 [M+H]$^+$.

2,6-Diethyl-4,4-difluoro-8-(2,3-dimethoxy-5-nitrophenyl)-1,3,5,7-tetramethyl-4-bora-3a,4a-diaza-s-indacene (4)

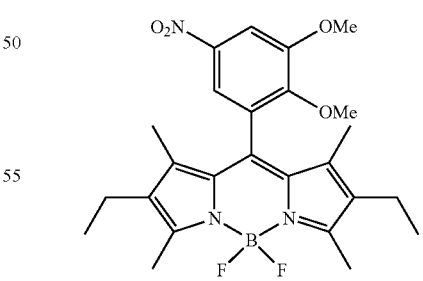

Compound 4 was prepared from 2,4-dimethyl-3-ethylpyrrole and 2,3-dimethoxy-5-nitrobenzaldehyde in 41% yield for three steps. $C_{25}H_{30}BF_2N_3O_4$, dark red solids, mp 185-187° C.; TLC (EtOAc/hexane, 1:4) $R_f$=0.35; $^1$H NMR (600 MHz, $CDCl_3$) δ 7.88 (1 H, d, J=2.3 Hz), 7.76 (1 H, d, J=2.3 Hz), 4.00 (3 H, s), 3.83 (3 H, s), 2.51 (6 H, s), 2.29 (4 H, q, J=7.6 Hz), 1.38 (6 H, s), 0.97 (6 H, t, J=7.6 Hz); $^{13}$C NMR (150 MHz, CDCl₃) δ 154.5, 152.8, 151.8, 143.8, 137.1, 133.4, 133.2, 130.3, 129.5, 117.8, 108.1, 60.8, 56.4, 17.0, 14.6, 12.6, 11.6; HRMS calcd for $C_{25}H_{31}BF_2N_3O_4$: 486.2376, found: m/z 486.2378 [M+H]⁺.

2,6-Diethyl-4,4-difluoro-8-(2,5-dimethoxy-3-nitrophenyl)-1,3,5,7-tetramethyl-4-bora-3a,4a-diaza-s-indacene (5)

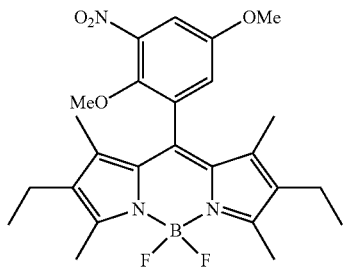

Compound 5 was prepared from 2,4-dimethyl-3-ethylpyrrole and 2,5-dimethoxy-3-nitrobenzaldehyde in 36% yield for three steps. $C_{25}H_{30}BF_2N_3O_4$, dark red solids, mp 181-183° C.; TLC (CH₂Cl₂/hexane, 3:7) R$_f$=0.5; ¹H NMR (600 MHz, CDCl₃) δ 7.41 (1 H, d, J=3.1 Hz), 6.98 (1 H, d, J=3.1 Hz), 3.83 (3 H, s), 3.71 (3 H, s), 2.52 (6 H, s), 2.30 (4 H, q, J=7.6 Hz), 1.44 (6 H, s), 0.98 (6 H, t, J=7.6 Hz); ¹³C NMR (150 MHz, CDCl₃) δ 155.6, 154.8, 145.0, 144.3, 137.3, 133.4, 133.2, 132.9, 130.3, 120.7, 110.4, 62.2, 56.2, 17.1, 14.6, 12.6, 11.7; HRMS calcd for $C_{25}H_{31}BF_2N_3O_4$: 486.2376, found: m/z 486.2378 [M+H]⁺.

2,6-Diethyl-4,4-difluoro-8-(2-morpholino-5-nitrophenyl)-1,3,5,7-tetramethyl-4-bora-3a,4a-diaza-s-indacene (6)

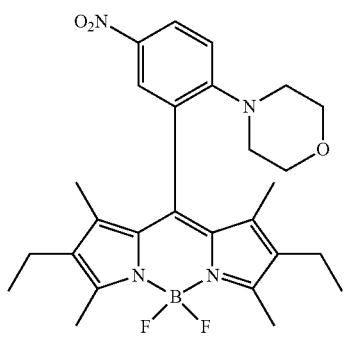

Compound 6 was prepared from 2,4-dimethyl-3-ethylpyrrole and 2-morpholino-5-nitrobenzaldehyde in 38% yield for three steps. $C_{27}H_{33}BF_2N_4O_3$, dark red solids, mp 179-181° C.; TLC (EtOAc/hexane, 3:7) R$_f$=0.25; ¹H NMR (600 MHz, CDCl₃) δ 8.24 (1 H, dd, J=9.1, 2.6 Hz), 8.02 (1 H, d, J=2.6 Hz), 6.96 (1 H, d, J=9.1 Hz), 3.84 (4 H, t, J=4.3 Hz), 3.24 (4 H, t, J=4.3 Hz), 2.52 (6 H, s), 2.31 (4 H, q, J=7.6 Hz), 1.42 (6 H, s), 0.99 (6 H, t, J=7.6 Hz); ¹³C NMR (150 MHz, CDCl₃) δ 155.1, 154.9, 141.1, 137.1, 136.0, 133.5, 129.8, 127.4, 126.2, 126.1, 117.4, 66.6, 50.4, 17.1, 14.6, 12.6, 12.1; HRMS calcd for $C_{27}H_{34}BF_2N_4O_3$: 511.2692, found: m/z 511.2695 [M+H]⁺.

2,6-Diethyl-4,4-difluoro-8-[2-(4-methylpiperazino)-5-nitrophenyl]-1,3,5,7-tetramethyl-4-bora-3a,4a-diaza-s-indacene (7)

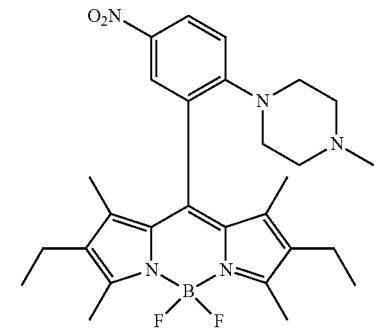

Compound 7 was prepared from 2,4-dimethyl-3-ethylpyrrole and 2-(4-methylpiperazino)-5-nitrobenzaldehyde in 48% yield for three steps. $C_{28}H_{36}BF_2N_5O_2$, dark red solids, mp 175-177° C.; TLC (EtOAc/hexane, 3:7) R$_f$=0.25; ¹H NMR (600 MHz, CDCl₃) δ 8.21 (1 H, dd, J=9.2, 2.8 Hz), 8.00 (1 H, d, J=2.8 Hz), 6.93 (1 H, d, J=9.2 Hz), 3.29 (4 H, t, J=4.7 Hz), 2.52 (6 H, s), 2.32 (4 H, q, J=7.6 Hz), 2.19 (4 H, t, J=4.7 Hz), 2.15 (3 H, s), 1.42 (6H, s), 0.99 (6 H, t, J=7.6 Hz); ¹³C NMR (150 MHz, CDCl₃) δ 155.1, 154.6, 140.6, 137.2, 136.4, 133.4, 129.9, 127.4, 126.1, 125.5, 117.5, 54.7, 49.8, 45.9, 17.1, 14.7, 12.6, 12.1; HRMS calcd for $C_{28}H_{37}BF_2N_5O_2$: 524.3008, found: m/z 524.3010 [M+H]⁺.

2,6-Diethyl-4,4-difluoro-8-(2-piperidino-5-nitrophenyl)-1,3,5,7-tetramethyl-4-bora-3a,4a-diaza-s-indacene (8)

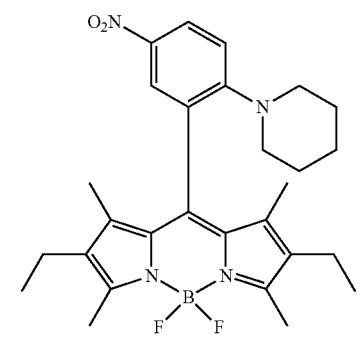

Compound 8 was prepared from 2,4-dimethyl-3-ethylpyrrole and 2-piperidino-5-nitrobenzaldehyde in 40% yield for three steps. $C_{28}H_{35}BF_2N_4O_2$, dark red solids, mp 201-203° C.; TLC (EtOAc/hexane, 1:9) R$_f$=0.38; ¹H NMR (600 MHz, CDCl₃) δ 8.19 (1 H, dd, J=9.2, 2.8 Hz), 7.97 (1 H, d, J=2.8 Hz), 6.91 (1 H, d, J=9.2 Hz), 3.23 (4 H, t, J=5.3 Hz), 2.52 (6 H, s), 2.30 (4 H, q, J=7.6 Hz), 1.48-1.44 (2 H, m), 1.43 (6 H, s), 1.37-1.34 (4 H, m), 0.98 (6 H, t, J=7.6 Hz); ¹³C NMR (150 MHz, CDCl₃) δ 156.0, 154.3, 139.9, 137.2, 137.0, 133.2, 130.0, 127.5, 126.1, 125.1, 117.3, 51.3, 25.8, 23.9, 17.1, 14.6, 12.6, 12.1; HRMS calcd for $C_{28}H_{36}BF_2N_4O_2$: 509.2899, found: m/z 509.2901 [M+H]⁺.

4,4-Difluoro-8-(2-methoxy-5-nitrophenyl)-1,3,5,7-tetramethyl-4-bora-3a,4a-diaza-s-indacene (9)

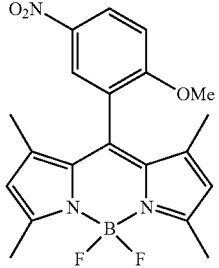

Compound 9 was prepared from 2,4-dimethylpyrrole and 2-methoxy-5-nitrobenzaldehyde in 39% yield for three steps. $C_{20}H_{20}BF_2N_3O_3$, dark red solids, mp 178-180° C.; TLC (EtOAc/hexane, 1:4) $R_f$=0.31; $^1$H NMR (600 MHz, CDCl$_3$) δ 8.42 (1 H, dd, J=9.1, 2.7 Hz), 8.17 (1H, d, J=2.7 Hz), 7.12 (1 H, d, J=9.1 Hz), 6.02 (2 H, s), 3.93 (3 H, s), 2.59 (6 H, s), 1.46 (6 H, s); $^{13}$C NMR (150 MHz, CDCl$_3$) δ 161.7, 156.1, 141.9, 135.0, 131.1, 126.9, 126.0, 124.8, 121.5, 118.9, 111.0, 56.7, 14.6, 14.2; HRMS calcd for $C_{20}H_{21}BF_2N_3O_3$: 400.1644, found: m/z 400.1640 [M+H]$^+$.

2,6-Diethoxycarbonyl-4,4-difluoro-8-(2-methoxy-5-nitrophenyl)-1,3,5,7-tetramethyl-4-bora-3a,4a-diaza-s-indacene (10)

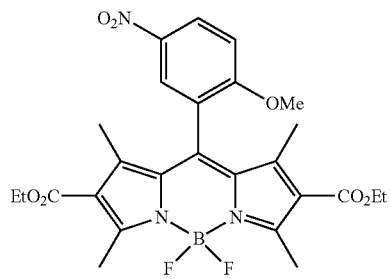

Compound 10 was prepared from 2,4-dimethy-4-ethoxycarbonylpyrrole and 2-methoxy-5-nitrobenzaldehyde in 60% yield for three steps. $C_{26}H_{28}BF_2N_3O_7$, orange-red solids, mp 181-183° C.; TLC (CH$_2$Cl$_2$/hexane, 7:3) $R_f$=0.18; $^1$H NMR (600 MHz, CDCl$_3$) δ 8.43 (1 H, dd, J=9.2, 2.8 Hz), 8.09 (1 H, d, J=2.8 Hz), 7.11 (1 H, d, J=9.2 Hz), 4.26 (4 H, q, J=7.1 Hz), 3.89 (3 H, s), 2.82 (6 H, s), 1.71 (6 H, s), 1.31 (6 H, t, J=7.1 Hz); $^{13}$C NMR (150 MHz, CDCl$_3$) δ 164.0, 161.4, 160.0, 146.4, 142.2, 139.2, 131.1, 127.6, 125.5, 124.3, 122.7, 111.3, 60.3, 56.8, 15.1, 14.2, 13.2; HRMS calcd for $C_{26}H_{29}BF_2N_3O_7$: 544.2067, found: m/z 544.2061 [M+H]$^+$.

2,6-Dicyano-4,4-difluoro-8-(2-methoxy-5-nitrophenyl)-1,3,5,7-tetramethyl-4-bora-3a,4a-diaza-s-indacene (11)

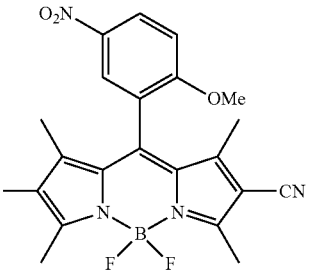

Compound 11 was prepared from 3-cyano-2,4-dimethylpyrrole$^{S7}$ and 2-methoxy-5-nitrobenzaldehyde in 13% Yield for three steps. $C_{22}H_{18}BF_2N_5O_3$, red solids, mp 278-280° C.; TLC (CH$_2$Cl$_2$/hexane, 7:3) $R_f$=0.18; $^1$H NMR (600 MHz, CDCl$_3$) δ 8.49 (1 H, dd, J=9.1, 2.6 Hz), 8.10 (1 H, d, J=2.6 Hz), 7.19 (1 H, d, J=9.1 Hz), 3.93 (3 H, s), 2.72 (6 H, s), 1.63 (6 H, s); $^{13}$C NMR (150 MHz, CDCl$_3$) δ 160.9, 160.2, 148.2, 142.2, 140.6, 131.2, 128.3, 125.1, 122.2, 113.2, 111.8, 106.8, 57.1, 13.9, 13.7; HRMS calcd for $C_{22}H_{19}BF_2N_5O_3$: 450.1549, found: m/z 450.1546 [M+H]$^+$.

General Synthetic Procedures and Product Characterization of Azido-BODIPYs (Az1-Az11).

A solution of nitro-BODIPY 1-11 (0.5 mmol) in a mixed solvent of EtOH (20 mL) and THF (20 mL) was purged with Ar for 10 min. Hydrazine monohydrate (0.3 mL) and 10% Pd/C (60 mg. 0.1 equiv) were added. The reaction mixture was heated to reflux for 30 min, and then Pd/C was removed by vacuum filtration. After evaporation of the solvent, the residue was purified by column chromatography on silica gel to afford red solids of amino-BODIPY. The crude product of amino-BODIPY Am1-Am11 was dissolved in CH$_2$Cl$_2$ (20 mL) in a 50 mL round-bottomed flask. Triethylamine (Et$_3$N, 1.5 mmol) and a solution of CuSO$_4$ (25 μmol in 0.1 mL of water) were added to the flask. A solution of freshly prepared triflyl azide (TfN$_3$) (1.5 mmol in 3 mL of CH$_2$Cl$_2$) was then added, and the mixture was brought to homogeneity by adding methanol (0.5 mL). After stirring for 3 h at room temperature, the mixture was poured into saturated aqueous NaHCO$_3$ (10 mL) and extracted with CH$_2$Cl$_2$ (3×10 mL). The combined organic extracts were dried over MgSO$_4$, filtered, and concentrated. The residue was purified by column chromatography on silica gel by elution with CH$_2$Cl$_2$/hexane, EtOAc/hexane or MeOH/CH$_2$Cl$_2$ to afford the corresponding azido-BODIPY product Az1-Az11.

8-(5-Amino-2-methoxyphenyl)-2,6-diethoxycarbonyl-4,4-difluoro-1,3,5,7-tetramethyl-4-bora-3a,4a-diaza-s-indacene (Am10)

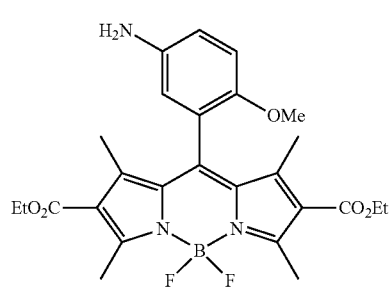

Compound Am10 was prepared from compound 10 in 83% yield. $C_{26}H_{30}BF_2N_3O_5$, dark red solids, mp 188-190° C.; TLC (EtOAc/hexane, 3:7) $R_f$=0.23; $^1$H NMR (600 MHz, CDCl$_3$) δ 6.82-6.77 (2 H, m), 6.45 (1 H, d, J=2.5 Hz), 4.25 (4 H, q, J=7.1 Hz), 3.66 (3 H, s), 3.52 (2 H, br s), 2.79 (6 H, s), 1.82 (6 H, s), 1.30 (6 H, t, J=7.1 Hz); $^{13}$C NMR (150 MHz, CDCl$_3$) δ 164.4, 158.9, 148.8, 147.3, 143.4, 141.4, 131.5, 123.7, 122.0, 117.4, 115.6, 112.8, 60.1, 56.0, 14.9, 14.3, 12.9; HRMS calcd for $C_{26}H_{31}BF_2N_3O_5$: 514.2325, found: m/z 514.2327 [M+H]$^+$.

8-(3-Azidophenyl)-2,6-diethyl-4,4-difluoro-1,3,5,7-tetramethyl-4-bora-3a,4a-diaza-s-indacene (Az1)

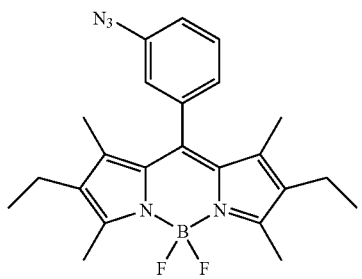

Compound Az1 was prepared from compound 1 in 47% yield for two steps. $C_{23}H_{26}BF_2N_5$, dark red solids, mp 151-153° C. (dec.); TLC (EtOAc/hexane, 1:9) $R_f$=0.38; $^1$H NMR (600 MHz, CDCl$_3$) δ 8.01 (1 H, d, J=7.9 Hz), 7.85 (1 H, s), 7.75 (1 H, t, J=7.7 Hz), 7.65 (1 H, d, J=7.1 Hz), 2.52 (6 H, s), 2.27 (4 H, q, J=7.4 Hz), 1.22 (6 H, s), 0.95 (6 H, t, J=7.4 Hz); $^{13}$C NMR (150 MHz, CDCl$_3$) δ 165.0, 154.7, 137.7, 137.4, 137.1, 135.3, 133.3, 130.5, 130.2, 121.2, 121.0, 17.0, 14.5, 12.6, 12.1; HRMS calcd for $C_{23}H_{27}BF_2N_5$: 422.2328, found: m/z 422.2330 [M+H]$^+$.

8-(5-Azido-2-methoxyphenyl)-2,6-diethyl-4,4-difluoro-1,3,5,7-tetramethyl-4-bora-3a,4a-diaza-s-indacene (Az2)

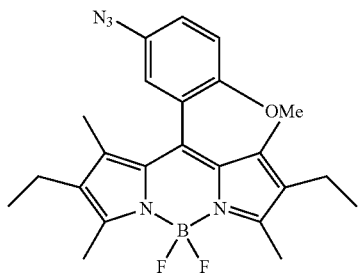

Compound Az2 was prepared from compound 2 in 59% yield for two steps. $C_{24}H_{28}BF_2N_5O$, dark red solids, mp 163-165° C. (dec.); TLC (EtOAc/hexane, 1:4) $R_f$=0.52; $^1$H NMR (600 MHz, CDCl$_3$) δ 7.08 (1 H, d, J=8.7 Hz), 6.95 (1 H, d, J=8.7 Hz), 6.84 (1 H, s), 3.74 (3 H, s), 2.50 (6 H, s), 2.28 (4 H, q, J=7.4 Hz), 1.36 (6 H, s), 0.97 (6 H, t, J=7.4 Hz); $^{13}$C NMR (150 MHz, CDCl$_3$) δ 154.1, 153.7, 137.6, 135.5, 133.4, 132.6, 130.6, 126.2, 120.5, 112.4, 56.0, 17.1, 14.6, 12.5, 11.2; HRMS calcd for $C_{24}H_{29}BF_2N_5O$: 452.2433, found: m/z 452.2429 [M+H]$^+$.

8-(3-Azido-4, 5-dimethoxyphenyl)-2,6-diethyl-4,4-difluoro-1,3,5,7-tetramethyl-4-bora-3a,4a-diaza-s-indacene (Az3)

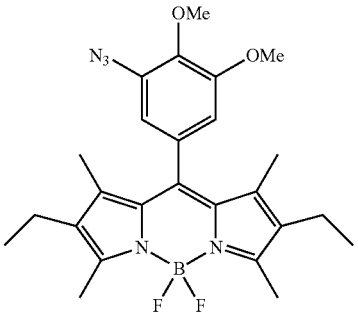

Compound Az3 was prepared from compound 3 in 51% yield for two steps. $C_{25}H_{30}BF_2N_5O_2$, orange-red solids, mp 156-158° C. (dec.); TLC (EtOAc/hexane, 1:4) $R_f$=0.41; $^1$H NMR (600 MHz, CDCl$_3$) δ 7.09 (1 H, d, J=1.4 Hz), 5.85 (1 H, d, J=1.4 Hz), 4.64 (3 H, s), 3.95 (3 H, s), 2.49 (6 H, s), 2.26 (4 H, q, J=7.5 Hz), 1.26 (6 H, s), 0.94 (6 H, t, J=7.5 Hz); $^{13}$C NMR (150 MHz, CDCl$_3$) δ 160.4, 155.2, 154.56, 154.53, 137.6, 137.3, 133.1, 130.4, 128.4, 118.2, 100.6, 65.6, 56.9, 17.0, 14.5, 12.5, 12.0; HRMS calcd for $C_{25}H_{31}BF_2N_5O_2$: 482.2539, found: m/z 482.2542 [M+H]$^+$.

8-(5-Azido-2, 3-dimethoxyphenyl)-2,6-diethyl-4,4-difluoro-1,3,5,7-tetramethyl-4-bora-3a,4a-diaza-s-indacene (Az4)

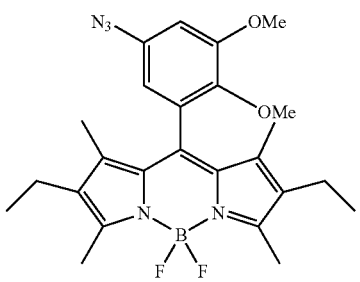

Compound Az4 was prepared from compound 4 in 54% yield for two steps. $C_{25}H_{30}BF_2N_5O_2$, dark red solids, mp 158-160° C. (dec.); TLC (EtOAc/hexane, 1:4) $R_f$=0.48; $^1$H NMR (600 MHz, CDCl$_3$) δ 8.18 (1 H, s), 6.82 (1 H, s), 3.94 (3 H, s), 3.88 (3 H, s), 2.54 (6 H, s), 2.29 (4 H, q, J=7.6 Hz), 1.43 (6 H, s), 0.97 (6 H, t, J=7.6 Hz); $^{13}$C NMR (150 MHz, CDCl$_3$) δ 163.1, 154.4, 153.1, 152.9, 137.3, 134.1, 133.2, 130.6, 129.3, 125.1, 97.6, 60.8, 56.1, 17.1, 14.6, 12.6, 11.7; HRMS calcd for $C_{25}H_{31}BF_2N_5O_2$: 482.2539, found: m/z 482.2541 [M+H]$^+$.

8-(3-Azido-2, 5-dimethoxyphenyl)-2,6-diethyl-4,4-difluoro-1,3,5,7-tetramethyl-4-bora-3a,4a-diaza-s-indacene (Az5)

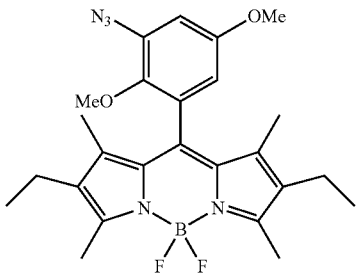

Compound Az5 was prepared from compound 5 in 54% yield for two steps. $C_{25}H_{30}BF_2N_5O_2$, dark red solids, mp 150-152° C. (dec.); TLC ($CH_2Cl_2$/hexane, 1:4) $R_f$=0.45; $^1$H NMR (600 MHz, CDCl$_3$) δ 7.16 (1 H, d, J=3.2 Hz), 5.81 (1 H, d, J=3.2 Hz), 4.42 (3 H, s), 3.72 (3 H, s), 2.55 (6 H, s), 2.32 (4 H, q, J=7.6 Hz), 1.52 (6 H, s), 0.99 (6 H, t, J=7.6 Hz); $^{13}$C NMR (150 MHz, CDCl$_3$) δ 160.0, 156.7, 154.7, 154.4, 137.3, 134.1, 133.1, 133.0, 130.6, 126.0, 90.7, 66.1, 55.8, 17.1, 14.6, 12.6, 11.8; HRMS calcd for $C_{25}H_{31}BF_2N_5O_2$: 482.2539, found: m/z 482.2543 [M+H]$^+$.

8-(5-Azido-2-morpholinophenyl)-2,6-diethyl-4,4-difluoro-1,3,5,7-tetramethyl-4-bora-3a,4a-diaza-s-indacene (Az6)

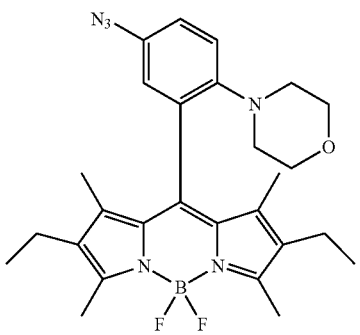

Compound Az6 was prepared from compound 6 in 62% yield for two steps. $C_{27}H_{33}BF_2N_6O$, dark red oil; TLC (EtOAc/hexane, 1:4) $R_f$=0.4; $^1$H NMR (600 MHz, CDCl$_3$) δ 7.06 (1 H, dd, J=8.7, 2.7 Hz), 7.01 (1 H, d, J=8.7 Hz), 6.81 (1 H, d, J=2.7 Hz), 3.48 (4 H, t, J=4.4 Hz), 2.94 (4 H, t, J=4.4 Hz), 2.51 (6 H, s), 2.30 (4 H, q, J=7.6 Hz), 1.39 (6 H, s), 0.97 (6 H, t, J=7.6 Hz); $^{13}$C NMR (150 MHz, CDCl$_3$) δ 153.8, 147.3, 137.4, 134.9, 132.9, 131.0, 130.2, 121.1, 120.6, 120.5, 67.1, 51.6, 17.1, 14.6, 12.6, 11.7; HRMS calcd for $C_{27}H_{34}BF_2N_6O$: 507.2855, found: m/z 507.2858 [M+H]$^+$.

8-[5-Azido-2-(4-methylpiperazino)phenyl]-2,6-diethyl-4,4-difluoro-1,3,5,7-tetramethyl-4-bora-3a,4a-diaza-s-indacene (Az7)

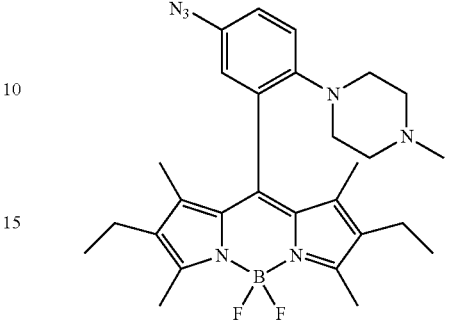

Compound Az7 was prepared from compound 7 in 72% yield for two steps. $C_{28}H_{36}BF_2N_7$, dark red foam; TLC (MeOH/CH$_2$Cl$_2$, 1:19) $R_f$=0.33; $^1$H NMR (600 MHz, CDCl$_3$) δ 7.06-7.01 (2 H, m), 6.80 (1 H, s), 2.99 (4 H, br s), 2.51 (6 H, s), 2.32-2.26 (8 H, m), 2.18 (3 H, s), 1.38 (6 H, s), 0.97 (6 H, t, J=7.4 Hz); $^{13}$C NMR (150 MHz, CDCl$_3$) δ 153.8, 146.8, 137.4, 135.3, 133.0, 131.2, 130.2, 121.4, 121.0, 120.5, 54.7, 50.1, 45.0, 17.1, 14.7, 12.6, 11.7; HRMS calcd for $C_{28}H_{37}BF_2N_7$: 520.3172, found: m/z 520.3177 [M+H]$^+$.

8-(5-Azido-2-piperidinophenyl)-2,6-diethyl-4,4-difluoro-1,3,5,7-tetramethyl-4-bora-3a,4a-diaza-s-indacene (Az8)

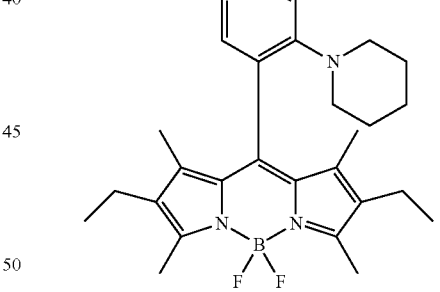

Compound Az8 was prepared from compound 8 in 69% yield for two steps. $C_{28}H_{35}BF_2N_6$, dark red oil; TLC (EtOAc/hexane, 1:4) $R_f$=0.67; $^1$H NMR (600 MHz, CDCl$_3$) δ 7.07 (1 H, dd, J=8.7, 2.6 Hz), 7.03 (1 H, d, J=8.7 Hz), 6.82 (1 H, d, J=2.6 Hz), 2.94 (4 H, t, J=5.2 Hz), 2.56 (6 H, s), 2.34 (4 H, q, J=7.6 Hz), 1.44 (6 H, s), 1.43-1.38 (6 H, m), 1.02 (6 H, t, J=7.6 Hz); $^{13}$C NMR (150 MHz, CDCl$_3$) δ 153.3, 148.9, 138.2, 137.5, 133.8, 132.6, 130.7, 130.4, 121.0, 120.8, 120.3, 52.6, 26.2, 24.1, 17.1, 14.6, 12.5, 11.7; HRMS calcd for $C_{28}H_{36}BF_2N_6$: 505.3063, found: m/z 505.3066 [M+H]$^+$.

8-(5-Azido-2-methoxyphenyl)-4,4-difluoro-1,3,5,7-tetramethyl-4-bora-3a,4a-diaza-s-indacene (Az9)

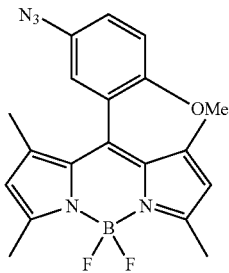

Compound Az9 was prepared from compound 9 in 71% yield for two steps. $C_{20}H_{20}BF_2N_5O$, dark red solids, mp 152-154° C. (dec.); TLC (EtOAc/hexane, 1:4) $R_f$=0.51; $^1$H NMR (600 MHz, CDCl$_3$) δ 7.08 (1 H, d, J=8.7 Hz), 6.96 (1 H, d, J=8.7 Hz), 6.84 (1 H, s), 5.95 (2 H, s), 3.74 (3 H, s), 2.53 (6 H, s), 1.46 (6 H, s); $^{13}$C NMR (150 MHz, CDCl$_3$) δ 155.4, 153.8, 142.3, 137.1, 133.5, 131.2, 125.3, 121.1, 120.7, 120.3, 112.5, 56.0, 14.6, 13.9; HRMS calcd for $C_{20}H_{21}BF_2N_5O$: 396.1807, found: m/z 396.1805 [M+H]$^+$.

8-(5-Azido-2-methoxyphenyl)-2,6-diethoxycarbonyl-4,4-difluoro-1,3,5,7-tetramethyl-4-bora-3a,4a-diaza-s-indacene (Az10)

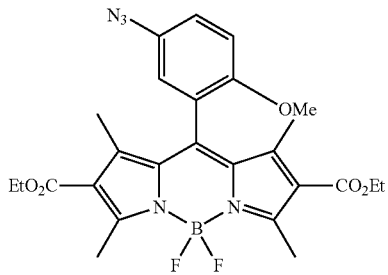

Compound Az10 was prepared from compound Am10 in 58% yield. $C_{26}H_{28}BF_2N_5O_5$, red solids, mp 86-88° C.; TLC (EtOAc/hexane, 3:7) $R_f$=0.41; $^1$H NMR (600 MHz, CDCl$_3$) δ 7.14 (1 H, dd, J=8.8, 2.8 Hz), 6.99 (1 H, d, J=8.8 Hz), 6.79 (1 H, d, J=2.8 Hz), 4.26 (4 H, q, J=7.1 Hz), 3.75 (3 H, s), 2.80 (6 H, s), 1.76 (6 H, s), 1.31 (6 H, t, J=7.1 Hz); $^{13}$C NMR (150 MHz, CDCl$_3$) δ 164.3, 159.4, 153.5, 146.9, 141.4, 134.2, 131.3, 124.7, 122.3, 121.4, 119.8, 112.7, 60.2, 56.1, 15.0, 14.3, 13.0; HRMS calcd for $C_{26}H_{29}BF_2N_5O_5$: 540.2230, found: m/z 540.2227 [M+H]$^+$.

8-(5-Azido-2-methoxyphenyl)-2,6-dicyano-4,4-difluoro-1,3,5,7-tetramethyl-4-bora-3a,4a-diaza-s-indacene (Az11)

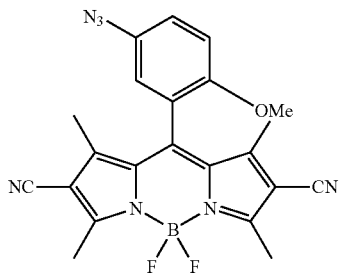

Compound Az11 was prepared from compound 11 in 61% yield for two steps. $C_{22}H_{18}BF_2N_7O$, red solids, mp 141-143° C. (dec.); TLC (CH$_2$Cl$_2$/hexane, 7:3) $R_f$=0.31; $^1$H NMR (600 MHz, CDCl$_3$) δ 7.21 (1 H, dd, J=8.9, 2.3 Hz), 7.06 (1 H, d, J=8.9 Hz), 6.77 (1 H, d, J=2.3 Hz), 3.77 (3 H, s), 2.70 (6 H, s), 1.67 (6 H, s); $^{13}$C NMR (150 MHz, CDCl$_3$) δ 158.6, 151.9, 147.7, 141.8, 133.6, 130.4, 121.6, 121.2, 118.2, 112.5, 112.1, 105.4, 55.3, 12.9, 12.4; HRMS calcd for $C_{22}H_{19}BF_2N_7O$: 446.1712, found: m/z 446.1714 [M+H]$^+$.

Procedure for Copper(I)-Catalyzed Azide-Alkyne Cycloaddition Reaction of Azido-BODIPY with 4-Pentyn-1-ol Azido-BODIPY (Az2 or Az9-Az11, 0.1 mmol) and 4-pentyn-1-ol (0.1 mmol) were dissolved in THF (5 mL). A freshly prepared 1 M solution of sodium ascorbate (0.2 mmol in 0.2 mL of water) was added, followed by addition of copper (II) pentahydrate (0.005 mmol in 0.1 mL of water). The mixture was brought to homogeneity by adding methanol (0.5 mL), and then stirred for 12 h at room temperature. TLC monitoring showed complete consumption of the reactants in 12 h. After evaporation of the solvents, the residue was purified by column chromatography on silica gel by elution with EtOAc/hexane to afford the corresponding triazole product T2 and T9-T11.

2,6-Diethyl-4,4-difluoro-8-{3-[4-(3-hydroxypropyl)-1H-1,2,3-triazol-1-yl]-2-methoxyphenyl}-1,3,5,7-tetramethyl-4-bora-3a,4a-diaza-s-indacene (T2)

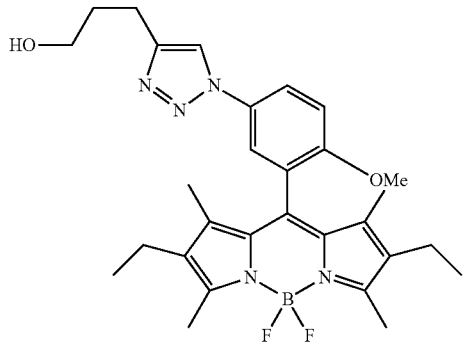

Compound T2 was prepared from compound Az2 in 71% yield. $C_{29}H_{36}BF_2N_5O_2$, red solids, mp 180-182° C.; TLC (EtOAc/hexane, 1:1) $R_f$=0.15; $^1$H NMR (600 MHz, CDCl$_3$) δ 7.89 (1 H, dd, J=8.9, 2.7 Hz), 7.66 (1 H, s), 7.46 (1 H, d, J=2.7 Hz), 7.10 (1 H, J=8.9 Hz), 3.83 (3 H, s), 3.73 (2 H, t, J=6.1 Hz), 2.88 (2 H, t, J=7.3 Hz), 2.51 (6 H, s), 2.28 (4 H, q, J=7.5 Hz), 1.98-1.96 (2 H, m), 1.38 (6 H, s), 0.97 (6 H, t, J=7.5 Hz); $^{13}$C NMR (150 MHz, CDCl$_3$) δ 156.8, 154.0, 148.3, 137.5, 134.7, 132.8, 131.3, 130.5, 125.9, 122.6, 121.9, 119.1, 112.0, 61.8, 56.1, 31.8, 22.0, 17.0, 14.6, 12.5, 11.4; HRMS calcd for $C_{29}H_{37}BF_2N_5O_2$: 536.3008, found: m/z 536.3005 [M+H]$^+$.

4,4-Difluoro-8-{3-[4-(3-hydroxypropyl)-1H-1,2,3-triazol-1-yl]-2-methoxyphenyl}-1,3,5,7-tetramethyl-4-bora-3a,4a-diaza-s-indacene (T9)

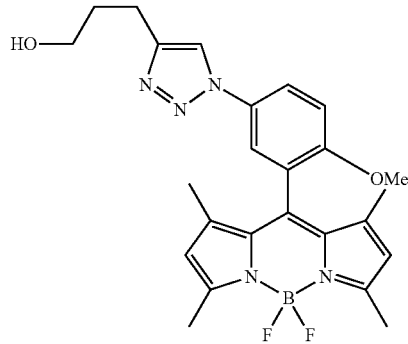

Compound T9 was prepared from compound Az9 in 79% yield. $C_{25}H_{28}BF_2N_5O_2$, red solids, mp 165-167° C.; TLC (EtOAc/hexane, 7:3) $R_f$=0.23; $^1H$ NMR (600 MHz, CDCl$_3$) δ 7.88 (1 H, d, J=8.8 Hz), 7.66 (1 H, s), 7.49 (1 H, s), 7.11 (1 H, d, J=8.8 Hz), 5.97 (2 H, s), 3.83 (3 H, s), 3.73 (2 H, q, J=5.3 Hz), 2.88 (2 H, t, J=7.3 Hz), 2.54 (6 H, s), 1.99-1.95 (2 H, m), 1.47 (6 H, s); $^{13}C$ NMR (150 MHz, CDCl$_3$) δ 156.5, 155.7, 148.4, 142.2, 136.3, 131.3, 131.2, 125.0, 122.7, 121.7, 121.2, 119.0, 112.1, 61.7, 56.1, 31.8, 22.0, 14.6, 14.1; HRMS calcd for $C_{25}H_{29}BF_2N_5O_2$: 480.2382, found: m/z 480.2379 [M+H]$^+$.

2,6-Diethoxycarbonyl-4,4-difluoro-8-{3-[4-(3-hydroxypropyl)-1H-1,2,3-triazol-1-yl]-2-methoxyphenyl}-1,3,5,7-tetramethyl-4-bora-3a,4a-diaza-s-indacene (T10)

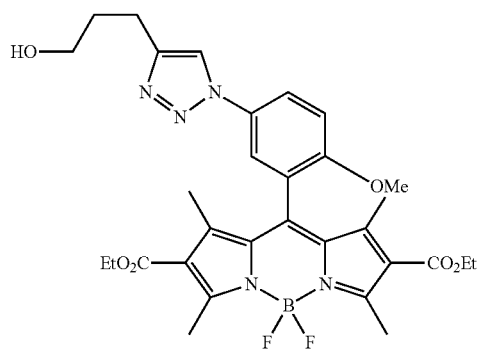

Compound T10 was prepared from compound Az10 in 90% yield. $C_{31}H_{36}BF_2N_5O_6$, red solids, mp 157-159° C.; TLC (EtOAc/hexane, 4:1) $R_f$=0.32; $^1H$ NMR (600 MHz, CDCl$_3$) δ 7.91 (1 H, dd, J=8.9, 2.6 Hz), 7.67 (1 H, s), 7.49 (1 H, d, J=2.6 Hz), 7.14 (1 H, d, J=8.9 Hz), 4.26 (4 H, q, J=7.1 Hz), 3.84 (3 H, s), 3.73 (2 H, q, J=5.8 Hz), 2.88 (2 H, t, J=7.3 Hz), 2.81 (6 H, s), 1.99-1.94 (2 H, m), 1.79 (6 H, s), 1.31 (6 H, t, J=7.1 Hz); $^{13}C$ NMR (150 MHz, CDCl$_3$) δ 164.2, 159.6, 156.3, 148.5, 146.7, 140.6, 131.7, 131.3, 124.5, 123.3, 122.5, 121.4, 119.0, 112.3, 61.6, 60.3, 56.3, 31.8, 21.9, 15.0, 14.2, 13.1; HRMS calcd for $C_{31}H_{37}BF_2N_5O_6$: 624.2805, found: m/z 624.2801 [M+H]$^+$.

2,6-Dicyano-4,4-difluoro-8-{3-[4-(3-hydroxypropyl)-1H-1,2,3-triazol-1-yl]-1,3,5,7-tetramethyl-4-bora-3a,4a-diaza-s-indacene (T11)

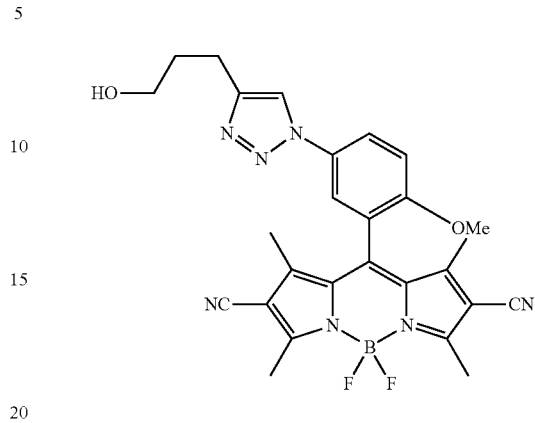

Compound T11 was prepared from compound Az11 in 78% yield. $C_{27}H_{26}BF_2N_7O_2$, red solids, mp 175-177° C. (dec.); TLC (EtOAc) $R_f$=0.42; $^1H$ NMR (600 MHz, CDCl$_3$) δ 7.90 (1H, dd, J=9.0, 2.3 Hz), 7.71 (1 H, s), 7.58 (1 H, d, J=2.3 Hz), 7.20 (1 H, d, J=9.0 Hz), 3.86 (3 H, s), 3.73 (2 H, t, J=6.1 Hz), 2.89 (2 H, t, J=7.3 Hz), 2.71 (6 H, s), 1.99-1.95 (2 H, m), 1.69 (6 H, s); $^{13}C$ NMR (150 MHz, CDCl$_3$) δ 159.9, 155.7, 148.7, 148.6, 142.0, 131.9, 131.4, 123.7, 122.5, 121.0, 118.9, 113.4, 112.6, 106.5, 61.7, 56.5, 31.8, 22.0, 13.9, 13.6; HRMS calcd for $C_{27}H_{27}BF_2N_7O_2$: 530.2287, found: m/z 530.2289 [M+H]$^+$.

Example 3

Detecting and Imaging Biomolecules

Spectroscopic Measurements

All spectroscopic measurements of the amino-BODIPY Am10, the azido-BODIPYs Az2 and Az9-Az11 as well as the corresponding triazolyl-BODIPYs T2 and T9-T11 were performed in ethanol using a cuvette with 1-cm path length at 25±0.1° C. All solutions were degassed under argon for several minutes prior to measurements. For each experiment, the slit width was 2.0 nm for both excitation and emission. The absorbance spectra were measured within an absorbance range of 0.07 to 0.7 (l=10 cm). Fluorescence quantum yield measurements were performed on a fluorometer and UV-Vis instrument. Relative quantum efficiencies were obtained by comparing the areas under corrected emission spectrum. The reported quantum yield was calculated as an average of 4 points according to the following equation:

$$\Phi_{sample}=\Phi_{standard}(A_{standard}/A_{sample})(F_{sample}/F_{standard}) (n_{sample}/n_{standard})^2$$

where "Φ" is the quantum yield, "A" is the absorbance at the excitation frequency, "F" is the integrated area under the emission curve, and "n" is the refractive index of the solvent used. Fluorescein ($\Phi_f$=0.85) in 0.1 M aqueous NaOH and Rhodamine 6G ($\Phi_f$=0.95) in ethanol are fluorescence standards. (Parker, C. A.; Rees, W. T. *Analyst* 1960, 85, 587-600; Kubin, R. F.; Fletcher, A. N. *J. Luminescence* 1982, 27, 455-462.)

Procedure of Fluorescence Screening of CuAAC Reaction in Microtiter Plate.

Figure 2:
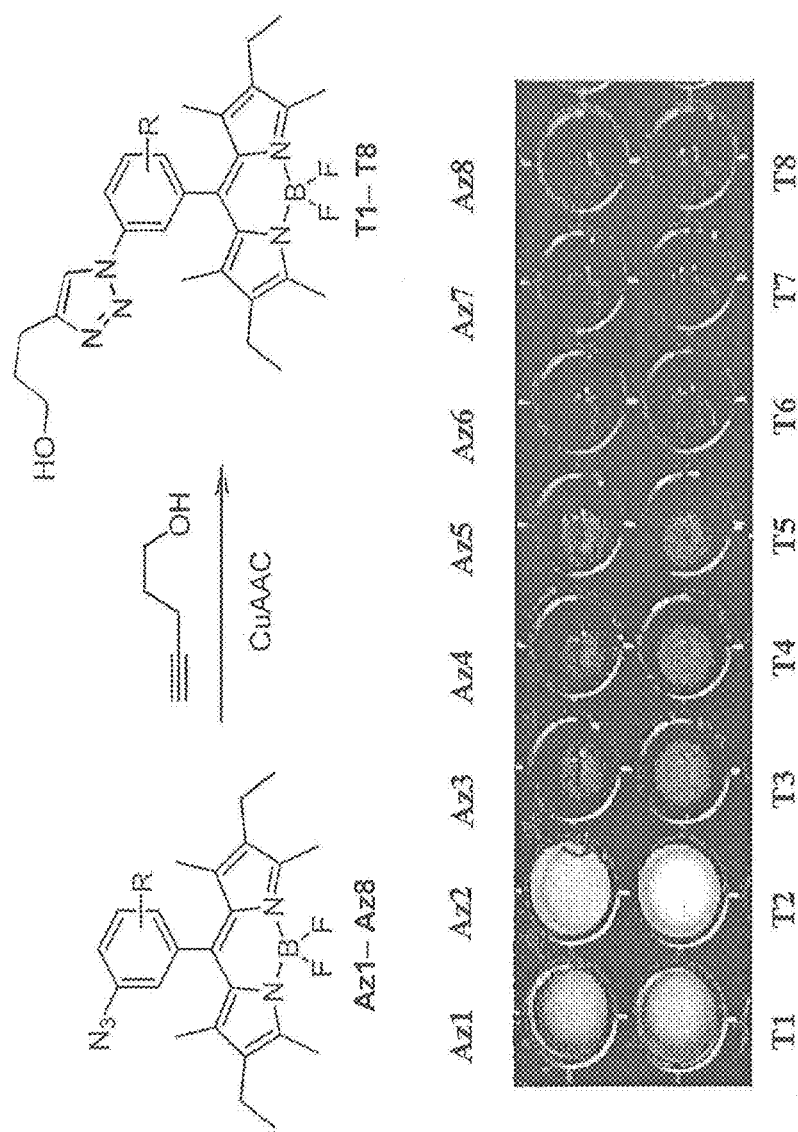
FIG. 2 shows the fluorescence screening of CuAAC reactions of Az1-Az8, giving the corresponding triazole derivatives T1-T8, in a microtier plate with UV lamp excitation ($\lambda_{ex}$=365 nm). Compounds Az1 to Az8 and T1 to T8 are sorted in an increasing order of electron density of the aryl moiety.

A 96-well black-bottom microtiter plate was used for the experiments, and fluorescence measurements were made using a Molecular Devices Spectramax M5 spectrometer. In the upper row, each well contained 200 μL of azido-BODIPY (Az1-Az8) (15 μM) in EtOH/water (1:1). In the bottom row, the overall volume in each well was 200 μL containing a solution of azido-BODIPY (Az1-Az8) (15 μM), 4-pentyn-1-ol (75 μM), CuSO$_4$ (150 μM), sodium ascorbate (300 μM) and tris-triazole ligand (150 μM) in EtOH/water (1:1). The plate was incubated for 6 h at room temperature as monitored by TLC or MS analysis, and then fluorescence measurements ($\lambda_{ex}$=488 nm) were taken in situ. The formation of the fluorescent or non-fluorescent triazole compounds could be discerned upon irradiation at 365 nm with a UV lamp (FIG. 2).

Protein Labeling with AzBOCEt (Az10)

Figure 5:
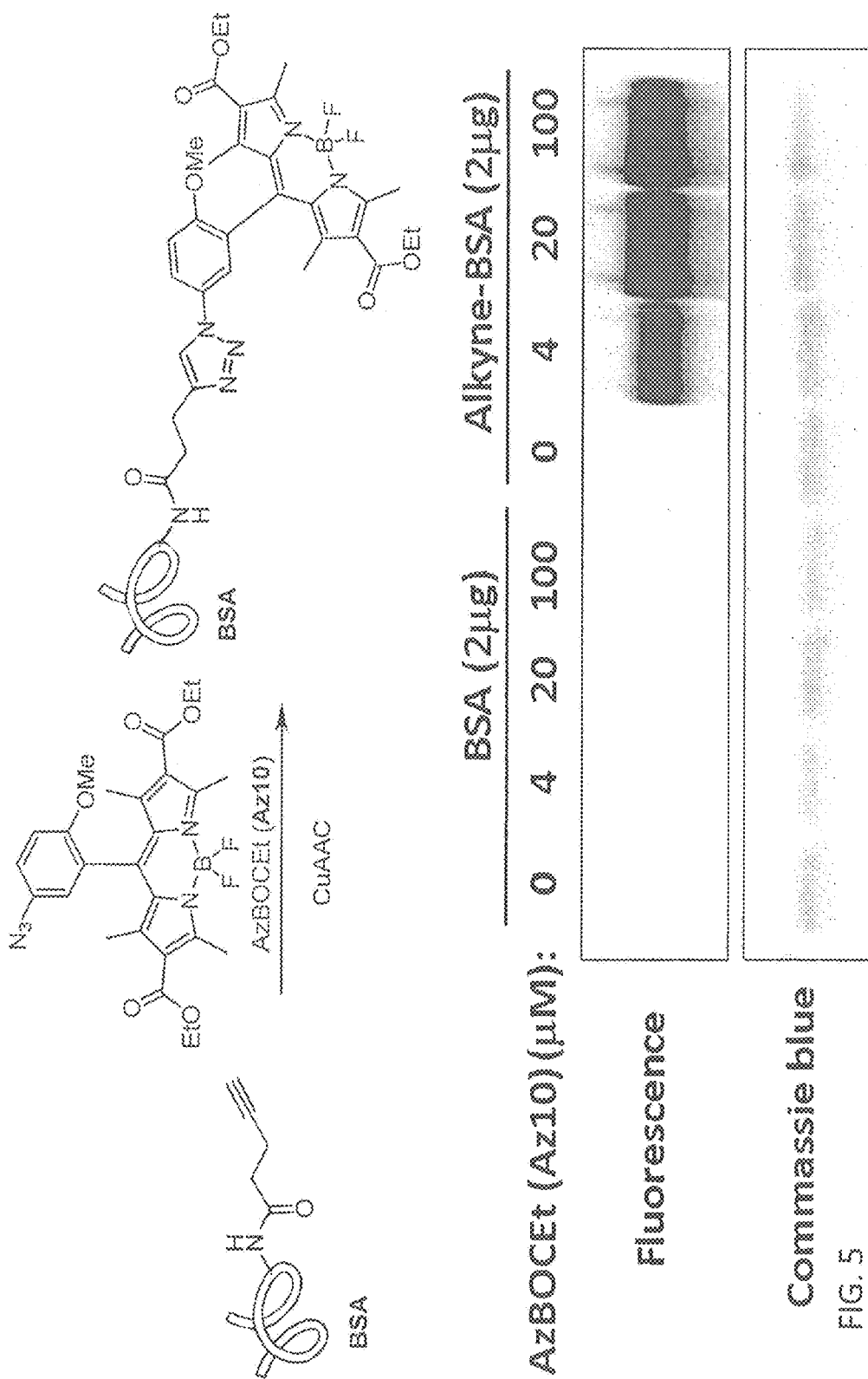
FIG. 5 shows alkyne-functionalized BSA labeling with AzBOCEt (Az10). The gel was analyzed by fluorescence imaging ($\lambda_{ex}$=488 nm; $\lambda_{em}$=526 nm). The total protein content was revealed by Coomassie blue stain.

For the protein labeling experiments, 60 μg/mL alkynyl-functionalized BSA and unmodified BSA in 90:10 pH 7.4 PBS/DMSO were incubated with 100 μM tris-triazole ligand, 1 mM CuSO$_4$, 2 mM freshly prepared sodium ascorbate, and 0 to 100 μM Az10 at room temperature for 1 h in the dark. Each mixture (30 μL) was mixed with 10 μL (4×) SDS loading dye containing 5% β-mercaptoethanol, and 40 μL of each was gradually loaded onto 4 to 12% Bis-Tris gel. The gel was run for 2.5 h at 100 V. The gel was imaged using a Typhoon 9400 Variable Mode Imager (Amersham BioScience) ($\lambda_{ex}$=488 nm; $\lambda_{em}$=526 nm) and stained with Coomassie blue (FIG. 5).

Microscopic Analysis of Fluorescence Labeling in Cells

CL1-5 cells were seeded on chamber slide (1×10$^4$ cells/1 mL per well), and incubated in culture medium (RPMI-1640 supplemented with 10% FBS, 100 U/mL penicillin, 100 μg/mL streptomycin, 1 mM L-glutamine and 1 mM sodium pyruvate) with 100 μM of respective alkynyl-sugar or control for 3 days. The alkynyl-sugars include peracetylated alkynyl-N-acetylmannosamine (Ac$_4$ManNAl), peracetylated alkynyl-N-acetylgalactosamine (Ac$_4$GalNAl) and peracetylated alkynyl-N-acetylglucosamine (Ac$_4$GlcNAl). The control sugars include peracetylated N-acetylmannosamine (Ac$_4$ManNAc), peracetylated N-acetylgalactosamine (Ac$_4$GalNAc) and peracetylated N-acetylglucosamine (Ac$_4$GlcNAc).

Figure 6A:
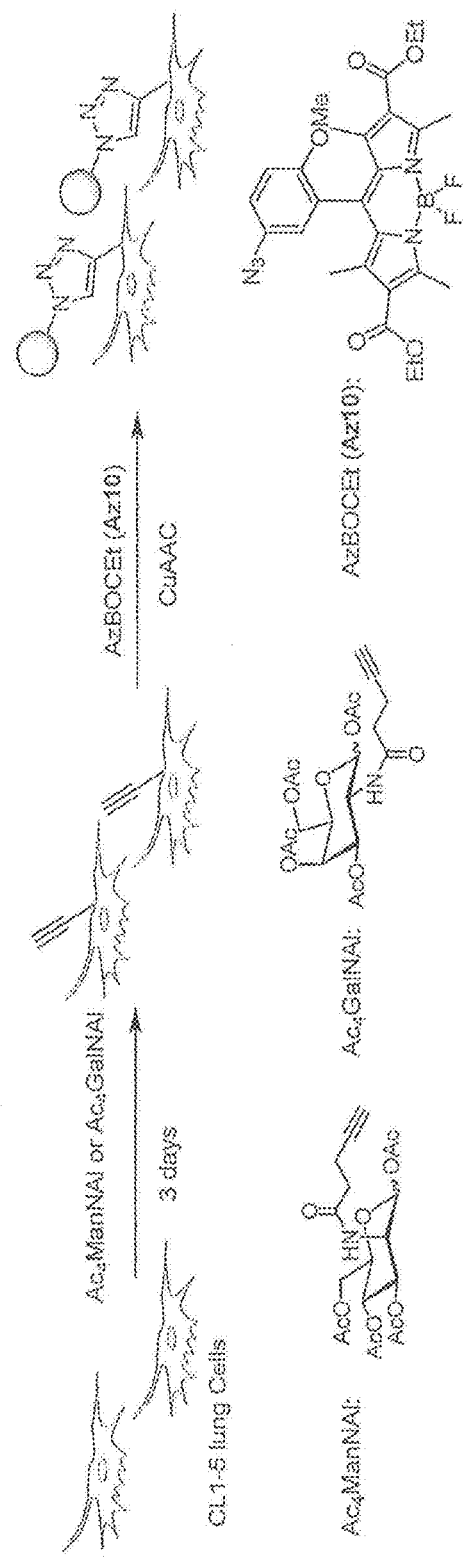
FIG. 6A, 6B, 6C shows the cell fluorescence labeling with AzBOCEt (Az10) and imaging by confocal microscopy.
Figure 6B:
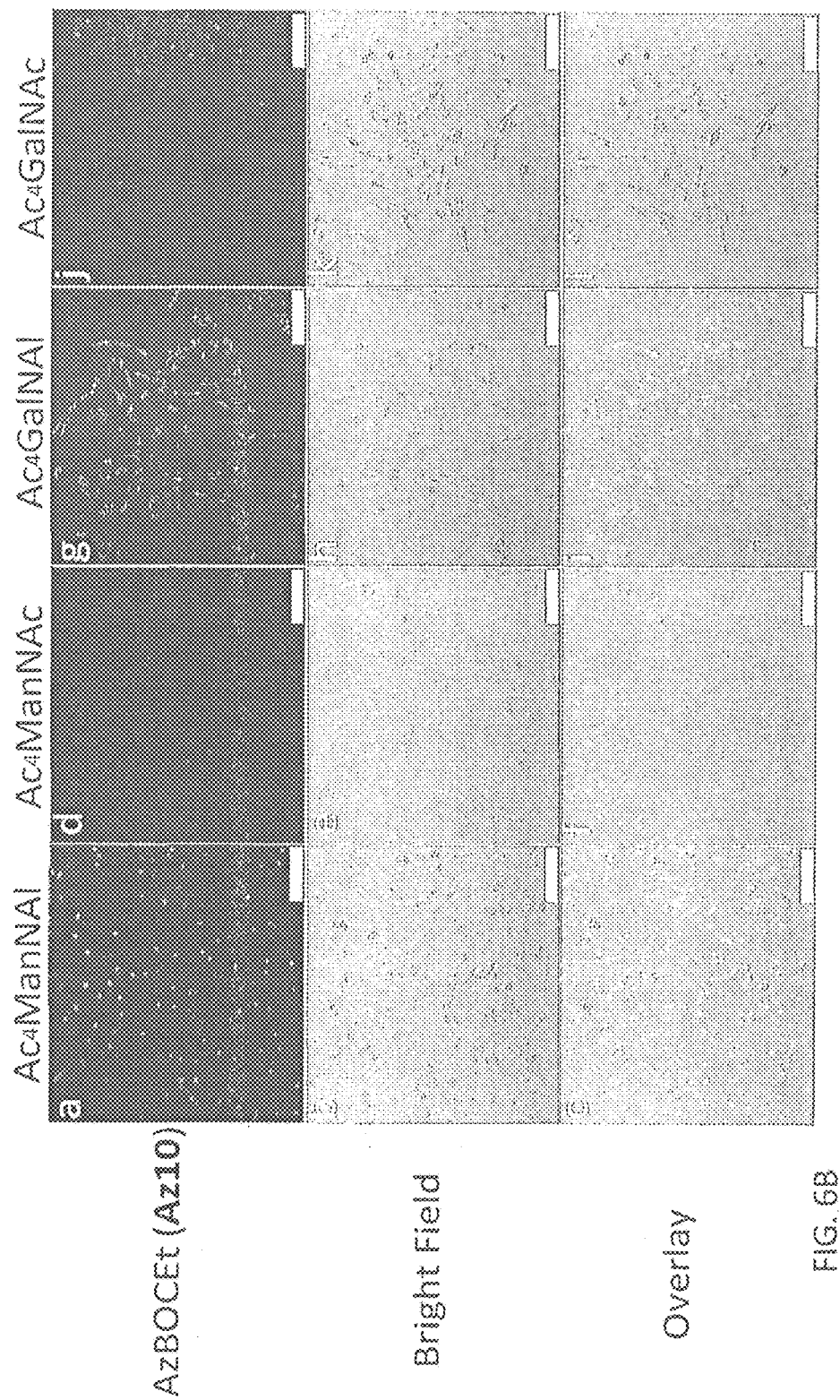
Figure 6C:
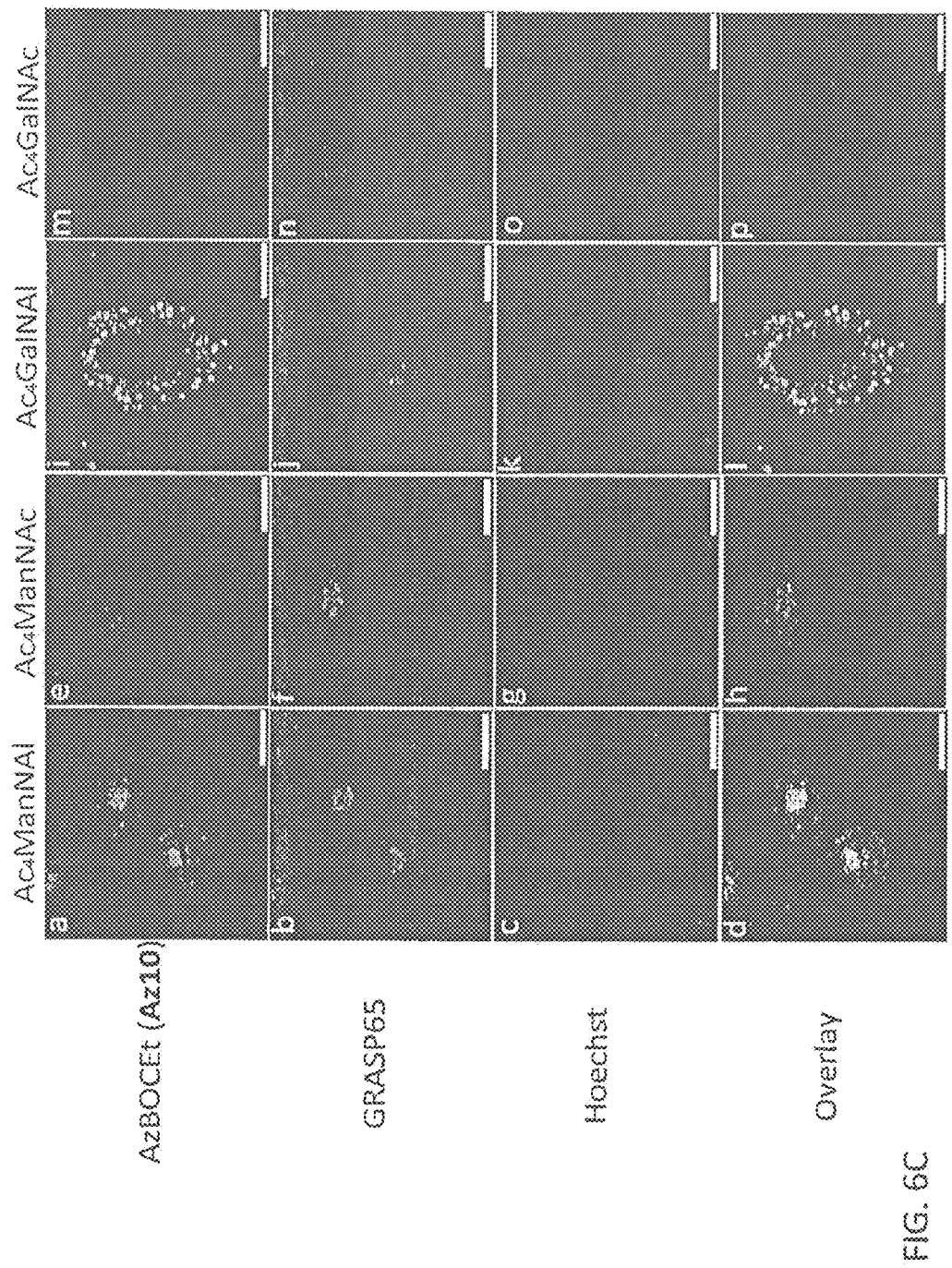

For detecting the labeling of AzBOCEt (Az10) to sugar analogs treated cells, The sugar-treated cells were washed with PBS, fixed with 3% paraformaldehyde in PBS at room temperature for 20 min, permeablized with 0.2% Triton X-100 in PBS at room temperature for 20 min, and blocked with 3% bovine serum albumin in PBS at room temperature for 30 min. To observe the fluorescence-labeled alkyne-tagged glycosyl conjugates in cells, the cells were incubated with 0.1 μM AzBOCEt (Az10), 100 μM tris-triazole ligand, 1 mM CuSO$_4$, and 2 mM sodium ascorbate in PBS buffer with 50% ethanol at room temperature for 1 h. Fluorescence images of cells were acquired at 496-nm excitation by using confocal laser-scanning microscope. To identify the location of alkynyl-glycans, the probe-labeled cells were further stained with anti-GRASP65 followed by Cy3-conjugated anti-rabbit for Golgi, and Hoechst for nucleus (FIG. 6).

Figure 7:
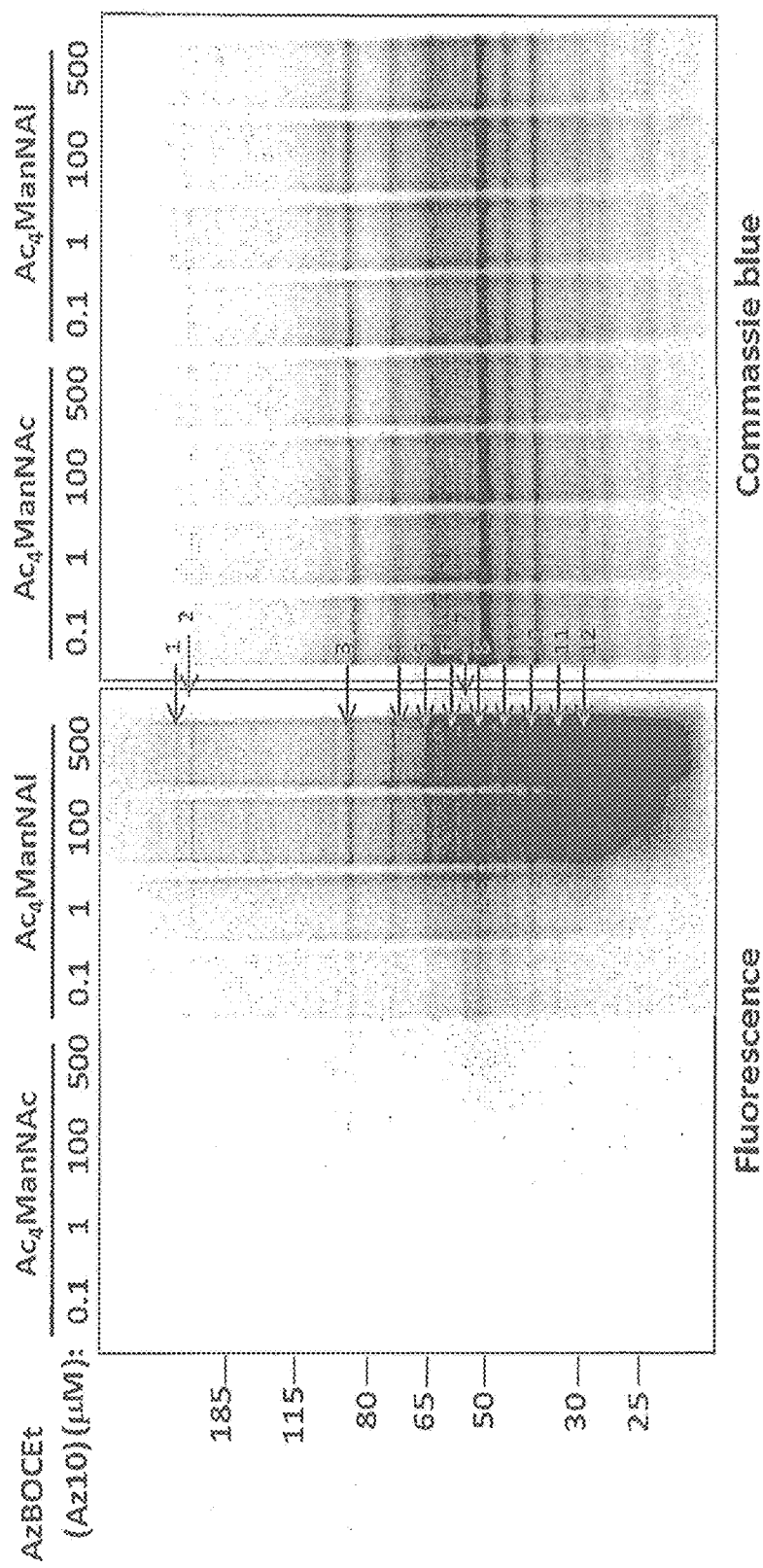
FIG. 7 shows the direct in-gel fluorescence detection of alkyne-tagged glycoproteins using CuAAC with AzBOCEt (Az10) from cell lysates. The gel was analyzed by fluorescence imaging ($\lambda_{ex}$=488 nm; $\lambda_{em}$=526 nm) and Coomassie blue staining to reveal the total protein content.
Figure 8A:
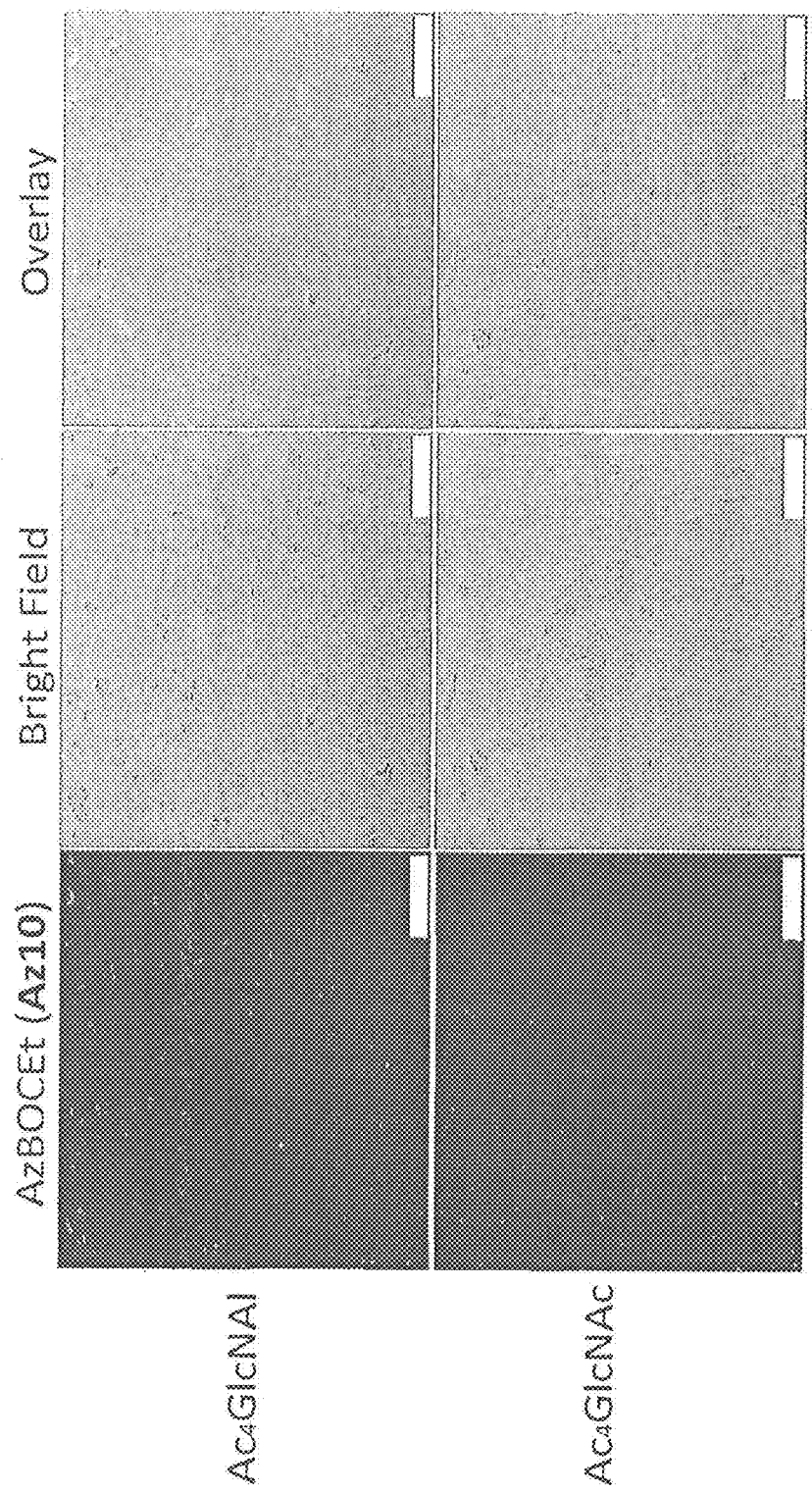
FIG. 8A, 8B shows the cell fluorescence labeling with AzBOCEt (Az10) and imaging by confocal microscopy. The CL1-5 cells were incubated with $Ac_4$GlcNAl or $Ac_4$GlcNAc for 3 days and then treated with 0.1 µM Az10 for 1 h under CuAAC conditions.
Figure 8B:
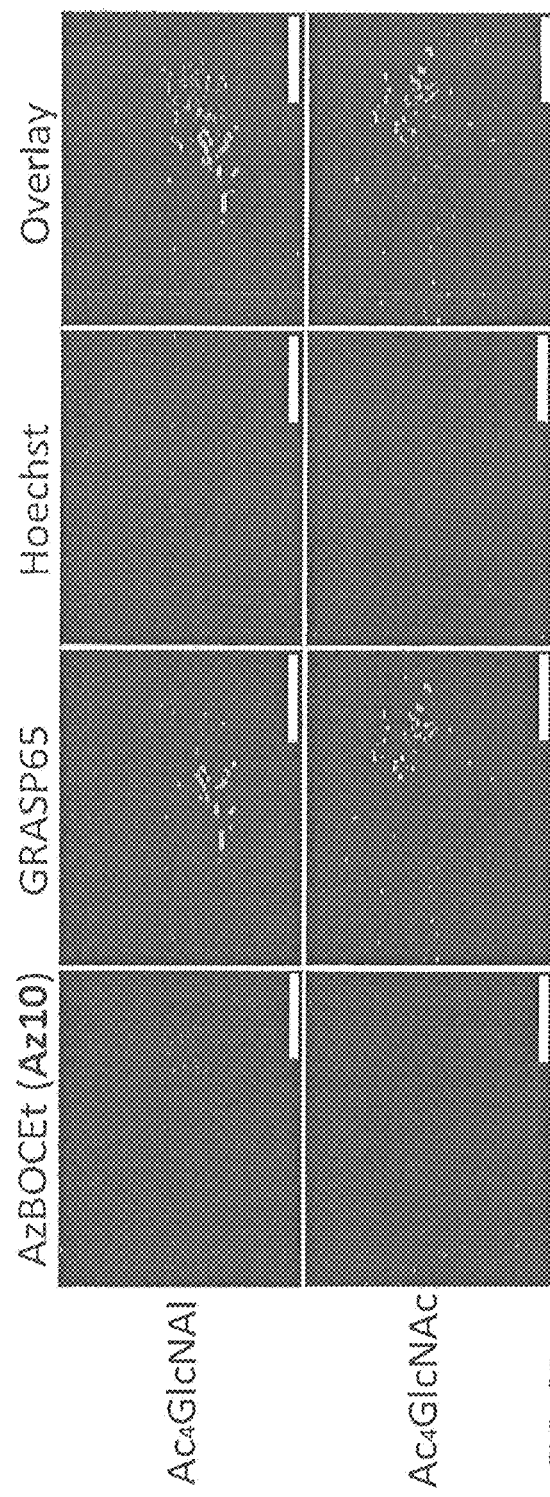

Detection and Identification of Alkyne-Tagged Sialyl Glycoproteins in Cell Extracts Cell extracts (20 μg) harvested from CL1-5 cells treated with 100 μM Ac$_4$ManNAc or Ac$_4$ManNAl for 3 days were incubated with indicated concentration of Az10, 100 M tris-triazole ligand,$^{S3}$ 1 mM CuSO$_4$, and 2 mM sodium ascorbate at room temperature for 1 h to proceed CuAAC reaction. The reacted extracts were further separated by SDS-PAGE and the fluorescence signals were detected with the Typhoon 9400 Variable Mode Imager (Amersham BioScience) ($\lambda_{ex}$=488 nm; $\lambda_{em}$=526 nm). The protein bands stained with Coomassie blue represented the loading control (FIG. 7).

The indicated 12 bands containing proteins labeled with fluorescence signal were excised and cut into small pieces. The gel pieces were destained with 50 mM NH$_4$HCO$_3$/CH$_3$CN 1:1 (v/v), and then rehydrated with 10 mM dithiothreitol (DTT) in 25 mM NH$_4$HCO$_3$ at 56° C. for 45 min. The excess DTT was removed and 55 mM iodoacetamide (IAA) in 25 mM NH$_4$HCO$_3$ was added at room temperature for 30 min in the dark for alkylation. The excess IAA was removed and the gels were washed twice with 50 mM NH$_4$HCO$_3$/CH$_3$CN 1:1 (v/v), and dried with CH$_3$CN after being dried using a vacuum centrifuge. Freshly prepared trypsin solution (5 ng/L in 25 mM NH$_4$HCO$_3$, 40 μL) was added to each gel pieces, and gel pieces were warmed to 37° C. for 18 h. The digested peptides were extracted twice with aqueous solution of 1% trifluoracetic acid (TFA) containing 50% CH$_3$CN (50 μL) under sonication for 10 min. The combined extracts and washes were concentrated using a vacuum centrifuge for 3 h to remove the volatiles. The digested peptides were analyzed and identified with a hybrid linear ion trap quadrupole fourier-transfer (LTQ-FT) mass spectrometer as shown in Table 2.

TABLE 2

Sialyl glycoproteins identified by mass spectrometry in cell extracts. Proteins are tabulated by accession number and number of peptides (# of Pep.) found for that proteins are listed.

| Band | No. | Gene name | Protein name | Accession number | # of Pep. |
|---|---|---|---|---|---|
| 1 | 1-1 | IGF2R | Cation-independent mannose-6-phosphate receptor | IPI00289819 | 13 |
| 4 | 4-1 | COLGALT1 | Procollagen galactosyltransferase 1 | IPI00168262 | 16 |
|  | 4-2 | PRKCSH | Glucosidase 2 subunit beta | IPI00026154 IPI00792916 | 19 |
|  | 4-3 | FKBP10 | Peptidyl-prolyl cis-trans isomerase FKBP10 | IPI00303300 | 22 |
|  | 4-4 | SLC1A1 | Neutral amino acid transporter B(0) | IPI00019472 IPI00922487 IPI00922776 | 6 |
|  | 4-5 | RPN1 | Ribophorin-1 | IPI00025874 | 1 |

TABLE 2-continued

Sialyl glycoproteins identified by mass spectrometry in cell extracts. Proteins are tabulated by accession number and number of peptides (# of Pep.) found for that proteins are listed.

| Band | No. | Gene name | Protein name | Accession number | # of Pep. |
|---|---|---|---|---|---|
| 5 | 5-1 | P4HA1 | Prolyl 4-hydroxylase subunit alpha-1 | IPI00009923 IPI00218682 IPI00916535 | 14 |
|  | 5-2 | OIT3 | Oncoprotein-induced transcript 3 protein | IPI00328215 IPI00855752 | 4 |
| 6 | 6-1 | NCLN | Nicalin | IPI00470649 IPI00607732 | 4 |
| 7 | 7-1 | ERO1L | ERO1-like protein alpha | IPI00386755 | 4 |
| 8 | 8-1 | NCEH1 | Neutral cholesterol ester hydrolase 1 | IPI00002230 IPI00790972 IPI00924788 | 4 |
|  | 8-2 | SERPINH1 | Serpin H1 | IPI00032140 | 3 |
|  | 8-3 | SIGLEC7 | Sialic acid-binding Ig-like lectin 7 | IPI00004288 IPI00220858 IPI00220860 IPI00220862 | 2 |
| 9 | 9-1 | ERLIN1 | Erlin-1 | IPI00007940 | 18 |
|  | 9-2 | DNAJB11 | DnaJ homolog subfamily B member 11 | IPI00074870 | 9 |
|  | 9-3 | AHSG | Alpha-2-HS-glycoprotein | IPI00953689 | 6 |
|  | 9-4 | RCN1 | Reticulocalbin-1 | IPI00015842 | 1 |
|  | 9-5 | IMPAD1 | Inositol monophosphatase 3 | IPI00787853 | 2 |
|  | 9-6 | IKBIP | Inhibitor of nuclear factor kappa-B kinase- interacting protein | IPI00043598 IPI00401792 IPI00797136 IPI00896464 | 4 |
| 10 | 10-1 | CTSL | Cathepsin L1 | IPI00012887 | 7 |
|  | 10-2 | TOR1B | Torsin-1B | IPI00023137 | 1 |
| 11 | 11-1 | SUMF2 | Sulfatase-modifying factor 2 | IPI00334513 IPI00334514 IPI00334516 IPI00783919 IPI00939930 | 5 |
|  | 11-2 | CNPY3 | Protein canopy homolog 3 | IPI00398366 IPI00551062 | 4 |
|  | 11-3 | PPT1 | Palmitoyl-protein thioesterase 1 | IPI00002412 | 2 |
|  | 11-4 | SSR1 | Translocon-associated protein subunit alpha | IPI00301021 IPI00449669 | 2 |
| 12 | 12-1 | PSMA1 | Proteasome subunit alpha type-1 | IPI00016832 IPI00472442 | 30 |
|  | 12-2 | CTXZ | Cathepsin Z | IPI00002745 | 3 |

Microscopic Analysis of Dual Fluorescence Labeling in Cells

Figure 9:
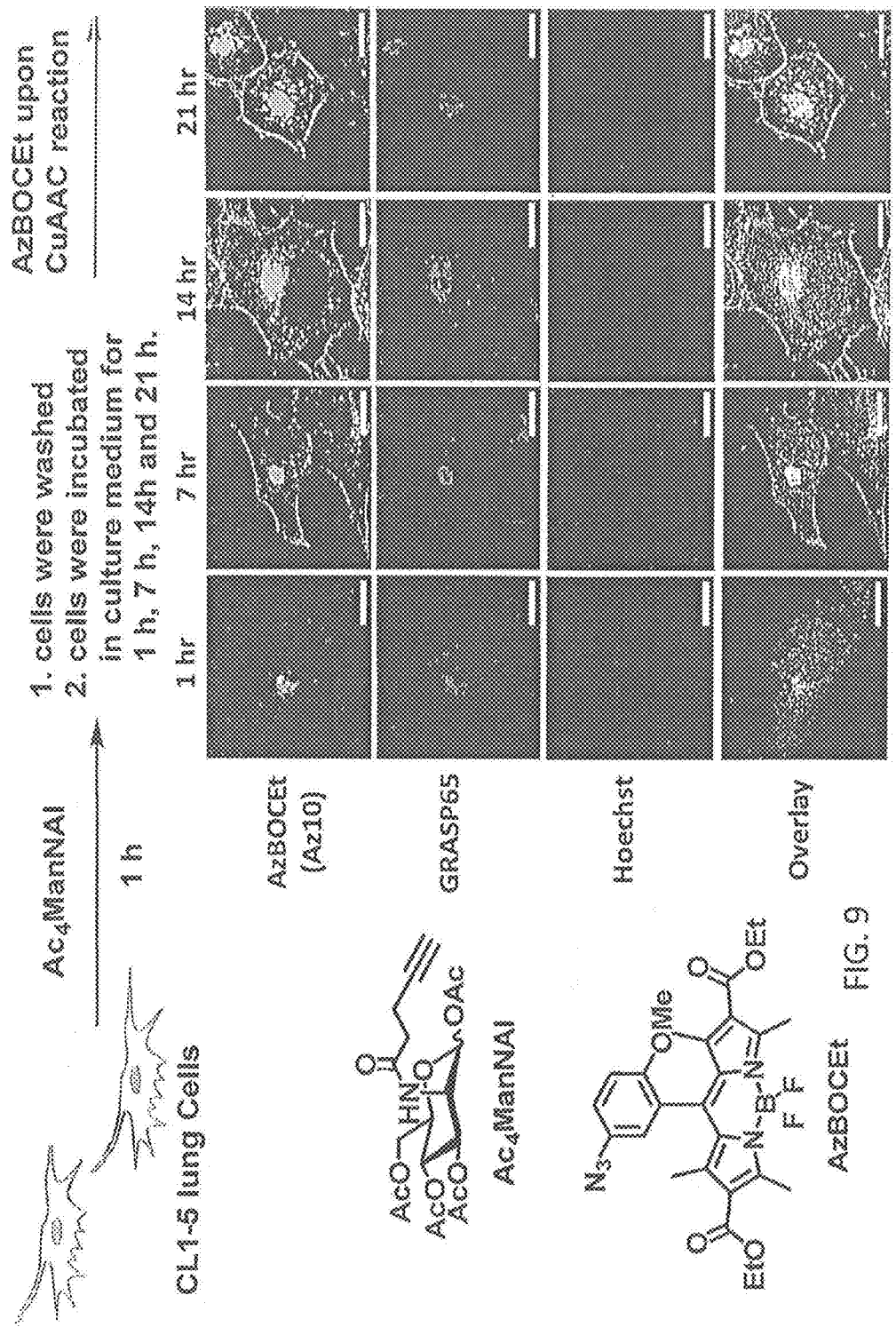
FIG. 9 shows Fluorescence imaging of glycan trafficking using AzBOCEt of CuAAC in cells. CL1-5 cells were incubated with 500 µM $Ac_4$ManNAl for 1 h and subsequently washed with PBS buffer to remove excess $Ac_4$ManNAl. The sugar-treated cells were incubated in culture medium for 1 h, 7 h, 14 h and 21 h, and then labeled with 0.1 µM Az10 for 1 h under CuAAC conditions, respectively.

CL1-5 cells were seeded on chamber slide (2.5×10$^4$ cells/0.5 mL per wells) and incubated in culture medium (RPMI-1640 supplemented with 10% FBS, 100 U/mL penicillin, 100 µg/mL streptomycin, 1 mM L-glutamine and 1 mM sodium pyruvate) for 3 days with either 100 µM of alkynyl-sugar (peracetylated alkynyl-N-acetylmannosamine, Ac$_4$ManNAl or azido-sugar (peracetylated azido-N-acetylglucosamine, Ac$_4$GlcNAz) or both or without sugar as negative control. Cells were washed three times with PBS and then incubated with 100 µM of coumOCT in PBS with 10% DMSO for 30 min at 37° C. After three washes with PBS with 10% DMSO, followed by fixed with 3% paraformaldehyde in PBS at room temperature for 20 min, the cells were incubated with 0.1 µM of AzBOCEt (Az10), 100 µM of ligand, 1 mM of CuSO$_4$, and 2 mM of sodium ascorbate in PBS with 50% ethanol at room temperature for 1 h and fluorescence images of cell were carried out using a confocal microscope (TCS-SP5-MP-SMD, Leica) (FIG. 9).

Example 4

Synthesis of Cyclooctyne-functionalized Fluorescent Probe 101

Scheme 100 shows the synthesis of compound 101 using 1-benzosuberone as the starting material. According to the previously reported procedure,[12] 1-benzosuberone was subject to regioselective nitration at 8-position. The nitro group was then reduced, followed by diazotization and hydroxylation under acid conditions to give alcohol 104. After protection of the hydroxyl group as a benzyl ether, the cyclic ketone 105 underwent a ring expansion by treatment with TMS-diazomethane in the presence of BF$_3$.OEt$_2$ to afford the cyclooctanone product 106 in 73% yield. Reduction of the carbonyl group with NaBH$_4$, followed by silylation, gave the silyl ether 107 in 96% yield. The benzyl group in 107 was removed by hydrogenation, and the phenol intermediate was treated with excess paraformaldehyde in the presence of Et$_3$N and MgCl$_2$ to form the salicylaldehyde 108. The coumarin scaffold in 109 was constructed by treatment of 108 with freshly prepared ketenylidenetriphenylphosphorane. After desilylation and oxidation, ketone 110 was obtained in 78% yield. The carbonyl group in compound 110 was converted to enol triflate, which was subsequently treated with a strong base NaHMDS to render an elimination reaction, giving the coumOCT probe 101.

Scheme 100. Synthesis of the SPAAC-based fluorescence-forming probe 101 and the corresponding triazoles 111 and 112.

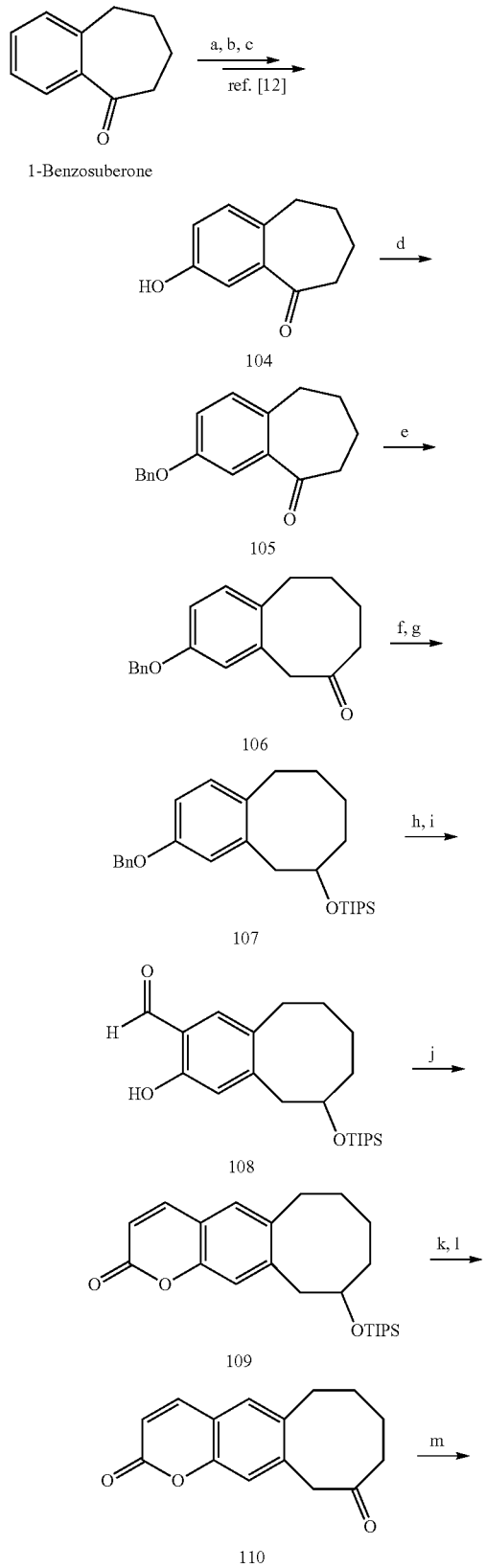

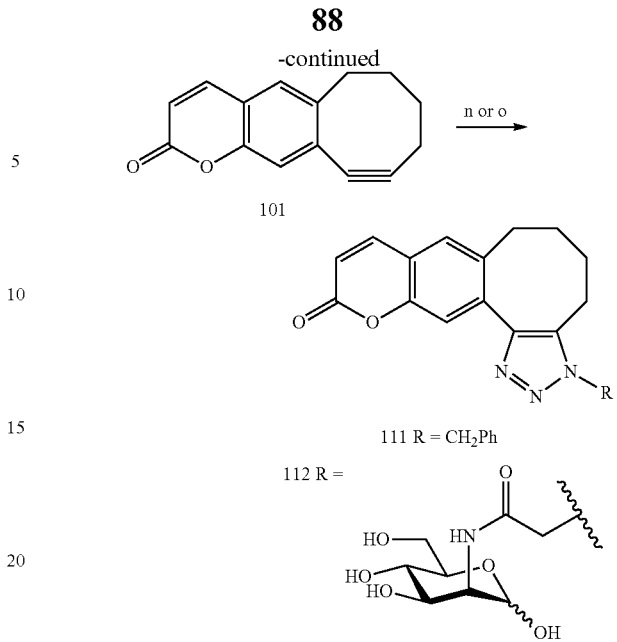

Reagents and conditions: (a) conc. H$_2$SO$_4$, KNO$_3$, 0° C., 1.5 h, 72%; (b) Sn, conc. HCl, C$_2$H$_5$OH, reflux, 50 min, 82%; (c) 10% aq. H$_2$SO$_4$, NaNO$_2$, 0° C. to rt, 72 h, 76%; (d) BnBr, K$_2$CO$_3$, DMF, rt, 24 h, 98%; (e) TMSCHN$_2$, BF$_3$OEt$_2$, CH$_2$Cl$_2$, 0° C., 12 h, 73%; (f) NaBH$_4$, CH$_3$OH, 0° C., 1 h; (g) TIPSOTf, 2,6-lutidine, CH$_2$Cl$_2$, rt, 1 h, 96% for two steps; (h) H$_2$, Pd/C, CH$_3$OH, EtOAc, 1 h; (i) paraformaldehyde, MgCl$_2$, Et$_3$N, CH$_3$CN, reflux, 12 h, 87% for two steps; (j) Ph$_3$P=C=C=O, toluene, 90° C., 1.5 h, 83%; (k) TBAF, THF, 0° C. to rt, 1 h; (l) (COCl)$_2$, DMSO, Et$_3$N, CH$_2$Cl$_2$, −78° C. to rt, 1 h, 78% for two steps; (m) NaHMDS, Tf$_2$NPh, −78° C. to rt, 2 h, 44%; (n) BnN$_3$ (1.5 equiv.), CH$_3$CN, rt, 2 h, 95%; (o) N-azidoacetylmannosamine (1.5 equiv.), MeOH, H$_2$O, rt, 2 h, 92%.

3-Nitro-6,7,8,9-tetrahydrobenzocyclohepten-5-one (A)

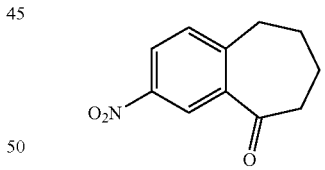

A solution of 1-benzosuberone (4.0 g, 25 mmol) in concentrated H$_2$SO$_4$ (28 mL) was cooled at 0° C., and a solution of KNO$_3$ (2.8 g, 27.7 mmol) in concentrated H$_2$SO$_4$ (7.5 mL) was added dropwise over a period of 30 min. The mixture was stirred for additional 1 h at 0° C., and then poured into crushed ice. The precipitate was filtered, washed with water and air-dried to yield a yellow solid. The crude product was purified by column chromatography on silica gel (EtOAc/hexane, 1:4) to afford the pure nitro product A (3.69 g, 72%). C$_{11}$H$_{11}$NO$_3$, white needles, mp 90-92° C. (lit.[S2] mp 89-90° C.); TLC (EtOAc/hexane, 1:4) R$_f$=0.31; $^1$H NMR (600 MHz, CDCl$_3$) δ 8.53 (1 H, d, J=2.5 Hz), 8.22 (1 H, dd, J=8.3, 2.5 Hz), 7.37 (1 H, d, J=8.3 Hz), 3.01 (2 H, t, J=6.4 Hz), 2.77 (2 H, t, J=6.1 Hz), 1.94-1.90 (2 H, m), 1.85-1.81 (2 H, m); $^{13}$C NMR (150 MHz, CDCl$_3$) δ 203.4, 148.0, 147.0, 139.8, 131.0, 126.2, 123.9, 40.4, 32.4, 24.7, 20.5; HRMS calcd for C$_{11}$H$_{12}$NO$_3$: 206.0812, found: m/z 206.0814 [M+H]$^+$.

3-Amino-6,7,8,9-tetrahydrobenzocyclohepten-5-one (B)

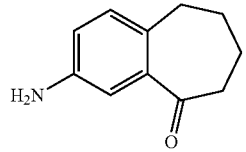 [SMILES: O=C1CCCCc2ccc([N+](=O)[O-])cc21]

A mixture of nitro compound A (2.05 g, 10 mmol) and Sn (8.31 g, 70 mmol) in concentrated HCl (45 mL) and ethanol (25 mL) was heated at reflux for 50 min. The mixture was cooled to room temperature, and basified with 30% NaOH aqueous solution. The mixture was filtered through a pad of Celite, and washed with ethanol. The filtrate was extracted with EtOAc (5×50 mL). The combined organic extracts were washed with brine (100 mL), dried over MgSO$_4$, filtered, and concentrated under reduced pressure to afford the analytically pure amino product B (1.44 g, 82%). C$_{11}$H$_{13}$NO, yellowish solid, mp 102-104° C. (lit.$^{S2}$ mp 103-105° C.); TLC (EtOAc/hexane, 3:7) R$_f$=0.29; $^1$H NMR (600 MHz, CDCl$_3$) δ 7.02 (1 H, d, J=2.6 Hz), 6.96 (1 H, d, J=8.0 Hz), 6.72 (1 H, dd, J=8.0, 2.6 Hz), 3.65 (2 H, br s, NH), 2.79 (2 H, t, J=5.5 Hz), 2.67 (2 H, t, J=6.6 Hz), 1.81-1.74 (4 H, m); $^{13}$C NMR (150 MHz, CDCl$_3$) δ 206.2, 144.9, 139.3, 131.6, 130.7, 118.8, 114.5, 40.8, 31.5, 25.4, 20.9; HRMS calcd for C$_{11}$H$_{14}$NO: 176.1070, found: m/z 176.1069 [M+H]$^+$.

3-Hydroxy-6,7,8,9-tetrahydrobenzocyclohepten-5-one (104)

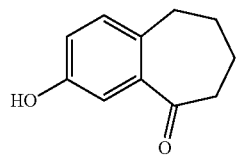 [SMILES: O=C1CCCCc2ccc(O)cc21]

A cold (0° C.) solution of amino compound B (1.45 g, 8.3 mmol) in H$_2$SO$_4$ (40 mL of 10% aqueous solution) was cautiously added an aqueous solution of NaNO$_2$ (687 mg, 9.96 mmol) in water (3 mL). The reaction mixture was stirred for 30 min at 0° C., and then sulfamic acid was added to destroy excess nitrous acid. The suspension was filtered and the filtrate was poured into a 10% aqueous solution of H$_2$SO$_4$ (100 mL) and toluene (50 mL). The mixture was stirred for 3 days at room temperature. The layers were then separated and the aqueous layer was extracted with EtOAc (5×30 mL). The combined organic extracts were washed with brine (100 mL), dried over MgSO$_4$, filtered, and concentrated under reduced pressure. The crude product was purified by column chromatography on silica gel (EtOAc/hexane, 1:4) to afford the analytically pure alcohol product 104 (1.11 g, 76%). C$_{11}$H$_{12}$O$_2$, yellow solid, mp 98-100° C. (lit.$^{S3}$ mp 96-99° C.); TLC (EtOAc/hexane, 3:7) R$_f$=0.37; $^1$H NMR (600 MHz, CDCl$_3$) δ 7.33 (1 H, d, J=2.8 Hz), 7.07 (1 H, d, J=8.2 Hz), 6.94 (1 H, dd, J=8.2, 2.8 Hz), 6.27 (1 H, s, OH), 2.84 (2 H, t, J=5.7 Hz), 2.72 (2 H, t, J=6.4 Hz), 1.86-1.76 (4 H, m); $^{13}$C NMR (150 MHz, CDCl$_3$) δ 206.7, 154.7, 139.2, 133.9, 131.3, 119.8, 114.9, 40.8, 31.6, 25.3, 20.8; HRMS calcd for C$_{11}$H$_{13}$O$_2$: 177.0910, found: m/z 177.0911 [M+H]$^+$.

3-Benzyloxy-6,7,8,9-tetrahydrobenzocyclohepten-5-one (105)

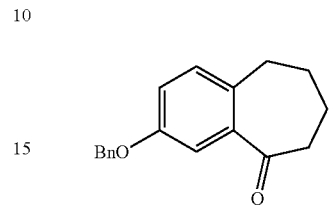

A solution of alcohol compound 104 (1.25 g, 7.1 mmol) in anhydrous DMF (10 mL) was treated with benzyl bromide (1 mL, 8.4 mmol) and potassium carbonate (2.1 g, 15.2 mmol). The suspension was vigorously stirred for 24 h at room temperature. The mixture was poured into water (20 mL) and extracted with Et$_2$O (4×30 mL), The combined organic extracts were washed with water (3×20 mL) and brine (100 mL), dried over MgSO$_4$, filtered, and concentrated under reduced pressure. The crude product was purified by column chromatography on silica gel (EtOAc/hexane, 1:9) to afford the pure benzyloxy product 105 (1.85 g, 98%). C$_{18}$H$_{18}$O$_2$, pale yellow oil; TLC (EtOAc/hexane, 1:9) R$_f$=0.37; $^1$H NMR (600 MHz, CDCl$_3$) δ 7.41 (2 H, d, J=7.2 Hz), 7.37-7.35 (3 H, m), 7.31 (1 H, d, J=7.4 Hz), 7.10 (1 H, d, J=8.3 Hz), 7.02 (1 H, dd, J=8.3, 2.9 Hz), 5.06 (2 H, s), 2.86 (2 H, t, J=5.8 Hz), 2.71 (2 H, t, J=6.2 Hz), 1.84-1.78 (4 H, m); $^{13}$C NMR (150 MHz, CDCl$_3$) δ 205.6, 157.4, 139.5, 136.7, 134.2, 131.0, 128.5 (2×), 127.9, 127.5 (2×), 119.7, 113.2, 70.1, 40.7, 31.6, 25.3, 20.8; HRMS calcd for C$_{18}$H$_{19}$O$_2$: 267.1380, found: m/z 267.1383 [M+H]$^+$.

3-Benzyloxy-7,8,9,10-tetrahydro-5H-benzocyclooocten-6-one (106)

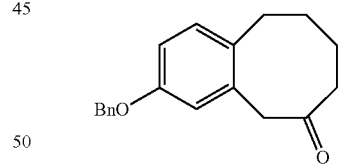

A stirred solution of (trimethylsilyl)diazomethane (5 mL, ca. 2 M solution in hexane, 10 mmol) in CH$_2$Cl$_2$ (10 mL) was added dropwise over a period of 1 h to a stirred solution of compound 105 (1.6 g, 6 mmol) and BF$_3$.OEt$_2$ (820 µL, 10 mmol) in CH$_2$Cl$_2$ (20 mL) at 0° C. The mixture was stirred for 12 h at 0° C., and then poured into crushed ice. The aqueous layer was extracted with CH$_2$Cl$_2$ (3×20 mL). The combined organic extracts were washed with brine (50 mL), dried over MgSO$_4$, and concentrated to give an orange oil that was purified by column chromatography on silica gel (EtOAc/hexane, 1:19) to afford pure cyclooctanone product 106 (1.23 g, 73%). C$_{19}$H$_{20}$O$_2$, colorless oil; TLC (EtOAc/hexane, 1:9) R$_f$=0.29; $^1$H NMR (600 MHz, CDCl$_3$) δ 7.40 (2 H, d, J=7.4 Hz), 7.37-7.34 (2 H, m), 7.31-7.29 (1 H, m), 7.09 (1 H, d, J=8.4 Hz), 6.84 (1 H, dd, J=8.4, 2.7 Hz), 6.75 (1 H, d, J=2.7 Hz), 5.01 (2 H, s), 3.72 (2 H, s), 2.74 (2 H, t, J=5.8 Hz), 2.31 (2 H, t, J=5.3 Hz), 1.81-1.77 (2 H, m), 1.72-1.68 (2 H, m); $^{13}$C NMR (150 MHz, CDCl$_3$) δ 211.8, 157.4, 136.9, 134.7, 133.4, 131.2, 128.5 (2×), 127.9, 127.5 (2×), 116.0, 114.4, 70.0, 48.8, 41.0, 32.3, 31.5, 24.7; HRMS calcd for C$_{19}$H$_{21}$O$_2$: 281.1536, found: m/z 281.1539 [M+H]$^+$.

3-Benzyloxy-6-triisopropylsilyloxy-5,6,7,8,9,10-hexahydrobenzocyclooctene (107)

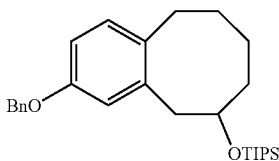

A cold (0° C.) solution of compound 106 (4.8 g, 17.1 mmol) in methanol (40 mL) was treated with NaBH$_4$ (970 mg, 25.7 mmol). The mixture was stirred for 1 h at the 0° C., and then concentrated under reduced pressure. The residue was dissolved in CH$_2$Cl$_2$ (80 mL), and washed with 1 M HCl aqueous solution (50 mL) and brine (50 mL). The organic layer was dried over MgSO$_4$, filtered, and concentrated to provide a crude alcohol product as colorless foam (4.8 g), which was used in the next step without further purification.

The above-prepared alcohol (4.8 g, 17.0 mmol) and 2,6-lutidine (8 mL, 68.7 mmol) were dissolved in anhydrous CH$_2$Cl$_2$ (50 mL), and cooled to 0° C. Triisopropylsilyl trifluoromethanesulfonate (9.2 mL 34.2 mmol) was added dropwise over a period of 3 min to the mixture. The mixture was stirred for 1 h at room temperature, and then diluted with CH$_2$Cl$_2$ (100 mL). The solution was washed with saturated aqueous NaHCO$_3$ (50 mL), 1 M HCl aqueous solution (50 mL), and brine (50 mL). The organic layer was dried over MgSO$_4$, filtered, and concentrated under reduced pressure. The residue was purified by column chromatography on silica gel (EtOAc/hexane, 1:9) to afford the pure silyl ether product 107 (7.2 g, 96% for two steps). C$_{28}$H$_{42}$O$_2$Si, colorless syrup; TLC (EtOAc/hexane, 1:9) R$_f$=0.51; $^1$H NMR (600 MHz, CDCl$_3$) δ 7.41 (2 H, d, J=7.4 Hz), 7.37-7.34 (2 H, m), 7.31-7.28 (1 H, m), 6.99 (1 H, dd, J=6.6, 2.5 Hz), 6.75-6.74 (2 H, m), 5.01 (2 H, s), 3.96-3.93 (1 H, m), 2.91-2.83 (2 H, m), 2.77-2.72 (1H, m), 2.65-2.61 (1 H, m), 1.76-1.72 (1 H, m), 1.71-1.64 (1 H, m), 1.50-1.41 (3 H, m), 1.18-1.15 (1 H, m), 1.07-1.05 (21 H, m); $^{13}$C NMR (150 MHz, CDCl$_3$) δ 156.8, 138.5, 137.3, 134.1, 130.1, 128.5 (2×), 127.8, 127.5 (2×), 116.7, 112.5, 73.8, 70.0, 40.9, 34.5, 32.3, 32.0, 20.8, 18.2 (6×), 12.4 (3×); HRMS calcd for C$_{28}$H$_{43}$O$_2$Si: 439.3032, found: m/z 439.3022 [M+H]$^+$.

3-Hydroxy-6-triisopropylsilyloxy-5,6,7,8,9,10-hexahydrobenzocyclocten-2-carboxaldehyde (108)

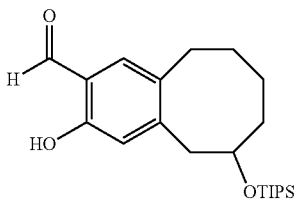

A solution of compound 107 (7.1 g, 16.2 mmol) in methanol (50 mL) and EtOAc (20 mL) was treated with Pd/C (100 mg) under an atmosphere of hydrogen. After stirring for 1 h, the mixture was filtered through Celite, and rinsed with EtOAc. The filtrate was concentrated under reduced pressure to give a light brown syrup (5.6 g), which was dissolved in anhydrous acetonitrile (150 mL) and treated with anhydrous MgCl$_2$ (4.64 g, 48.6 mmol), triethylamine (13.5 mL, 97.2 mmol) and paraformaldehyde (4.86 g, 162 mmol). The suspension was heated at reflux for 12 h. The mixture was cooled to room temperature, and the deep-yellow suspension was acidified with a 1 M HCl aqueous solution (200 mL). The solution was extracted with EtOAc (5×150 mL). The combined organic extracts were washed with brine (200 mL), dried over MgSO$_4$, filtered, and concentrated under reduced pressure. The crude product was purified by column chromatography on silica gel (EtOAc/hexane, 1:19) to afford the pure salicylaldehyde product 108 (5.3 g, 87% for two steps). C$_{22}$H$_{36}$O$_3$Si, pale yellow syrup; TLC (EtOAc/hexane, 1:9) R$_f$=0.71; $^1$H NMR (600 MHz, CDCl$_3$) δ 10.77 (1 H, s), 9.79 (1 H, s), 7.24 (1 H, s), 6.76 (1H, s), 4.03-3.99 (1 H, m), 2.94-2.88 (2 H, m), 2.81-2.76 (1 H, m), 2.71-2.67 (1 H, m), 1.80-1.75 (1 H, m), 1.72-1.66 (1 H, m), 1.52-1.46 (2 H, m), 1.43-1.38 (1 H, m), 1.24-1.16 (1 H, m), 1.07-1.05 (21 H, m); $^{13}$C NMR (150 MHz, CDCl$_3$) δ 195.9, 159.5, 148.2, 133.8, 133.7, 119.5, 118.8, 73.2, 41.0, 34.4, 32.2, 32.1, 20.6, 18.1 (6×), 12.4 (3×); HRMS calcd for C$_{22}$H$_{37}$O$_3$Si: 377.2506, found: m/z 377.2511 [M+H]$^+$.

6,7,8,9,10,11-Hexahydro-10-triisopropylsilyloxy-cycloocta[g]chromen-2 (2H)-one (109)

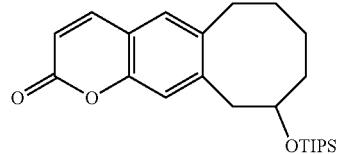

Preparation of ketenylidenetriphenylphosphorane: A stirred solution of carbethoxymethylenetriphenylphosphorane (10 g, 30 mmol) in anhydrous toluene (200 mL) was added dropwise a solution of sodium hexamethyldisilazide (17.5 mL, 2 M solution in THF, 35 mmol) at 0° C. Once the addition was complete, the mixture was heated at 60° C. for 24 h. The reaction was then allowed to cool to room temperature and filtered out. The filtrate was concentrated under reduced pressure, and then poured into ether (200 mL). The precipitate was filtered, washed with ether, and air-dried to afford ketenylidenetriphenylphosphorane (5.8 g, 64%) as pale yellow solids.

A stirred solution of salicylaldehyde 108 (4.3 g, 11.42 mmol) in anhydrous toluene (100 mL) was added the fresh prepared ketenylidenetriphenylphosphorane (5.2 g, 17.2 mmol) at room temperature. The mixture was heated at 90° C. for 1.5 h, and then concentrated under reduced pressure. The residue was purified by column chromatography on silica gel (EtOAc/hexane, 1:9) to afford the pure coumarin product 109 (3.8 g, 83%). C$_{24}$H$_{36}$O$_3$Si, colorless solid, mp 103-105° C.; TLC (EtOAc/hexane, 1:9) R$_f$=0.25; $^1$H NMR (600 MHz, CDCl$_3$) δ 7.61 (1 H, d, J=9.5 Hz), 7.18 (1 H, s), 7.10 (1 H, s), 6.33 (1 H, d, J=9.5 Hz), 4.02 (1 H, dd, J=11.9, 5.5 Hz), 3.00-2.94 (2 H, m), 2.86-2.81 (1 H, m), 2.76-2.72 (1 H, m), 1.80-1.73 (1 H, m), 1.69-1.64 (1 H, m), 1.60-1.55 (1 H, m), 1.47-1.43 (2 H, m), 1.20-1.13 (1 H, m), 1.11-1.03 (21 H, m); $^{13}$C NMR (150 MHz, CDCl$_3$) δ 161.3, 152.3, 143.3, 142.4, 138.4, 127.8, 118.1, 117.3, 115.7, 73.3, 40.8, 34.5, 32.4, 32.0, 20.6, 18.1 (6×), 12.4 (3×); HRMS calcd for C$_{24}$H$_{37}$O$_3$Si: 401.2506, found: m/z 401.2511 [M+H]$^+$.

6,7,8,9-Tetrahydro-11H-10-oxo-cycloocta[g]chromen-2 (2 H)-one (110)

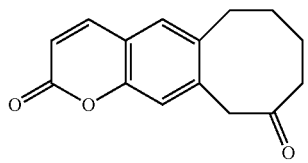 [SMILES: O=C1CCCCc2cc3ccc(=O)oc3cc2C1]

A cold (0° C.) solution of compound 109 (3.0 g, 7.5 mmol) in THF (20 mL) was treated with a solution of tetrabutylammonium fluoride (10 mL, 1 M solution in THF, 10 mmol). After stirring for 1 h at room temperature, the mixture was concentrated under reduced pressure. The residual oil was filtered through a short pad of silica gel (EtOAc/hexane, 1:4) and the filtrate was concentrated to give a colorless solid (1.67 g).

A solution of DMSO (1.5 mL, 21.2 mmol) in anhydrous CH$_2$Cl$_2$ (10 mL) was added dropwise to a stirred solution of oxalyl chloride (0.89 mL, 10.3 mmol) in anhydrous CH$_2$Cl$_2$ (10 mL) at −78° C. under an atmosphere of nitrogen. The mixture was stirred for 30 min at −78° C., and the above-prepared alcohol (1.67 g) in anhydrous CH$_2$Cl$_2$ (10 mL) was added dropwise. The mixture was stirred for additional 30 min at −78° C., and triethylamine (7.1 mL, 50.4 mmol) was added. The mixture was allowed to warm to 0° C. for 30 min, and then poured into water (40 mL). The aqueous layer was extracted with CH$_2$Cl$_2$ (5×50 mL). The combined organic extracts were washed with water (100 mL) and brine (100 mL), dried over MgSO$_4$, filtered, and concentrated under reduced pressure. The crude product was purified by column chromatography on silica gel (EtOAc/hexane, 1:4) to afford the desired product 110 (1.45 g, 78% for two steps). C$_{15}$H$_{14}$O$_3$, colorless solid, mp 127-129° C.; TLC (EtOAc/hexane, 3:7) R$_f$=0.32; $^1$H NMR (600 MHz, CDCl$_3$) δ 7.63 (1 H, d, J=9.5 Hz), 7.29 (1 H, s), 7.09 (1 H, s), 6.34 (1 H, d, J=9.5 Hz), 3.82 (2 H, s), 2.84 (2 H, t, J=5.7 Hz), 2.31 (2 H, t, J=5.6 Hz), 1.86-1.84 (2 H, m), 1.73-1.71 (2H, m); $^{13}$C NMR (150 MHz, CDCl$_3$) δ 209.9, 160.7, 152.6, 142.8, 138.2, 137.7, 129.0, 118.4, 117.7, 116.6, 48.8, 41.1, 32.3, 31.4, 24.5; HRMS calcd for C$_{15}$H$_{15}$O$_3$: 243.1016, found: m/z 243.1016 [M+H]$^+$.

6,7,8,9-Tetrahydro-10,11-didehydro-cycloocta[g]chromen-2(2H)-one (101)

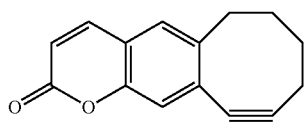 [SMILES: O=c1ccc2cc3c(cc2o1)C#CCCCC3]

A cold (−78° C.) solution of compound 110 (245 mg, 1 mmol) and N-phenyl bis(trifluoromethanesulfonimide) (393 mg, 1.1 mmol) in anhydrous THF (10 mL) was added a solution of sodium hexamethyldisilazide (0.55 mL, 2 M solution in THF, 1.1 mmol) via syringe over a period of 5 min. The mixture was stirred for 1 h at −78° C., and another batch of sodium hexamethyldisilazide (0.55 mL, 2 M solution in THF, 1.1 mmol) was added. The mixture was allowed to warm to 0° C., stirred for additional 1 h, and then quenched with methanol (1 mL). The mixture was concentrated under reduced pressure to give a yellow syrup, which was purified by column chromatography on silica gel (EtOAc/hexane, 1:9) to afford the target product 101 (72 mg, 44%). C$_{15}$H$_{12}$O$_2$, light-yellow solid, mp 98-100° C.; TLC (EtOAc/hexane, 3:7) R$_f$=0.42; $^1$H NMR (600 MHz, CDCl$_3$) δ 7.60 (1 H, d, J=9.5 Hz), 7.23 (1 H, s), 7.06 (1 H, s), 6.35 (1 H, d, J=9.5 Hz), 2.81 (2 H, br s), 2.61 (2 H, t, J=56.7 Hz), 2.13 (2 H, br s), 1.74 (2 H, br s); $^{13}$C NMR (150 MHz, CDCl$_3$) δ 161.1, 152.6, 147.4, 143.3, 128.6, 127.1, 117.5, 117.4, 116.1, 113.9, 92.5, 38.3, 33.5, 25.5, 20.5; HRMS calcd for C$_{15}$H$_{13}$O$_2$: 225.0910, found: m/z 225.0910 [M+H]$^+$.

10-Benzyl-6,7,8,9-tetrahydro-cyclooctatriazolo[5,4-g]chromen-2(2H)-one (111)

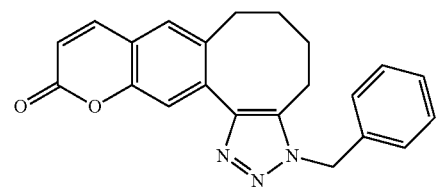 [SMILES: O=c1ccc2cc3c(cc2o1)-c1nnn(Cc2ccccc2)c1CCCC3]

A solution of compound 101 (50 mg, 0.22 mmol) in CH$_3$CN (5 mL) was treated with benzyl azide (44 μL, 0.33 mmol). After stirring for 2 h at room temperature, the mixture was concentrated under reduced pressure. The residue was purified by column chromatography on silica gel (EtOAc/hexane, 3:7) to afford the desired triazole product 111 (75 mg, 95%). C$_{22}$H$_{19}$N$_3$O$_2$, colorless solid, mp 60-62° C.; TLC (EtOAc/hexane, 1:1) R$_f$=0.35; $^1$H NMR (600 MHz, CDCl$_3$) δ 7.75 (1 H, s), 7.65 (1 H, d, J=9.4 Hz), 7.37-7.32 (3 H, m), 7.24 (1 H, s), 7.20-7.19 (2 H, m), 6.39 (1 H, d, J=9.4 Hz), 5.50 (2 H, s), 2.69-2.67 (2 H, m), 2.65-2.63 (2 H, m), 1.79-1.75 (2 H, m), 1.67-1.64 (2 H, m); $^{13}$C NMR (150 MHz, CDCl$_3$) δ 161.0, 152.4, 143.1, 136.1, 135.3, 135.0, 134.4, 129.0 (2×), 128.7, 128.4, 128.1, 127.1 (2×), 126.9, 116.7, 116.4, 51.9, 30.8, 30.6, 23.9, 20.0; HRMS calcd for C$_{22}$H$_{20}$N$_3$O$_2$: 358.1550, found: m/z 358.1548 [M+H]$^+$.

N-[2-(11-Oxo-4,6,7,11-tetrahydrochromeno[7',6':3,4]cycloocta[1,2-d][1,2,3]triazol-3(5H)-yl)]acetamido-2-deoxy-α,β-D-mannopyranose (112)

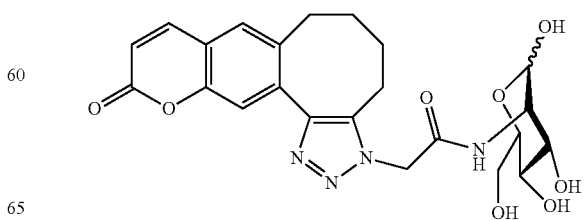

A solution of compound 101 (50 mg, 0.22 mmol) in MeOH (5 mL) and water (1 mL) was treated with N-azidoacetylmannosamine (142 mg, 0.33 mmol). After stirring for 2 h at room temperature, the mixture was concentrated under reduced pressure. The residue was purified by column chromatography on silica gel (MeOH/CH$_2$Cl$_2$, 1:9) to afford the desired triazole product 112 (98 mg, 92%). C$_{23}$H$_{26}$N$_4$O$_8$, colorless solid, mp 170-172° C. (dec.); TLC (MeOH/CH$_2$Cl$_2$, 1:8) R$_f$=0.25; $^1$H NMR (600 MHz, DMSO-d$_6$) δ 8.04 (1 H, d, J=9.5 Hz),7.59 (1 H, s), 7.52 (1 H, s), 6.48 (1 H, d, J=9.5 Hz), 5.15 (1 H, d, J=2.9 Hz), 5.11 (1 H, d, J=6.9 Hz), 4.98-4.85 (1 H, m), 4.89-4.81 (2 H, m), 4.44-4.38 (1 H, m), 3.61-3.59 (3 H, m), 3.53-3.45 (2 H, m), 3.42-3.37 (1 H, m), 3.16-3.14 (2 H, m), 2.86-2.82 (2 H, m), 2.72-2.70 (2 H, m), 1.78 (2 H, br s), 1.61 (2 H, br t, J=5.5 Hz); $^{13}$C NMR (150 MHz, DMSO-d$_6$) δ 165.2, 160.1, 151.9, 143.8, 140.6, 137.0, 135.9, 134.7, 128.8, 118.6, 116.1, 115.2, 92.5, 90.4, 72.9, 72.1, 71.0, 70.5, 68.2, 67.5, 61.5, 61.0, 54.7, 54.2, 50.0, 49.9, 30.6, 29.9, 22.8, 19.6; HRMS calcd for C$_{23}$H$_{27}$N$_4$O$_8$: 487.1829, found: m/z 487.1827 [M+H]$^+$.

Example 5

Figure 17:
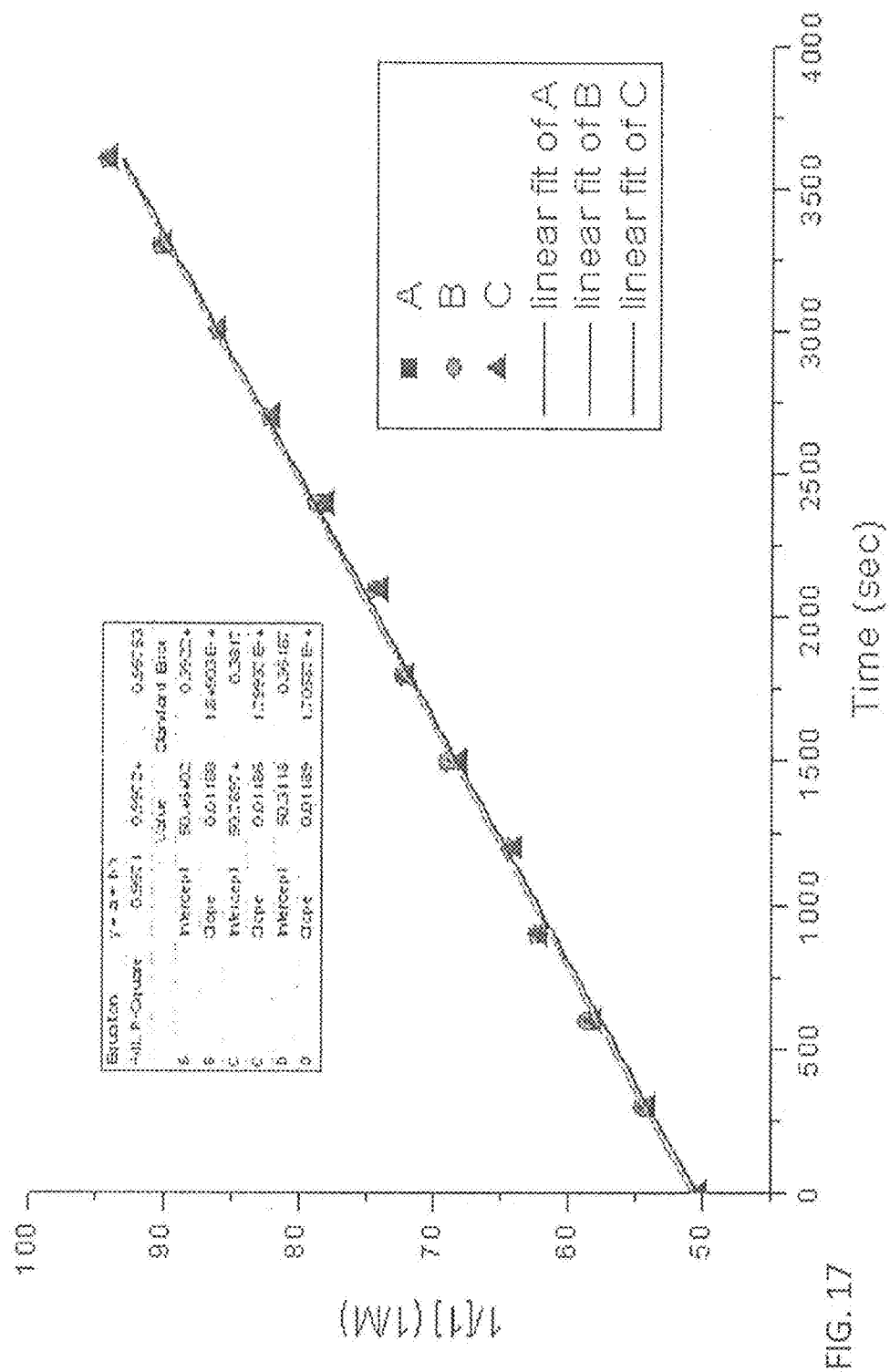
FIG. 17 shows a plot of the inverse flourogenic probe concentration as a function of reaction time of 101 and a model azide molecule.
Figure 18:
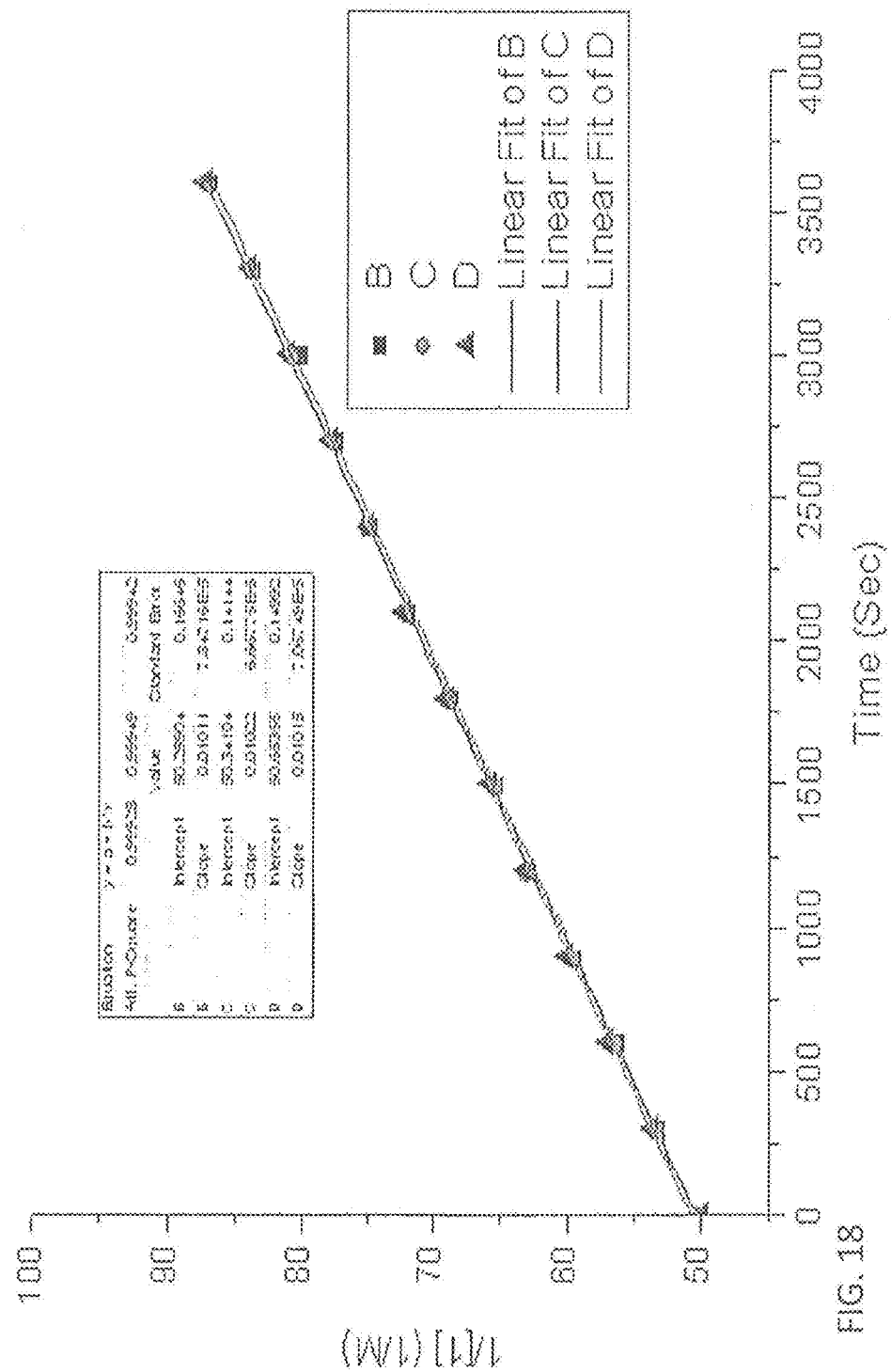
FIG. 18 shows a plot of the inverse flourogenic probe concentration as a function of reaction time of 101 and a model azide-containing glycan. Plot of 1/[101] vs. time for the reaction of compound 101 and N-azidoacetylmannosamine in a solution of $CD_3OD-D_2O$ (5:1, v/v) as monitored by $^1$H-NMR.

Measuring Reaction Scope and Kinetics of Cyclooctyne-fused Fluorogenic Probe Using on a Model Substrate To evaluate the feasibility of compound 101 as a reagent for the SPAAC-based fluorescence labeling, its reaction scope and kinetics using benzyl azide as a model substrate was first studied. The SPAAC reaction of 101 with benzyl azide in acetonitrile was completed in 2 h at room temperature to give triazole 111 in 95% yield (Scheme 100). The reactivity of 101 with benzyl azide (1:1) in CD$_3$CN was determined by integration of multiple chemical shifts in the $^1$H-NMR spectrum to yield a second-order rate constant of 0.012 M$^{-1}$s$^{-1}$ at 25° C. We also observed the cycloaddition reaction between 101 and N-azidoacetylmannosamine (ManNAz), proceeding similarly to give triazole 112 with a second-order rate constant of 0.010 M$^{-1}$s$^{-1}$ at 25° C. in a solution of CD$_3$OD-D$_2$O (5:1, v/v) (FIGS. 17 and 18).

Figure 16B:
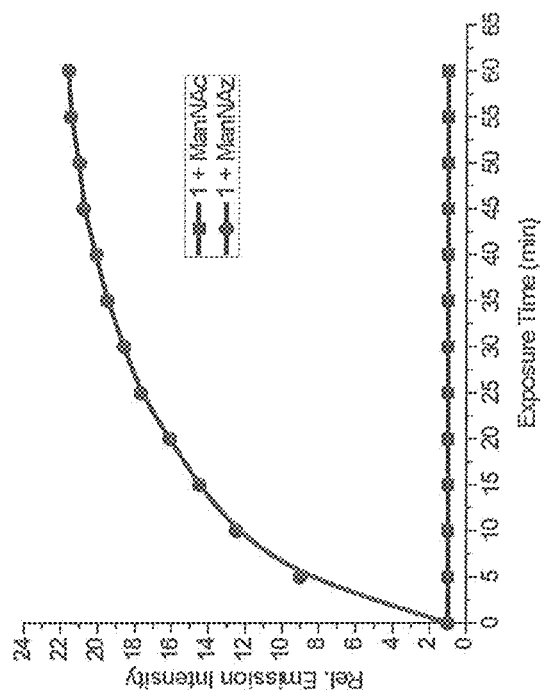
FIG. 16A, 16B shows the absorbance and emission spectra and time-course during reaction of fluorogenic probes.
Figure 16A:
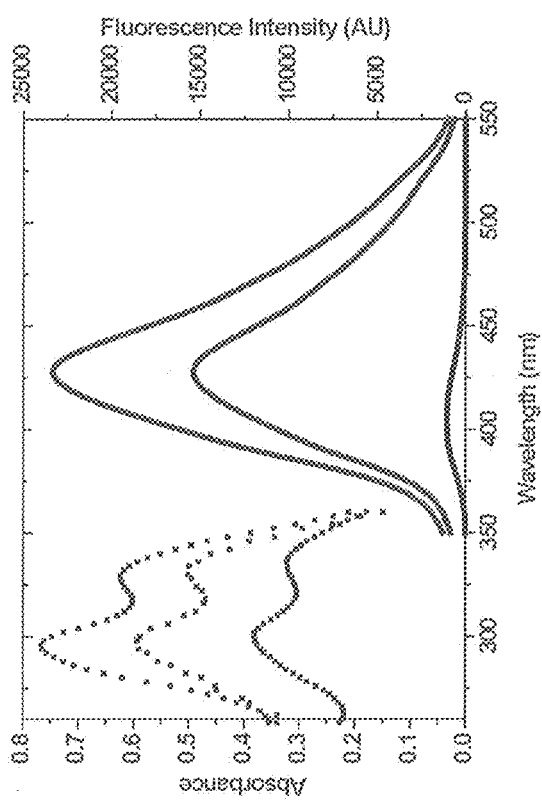

Table 3 shows the absorption and fluorescence data of 101, 111 and 112 recorded under simulated physiological conditions (PBS buffer containing 10% DMSO, pH 7.4). Formation of triazoles 111 and 112 were accompanied by a significant increase in fluorescence intensity with a large Stokes shift into a standard range for coumarin emission (FIG. 16a). Upon excitation at 330 nm, probe 101 produced a weak emission band centered at 405 nm with a low quantum yield (Φ$_f$=0.011), whereas both triazoles 111 and 112 exhibited a strong fluorescence at 435 nm with a quantum yield of 0.23 and 0.21, respectively.

To probe the SPAAC reaction under the conditions that would be more typical for biomolecule labeling, we investigated the fluorescence response and time course for the reaction of 101 with ManNAz. The experiments indicated that more than 90% of ManNAz was consumed in 40 min, and the fluorescence intensity reached a plateau in less than 1 h (FIG. 16b).

TABLE 3

Spectroscopic properties of probe 101 and triazoles 111, 112

| | Absorption (λ$_{max}$, nm) | ε (M$^{-1}$cm$^{-1}$)[a] | Emission (λ$_{max}$, nm) | Stokes shift (cm$^{-1}$) | Φ$_f$[b] |
|---|---|---|---|---|---|
| 101 | 336 | 7800 | 405 | 5070 | 0.011 |
| 111 | 328 | 12200 | 435 | 7500 | 0.23 |
| 112 | 330 | 10800 | 435 | 7320 | 0.21 |

[a]Extinction coefficient; measured at 340 nm for 101, and at 330 nm for 111 and 112.
[b]Fluorescence quantum yield; using quinine sulfate (Φ$_f$ = 0.54 ± 0.03) as standard.

FIG. 16 describes (a) Absorption and Fluorescence emission spectra (λ$_{ex}$=330 nm) of 101 (black), 111 (blue) and 112 (red) (45 μM, PBS buffer containing 10% DMSO, pH 7.4). (b) Time course of normalized fluorescence intensity at 435 nm (λ$_{ex}$=330 nm) for the ligation reaction of 101 (30 μM) with N-azidoacetylmannosamine (30 μM) in PBS buffer containing 10% DMSO.

Part A: Compound 101 and benzyl azide were predissolved in CD$_3$CN, and then mixed at equimolar concentration of 20 mM. The reaction was monitored by $^1$H-NMR analysis over a period of 1 h. The concentration of each component was determined, based on the concentration of initial compound 101, by integration at multiple chemical shifts in the $^1$H-NMR spectrum. By plotting 1/[101] (M$^{-1}$) vs. time (sec), a second order rate constant in unit of M$^{-1}$s$^{-1}$ was determined using linear regression analysis. This procedure was repeated 3 times with a concentrated of 20 mM to afford a rate constant of 0.012 M$^{-1}$s$^{-1}$ at 25° C. (FIG. 17).

FIG. 17 describes a Plot of 1/[101] vs. time for the reaction of compound 101 and benzyl azide in CD$_3$CN as monitored by $^1$H-NMR.

Part B: Compound 101 and N-azidoacetylmannosamine were predissolved in CD$_3$OD/D$_2$O (5:1, v/v), and then mixed at equimolar concentration of 20 mM. The reaction was monitored by $^1$H-NMR analysis over a period of 1 h. The concentration of each component was determined, based on the concentration of initial compound 101, by integration at multiple chemical shifts in the $^1$H-NMR spectrum. By plotting 1/[101] (M$^{-1}$) vs. time (sec), a second order rate constant in unit of M$^{-1}$s$^{-1}$ was determined using linear regression analysis. This procedure was repeated 3 times with a concentrated of 20 mM to afford a rate constant of 0.010 M$^{-1}$s$^{-1}$ at 25° C. (FIG. 18).

FIG. 18 describes a Plot of 1/[101] vs. time for the reaction of compound 101 and N-azidoacetylmannosamine in a solution of CD$_3$OD-D$_2$O (5:1, v/v) as monitored by $^1$H-NMR.

Example 6

Live Cell Imaging of Stained Samples Using Cyclooctyne-fused Fluorogenic Probe 101

Figure 19:
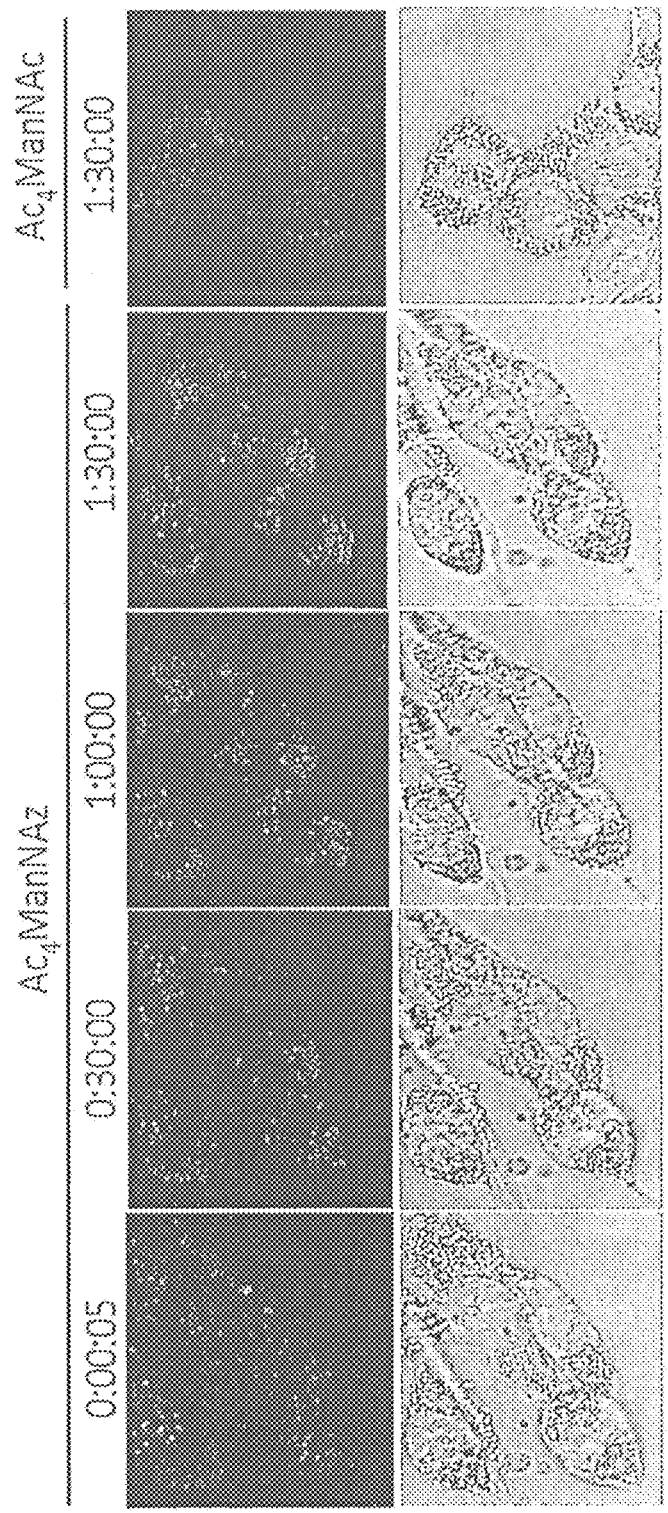
FIG. 19 shows time-lapse fluorescence and overlaid images of living CL1-5 cells incubated with 200 µM of $Ac_4$ManNAz and labeled with 100 µM of probe 101 under no-wash and no-fixation conditions.
Figure 20:
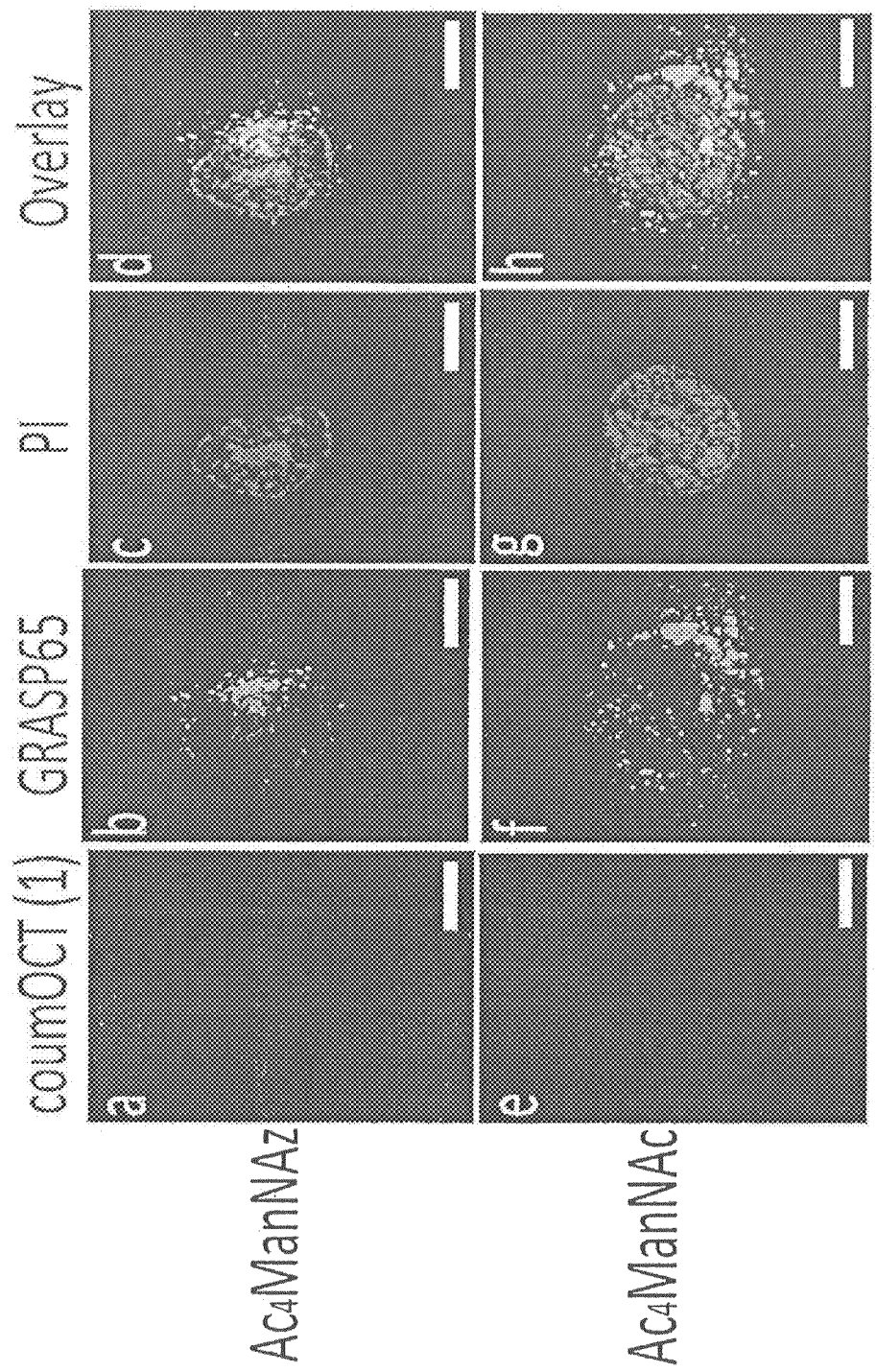
FIG. 20 shows localization of probe-labeled sialyl glycoconjugates in CL1-5 cells as visualized by confocal microscopy.
Figure 22:
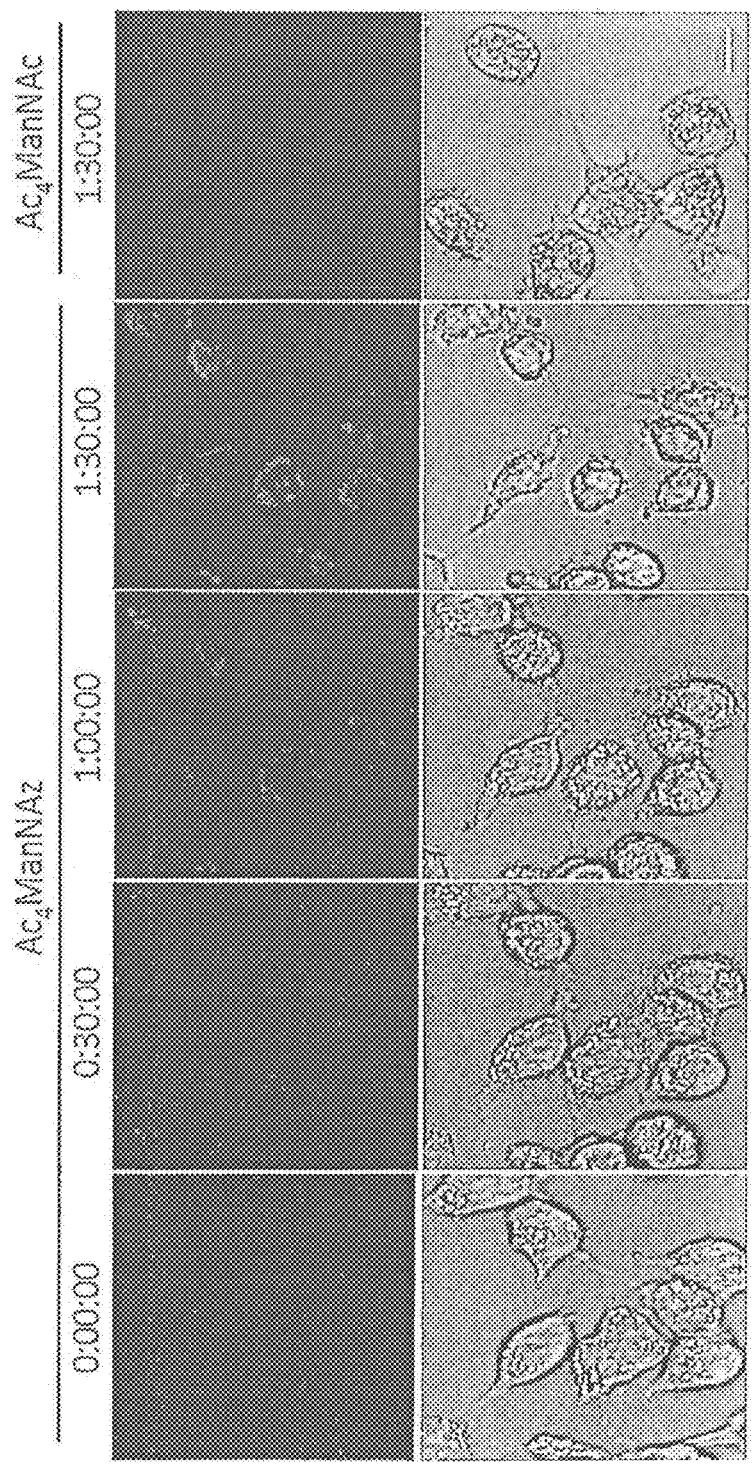
FIG. 22 shows time-lapse fluorescence and overlaid images of living CL1-5 cells incubated with 200 µM of $Ac_4$ManNAz and labeled with 100 µM of probe 101.

The performance of 101 in live cell imaging was evaluated. For this purpose, highly sialylated lung cancer cells, CL1-5, were cultured in the presence of peracetylated N-azidoacetylmannosamine (Ac$_4$ManNAz) for 3 days to metabolically produce the azido-sialic acid expressed cells. As a negative control, CL1-5 cells were grown in the presence of peracetylated N-acetylmannosamine (Ac$_4$ManNAc). A time course experiment was conducted by exposing the cells at 30-min intervals under no-wash and no-fixation conditions (FIG. 19, FIG. 22). The Ac$_4$ManNAz treated cells showed a time-dependent increase of fluorescence intensity (upper row: cyan, bottom row: blue) and then reached saturation for 1.5 h incubation. In contrast, the control cells exhibited almost no fluorescence staining, supporting that background labeling is negligible. Furthermore, the localization of azido-containing glycoconjugates in living cells was visualized by confocal microscopy. The cells labeled by probe 101 were subsequently stained with anti-GRASP65 followed by FITC-conjugated anti-rabbit for Golgi and propidium iodide (PI, a nuclei marker). The blue fluorescent signal derived from the coumarin probe apparently showed in $Ac_4ManNAz$ treated cells without addition of $Ac_4ManNAc$ (FIG. 20). The labeled sialylated glycoconjugates were visualized in the cytosol using coumOCT probe (blue fluorescence), and significantly overlapped with the Golgi apparatus (green staining), but not in the nucleus (red staining).

FIG. 19 describes Time-lapse fluorescence and overlaid images of living CL1-5 cells incubated with 200 μM of $Ac_4ManNAz$ and labeled with 100 μM of probe 101 under no-wash and no-fixation conditions: fluorescence image of cells (upper row) and bright field overlaid image of cells (bottom row). Control: cells incubated with $Ac_4ManNAc$. (Scale bar: 10 μm)

FIG. 20 describes localization of probe-labeled sialyl glycoconjugates in CL1-5 cells as visualized by confocal microscopy. Cells incubated with 200 μM of $Ac_4ManNAz$ or $Ac_4ManNAc$ were labeled with 100 μM of 101 (blue) and stained with anti-GRASP65 followed by FITC-conjugated anti-rabbit (for Golgi, green) and propidium iodide (for nucleus, red). (Scale bar: 10 μm)

Figure 21:
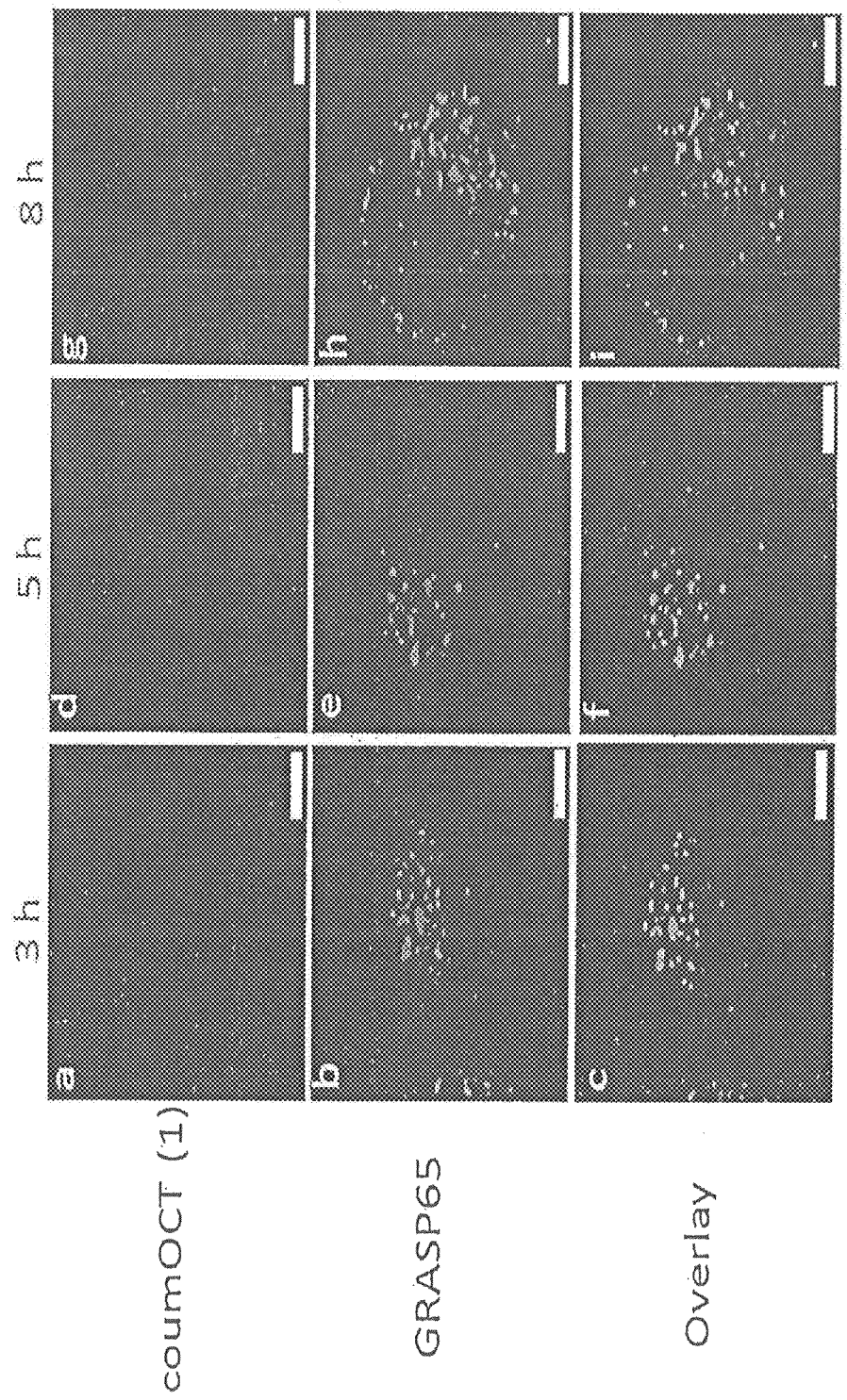
FIG. 21 shows high contrast fluorescence imaging of glycoconjugates trafficking using coumOCT (101) of SPAAC in cells.
Figure 23:
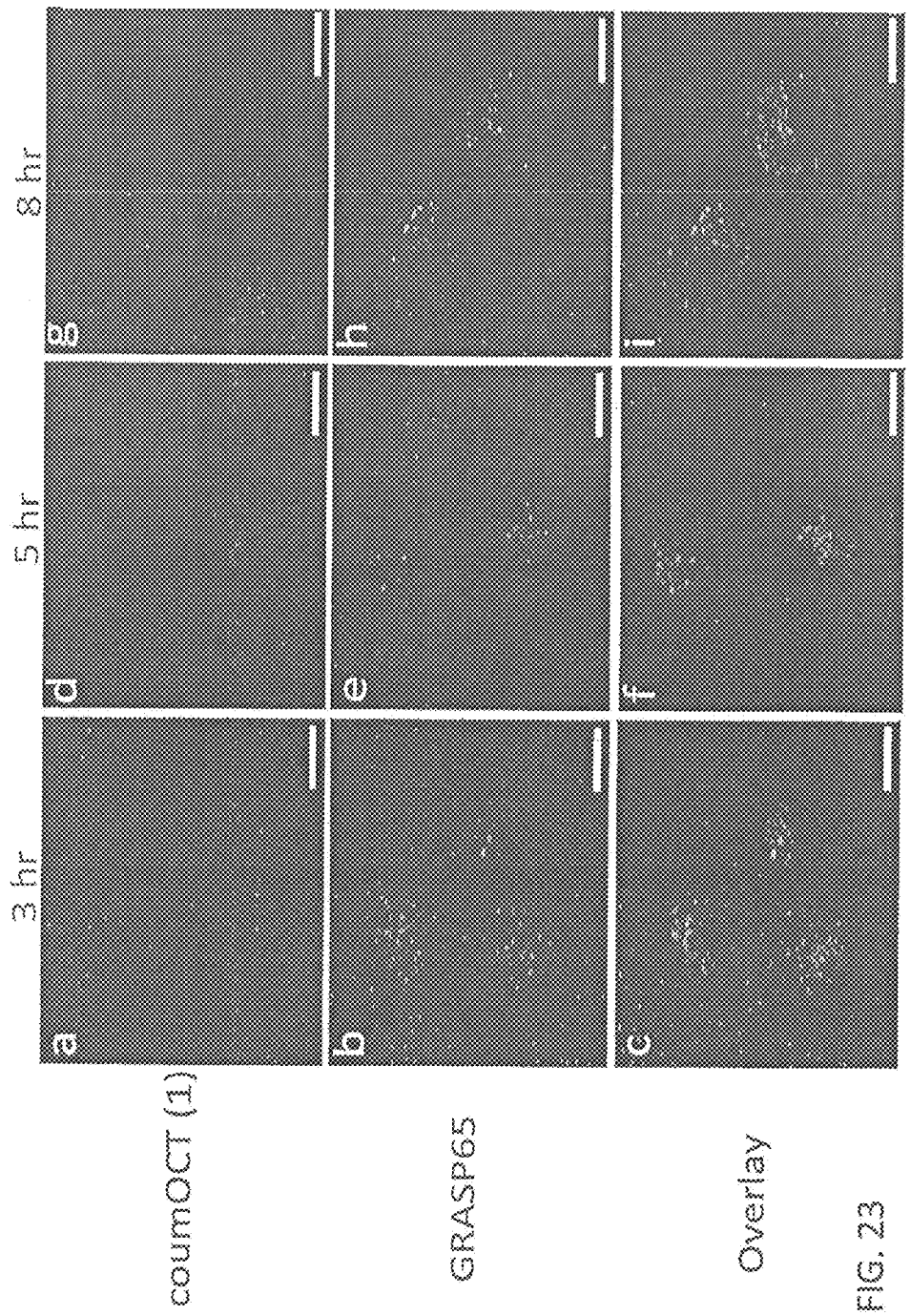
FIG. 23 shows fluorescence imaging of glycoconjugates trafficking using coumOCT (101) of SPAAC in cells.

Surprisingly, the blue fluorescence was observed not only on the cell surface but also inside the cells in the time-lapse experiment. We therefore examined whether coumOCT 101 could be a cell-permeable probe that could be utilized for direct intracellular labeling in live cells. Toward this goal, CL1-5 cells were incubated with $Ac_4ManNAz$ for 1 h and subsequently removed excess $Ac_4ManNAz$. We then performed the imaging to monitor the trafficking of the sialylated glycoconjugates. As shown in FIG. 21, the sialylated glycoconjugates were readily imaged by using coumOCT and significantly overlapped with the Golgi apparatus (red) at initial stage. However, the appearance of blue fluorescence signal was detected on the cell surface after 5 h. The intensity of fluorescence increased over time, and reached saturation at 8 h (FIG. 21 and FIG. 23). Our results indicate that coumOCT is not only a cell-permeable probe but also specific for direct labeling of endogenous azido-bearing glycoconjugates in live cells.

FIG. 21 describes fluorescence imaging of glycoconjugates trafficking using coumOCT (1) of SPAAC in cells. CL1-5 cells were incubated with 500 μM of $Ac_4ManNAz$ for 1 h and subsequently washed with PBS buffer to remove excess $Ac_4ManNAz$. The sugar-treated cells were incubated in culture medium for 3 h, 5 h and 8 h, and then labeled with 100 μM of probe 101 for 0.5 h under SPAAC conditions, respectively. The Golgi was labeled with anti-GRASP65 followed by Cy3-conjugated anti-rabbit. (Scale bar: 5 μm)

Time Course Measurements by Fluorescence Spectroscopy.

A solution of probe 101 (0.075 μmol) and N-azidoacetylmannosamine (0.075 μmol) in a mixture of 10% DMSO in PBS buffer (2.5 mL) was incubated at 37° C. The fluorescence emission intensity at 435 nm upon excitation at 330 nm was monitored in 5 min intervals. For each point the fluorescence intensity was measured over a period of 5 sec and averaged over a total of 3 points. In a control experiment the same conditions were used except that N-acetylmannosamine (0.075 μmol) was added to the solution.

Time-Lapse Microscopic Analysis of Fluorescence Labeling in Live Cells.

To observe the fluorescence labeled azido-glycoconjugates in cells, CL1-5 cells were seeded on chamber slide ($2.5 \times 10^4$ cells/0.5 mL per wells) and incubated in culture medium (RPMI-1640 supplemented with 10% FBS, 100 U/mL penicillin, 100 μg/mL streptomycin, 1 mM L-glutamine and 1 mM sodium pyruvate) with either 200 μM of control sugar (peracetylated N-acetylmannosamine, $Ac_4ManNAc$) or azido-sugar (peracetylated N-azidoacetylmannosamine, $Ac_4ManNAz$) for 3 days.

For Time-lapse imaging of live cells, experiments were carried out using a confocal microscope (TCS-SP5-MP-SMD, Leica) equipped with an incubator to keep the cells in culture conditions. Prewashed cells were incubated with 100 μM of probe 101 in PBS with 10% DMSO and fluorescence imaging of live cells from the previous experiment over 1.5 h. The images were acquired at 450 nm emission and in 5-min intervals.

For comparing the localization of azido-glycoconjugates, probe-labeled cells were washed with PBS, fixed with 3% paraformaldehyde in PBS at room temperature for 20 min, permeablized with 0.2% Triton X-100 in PBS at room temperature for 20 min, and blocked with 3% bovine serum albumin in PBS at room temperature for 30 min. Cells were stained with anti-GRASP65 followed by FITC-conjugated anti-rabbit for Golgi, and propidium iodide (PI) for nucleus.

FIG. 22 describes time-lapse fluorescence and overlaid images of living CL1-5 cells incubated with 200 μM of $Ac_4ManNAz$ and labeled with 100 μM of probe 101 under no-wash and no-fixation conditions: fluorescence image of cells (upper row) and bright field overlaid image of cells (bottom row). Control: cells incubated with $Ac_4ManNAc$. (Scale bar: 25 μm)

Microscopic Analysis of Sialylconjugates Trafficking by Fluorescence Labeling in Live Cells.

To observe the fluorescence labeled sialylconjugates in cells dependent on different time, CL1-5 cells were seeded on chamber slide ($2.5 \times 10^4$ cells/0.5 mL per wells) and incubated in culture medium (RPMI-1640 supplemented with 10% FBS, 100 U/mL penicillin, 100 μg/mL streptomycin, 1 mM L-glutamine and 1 mM sodium pyruvate) with 500 μM of azido-sugar (peracetylated N-azidoacetylmannosamine, $Ac_4ManNAz$) for 1 h. Cells were washed three times with PBS and then incubated in culture medium. After 3 h, 5 h and 8 h, cells were incubated with 100 μM of coumOCT (101) in PBS with 10% DMSO for 30 min at 37° C. For fluorescence imaging of live cells, experiments were carried out using a confocal microscope (TCS-SP5-MP-SMD, Leica) equipped with an incubator to keep the cells in culture conditions.

For comparing the localization of sialylconjugates, probe-labeled cells were washed with PBS, fixed with 3% paraformaldehyde in PBS at room temperature for 20 min, permeablized with 0.2% Triton X-100 in PBS at room temperature for 20 min, and blocked with 3% bovine serum albumin in PBS at room temperature for 30 min. Cells were further stained with anti-GRASP65 followed by Cy3-conjugated anti-rabbit for Golgi.

FIG. 23 describes fluorescence imaging of glycoconjugates trafficking using coumOCT (101) of SPAAC in cells. CL1-5 cells were incubated with 500 μM of $Ac_4ManNAz$ for 1 h and subsequently washed with PBS buffer to remove excess $Ac_4ManNAz$. The sugar-treated cells were incubated in culture medium for 3 h, 5 h and 8 h, and then labeled with 100 μM of probe 101 for 0.5 h under SPAAC conditions, respectively. The Golgi was labeled with anti-GRASP65 followed by Cy3-conjugated anti-rabbit. (Scale bar: 10 μm)

Example 7

Dual-labeling Experiment

A dual-labeling experiment was performed using SPAAC in combination with CuAAC for the concurrent fluorescence labeling of two different metabolically incorporated glycoconjugates. Peracetylated N-acetylmannosamine ($Ac_4$ManNAc) and peracetylated N-acetylglucosamine ($Ac_4$GlcNAc) were employed as the control sugars. ManNAc is converted metabolically to sialic acid that is found as a terminal monosaccharide of glycoproteins and glycolipids in cell, whereas GlcNAz is an internal monosaccharide that abundant in the N- and O-linked glycans produced in the endoplasmic reticulum and Golgi. CL1-5 cells were incubated in the presence of both alkyne-containing sugar ($Ac_4$ManNAl) and azido-containing sugar ($Ac_4$GlcNAz) for three days. The cells were stained by SPAAC with coumOCT (for azido sugars), followed by CuAAC with AzBOCEt[6j] (for alkynyl sugars), and investigated by confocal microscopy (FIG. 24).

The cells treated both azido- and alkynyl-sugars showed a distinct pattern (FIG. 24a, 24b, 24c) in both fluorescence channels, whereas omission of either sugar resulted in no labeling in the corresponding channel (FIG. 24d, 24e, 24f and FIG. 24g, 24h, 24i). Interestingly, the imaging experiments revealed that ManNAl and GlcNAz labeled species exhibited considerably at the same localization, possibly in the Golgi. In addition, the expressed alkynyl-labeled sialylated glycoconjugates were observed clearly on the cell surface and partially in the cytosol on AzBOCEt labeling, whereas the GlcNAz-labeled glycans were shown only in the cytosol using coumOCT probe. Although sialic acid is usually attached to N- and O-linked glycans by terminal glycosylation, incorporation of unnatural GlcNAz to glycoproteins may affect the specificity and efficiency of glycosyltransferase for further glycosylations. Thus, the immature aberrant glycoproteins may be transported to cytosol for degradation. These findings validate that coumOCT and AzBOCEt can be employed as fluorescence-forming probes for simultaneous detection of azido- and alkyne-labeled metabolically incorporated glycoconjugates within a single cell by SPAAC and CuAAC triazole formation chemistries.

Figure 24A:
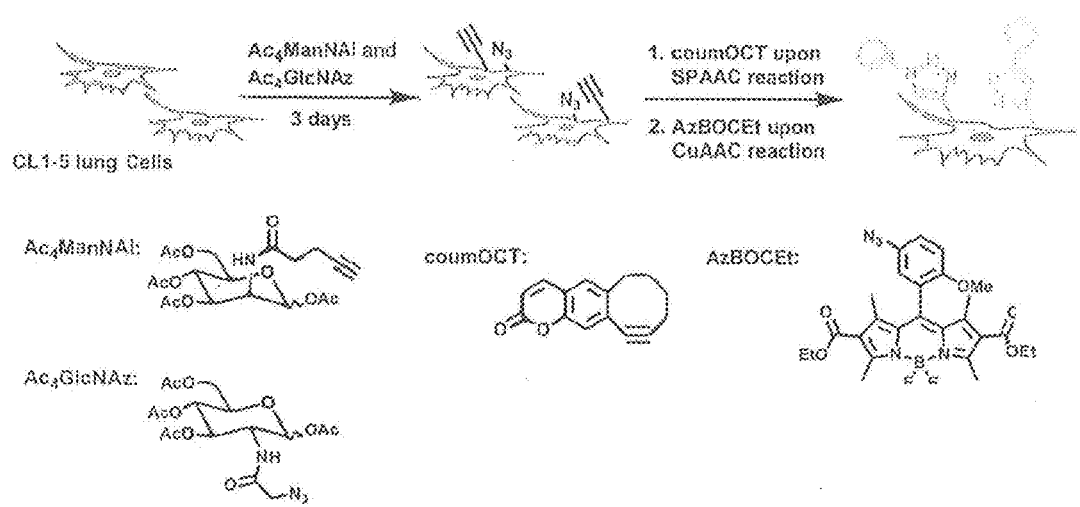
FIG. 24A, 24B shows dual fluorescence labeling in cells with coumOCT (1), AzBOCEt and imaging by confocal microscopy. Dual fluorescence labeling in cells with coumOCT (1), AzBOCEt and imaging by confocal microscopy.
Figure 24B:
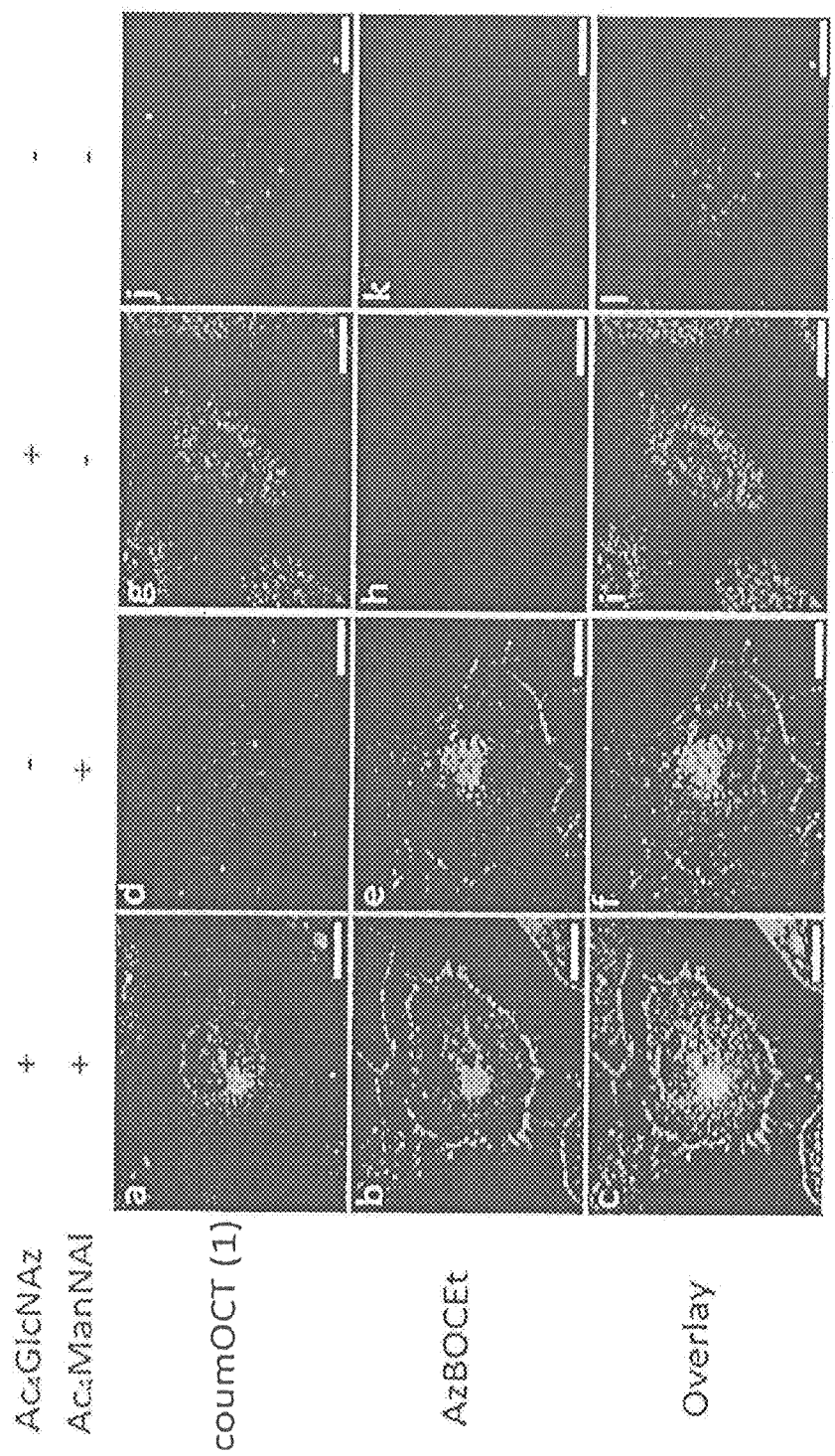

FIG. 24A, 24B shows dual fluorescence labeling in cells with coumOCT (1), AzBOCEt and imaging by confocal microscopy. (A) Illustration of the cell labeling experiments using $Ac_4$ManNAl, $Ac_4$GlcNAz, 101 and AzBOCEt. CL1-5 cells were incubated with 100 μM of $Ac_4$ManNAl and $Ac_4$GlcNAz or control sugars ($Ac_4$ManNAc and $Ac_4$GlcNAc) for 3 days, which were treated with 100 μM of probe 101 for 0.5 h under SPAAC conditions, and then incubated with 0.1 μM of AzBOCEt for 1 h under CuAAC conditions. (B) Dual fluorescence imaging in CL1-5 cells. These glycoconjugates were labeled with probe 101 (cyan) for azido-containing glycoconjugates and AzBOCEt (green) for alkyne-containing glycoconjugates. (Scale bar: 10 μm) Microscopic Analysis of Dual Fluorescence Labeling in Cells.

CL1-5 cells were seeded on chamber slide ($2.5 \times 10^4$ cells/0.5 mL per wells) and incubated in culture medium (RPMI-1640 supplemented with 10% FBS, 100 U/mL penicillin, 100 μg/mL streptomycin, 1 mM L-glutamine and 1 mM sodium pyruvate) for 3 days with either 100 μM of alkynyl-sugar (peracetylated alkynyl-N-acetylmannosamine, $Ac_4$ManNAl or azido-sugar (peracetylated N-azidoacetylglucosamine, $Ac_4$GlcNAz) or both or without sugar as negative control. Cells were washed three times with PBS and then incubated with 100 μM of coumOCT (101) in PBS with 10% DMSO for 30 min at 37° C. After three washes with PBS with 10% DMSO, followed by fixed with 3% paraformaldehyde in PBS at room temperature for 20 min, the cells were incubated with 0.1 μM of AzBOCEt, 100 μM of ligand, 1 mM of $CuSO_4$, and 2 mM of sodium ascorbate in PBS with 50% ethanol at room temperature for 1 h and fluorescence images of cell were carried out using a confocal microscope (TCS-SP5-MP-SMD, Leica).

Example 8

Figure 25:
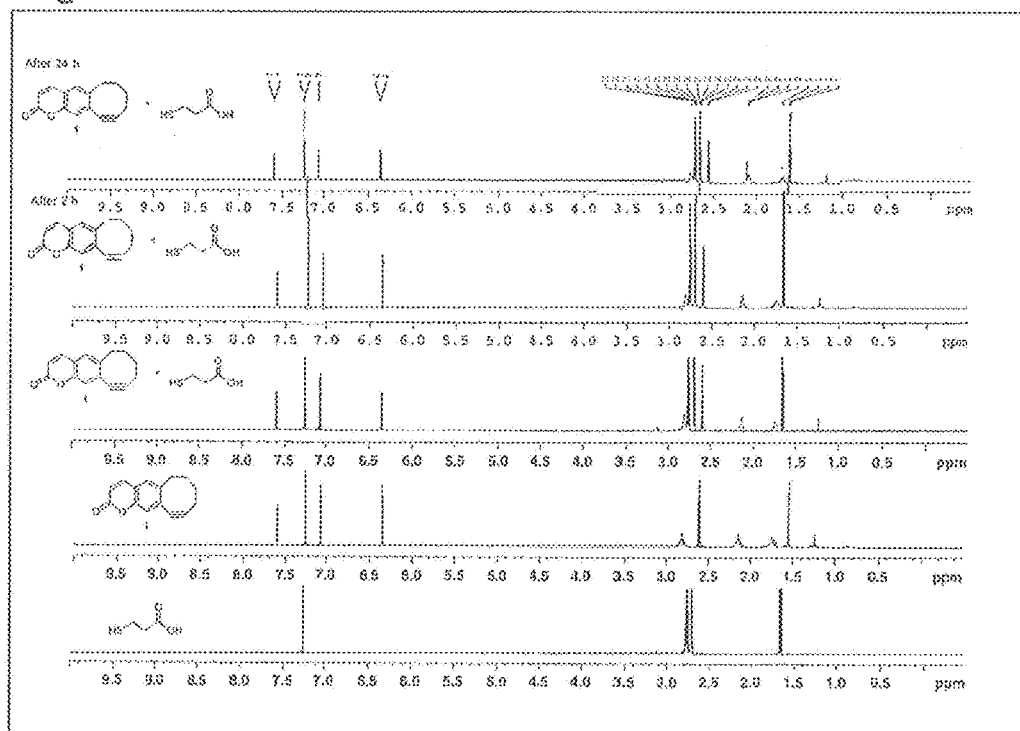
FIG. 25 shows $^1$H-NMR spectrum in $CDCl_3$ of compound 101 and 3-mercaptopropionic acid.

Stability of Compound (101) and Compound (111) in Presence of 3-Mercaptopropionic Acid A potential problematic side reaction of cyclooctynes is the addition with proteinic or endogenous thiols to the corresponding vinyl sulfides. To test whether potential non-specific stainings of 101 and the corresponding triazole 111 may occur due to additions of the SH groups to the triple bond or double bond by proteinic or endogenous thiols, the experiment was performed by incubation of 101 and 111 with 3-mercaptopropionic acid in $CDCl_3$ (FIGS. 25 and 26). The NMR spectral analyses suggested that 101 and 111 were inactive to the thiol-yne or thiol-ene addition with 3-mercaptopropionic acid. These results show that the application of 101 as a fluorescence-forming probe allows the surprising detection of metabolically incorporated glycoconjugates in living cells without non-specific staining by thiol-yne addition, and the formed triazoles would not undergo thiol-ene addition to quench fluorescence.

A solution of compound 101 and compound 111 (25 mM in $CDCl_3$) was incubated with a solution of 3-mercaptopropionic acid (32 mM in $CDCl_3$) at room temperature (25° C.). The reaction was monitored by $^1$H-NMR analysis over a period of 24 h. $^1$H-NMR analysis suggested that compound 101 and compound 111 have high stability in the presence of thiols due to no substitution effect on compound 101 and compound 111 with 3-mercaptopropionic acid by $^1$H-NMR analysis (FIG. 25 and FIG. 26).

FIG. 25 show $^1$H-NMR spectrum in $CDCl_3$ of compound 101 and 3-mercaptopropionic acid alone, and $^1$H-NMR spectrum of compound 101 was treated with 3-mercaptopropionic acid at 25° C. for 0 h, 2 h and 24 h.

FIG. 26 shows $^1$H-NMR spectrum in $CDCl_3$ of compound 111 and 3-mercaptopropionic acid alone, and $^1$H-NMR spectrum of compound 111 was treated with 3-mercaptopropionic acid at 25° C. for 24 h.

This disclosure describes a new SPAAC-based fluorescence-forming probe coumOCT (101) for real-time imaging in living cells under no-wash and no-fixation conditions. The SPAAC reactions of 101 with benzyl azide and N-azidoacetylmannosamine proceeded with a rate constant of 0.012 $M^{-1}s^{-1}$ in $CD_3CN$ and 0.010 $M^{-1}s^{-1}$ in a solution of $CD_3OD$-$D_2O$ (5:1, v/v), respectively. The triazole products 111 and 112 showed 20-fold increase in quantum yield ($\Phi_f$=0.23 and $\Phi_f$=0.21) compared to unreacted 101. Furthermore, this disclosure establishes that 101 is a fluorescence turn-on probe for imaging azido-containing glycoconjugates in living cells. The SPAAC reaction is spontaneous and no washing steps are needed. Moreover, probe 101 is nontoxic and cell-permeable with no problem of background labeling, which allows the simultaneous labeling of two different sugars in combination with AzBOCEt under CuAAC. This disclosure represents a significant advance in cell imaging, and should be potentially applicable to real-time detection of biochemical events in vivo.

Example 9

Synthesis of CoumFSA (601)

Sialic acid (Neu5Ac) was treated with acetyl chloride to give the chloride intermediate in more than 90% yield according to $^1$H NMR analysis. The crude product was dissolved in pyridine and heated to 50° C., followed by concentration and trituration to remove pyridine hydrochloride, giving the glycal 201 with 78% overall yield from sialic acid. Neu5Boc2en 203 was synthesized from compound 201 by treating it with $Boc_2O$ to produce N-acetyl-N-Boc protected product 202, which was deacetyled under Zemplén condition followed by acetylation provided N-Boc protected compound 203. Bromohydroxylation of 203 with N-bromosuccinimide (NBS) and water in MeCN at 80° C. gave the bromohydrins 204a and 204b (91%; 204a/204b=3.1:1). Treatment of 204a with 1,8-diazabicyclo[5.4.0]undec-7-ene (DBU) gave the epoxide 205 (86%). Glycosyl bromide 206 with a hydroxyl group at C-3 was prepared from 205. The alpha-glycoside 207 was obtained in 52% yield with sodium methylumbelliferone in anhydrous DMF. After removal of the Boc group of 207 with trifluoroacetic acid (TFA) in water, the obtained amine salt was treated with 4-pentynoic acid in the presence of base DIPEA and coupling reagent HBTU in DMF to afford the alkynyl product 208. The fluoro compound 209 was carried out by conversion of 208 into the triflate allowed reaction with tris(dimethylamino)sulfonium difluorotrimethyl silicate (TASF) in refluxing THF. Deprotection of 209 under alkaline condition produced CoumFSA (601) in 75% yield after purification on a reverse-phase column.

Example 10

Synthesis of DFSA (501)

Fluorohydroxylation of compound 203 with Selectfluor in aqueous $MeNO_2$ at room temperature gave the fluorohydrins 210a and 210b (59%; 210a/210b=1.3:1). Treatment of 210a with diethylaminosulfur trifluoride (DAST) gave the difluoro compounds 211a and 211b (75%; 211a/211b=5.3:1). After removal of the Boc group of 211a with trifluoroacetic acid (TFA) in water, the obtained amine salt was treated with 4-pentynoic acid in the presence of base DIPEA and coupling reagent HBTU in DMF to afford the alkynyl product 212. Deprotection of 212 under alkaline condition produced DFSA (501) in 55% yield after purification on a reverse-phase column.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present present disclosure, as defined in the following claims.

REFERENCES

Rostovtsev, V. V.; Green, L. G.; Fokin, V. V.; Sharpless, K. B. "A stepwise Huisgen cycloaddition process: copper(I)-catalyzed regioselective "ligation" of azides and terminal alkynes." *Angew. Chem. Int. Ed.* 2002, 41, 2596-2599.

Zhou, Z.; Fahrni, C. J. A "Fluorogenic probe for the copper(I)-catalyzed azide-alkyne ligation reaction: Modulation of the fluorescence emission via $3(n,\pi^*)–1(\pi,\pi^*)$ Inversion." *J. Am. Chem. Soc.* 2004, 126, 8862-8863.

Sivakumar, K.; Xie, F.; Cash, B. M.; Long, S.; Barnhill, H. N.; Wang, Q. "A fluorogenic 1,3-dipolar cycloaddition reaction of 3-azidocoumarins and acetylenes." *Org. Lett.* 2004, 24, 4603-4606.

Prescher, J. A.; Bertozzi, C. R. "Chemistry in living systems." *Nat. Chem. Biol.* 2005, 1, 13-21.

Sawa, M.; Hsu, T.-L.; Itoh, T.; Sugiyama, M.; Hanson, S. R.; Vogt, P. K.; Wong, C.-H. "Glycoproteomic probes for fluorescent imaging of fucosylated glycans in vivo." *Proc. Nat. Acad. Sci. U.S.A.*, 2006, 103, 12371-12376.

Hsu, T.-L.; Hanson, S. R.; Kishikawa, K.; Wang, S.-K.; Sawa, M.; Wong, C.-H. "Alkynyl sugar analogs for the labeling and visualization of glycoconjugates in cells." *Proc. Natl. Acad. Sci. U.S.A* 2007, 104, 2614-2619.

Loudet, A.; Burgess, K. "BODIPY dyes and their derivatives: syntheses and spectroscopic properties." *Chem. Rev.* 2007, 107, 4891-4932.

Wu, P.; Fokin, V. V. "Catalytic azide-alkyne cycloaddition: reactivity and Applications." *Aldrichim. Acta* 2007, 40, 7-17.

Ulrich, G.; Ziessel, R.; Harriman, A. "The chemistry of fluorescent bodipy dyes: Versatility unsurpassed." *Angew. Chem. Int. Ed.* 2008, 47, 1184-1201.

Li, L.; Han, J.; Nguyen, B.; Burgess, K. "Syntheses and spectral properties of functionalized, water-soluble BODIPY derivatives." *J. Org. Chem.* 2008, 73, 1963-1970.

Xie, F.; Sivakumar, K.; Zeng, Q. B.; Bruckman, M. A.; Hodges, B.; Wang, Q. "A fluorogenic 'click' reaction of azidoanthracene derivatives." *Tetrahedron* 2008, 64, 2906-2914.

Baskin, J. M.; Amacher, S. L.; Bertozzi, C. R." In vivo imaging of membrane-associated glycans in developing zebrafish." *Science* 2008, 320, 664-667.

Best, M. D. "Click chemistry and bioorthogonal reactions: unprecedented selectivity in the labeling of biological molecules." *Biochemistry* 2009, 48, 6571-6584.

Sletten, E. M.; Bertozzi, C. R. "Bioorthogonal chemistry: fishing for selectivity in a sea of Functionality." *Angew. Chem. Int. Ed.* 2009, 48, 6974-6998.

Li, J.; Hu, M.; Yao, S. Q. "Rapid synthesis, screening, and identification of xanthone and xanthene-based fluorophores using click chemistry." *Org. Lett.* 2009, 11, 3008-3011.

Le Droumaguet, C.; Wang, C.; Wang, Q. "Fluorogenic click reaction." *Chem. Soc. Rev.* 2010, 39, 1233-1239.

Qi, J.; Han, M.-S.; Chang, Y.-C.; Tung, C.-H. "Developing visible fluorogenic 'click-on' dyes for cellular imaging." *Bioconjugate Chem.* 2011, 22, 1758-1762.

Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." *Sci. China Chemistry* 2012, 55, 125-130.

Boens, N.; Leen, V.; Dehaen, W. "Fluorescent indicators based on BODIPY." *Chem. Soc. Rev.* 2012, 41, 1130-1172.

Shieh, P.; Hangauer, M. J.; Bertozzi, C. R. "Fluorogenic azidofluoresceins for biological imaging." *J. Am. Chem. Soc.* 2012, 134, 17428-17431.

Kamkaew, A.; Lim, S. H.; Lee, H. B.; Kiew, L. V.; Chung, L. Y.; Burgess, K. "BODIPY dyes in photodynamic therapy." *Chem. Soc. Rev.* 2013, 42, 77-88.

Herner, A.; Nikić, I.; Kállay, M.; Lemke, E. A.; Kele, P. "A new family of bioorthogonally applicable fluorogenic labels." *Org. Biomol. Chem.* 2013, 11, 3297-3306.

Chauhan, D. P.; Saha, T.; Lahiri, M.; Talukdar, P. "BODIPY based 'click on' fluorogenic dyes: application in live cell imaging." *Tetrahedron Lett.* 2014, 55, 244-247.

We claim:

1. A compound of formula (V) or (VI):

Formula (V)

Formula (VI)

wherein L is selected from the group consisting of umbelliferyl, coumarin oxide, triflate, mesylate, tosylate, alkoxy, phenoxy, benzoate, pentafluorophenoxy, or 4-nitrophenoxy.

2. The compound of claim 1, wherein L is umbelliferyl.

3. The compound of claim 2, wherein the compound is compound 601:

4. A method for imaging the active site of a sialidase enzyme comprising:
  (a) contacting a compound of claim 1 with a sample suspected of comprising the sialidase enzyme under conditions for ligation of the compound to an active site of the sialidase enzyme to form a covalent bond product,
  (b) contacting the covalent bond product with an azide-containing fluorogenic probe of formula (I) to form a fluorogenic triazole product,
  (c) measuring a fluorescent signal released from the triazole product;
wherein the azide-containing fluorogenic probe of formula (I) has the formula:

wherein each instance of $G^1$, $G^2$, $G^3$, $G^5$, $G^6$, $G^7$ and $G^8$ is independently hydrogen, optionally substituted $C_{1-6}$alkyl, optionally substituted $C_{1-6}$alkenyl, optionally substituted $C_{1-6}$alkynyl, optionally substituted aryl, optionally substituted acyl, $-OR^A$, $-CH_2OR^A$, $-OC(O)R^A$, $-SR^A$, $-N(R^B)_2$, $-N(R^A)C(O)R^A$, $-C(O)N(R^B)_2$, $-CN$, $-NO_2$, $-C(O)R^A$, $-C(O)OR^A$, $-S(O)R^A$, $-SO_2R^A$, $-SO_3R^A$, $-SO_2N(R^B)_2$, and $-NHSO_2R^B$;

each $R^A$ is independently selected from hydrogen, optionally substituted $C_1$-$C_6$alkyl, optionally substituted alkenyl, optionally substituted alkynyl, optionally substituted heterocyclyl, and optionally substituted aryl;

each $R^B$ is independently selected from hydrogen, optionally substituted $C_1$-$C_6$alkyl, optionally substituted alkenyl, optionally substituted alkynyl, optionally substituted heterocyclyl, and optionally substituted aryl, or two $R^B$ taken together with the intervening nitrogen form a heterocycle;

each instance of $G^{4a}$ and $G^{4b}$ is fluoro, alkyl, alkoxy, aryloxy, or alkynyl, wherein alkyl and alkoxy groups are unbranched, saturated, and have 1-4 carbon atoms; aryl groups and aryl groups of aryloxy can be either carbocyclic aryl or heterocyclic aryl; carbocyclic aryl groups have a total of 6-20 carbon atoms, including carbon atoms of substituents; heterocyclic aryl groups have a total of 5-20 carbon atoms, including carbon atoms of substituents; carboalkoxy groups are alkyl esters of a carboxylic acid wherein alkyl groups are as defined above; each alkyl, aryl, alkoxy, aryloxy, benzo, and carboalkoxy, independently, may be unsubstituted or substituted with one or more substituent; alkyl substituents are halo, hydroxyl, amino, or aryl; aryl substituents are halo, hydroxyl, amino, alkyl, aryl, nitro, or carboxyl; and halo substituents are fluoro or chloro; and n is 0, 1, 2, 3, or 4.

5. A method for detecting the active site of a sialidase enzyme in a sample, comprising:
(a) contacting the compound of claim 1, wherein L is coumarin oxide, with a sample suspected of having an sialidase enzyme molecule to release coumarin;
(b) measuring the level of a fluorescent signal released from the released coumarin in the sample mixture, and
(c) determining the presence of the sialidase enzyme molecule in the sample, wherein an enhanced fluorescent signal as compared to a level of the fluorescent signal in the absence of said compound indicates presence of the azide-containing molecule.

6. A method for detecting the active site of a sialidase enzyme in a sample, comprising:
(a) contacting the compound of claim 2 with a sample suspected of having an sialidase enzyme molecule to release an umbelliferyl moiety;
(b) measuring the level of a fluorescent signal released from the released umbelliferyl moiety in the sample mixture, and
(c) determining the presence of the sialidase enzyme molecule in the sample, wherein an enhanced fluorescent signal as compared to a level of the fluorescent signal in the absence of said compound indicates presence of the azide-containing molecule.

7. A method for detecting the active site of a sialidase enzyme in a sample, comprising:
(a) contacting the compound of claim 3 with a sample suspected of having an sialidase enzyme molecule to release coumarin;
(b) measuring the level of a fluorescent signal released from the released coumarin in the sample mixture, and
(c) determining the presence of the sialidase enzyme molecule in the sample, wherein an enhanced fluorescent signal as compared to a level of the fluorescent signal in the absence of said compound indicates presence of the azide-containing molecule.

* * * * *